US012617855B2

(12) United States Patent
Alonso et al.

(10) Patent No.: US 12,617,855 B2
(45) Date of Patent: May 5, 2026

(54) ANTI-PD-L1 ANTIBODIES

(71) Applicant: BOLT BIOTHERAPEUTICS, INC., Redwood City, CA (US)

(72) Inventors: Michael N. Alonso, Redwood City, CA (US); David Dornan, Redwood City, CA (US); Karla Henning, Redwood City, CA (US); Justin Kenkel, Redwood City, CA (US); Marcin Kowanetz, Redwood City, CA (US); Heidi Leblanc, Redwood City, CA (US); William Mallet, Redwood City, CA (US)

(73) Assignee: BOLT BIOTHERAPEUTICS, INC., Redwood City, CA (US)

( * ) Notice: Subject to any disclaimer, the term of this patent is extended or adjusted under 35 U.S.C. 154(b) by 818 days.

(21) Appl. No.: 17/794,484

(22) PCT Filed: Jan. 21, 2021

(86) PCT No.: PCT/US2021/014346
§ 371 (c)(1),
(2) Date: Jul. 21, 2022

(87) PCT Pub. No.: WO2021/150701
PCT Pub. Date: Jul. 29, 2021

(65) Prior Publication Data
US 2023/0086603 A1 Mar. 23, 2023

Related U.S. Application Data

(60) Provisional application No. 62/963,771, filed on Jan. 21, 2020.

(51) Int. Cl.
*C07K 16/28* (2006.01)
*C07K 14/495* (2006.01)

(52) U.S. Cl.
CPC ........ *C07K 16/2827* (2013.01); *C07K 14/495* (2013.01); *C07K 2317/31* (2013.01); *C07K 2317/52* (2013.01); *C07K 2317/565* (2013.01); *C07K 2317/73* (2013.01); *C07K 2317/77* (2013.01); *C07K 2317/92* (2013.01)

(58) Field of Classification Search
CPC .............. C07K 16/2827; C07K 14/495; C07K 2317/31; C07K 2317/52; C07K 2317/565; C07K 2317/73; C07K 2317/77; C07K 2317/92; C07K 2317/76; A61P 31/12; A61P 35/00; A61P 37/06; A61K 2039/505
See application file for complete search history.

(56) References Cited

U.S. PATENT DOCUMENTS

| | | | | |
|---|---|---|---|---|
| 2006/0110383 A1* | 5/2006 | Honjo | ..................... | A61P 31/10 |
| | | | | 514/19.5 |
| 2015/0225483 A1 | 8/2015 | Lo | | |

FOREIGN PATENT DOCUMENTS

| | | | |
|---|---|---|---|
| CN | 110337448 A | 10/2019 | |
| JP | 2017-506217 A | 3/2017 | |
| JP | 2019-528251 A | 10/2019 | |
| JP | 2019-534008 A | 11/2019 | |
| WO | WO 2018/017673 A1 | 1/2018 | |
| WO | WO 2018/085358 A1 | 5/2018 | |
| WO | WO 2018/119475 A1 | 6/2018 | |
| WO | WO 2020/252294 A1 | 12/2020 | |
| WO | WO 2021/150702 A1 | 7/2021 | |

OTHER PUBLICATIONS

McCarthy et al. (J. Immunol. Methods, 251(1-2): 137-149, 2001).*
Lin et al. (African Journal of Biotechnology, 10(79):18294-18302, 2011).*
Li et al., "Eradication of Triple-Negative Breast Cancer Cells by Targeting Glycosylated PD-L1," *Cancer Cell*, 33(2): 187-201 (2018).
European Patent Office, International Search Report in International Patent Application No. PCT/US2021/014346 (Jul. 19, 2021).
European Patent Office, International Search Report in International Patent Application No. PCT/US2021/014347 (Jul. 5, 2021).
Dondelinger et al., "Understanding the Significance and Implications of Antibody Numbering and Antigen-Binding Surface/Residue Definition," *Frontiers in Immunology*, 9: 2278 (2018).
Sela-Culang et al., "The structural basis of antibody-antigen recognition," *Frontiers in Immunology*, 4: 302 (2013).
Brown et al., "Tolerance of single, but not multiple, amino acid replacements in antibody Vh Cdr 2: a means of minimizing B cell wastage from somatic hypermutation?," J. Immunol., 156(9): 3285-3291 (1996).
Chen et al., "Generation and Analysis of Random Point Mutations in an Antibody CDR2 Sequence: Many Mutated Antibodies Lose their Ability to Bind Antigen," J. Exp. Med., 176: 855-866 (1992).

* cited by examiner

*Primary Examiner* — Nelson B Moseley, II
(74) *Attorney, Agent, or Firm* — Leydig, Voit & Mayer, Ltd.

(57) ABSTRACT

The invention relates to programmed death-ligand 1 (PD-L1) binding agents, nucleic acids comprising the inventive binding agents, vectors and cells comprising the inventive nucleic acids, and compositions thereof. The invention also relates to methods of producing the inventive binding agents, methods for treating a disease, disorder, or condition in a mammal, and methods for enhancing or reducing or inhibiting an immune response in a mammal.

29 Claims, 4 Drawing Sheets

Specification includes a Sequence Listing.

ANTI-PD-L1 ANTIBODIES

CROSS-REFERENCE TO RELATED APPLICATION

This patent application is the U.S. national phase of International Patent Application No. PCT/US2021/014346, filed Jan. 21, 2021, which claims the benefit of U.S. Provisional Patent Application No. 62/963,771, filed Jan. 21, 2020, which is incorporated by reference in its entirety herein.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 187,026 Byte ASCII (Text) file named "763639_ST25.txt" created Jul. 19, 2022.

BACKGROUND OF THE INVENTION

Programmed Death-Ligand 1 (PD-L1, cluster of differentiation 274, CD274, B7-homolog 1, or B7-H1) belongs to the B7 protein superfamily, and is a ligand of programmed cell death protein 1 (PD-1, PDCD1, cluster of differentiation 279, or CD279). PD-L1 can also interact with B7.1 (CD80) and such interaction is believed to inhibit T cell priming. The PD-L1/PD-1 axis plays a large role in suppressing the adaptive immune response. More specifically, it is believed that engagement of PD-L1 with its receptor, PD-1, delivers a signal that inhibits activation and proliferation of T-cells. Agents that bind to PD-L1 and prevent the ligand from binding to the PD-1 receptor prevent this immunosuppression, and can, therefore, enhance an immune response when desired, such as for the treatment of cancers, or infections. PD-L1/PD-1 pathway also contributes to preventing autoimmunity and therefore agonistic agents against PD-L1 or agents that deliver immune inhibitory payloads may help treatment of autoimmune disorders.

Several antibodies targeting PD-L1 have been developed for the treatment of cancer, including atezolizumab (TECENTRIQ™), durvalumab (IMFINZI™), and avelumab (BAVENCIO™). Nevertheless, there continues to be a need for new PD-L1-binding agents, including agents that bind PD-L1 with high affinity and effectively prevent PD-L1/PD-1 signaling and agents that can deliver therapeutic payloads to PD-L1 expressing cells. In addition, there is a need for new PD-L1-binding agents to treat autoimmune disorders and infections.

BRIEF SUMMARY OF THE INVENTION

Provided herein are PD-L1 binding agents comprising an immunoglobulin heavy chain variable region polypeptide and an immunoglobulin light chain variable region polypeptide. In some embodiments, the PD-L1 binding agents comprise an immunoglobulin heavy chain variable region of any one of SEQ ID NOs: 223-264, 324-334, or 361-365, or at least the CDRs thereof; and an immunoglobulin light chain variable region of any one of SEQ ID NOs: 265-306, 335-344, or 366-370 or at least the CDRs thereof. In other embodiments, the PD-L1 binding agents comprise an immunoglobulin heavy chain variable region polypeptide with an amino acid sequence that is at least 90% identical to any one of SEQ ID NOs: 223-264, 324-334, or 361-365, and an immunoglobulin light chain variable region polypeptide with an amino acid sequence that is at least 90% identical to any one of SEQ ID NOs: 265-306, 335-344, or 366-370. In yet other embodiments, the PD-L1 binding agent, the immunoglobulin heavy chain variable region polypeptide comprises a complementarity determining region 1 (HCDR1) comprising any one of SEQ ID NOs: 1-23, 309, or 345, a complementarity determining region 2 (HCDR2) comprising any one of SEQ ID NOs: 24-57, 310-314, or 346-349, and a complementarity determining region 3 (HCDR3) comprising any one of SEQ ID NOs: 58-95, 315-318, or 350-354; and/or the immunoglobulin light chain variable region polypeptide comprises a complementarity determining region 1 (LCDR1) comprising any one of SEQ ID NOs: 96-128, 319-323, 355, or 356, a complementarity determining region 2 (LCDR2) comprising any one of SEQ ID NOs: 129-151 or 357-359, and a complementarity determining region 3 (LCDR3) comprising any one of SEQ ID NOs: 152-176 or 360. Also provided are nucleic acids encoding the PD-L1 binding agents, or the individual heavy and light chains thereof vectors and cells comprising the nucleic acids; and compositions comprising the binding agents or nucleic acids.

Also provided is a method of preparing a binding agent as described herein, which method comprises expressing in a cell one or more nucleic acids encoding the heavy and light chain variable region polypeptides of the binding agent.

Further provided is a method of delivering a payload to a cell expressing PD-L1 comprising administering to the cell, or mammal comprising the cell, a PD-L1 binding agent provided herein conjugated to the payload.

Also provided is a method for enhancing or reducing or inhibiting an immune response in a mammal, and a method for treating a disease, disorder, or condition in a mammal that is responsive to PD-L1 inhibition, which methods comprise administering a binding agent as described herein, or conjugate thereof, to the mammal.

Additional aspects and embodiments of the invention are as provided in the following detailed description.

BRIEF DESCRIPTION OF THE SEVERAL VIEWS OF THE DRAWING(S)

DETAILED DESCRIPTION OF THE INVENTION

Figure 1:
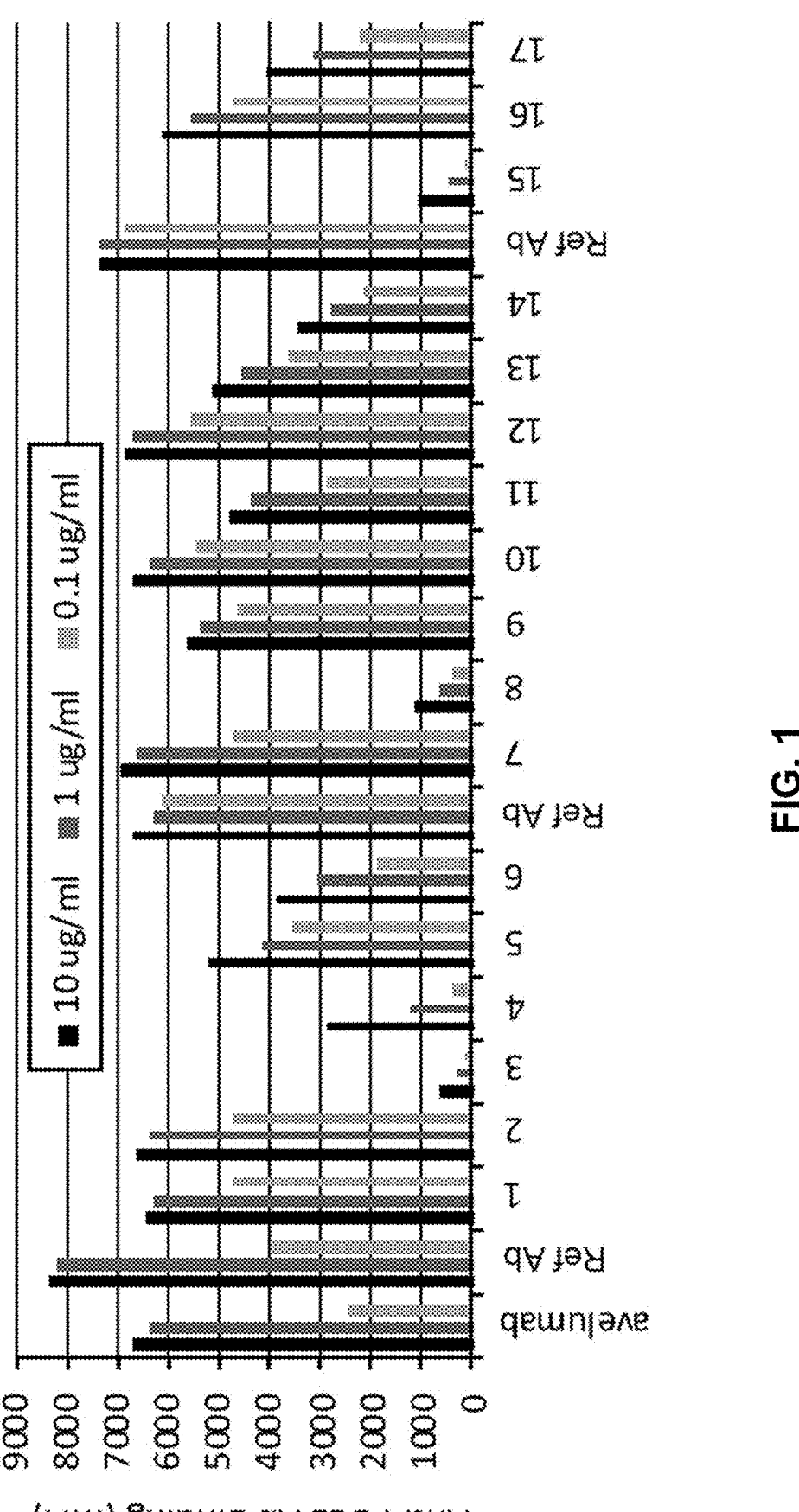
FIG. 1 depicts experimental data illustrating the affinity for binding agents of an embodiment of the invention for human PD-L1 on JIMT-1 cell surface.

The invention provides a PD-L1 binding agent comprising an immunoglobulin heavy chain variable region polypeptide and an immunoglobulin light chain variable region polypeptide.

The PD-L1 binding agent specifically binds PD-L1. The binding specificity of the agent allows for targeting PD-L1 expressing cells, for instance, to deliver therapeutic payloads to such cells.

In some embodiments, the PD-L1 binding agent binds PD-L1 without substantially inhibiting or preventing PD-L1 from binding to its receptor, PD-1. However, in other embodiments, the PD-L1 binding agent can completely or partially block (inhibit or prevent) binding of PD-L1 to its receptor, PD-1, such that the antibody can be used to inhibit PD-L1/PD-1 signaling (e.g., for therapeutic purposes).

Furthermore, in some embodiments, the PD-L1 binding agents provided herein cause cellular internalization of PD-L1 or the PD-L1/PD-L1 binding agent complex upon binding to PD-L1 on the cell surface. Without wishing to be bound by any particular theory or mechanism of action, it is believed that the PD-L1 binding agents according to this embodiment cause PD-L1 internalization upon binding, and remain bound to PD-L1 during internalization resulting in internalization of the binding agent along with PD-L1. Cellular internalization of PD-L1 and bound PD-L1 binding agent can be determined by any suitable method, such as assaying for persistence on the cell surface and/or detection of internalized antibodies. In some embodiments, the PD-L1 binding agent internalizes strongly enough that at least about 20% or 25% (e.g., at least about 35%, at least about 50%, at least about 75%, or at least about 90%) of the PD-L1 binding agent that binds PD-L1 on the cell surface is internalized (e.g., using a surface persistence assay, about 75% or less, about 65% or less, about 50% or less, about 35% or less or about 20% or less of PD-L1 binding agent molecules bound to PD-L1 on the cell surface at the beginning of the assay remain bound at the end of the assay). Persistence can be tested over a suitable length of time long enough to allow internalization to occur. In some embodiments, the internalization occurs within about 2 days, or even within about one day (24 hours or less) or even within about 12 hours or less.

In some embodiments, the PD-L1 binding agent binds to human PD-L1, for example, a protein comprising SEQ ID NO: 307 (MRIFAVFIFMTYWHLLNAFTVTVPKDLY-VVEYGSNMTIECKFPVEKQLDLAALIVY WEMEDKNIIQFVH-GEEDLKVQHSSYRQRARLLKDQLSLG-NAALQITDVKLQDAGVY RCMISYGGA-DYKRITVKVNAPYNKINQRILVVDPVTSEHELTCQAE-GYPKAEVIWTS SDHQVLSGKTTTTNSKREEKLFNVTSTLRINTTTNEI-FYCTFRRLDPEENHTAELVIPE LPLAHPPNERTHLVIL-GAILLCLGVALTFI-FRLRKGRMMDVKKCGIQDTNSKKQSDTH LEET). However, binding agents that bind to any PD-L1 homolog or paralog also are encompassed. In some embodiments, the PD-L1 protein comprises at least about 70%, about 75%, about 80%, about 85%, about 90%, about 91%, about 92%, about 93%, about 94%, about 95%, about 96%, about 97%, about 98%, about 99%, or more sequence identity to SEQ ID NO: 307. In some embodiments, the binding agent binds human PD-L1 and cynomolgus PD-L1; or human, cynomolgus and mouse PD-L1.

Nucleic acid or amino acid sequence "identity," as referenced herein, can be determined by comparing a nucleic acid or amino acid sequence of interest to a reference nucleic acid or amino acid sequence. The percent identity is the number of nucleotides or amino acid residues that are the same (i.e., that are identical) as between the optimally aligned sequence of interest and the reference sequence divided by the length of the longest sequence (i.e., the length of either the sequence of interest or the reference sequence, whichever is longer). Alignment of sequences and calculation of percent identity can be performed using available software programs. Examples of such programs include CLUSTAL-W, T-Coffee, and ALIGN (for alignment of nucleic acid and amino acid sequences), BLAST programs (e.g., BLAST 2.1, BL2SEQ, BLASTp, BLASTn, and the like) and FASTA programs (e.g., FASTA3x, FAS™, and SSEARCH) (for sequence alignment and sequence similarity searches). Sequence alignment algorithms also are disclosed in, for example, Altschul et al., *J. Molecular Biol.*, 215(3): 403-410 (1990), Beigert et al., *Proc. Natl. Acad. Sci. USA*, 106(10): 3770-3775 (2009), Durbin et al., eds., *Biological Sequence Analysis: Probalistic Models of Proteins and Nucleic Acids*, Cambridge University Press, Cambridge, UK (2009), Sod-ing, *Bioinformatics*, 21(7): 951-960 (2005), Altschul et al., *Nucleic Acids Res.*, 25(17): 3389-3402 (1997), and Gusfield, *Algorithms on Strings, Trees and Sequences*, Cambridge University Press, Cambridge UK (1997)). Percent (%) identity of sequences can be also calculated, for example, as $100\times[(\text{identical positions})/\min(\text{TG}_A, \text{TG}_B)]$, where $\text{TG}_A$ and $\text{TG}_B$ are the sum of the number of residues and internal gap positions in peptide sequences A and B in the alignment that minimizes $\text{TG}_A$ and $\text{TG}_B$. See, e.g., Russell et al., *J. Mol Biol.*, 244: 332-350 (1994).

The binding agent comprises Ig heavy and light chain variable region polypeptides that together form the antigen binding site. Each of the heavy and light chain variable regions are polypeptides comprising three complementarity determining regions (CDR1, CDR2, and CDR3) connected by framework regions. The binding agent can be any of a variety of types of binding agents known in the art that comprise Ig heavy and light chains. For instance, the binding agent can be an antibody, an antigen-binding antibody "fragment," or a T-cell receptor.

In some embodiments, the binding agent is a whole (or complete) antibody, which comprises an antigen binding domain comprising the Ig heavy and light variable domains as well as a fragment crystallizable (Fc) domain. An exemplary antibody structure is a tetramer composed of two pairs of polypeptide chains, each pair having one "light" (a smaller chain, such as about 25 kDa) and one "heavy" chain (a larger chain, such as about 50-70 kDa), typically connected by disulfide bonds. Each chain is composed of structural domains, which are referred to as immunoglobulin domains. These domains are classified into different categories by size and function, e.g., variable domains or regions on the light and heavy chains ($V_L$ and $V_H$, respectively) and constant domains or regions on the light and heavy chains ($C_L$ and $C_H$, respectively). The N-terminus of each chain defines a variable region, typically about 100 to 110 or more amino acids (but not limited thereto), referred to as the paratope, primarily responsible for antigen recognition, i.e., the antigen binding domain. Light chains are classified as either kappa or lambda. Heavy chains are classified as gamma, mu, alpha, delta, or epsilon, which in turn define the immunoglobulin classes, IgG, IgM, IgA, IgD and IgE, respectively. The classes can be further divided into subclasses. For instance, there are four IgG subclasses (IgG1, IgG2, IgG3, and IgG4) in humans, named in order of their abundance in serum (i.e., IgG1 is the most abundant).

In some embodiments, the binding agent is an antigen-binding antibody "fragment," which is a construct that comprises at least an antigen-binding region of an antibody, alone or with other components that together constitute the antigen-binding construct. Many different types of antibody "fragments" are known in the art, including, for instance, (i) a Fab fragment, which is a monovalent fragment consisting of the $V_L$, $V_H$, $C_L$, and $CH_1$ domains, (ii) a $F(ab')_2$ fragment, which is a bivalent fragment comprising two Fab fragments linked by a disulfide bridge at the hinge region, (iii) a Fv fragment consisting of the $V_L$ and $V_H$ domains of a single arm of an antibody, (iv) a Fab' fragment, which results from breaking the disulfide bridge of an F(ab')$_2$ fragment using mild reducing conditions, (v) a disulfide-stabilized Fv fragment (dsFv), and (vi) a single chain Fv (scFv), which is a monovalent molecule consisting of the two domains of the Fv fragment (i.e., $V_L$ and $V_H$) joined by a synthetic linker which enables the two domains to be synthesized as a single polypeptide chain.

The antibody or antibody fragments can be part of a larger construct, for example, a conjugate or fusion construct of the antibody fragment to additional regions. For instance, in some embodiments, the antibody fragment can be fused to an Fc region as described herein. In other embodiments, the antibody fragment (e.g., a Fab or scFv) can be part of a chimeric antigen receptor or chimeric T-cell receptor, for instance, by fusing to a transmembrane domain (optionally with an intervening linker or "stalk" (e.g., hinge region)) and optional intercellular signaling domain. For instance, the antibody fragment can be fused to the gamma and/or delta chains of a t-cell receptor, so as to provide a T-cell receptor like construct that binds PD-L1. In yet another embodiment, the antibody fragment is part of a bispecific T-cell engager (BiTEs) comprising a CD1 or CD3 binding domain and linker.

The antibody or antigen-binding antibody fragment can be monospecific for PD-L1, or can be bispecific or multispecific. For instance, in bivalent or multivalent antibodies or antibody fragments, the binding domains can be different targeting different epitopes of the same antigen or targeting different antigens. Methods of constructing multivalent binding constructs are known in the art. Bispecific and multispecific antibodies are known in the art. Furthermore, a diabody, triabody, or tetrabody can be provided, which is a dimer, trimer, or tetramer of polypeptide chains each comprising a $V_H$ connected to a $V_L$ by a peptide linker that is too short to allow pairing between the $V_H$ and $V_L$ on the same polypeptide chain, thereby driving the pairing between the complementary domains on different $V_H$-$V_L$ polypeptide chains to generate a multimeric molecule having two, three, or four functional antigen binding sites. Also, bis-scFv fragments, which are small scFv fragments with two different variable domains can be generated to produce bispecific bis-scFv fragments capable of binding two different epitopes. Fab dimers (Fab2) and Fab trimers (Fab3) can be produced using genetic engineering methods to create multispecific constructs based on Fab fragments.

The PD-L1-binding agent also can be an antibody conjugate. In this respect, the PD-L1-binding agent can be a conjugate of (1) an antibody, an alternative scaffold, or fragments thereof, and (2) a protein or non-protein moiety. For example, the PD-L1 binding agent can be conjugated to a peptide, a fluorescent molecule, chemotherapeutic or other cytotoxic payload, immune-activating or immune-suppressive agent.

The PD-L1-binding agent can be, or can be obtained from, a human antibody, a non-human antibody, a humanized antibody, or a chimeric antibody, or corresponding antibody fragments. A "chimeric" antibody is an antibody or fragment thereof typically comprising human constant regions and non-human variable regions. A "humanized" antibody is a monoclonal antibody typically comprising a human antibody scaffold but with non-human origin amino acids or sequences in at least one CDR (e.g., 1, 2, 3, 4, 5, or all six CDRs).

Methods for generating such antibodies are known in the art and are described in, for example, Köhler and Milstein,

6

Eur. J. Immunol., 5: 511-519 (1976); Harlow and Lane (eds.), Antibodies: A Laboratory Manual, CSH Press (1988); and Janeway et al. (eds.), Immunobiology, 9th Ed., Garland Publishing, New York, NY (2017). In certain embodiments, a human or chimeric antibody or antibody fragment can be generated using a transgenic animal (e.g., a mouse) wherein one or more endogenous immunoglobulin genes are replaced with one or more human immunoglobulin genes. Examples of transgenic mice wherein endogenous antibody genes are effectively replaced with human antibody genes include, but are not limited to, the Medarex HUMAB-MOUSE™, the Kirin TC MOUSE™ and the Kyowa Kirin KM-MOUSE™ (see, e.g., Lonberg, Nat. Biotechnol., 23(9): 1117-25 (2005), and Lonberg, Handb. Exp. Pharmacol., 181: 69-97 (2008)). A humanized antibody can be generated using any suitable method known in the art (see, e.g., An, Z. (ed.), Therapeutic Monoclonal Antibodies: From Bench to Clinic, John Wiley & Sons, Inc., Hoboken, New Jersey (2009)), including, e.g., grafting of non-human CDRs onto a human antibody scaffold (see, e.g., Kashmiri et al., Methods, 36(1): 25-34 (2005); and Hou et al., J. Biochem., 144(1): 115-120 (2008) and use of phage display (see, e.g., Fellouse, et al., Journal of Molecular Biology, 373(4): 924-940 (2007) and Glanville, et al., PNAS, 106(48): 20216-20221 (2009)).

In an embodiment, the PD-L1 binding agent comprises an immunoglobulin heavy chain variable region of any one of SEQ ID NOs: 223-264, 324-334, or 361-365, a sequence that is at least about 90%, at least about 91%, at least about 92%, at least about 93%, at least about 94%, at least about 95%, at least about 96%, at least about 97%, at least about 98%, or at least about 99% identical to SEQ ID NOs: 223-264, 324-334, or 361-365, or at least the CDRs thereof; and/or an immunoglobulin light chain variable region of any one of SEQ ID NOs: 265-306, 335-344, or 366-370, a sequence that is at least about 90%, at least about 91%, at least about 92%, at least about 93%, at least about 94%, at least about 95%, at least about 96%, at least about 97%, at least about 98%, or at least about 99% identical to SEQ ID NOs: 265-306, 335-344, or 366-370, or at least the CDRs thereof.

By way of further illustration, the PD-L1 binding agent can comprise:

(1) an immunoglobulin heavy chain variable region of SEQ ID NO: 223, or at least the CDRs thereof, and/or an immunoglobulin light chain variable region of SEQ ID NO: 265, or at least the CDRs thereof;

(2) an immunoglobulin heavy chain variable region of SEQ ID NO: 224, or at least the CDRs thereof, and/or an immunoglobulin light chain variable region of SEQ ID NO: 266, or at least the CDRs thereof.

(3) an immunoglobulin heavy chain variable region of SEQ ID NO: 225, or at least the CDRs thereof, and/or an immunoglobulin light chain variable region of SEQ ID NO: 267, or at least the CDRs thereof;

(4) an immunoglobulin heavy chain variable region of SEQ ID NO: 226, or at least the CDRs thereof, and/or an immunoglobulin light chain variable region of SEQ ID NO: 268, or at least the CDRs thereof;

(5) an immunoglobulin heavy chain variable region of SEQ ID NO: 227, or at least the CDRs thereof, and/or an immunoglobulin light chain variable region of SEQ ID NO: 269, or at least the CDRs thereof;

(6) an immunoglobulin heavy chain variable region of SEQ ID NO: 228, or at least the CDRs thereof, and/or an immunoglobulin light chain variable region of SEQ ID NO: 270, or at least the CDRs thereof;

(7) an immunoglobulin heavy chain variable region of SEQ ID NO: 229, or at least the CDRs thereof, and/or an immunoglobulin light chain variable region of SEQ ID NO: 271, or at least the CDRs thereof;

(8) an immunoglobulin heavy chain variable region of SEQ ID NO: 230, or at least the CDRs thereof, and/or an immunoglobulin light chain variable region of SEQ ID NO: 272, or at least the CDRs thereof;

(9) an immunoglobulin heavy chain variable region of SEQ ID NO: 231, or at least the CDRs thereof, and/or an immunoglobulin light chain variable region of SEQ ID NO: 273, or at least the CDRs thereof;

(10) an immunoglobulin heavy chain variable region of SEQ ID NO: 232, or at least the CDRs thereof, and/or an immunoglobulin light chain variable region of SEQ ID NO: 274, or at least the CDRs thereof;

(11) an immunoglobulin heavy chain variable region of SEQ ID NO: 233, or at least the CDRs thereof, and/or an immunoglobulin light chain variable region of SEQ ID NO: 275, or at least the CDRs thereof;

(12) an immunoglobulin heavy chain variable region of SEQ ID NO: 234, or at least the CDRs thereof, and/or an immunoglobulin light chain variable region of SEQ ID NO: 276, or at least the CDRs thereof;

(13) an immunoglobulin heavy chain variable region of SEQ ID NO: 235, or at least the CDRs thereof, and/or an immunoglobulin light chain variable region of SEQ ID NO: 277, or at least the CDRs thereof;

(14) an immunoglobulin heavy chain variable region of SEQ ID NO: 236, or at least the CDRs thereof, and/or an immunoglobulin light chain variable region of SEQ ID NO: 278, or at least the CDRs thereof;

(15) an immunoglobulin heavy chain variable region of SEQ ID NO: 237, or at least the CDRs thereof, and/or an immunoglobulin light chain variable region of SEQ ID NO: 279, or at least the CDRs thereof;

(16) an immunoglobulin heavy chain variable region of SEQ ID NO: 238, or at least the CDRs thereof, and/or an immunoglobulin light chain variable region of SEQ ID NO: 280, or at least the CDRs thereof;

(17) an immunoglobulin heavy chain variable region of SEQ ID NO: 239, or at least the CDRs thereof, and/or an immunoglobulin light chain variable region of SEQ ID NO: 281, or at least the CDRs thereof;

(18) an immunoglobulin heavy chain variable region of SEQ ID NO: 240, or at least the CDRs thereof, and/or an immunoglobulin light chain variable region of SEQ ID NO: 282, or at least the CDRs thereof;

(19) an immunoglobulin heavy chain variable region of SEQ ID NO: 241, or at least the CDRs thereof, and/or an immunoglobulin light chain variable region of SEQ ID NO: 283, or at least the CDRs thereof;

(20) an immunoglobulin heavy chain variable region of SEQ ID NO: 242, or at least the CDRs thereof, and/or an immunoglobulin light chain variable region of SEQ ID NO: 284, or at least the CDRs thereof;

(21) an immunoglobulin heavy chain variable region of SEQ ID NO: 243, or at least the CDRs thereof, and/or an immunoglobulin light chain variable region of SEQ ID NO: 285, or at least the CDRs thereof;

(22) an immunoglobulin heavy chain variable region of SEQ ID NO: 244, or at least the CDRs thereof, and/or an immunoglobulin light chain variable region of SEQ ID NO: 286, or at least the CDRs thereof;

(23) an immunoglobulin heavy chain variable region of SEQ ID NO: 245, or at least the CDRs thereof, and/or an immunoglobulin light chain variable region of SEQ ID NO: 287, or at least the CDRs thereof;

(24) an immunoglobulin heavy chain variable region of SEQ ID NO: 246, or at least the CDRs thereof, and/or an immunoglobulin light chain variable region of SEQ ID NO: 288, or at least the CDRs thereof;

(25) an immunoglobulin heavy chain variable region of SEQ ID NO: 247, or at least the CDRs thereof, and/or an immunoglobulin light chain variable region of SEQ ID NO: 289, or at least the CDRs thereof;

(26) an immunoglobulin heavy chain variable region of SEQ ID NO: 248, or at least the CDRs thereof, and/or an immunoglobulin light chain variable region of SEQ ID NO: 290, or at least the CDRs thereof;

(27) an immunoglobulin heavy chain variable region of SEQ ID NO: 249, or at least the CDRs thereof, and/or an immunoglobulin light chain variable region of SEQ ID NO: 291, or at least the CDRs thereof;

(28) an immunoglobulin heavy chain variable region of SEQ ID NO: 250, or at least the CDRs thereof, and/or an immunoglobulin light chain variable region of SEQ ID NO: 292, or at least the CDRs thereof;

(29) an immunoglobulin heavy chain variable region of SEQ ID NO: 251, or at least the CDRs thereof, and/or an immunoglobulin light chain variable region of SEQ ID NO: 293, or at least the CDRs thereof;

(30) an immunoglobulin heavy chain variable region of SEQ ID NO: 252, or at least the CDRs thereof, and/or an immunoglobulin light chain variable region of SEQ ID NO: 294, or at least the CDRs thereof;

(31) an immunoglobulin heavy chain variable region of SEQ ID NO: 253, or at least the CDRs thereof, and/or an immunoglobulin light chain variable region of SEQ ID NO: 295, or at least the CDRs thereof;

(32) an immunoglobulin heavy chain variable region of SEQ ID NO: 254, or at least the CDRs thereof, and/or an immunoglobulin light chain variable region of SEQ ID NO: 296, or at least the CDRs thereof;

(33) an immunoglobulin heavy chain variable region of SEQ ID NO: 255, or at least the CDRs thereof, and/or an immunoglobulin light chain variable region of SEQ ID NO: 297, or at least the CDRs thereof;

(34) an immunoglobulin heavy chain variable region of SEQ ID NO: 256, or at least the CDRs thereof, and/or an immunoglobulin light chain variable region of SEQ ID NO: 298, or at least the CDRs thereof;

(35) an immunoglobulin heavy chain variable region of SEQ ID NO: 257, or at least the CDRs thereof, and/or an immunoglobulin light chain variable region of SEQ ID NO: 299, or at least the CDRs thereof;

(36) an immunoglobulin heavy chain variable region of SEQ ID NO: 258, or at least the CDRs thereof, and/or an immunoglobulin light chain variable region of SEQ ID NO: 300, or at least the CDRs thereof;

(37) an immunoglobulin heavy chain variable region of SEQ ID NO: 259, or at least the CDRs thereof, and/or an immunoglobulin light chain variable region of SEQ ID NO: 301, or at least the CDRs thereof;

(38) an immunoglobulin heavy chain variable region of SEQ ID NO: 260, or at least the CDRs thereof, and/or an immunoglobulin light chain variable region of SEQ ID NO: 302, or at least the CDRs thereof;

(39) an immunoglobulin heavy chain variable region of SEQ ID NO: 261, or at least the CDRs thereof, and/or an immunoglobulin light chain variable region of SEQ ID NO: 303, or at least the CDRs thereof;

(40) an immunoglobulin heavy chain variable region of SEQ ID NO: 262, or at least the CDRs thereof, and/or an immunoglobulin light chain variable region of SEQ ID NO: 304, or at least the CDRs thereof;

(41) an immunoglobulin heavy chain variable region of SEQ ID NO: 263, or at least the CDRs thereof, and/or an immunoglobulin light chain variable region of SEQ ID NO: 305, or at least the CDRs thereof;

(42) an immunoglobulin heavy chain variable region of SEQ ID NO: 164, or at least the CDRs thereof, and/or an immunoglobulin light chain variable region of SEQ ID NO: 306, or at least the CDRs thereof;

(43) an immunoglobulin heavy chain variable region of SEQ ID NO: 324, or at least the CDRs thereof, and/or an immunoglobulin light chain variable region of SEQ ID NO: 281, or at least the CDRs thereof;

(44) an immunoglobulin heavy chain variable region of SEQ ID NO: 325 (wherein X can be any amino acid), or at least the CDRs thereof, and/or an immunoglobulin light chain variable region of SEQ ID NO: 281, or at least the CDRs thereof;

(45) an immunoglobulin heavy chain variable region of SEQ ID NO: 326 (wherein X can be any amino acid), or at least the CDRs thereof, and/or an immunoglobulin light chain variable region of SEQ ID NO: 281, or at least the CDRs thereof;

(46) an immunoglobulin heavy chain variable region of SEQ ID NO: 327, or at least the CDRs thereof, and/or an immunoglobulin light chain variable region of SEQ ID NO: 281, or at least the CDRs thereof;

(47) an immunoglobulin heavy chain variable region of SEQ ID NO: 328, or at least the CDRs thereof, and/or an immunoglobulin light chain variable region of SEQ ID NO: 281, or at least the CDRs thereof;

(48) an immunoglobulin heavy chain variable region of SEQ ID NO: 329, or at least the CDRs thereof, and/or an immunoglobulin light chain variable region of SEQ ID NO: 281, or at least the CDRs thereof;

(49) an immunoglobulin heavy chain variable region of SEQ ID NO: 329, or at least the CDRs thereof, and/or an immunoglobulin light chain variable region of SEQ ID NO: 281, or at least the CDRs thereof;

(50) an immunoglobulin heavy chain variable region of SEQ ID NO: 330, or at least the CDRs thereof, and/or an immunoglobulin light chain variable region of SEQ ID NO: 281, or at least the CDRs thereof;

(51) an immunoglobulin heavy chain variable region of SEQ ID NO: 331, or at least the CDRs thereof, and/or an immunoglobulin light chain variable region of SEQ ID NO: 281, or at least the CDRs thereof;

(52) an immunoglobulin heavy chain variable region of SEQ ID NO: 332, or at least the CDRs thereof, and/or an immunoglobulin light chain variable region of SEQ ID NO: 281, or at least the CDRs thereof;

(53) an immunoglobulin heavy chain variable region of SEQ ID NO: 333, or at least the CDRs thereof, and/or an immunoglobulin light chain variable region of SEQ ID NO: 281, or at least the CDRs thereof;

(54) an immunoglobulin heavy chain variable region of SEQ ID NO: 334, or at least the CDRs thereof, and/or an immunoglobulin light chain variable region of SEQ ID NO: 281, or at least the CDRs thereof;

(55) an immunoglobulin heavy chain variable region of SEQ ID NO: 328, or at least the CDRs thereof, and/or an immunoglobulin light chain variable region of SEQ ID NO: 335, or at least the CDRs thereof;

(56) an immunoglobulin heavy chain variable region of SEQ ID NO: 328, or at least the CDRs thereof, and/or an immunoglobulin light chain variable region of SEQ ID NO: 336, or at least the CDRs thereof;

(57) an immunoglobulin heavy chain variable region of SEQ ID NO: 328, or at least the CDRs thereof, and/or an immunoglobulin light chain variable region of SEQ ID NO: 337, or at least the CDRs thereof;

(58) an immunoglobulin heavy chain variable region of SEQ ID NO: 328, or at least the CDRs thereof, and/or an immunoglobulin light chain variable region of SEQ ID NO: 338, or at least the CDRs thereof;

(59) an immunoglobulin heavy chain variable region of SEQ ID NO: 328, or at least the CDRs thereof, and/or an immunoglobulin light chain variable region of SEQ ID NO: 339, or at least the CDRs thereof;

(60) an immunoglobulin heavy chain variable region of SEQ ID NO: 328, or at least the CDRs thereof, and/or an immunoglobulin light chain variable region of SEQ ID NO: 340, or at least the CDRs thereof;

(61) an immunoglobulin heavy chain variable region of SEQ ID NO: 328, or at least the CDRs thereof, and/or an immunoglobulin light chain variable region of SEQ ID NO: 341, or at least the CDRs thereof;

(62) an immunoglobulin heavy chain variable region of SEQ ID NO: 328, or at least the CDRs thereof, and/or an immunoglobulin light chain variable region of SEQ ID NO: 342, or at least the CDRs thereof;

(63) an immunoglobulin heavy chain variable region of SEQ ID NO: 328, or at least the CDRs thereof, and/or an immunoglobulin light chain variable region of SEQ ID NO: 343, or at least the CDRs thereof;

(64) an immunoglobulin heavy chain variable region of SEQ ID NO: 328, or at least the CDRs thereof, and/or an immunoglobulin light chain variable region of SEQ ID NO: 344, or at least the CDRs thereof;

(65) an immunoglobulin heavy chain variable region of SEQ ID NO: 328, or at least the CDRs thereof, and/or an immunoglobulin light chain variable region of SEQ ID NO: 281, or at least the CDRs thereof;

(66) an immunoglobulin heavy chain variable region of SEQ ID NO: 361, or at least the CDRs thereof, and/or an immunoglobulin light chain variable region of SEQ ID NO: 366, or at least the CDRs thereof;

(67) an immunoglobulin heavy chain variable region of SEQ ID NO: 362, or at least the CDRs thereof, and/or an immunoglobulin light chain variable region of SEQ ID NO: 367, or at least the CDRs thereof;

(68) an immunoglobulin heavy chain variable region of SEQ ID NO: 363, or at least the CDRs thereof, and/or an immunoglobulin light chain variable region of SEQ ID NO: 368, or at least the CDRs thereof;

(69) an immunoglobulin heavy chain variable region of SEQ ID NO: 364, or at least the CDRs thereof, and/or an immunoglobulin light chain variable region of SEQ ID NO: 369, or at least the CDRs thereof;

(70) an immunoglobulin heavy chain variable region of SEQ ID NO: 365, or at least the CDRs thereof, and/or an immunoglobulin light chain variable region of SEQ ID NO: 370, or at least the CDRs thereof; and/or

(71) an immunoglobulin heavy chain variable region of Table 4 and/or an immunoglobulin light chain variable region of Table 4, or at least the CDRs thereof.

The CDRs of a given heavy or light chain Ig sequence can be determined in accordance with any of the various known Ig numbering schemes (e.g., Kabat, Chothia, Martin (Enhanced Chothia), IGMT, AbM). In certain embodiments, the PD-L1 binding agent comprises one or more of the following CDRs:

a HCDR1 comprising or consisting of any one of SEQ ID NOs: 1-23, 309, or 345 or a sequence that is at least about 90%, at least about 91%, at least about 92%, at least about 93%, at least about 94%, at least about 95%, at least about 96%, at least about 97%, at least about 98%, or at least about 99% identical to any one of SEQ ID NOs: 1-23, 309, or 345;

a HCDR2 comprising or consisting of any one of SEQ ID NOs: 24-57, 310-314, or 346-349, or a sequence that is at least about 90%, at least about 91%, at least about 92%, at least about 93%, at least about 94%, at least about 95%, at least about 96%, at least about 97%, at least about 98%, or at least about 99% identical to any one of SEQ ID NOs: 24-57, 310-314, or 346-349; and a HCDR3 comprising or consisting of any one of SEQ ID NOs: 58-95, 315-318, or 350-354, or a sequence that is at least about 90%, at least about 91%, at least about 92%, at least about 93%, at least about 94%, at least about 95%, at least about 96%, at least about 97%, at least about 98%, or at least about 99% identical to any one of SEQ ID NOs: 58-95, 315-318, or 350-354; and/or the immunoglobulin light chain polypeptide comprises a LCDR1 comprising or consisting of any one of SEQ ID NOs: 96-128, 319-323, 355, or 356, or a sequence that is at least about 90%, at least about 91%, at least about 92%, at least about 93%, at least about 94%, at least about 95%, at least about 96%, at least about 97%, at least about 98%, or at least about 99% identical to any one of SEQ ID NOs: 96-128, 319-323, 355, or 356;

a LCDR2 comprising or consisting of any one of SEQ ID NOs: 129-151 or 357-359 or a sequence that is at least about 90%, at least about 91%, at least about 92%, at least about 93%, at least about 94%, at least about 95%, at least about 96%, at least about 97%, at least about 98%, or at least about 99% identical to any one of SEQ ID NOs: 129-151 or 357-359; and a LCDR3 comprising or consisting of any one of SEQ ID NOs: 152-176 or 360 or a sequence that is at least about 90%, at least about 91%, at least about 92%, at least about 93%, at least about 94%, at least about 95%, at least about 96%, at least about 97%, at least about 98%, or at least about 99% identical to any one of SEQ ID NOs: 152-176 or 360.

In particular embodiments, the binding agent comprises an immunoglobulin heavy chain polypeptide and an immunoglobulin light chain polypeptide, wherein:

(1) the immunoglobulin heavy chain polypeptide comprises a HCDR1 comprising or consisting of SEQ ID NO: 1, a HCDR2 comprising or consisting of SEQ ID NO: 24, and a HCDR3 comprising or consisting of SEQ ID NO: 58; and/or the immunoglobulin light chain polypeptide comprises a LCDR1 comprising or consisting of SEQ ID NO: 96, a LCDR2 comprising or consisting of SEQ ID NO: 129, and a LCDR3 comprising or consisting of SEQ ID NO: 152;

(2) the immunoglobulin heavy chain polypeptide comprises a HCDR1 comprising or consisting of SEQ ID NO: 2, a HCDR2 comprising or consisting of SEQ ID NO: 25, and a HCDR3 comprising or consisting of SEQ ID NO: 59; and/or the immunoglobulin light chain polypeptide comprises a LCDR1 comprising or consisting of SEQ ID NO: 97, a LCDR2 comprising or consisting of SEQ ID NO: 129, and a LCDR3 comprising or consisting of SEQ ID NO: 153;

(3) the immunoglobulin heavy chain polypeptide comprises a HCDR1 comprising or consisting of SEQ ID NO: 3, a HCDR2 comprising or consisting of SEQ ID NO: 26, and a HCDR3 comprising or consisting of SEQ ID NO: 60; and/or the immunoglobulin light chain polypeptide comprises a LCDR1 comprising or consisting of SEQ ID NO: 98, a LCDR2 comprising or consisting of SEQ ID NO: 129, and a LCDR3 comprising or consisting of SEQ ID NO: 154;

(4) the immunoglobulin heavy chain polypeptide comprises a HCDR1 comprising or consisting of SEQ ID NO: 4, a HCDR2 comprising or consisting of SEQ ID NO: 27, and a HCDR3 comprising or consisting of SEQ ID NO: 61; and/or the immunoglobulin light chain polypeptide comprises a LCDR1 comprising or consisting of SEQ ID NO: 99, a LCDR2 comprising or consisting of SEQ ID NO: 130, and a LCDR3 comprising or consisting of SEQ ID NO: 155;

(5) the immunoglobulin heavy chain polypeptide comprises a HCDR1 comprising or consisting of SEQ ID NO: 5, a HCDR2 comprising or consisting of SEQ ID NO: 28, and a HCDR3 comprising or consisting of SEQ ID NO: 62; and/or the immunoglobulin light chain polypeptide comprises a LCDR1 comprising or consisting of SEQ ID NO: 100, a LCDR2 comprising or consisting of SEQ ID NO: 129, and a LCDR3 comprising or consisting of SEQ ID NO: 153;

(6) the immunoglobulin heavy chain polypeptide comprises a HCDR1 comprising or consisting of SEQ ID NO: 6, a HCDR2 comprising or consisting of SEQ ID NO: 29, and a HCDR3 comprising or consisting of SEQ ID NO: 63; and/or the immunoglobulin light chain polypeptide comprises a LCDR1 comprising or consisting of SEQ ID NO: 101, a LCDR2 comprising or consisting of SEQ ID NO: 131, and a LCDR3 comprising or consisting of SEQ ID NO: 156;

(7) the immunoglobulin heavy chain polypeptide comprises a HCDR1 comprising or consisting of SEQ ID NO: 7, a HCDR2 comprising or consisting of SEQ ID NO: 30, and a HCDR3 comprising or consisting of SEQ ID NO: 64; and/or the immunoglobulin light chain polypeptide comprises a LCDR1 comprising or consisting of SEQ ID NO: 102, a LCDR2 comprising or consisting of SEQ ID NO: 132, and a LCDR3 comprising or consisting of SEQ ID NO: 157;

(8) the immunoglobulin heavy chain polypeptide comprises a HCDR1 comprising or consisting of SEQ ID NO: 2, a HCDR2 comprising or consisting of SEQ ID NO: 31, and a HCDR3 comprising or consisting of SEQ ID NO: 65; and/or the immunoglobulin light chain polypeptide comprises a LCDR1 comprising or consisting of SEQ ID NO: 103, a LCDR2 comprising or consisting of SEQ ID NO: 133, and a LCDR3 comprising or consisting of SEQ ID NO: 155;

(9) the immunoglobulin heavy chain polypeptide comprises a HCDR1 comprising or consisting of SEQ ID NO: 8, a HCDR2 comprising or consisting of SEQ ID NO: 32, and a HCDR3 comprising or consisting of SEQ ID NO: 66; and/or the immunoglobulin light chain polypeptide comprises a LCDR1 comprising or consisting of SEQ ID NO: 104, a LCDR2 comprising or consisting of SEQ ID NO: 134, and a LCDR3 comprising or consisting of SEQ ID NO: 158;

(10) the immunoglobulin heavy chain polypeptide comprises a HCDR1 comprising or consisting of SEQ ID NO: 9, a HCDR2 comprising or consisting of SEQ ID NO: 33, and a HCDR3 comprising or consisting of SEQ ID NO: 67; and/or the immunoglobulin light chain polypeptide comprises a LCDR1 comprising or consisting of SEQ ID NO: 97, a LCDR2 comprising or consisting of SEQ ID NO: 135, and a LCDR3 comprising or consisting of SEQ ID NO: 159;

(11) the immunoglobulin heavy chain polypeptide comprises a HCDR1 comprising or consisting of SEQ ID NO: 7, a HCDR2 comprising or consisting of SEQ ID NO: 34, and a HCDR3 comprising or consisting of SEQ ID NO: 64; and/or the immunoglobulin light chain polypeptide comprises a LCDR1 comprising or consisting of SEQ ID NO: 102, a LCDR2 comprising or consisting of SEQ ID NO: 132, and a LCDR3 comprising or consisting of SEQ ID NO: 160;

(12) the immunoglobulin heavy chain polypeptide comprises a HCDR1 comprising or consisting of SEQ ID NO: 10, a HCDR2 comprising or consisting of SEQ ID NO: 35, and a HCDR3 comprising or consisting of SEQ ID NO: 68; and/or the immunoglobulin light chain polypeptide comprises a LCDR1 comprising or consisting of SEQ ID NO: 105, a LCDR2 comprising or consisting of SEQ ID NO: 136, and a LCDR3 comprising or consisting of SEQ ID NO: 161;

(13) the immunoglobulin heavy chain polypeptide comprises a HCDR1 comprising or consisting of SEQ ID NO: 2, a HCDR2 comprising or consisting of SEQ ID NO: 25, and a HCDR3 comprising or consisting of SEQ ID NO: 69; and/or the immunoglobulin light chain polypeptide comprises a LCDR1 comprising or consisting of SEQ ID NO: 106, a LCDR2 comprising or consisting of SEQ ID NO: 129, and a LCDR3 comprising or consisting of SEQ ID NO: 162;

(14) the immunoglobulin heavy chain polypeptide comprises a HCDR1 comprising or consisting of SEQ ID NO: 11, a HCDR2 comprising or consisting of SEQ ID NO: 36, and a HCDR3 comprising or consisting of SEQ ID NO: 70; and/or the immunoglobulin light chain polypeptide comprises a LCDR1 comprising or consisting of SEQ ID NO: 107, a LCDR2 comprising or consisting of SEQ ID NO: 129, and a LCDR3 comprising or consisting of SEQ ID NO: 163;

(15) the immunoglobulin heavy chain polypeptide comprises a HCDR1 comprising or consisting of SEQ ID NO: 12, a HCDR2 comprising or consisting of SEQ ID NO: 37, and a HCDR3 comprising or consisting of SEQ ID NO: 71; and/or the immunoglobulin light chain polypeptide comprises a LCDR1 comprising or consisting of SEQ ID NO: 108, a LCDR2 comprising or consisting of SEQ ID NO: 137, and a LCDR3 comprising or consisting of SEQ ID NO: 164;

(16) the immunoglobulin heavy chain polypeptide comprises a HCDR1 comprising or consisting of SEQ ID NO: 1, a HCDR2 comprising or consisting of SEQ ID NO: 38, and a HCDR3 comprising or consisting of SEQ ID NO: 72; and/or the immunoglobulin light chain polypeptide comprises a LCDR1 comprising or consisting of SEQ ID NO: 109, a LCDR2 comprising or consisting of SEQ ID NO: 138, and a LCDR3 comprising or consisting of SEQ ID NO: 165;

(17) the immunoglobulin heavy chain polypeptide comprises a HCDR1 comprising or consisting of SEQ ID NO: 13, a HCDR2 comprising or consisting of SEQ ID NO: 39, and a HCDR3 comprising or consisting of SEQ ID NO: 73; and/or the immunoglobulin light chain polypeptide comprises a LCDR1 comprising or consisting of SEQ ID NO: 98, a LCDR2 comprising or consisting of SEQ ID NO: 129, and a LCDR3 comprising or consisting of SEQ ID NO: 155;

(18) the immunoglobulin heavy chain polypeptide comprises a HCDR1 comprising or consisting of SEQ ID NO: 2, a HCDR2 comprising or consisting of SEQ ID NO: 40, and a HCDR3 comprising or consisting of SEQ ID NO: 74; and/or the immunoglobulin light chain polypeptide comprises a LCDR1 comprising or consisting of SEQ ID NO: 110, a LCDR2 comprising or consisting of SEQ ID NO: 137, and a LCDR3 comprising or consisting of SEQ ID NO: 166;

(19) the immunoglobulin heavy chain polypeptide comprises a HCDR1 comprising or consisting of SEQ ID NO: 14, a HCDR2 comprising or consisting of SEQ ID NO: 41, and a HCDR3 comprising or consisting of SEQ ID NO: 75; and/or the immunoglobulin light chain polypeptide comprises a LCDR1 comprising or consisting of SEQ ID NO: 111, a LCDR2 comprising or consisting of SEQ ID NO: 129, and a LCDR3 comprising or consisting of SEQ ID NO: 165;

(20) the immunoglobulin heavy chain polypeptide comprises a HCDR1 comprising or consisting of SEQ ID NO: 15, a HCDR2 comprising or consisting of SEQ ID NO: 42, and a HCDR3 comprising or consisting of SEQ ID NO: 74; and/or the immunoglobulin light chain polypeptide comprises a LCDR1 comprising or consisting of SEQ ID NO: 97, a LCDR2 comprising or consisting of SEQ ID NO: 139, and a LCDR3 comprising or consisting of SEQ ID NO: 152;

(21) the immunoglobulin heavy chain polypeptide comprises a HCDR1 comprising or consisting of SEQ ID NO: 14, a HCDR2 comprising or consisting of SEQ ID NO: 43, and a HCDR3 comprising or consisting of SEQ ID NO: 76; and/or the immunoglobulin light chain polypeptide comprises a LCDR1 comprising or consisting of SEQ ID NO: 112, a LCDR2 comprising or consisting of SEQ ID NO: 137, and a LCDR3 comprising or consisting of SEQ ID NO: 155;

(22) the immunoglobulin heavy chain polypeptide comprises a HCDR1 comprising or consisting of SEQ ID NO: 16, a HCDR2 comprising or consisting of SEQ ID NO: 44, and a HCDR3 comprising or consisting of SEQ ID NO: 77; and/or the immunoglobulin light chain polypeptide comprises a LCDR1 comprising or consisting of SEQ ID NO: 113, a LCDR2 comprising or consisting of SEQ ID NO: 140, and a LCDR3 comprising or consisting of SEQ ID NO: 165;

(23) the immunoglobulin heavy chain polypeptide comprises a HCDR1 comprising or consisting of SEQ ID NO: 9, a HCDR2 comprising or consisting of SEQ ID NO: 45, and a HCDR3 comprising or consisting of SEQ ID NO: 78; and/or the immunoglobulin light chain polypeptide comprises a LCDR1 comprising or consisting of SEQ ID NO: 114, a LCDR2 comprising or consisting of SEQ ID NO: 141, and a LCDR3 comprising or consisting of SEQ ID NO: 165;

(24) the immunoglobulin heavy chain polypeptide comprises a HCDR1 comprising or consisting of SEQ ID NO: 17, a HCDR2 comprising or consisting of SEQ ID NO: 46, and a HCDR3 comprising or consisting of SEQ ID NO: 79; and/or the immunoglobulin light chain polypeptide comprises a LCDR1 comprising or consisting of SEQ ID NO: 98, a LCDR2 comprising or consisting of SEQ ID NO: 129, and a LCDR3 comprising or consisting of SEQ ID NO: 155;

(25) the immunoglobulin heavy chain polypeptide comprises a HCDR1 comprising or consisting of SEQ ID NO: 9, a HCDR2 comprising or consisting of SEQ ID NO: 25, and a HCDR3 comprising or consisting of SEQ ID NO: 80; and/or the immunoglobulin light chain polypeptide comprises a LCDR1 comprising or consisting of SEQ ID NO: 115, a LCDR2 comprising or consisting of SEQ ID NO: 142, and a LCDR3 comprising or consisting of SEQ ID NO: 165;

(26) the immunoglobulin heavy chain polypeptide comprises a HCDR1 comprising or consisting of SEQ ID NO: 17, a HCDR2 comprising or consisting of SEQ ID NO: 41, and a HCDR3 comprising or consisting of SEQ ID NO: 81; and/or the immunoglobulin light chain polypeptide comprises a LCDR1 comprising or consisting of SEQ ID NO: 116, a LCDR2 comprising or consisting of SEQ ID NO: 143, and a LCDR3 comprising or consisting of SEQ ID NO: 167;

(27) the immunoglobulin heavy chain polypeptide comprises a HCDR1 comprising or consisting of SEQ ID NO: 7, a HCDR2 comprising or consisting of SEQ ID NO: 47, and a HCDR3 comprising or consisting of SEQ ID NO: 82; and/or the immunoglobulin light chain polypeptide comprises a LCDR1 comprising or consisting of SEQ ID NO: 117, a LCDR2 comprising or consisting of SEQ ID NO: 144, and a LCDR3 comprising or consisting of SEQ ID NO: 155;

(28) the immunoglobulin heavy chain polypeptide comprises a HCDR1 comprising or consisting of SEQ ID NO: 2, a HCDR2 comprising or consisting of SEQ ID NO: 41, and a HCDR3 comprising or consisting of SEQ ID NO: 83; and/or the immunoglobulin light chain polypeptide comprises a LCDR1 comprising or consisting of SEQ ID NO: 118, a LCDR2 comprising or consisting of SEQ ID NO: 131, and a LCDR3 comprising or consisting of SEQ ID NO: 168;

(29) the immunoglobulin heavy chain polypeptide comprises a HCDR1 comprising or consisting of SEQ ID NO: 18, a HCDR2 comprising or consisting of SEQ ID NO: 48, and a HCDR3 comprising or consisting of SEQ ID NO: 84; and/or the immunoglobulin light chain polypeptide comprises a LCDR1 comprising or consisting of SEQ ID NO: 119, a LCDR2 comprising or consisting of SEQ ID NO: 145, and a LCDR3 comprising or consisting of SEQ ID NO: 165;

(30) the immunoglobulin heavy chain polypeptide comprises a HCDR1 comprising or consisting of SEQ ID NO: 19, a HCDR2 comprising or consisting of SEQ ID NO: 49, and a HCDR3 comprising or consisting of SEQ ID NO: 85; and/or the immunoglobulin light chain polypeptide comprises a LCDR1 comprising or consisting of SEQ ID NO: 120, a LCDR2 comprising or consisting of SEQ ID NO: 146, and a LCDR3 comprising or consisting of SEQ ID NO: 155;

(31) the immunoglobulin heavy chain polypeptide comprises a HCDR1 comprising or consisting of SEQ ID NO: 2, a HCDR2 comprising or consisting of SEQ ID NO: 50, and a HCDR3 comprising or consisting of SEQ ID NO: 86; and/or the immunoglobulin light chain polypeptide comprises a LCDR1 comprising or consisting of SEQ ID NO: 121, a LCDR2 comprising or consisting of SEQ ID NO: 147, and a LCDR3 comprising or consisting of SEQ ID NO: 169;

(32) the immunoglobulin heavy chain polypeptide comprises a HCDR1 comprising or consisting of SEQ ID NO: 2, a HCDR2 comprising or consisting of SEQ ID NO: 51, and a HCDR3 comprising or consisting of SEQ ID NO: 87; and/or the immunoglobulin light chain polypeptide comprises a LCDR1 comprising or consisting of SEQ ID NO: 122, a LCDR2 comprising or consisting of SEQ ID NO: 137, and a LCDR3 comprising or consisting of SEQ ID NO: 155;

(33) the immunoglobulin heavy chain polypeptide comprises a HCDR1 comprising or consisting of SEQ ID NO: 20, a HCDR2 comprising or consisting of SEQ ID NO: 44, and a HCDR3 comprising or consisting of SEQ ID NO: 88; and/or the immunoglobulin light chain polypeptide comprises a LCDR1 comprising or consisting of SEQ ID NO: 123, a LCDR2 comprising or consisting of SEQ ID NO: 148, and a LCDR3 comprising or consisting of SEQ ID NO: 170;

(34) the immunoglobulin heavy chain polypeptide comprises a HCDR1 comprising or consisting of SEQ ID NO: 3, a HCDR2 comprising or consisting of SEQ ID NO: 52, and a HCDR3 comprising or consisting of SEQ ID NO: 60; and/or the immunoglobulin light chain polypeptide comprises a LCDR1 comprising or consisting of SEQ ID NO: 98, a LCDR2 comprising or consisting of SEQ ID NO: 129, and a LCDR3 comprising or consisting of SEQ ID NO: 171;

(35) the immunoglobulin heavy chain polypeptide comprises a HCDR1 comprising or consisting of SEQ ID NO: 2, a HCDR2 comprising or consisting of SEQ ID NO: 53, and a HCDR3 comprising or consisting of SEQ ID NO: 89; and/or the immunoglobulin light chain polypeptide comprises a LCDR1 comprising or consisting of SEQ ID NO: 97, a LCDR2 comprising or consisting of SEQ ID NO: 147, and a LCDR3 comprising or consisting of SEQ ID NO: 172;

(36) the immunoglobulin heavy chain polypeptide comprises a HCDR1 comprising or consisting of SEQ ID NO: 21, a HCDR2 comprising or consisting of SEQ ID NO: 38, and a HCDR3 comprising or consisting of SEQ ID NO: 90; and/or the immunoglobulin light chain polypeptide comprises a LCDR1 comprising or consisting of SEQ ID NO: 109, a LCDR2 comprising or consisting of SEQ ID NO: 150, and a LCDR3 comprising or consisting of SEQ ID NO: 165;

(37) the immunoglobulin heavy chain polypeptide comprises a HCDR1 comprising or consisting of SEQ ID NO: 22, a HCDR2 comprising or consisting of SEQ ID NO: 41, and a HCDR3 comprising or consisting of SEQ ID NO: 91; and/or the immunoglobulin light chain polypeptide comprises a LCDR1 comprising or consisting of SEQ ID NO: 124, a LCDR2 comprising or consisting of SEQ ID NO: 151, and a LCDR3 comprising or consisting of SEQ ID NO: 173;

(38) the immunoglobulin heavy chain polypeptide comprises a HCDR1 comprising or consisting of SEQ ID NO: 2, a HCDR2 comprising or consisting of SEQ ID NO: 54, and a HCDR3 comprising or consisting of SEQ ID NO: 92; and/or the immunoglobulin light chain polypeptide comprises a LCDR1 comprising or consisting of SEQ ID NO: 126, a LCDR2 comprising or consisting of SEQ ID NO: 129, and a LCDR3 comprising or consisting of SEQ ID NO: 165;

(39) the immunoglobulin heavy chain polypeptide comprises a HCDR1 comprising or consisting of SEQ ID NO: 2, a HCDR2 comprising or consisting of SEQ ID NO: 55, and a HCDR3 comprising or consisting of SEQ ID NO: 93; and/or the immunoglobulin light chain polypeptide comprises a LCDR1 comprising or consisting of SEQ ID NO: 97, a LCDR2 comprising or consisting of SEQ ID NO: 149, and a LCDR3 comprising or consisting of SEQ ID NO: 174;

(40) the immunoglobulin heavy chain polypeptide comprises a HCDR1 comprising or consisting of SEQ ID NO: 23, a HCDR2 comprising or consisting of SEQ ID NO: 56, and a HCDR3 comprising or consisting of SEQ ID NO: 94; and/or the immunoglobulin light chain polypeptide comprises a LCDR1 comprising or consisting of SEQ ID NO: 125, a LCDR2 comprising or consisting of SEQ ID NO: 142, and a LCDR3 comprising or consisting of SEQ ID NO: 175;

(41) the immunoglobulin heavy chain polypeptide comprises a HCDR1 comprising or consisting of SEQ ID NO: 14, a HCDR2 comprising or consisting of SEQ ID NO: 43, and a HCDR3 comprising or consisting of SEQ ID NO: 76; and/or the immunoglobulin light chain polypeptide comprises a LCDR1 comprising or consisting of SEQ ID NO: 127, a LCDR2 comprising or consisting of SEQ ID NO: 137, and a LCDR3 comprising or consisting of SEQ ID NO: 176;

(42) the immunoglobulin heavy chain polypeptide comprises a HCDR1 comprising or consisting of SEQ ID NO: 3, a HCDR2 comprising or consisting of SEQ ID NO: 57, and a HCDR3 comprising or consisting of SEQ ID NO: 95; and/or the immunoglobulin light chain polypeptide comprises a LCDR1 comprising or consisting of SEQ ID NO: 128, a LCDR2 comprising or consisting of SEQ ID NO: 137, and a LCDR3 comprising or consisting of SEQ ID NO: 155;

(43) the immunoglobulin heavy chain polypeptide comprises a HCDR1 comprising or consisting of SEQ ID NO: 17, a HCDR2 comprising or consisting of SEQ ID NO: 46, and a HCDR3 comprising or consisting of SEQ ID NO: 79; and/or the immunoglobulin light chain polypeptide comprises a LCDR1 comprising or consisting of SEQ ID NO: 98, a LCDR2 comprising or consisting of SEQ ID NO: 129, and a LCDR3 comprising or consisting of SEQ ID NO: 155;

(44) the immunoglobulin heavy chain polypeptide comprises a HCDR1 comprising or consisting of SEQ ID NO: 14, a HCDR2 comprising or consisting of SEQ ID NO: 310, and a HCDR3 comprising or consisting of SEQ ID NO: 315 (ERFLGGXMDV, wherein X can be any amino acid); and/or the immunoglobulin light chain polypeptide comprises a LCDR1 comprising or consisting of SEQ ID NO: 98, a LCDR2 comprising or consisting of SEQ ID NO: 129, and a LCDR3 comprising or consisting of SEQ ID NO: 155;

(45) the immunoglobulin heavy chain polypeptide comprises a HCDR1 comprising or consisting of SEQ ID NO: 17, a HCDR2 comprising or consisting of SEQ ID NO: 311, and a HCDR3 comprising or consisting of SEQ ID NO: 316 (EAVAGPXMDV, wherein X can be any amino acid); and/or the immunoglobulin light chain polypeptide comprises a LCDR1 comprising or consisting of SEQ ID NO: 98, a LCDR2 comprising or consisting of SEQ ID NO: 129, and a LCDR3 comprising or consisting of SEQ ID NO: 155;

(46) the immunoglobulin heavy chain polypeptide comprises a HCDR1 comprising or consisting of SEQ ID NO: 17, a HCDR2 comprising or consisting of SEQ ID NO: 310, and a HCDR3 comprising or consisting of SEQ ID NO: 317; and/or the immunoglobulin light chain polypeptide comprises a LCDR1 comprising or consisting of SEQ ID NO: 98, a LCDR2 comprising or consisting of SEQ ID NO: 129, and a LCDR3 comprising or consisting of SEQ ID NO: 155;

(47) the immunoglobulin heavy chain polypeptide comprises a HCDR1 comprising or consisting of SEQ ID NO: 309, a HCDR2 comprising or consisting of SEQ ID NO: 312, and a HCDR3 comprising or consisting of SEQ ID NO: 318; and/or the immunoglobulin light chain polypeptide comprises a LCDR1 comprising or consisting of SEQ ID NO: 98, a LCDR2 comprising or consisting of SEQ ID NO: 129, and a LCDR3 comprising or consisting of SEQ ID NO: 155;

(48) the immunoglobulin heavy chain polypeptide comprises a HCDR1 comprising or consisting of SEQ ID NO: 17, a HCDR2 comprising or consisting of SEQ ID NO: 46, and a HCDR3 comprising or consisting of SEQ ID NO: 79; and/or the immunoglobulin light chain polypeptide comprises a LCDR1 comprising or consisting of SEQ ID NO: 98, a LCDR2 comprising or consisting of SEQ ID NO: 129, and a LCDR3 comprising or consisting of SEQ ID NO: 155;

(49) the immunoglobulin heavy chain polypeptide comprises a HCDR1 comprising or consisting of SEQ ID NO: 17, a HCDR2 comprising or consisting of SEQ ID NO: 46, and a HCDR3 comprising or consisting of SEQ ID NO: 79; and/or the immunoglobulin light chain polypeptide comprises a LCDR1 comprising or consisting of SEQ ID NO: 98, a LCDR2 comprising or consisting of SEQ ID NO: 129, and a LCDR3 comprising or consisting of SEQ ID NO: 155;

(50) the immunoglobulin heavy chain polypeptide comprises a HCDR1 comprising or consisting of SEQ ID NO: 17, a HCDR2 comprising or consisting of SEQ ID NO: 51, and a HCDR3 comprising or consisting of SEQ ID NO: 79; and/or the immunoglobulin light chain polypeptide comprises a LCDR1 comprising or consisting of SEQ ID NO: 98, a LCDR2 comprising or consisting of SEQ ID NO: 129, and a LCDR3 comprising or consisting of SEQ ID NO: 155;

(51) the immunoglobulin heavy chain polypeptide comprises a HCDR1 comprising or consisting of SEQ ID NO: 17, a HCDR2 comprising or consisting of SEQ ID NO: 313, and a HCDR3 comprising or consisting of SEQ ID NO: 79; and/or the immunoglobulin light chain polypeptide comprises a LCDR1 comprising or consisting of SEQ ID NO: 98, a LCDR2 comprising or consisting of SEQ ID NO: 129, and a LCDR3 comprising or consisting of SEQ ID NO: 155;

(52) the immunoglobulin heavy chain polypeptide comprises a HCDR1 comprising or consisting of SEQ ID NO: 17, a HCDR2 comprising or consisting of SEQ ID NO: 51, and a HCDR3 comprising or consisting of SEQ ID NO: 79; and/or the immunoglobulin light chain polypeptide comprises a LCDR1 comprising or consisting of SEQ ID NO: 98, a LCDR2 comprising or consisting of SEQ ID NO: 129, and a LCDR3 comprising or consisting of SEQ ID NO: 155;

(53) the immunoglobulin heavy chain polypeptide comprises a HCDR1 comprising or consisting of SEQ ID NO: 17, a HCDR2 comprising or consisting of SEQ ID NO: 311, and a HCDR3 comprising or consisting of SEQ ID NO: 79; and/or the immunoglobulin light chain polypeptide comprises a LCDR1 comprising or consisting of SEQ ID NO: 98, a LCDR2 comprising or consisting of SEQ ID NO: 129, and a LCDR3 comprising or consisting of SEQ ID NO: 155;

(54) the immunoglobulin heavy chain polypeptide comprises a HCDR1 comprising or consisting of SEQ ID NO: 309, a HCDR2 comprising or consisting of SEQ ID NO: 314, and a HCDR3 comprising or consisting of SEQ ID NO: 318; and/or the immunoglobulin light chain polypeptide comprises a LCDR1 comprising or consisting of SEQ ID NO: 98, a LCDR2 comprising or consisting of SEQ ID NO: 129, and a LCDR3 comprising or consisting of SEQ ID NO: 155;

(55) the immunoglobulin heavy chain polypeptide comprises a HCDR1 comprising or consisting of SEQ ID NO: 309, a HCDR2 comprising or consisting of SEQ ID NO: 312, and a HCDR3 comprising or consisting of SEQ ID NO: 318; and/or the immunoglobulin light chain polypeptide comprises a LCDR1 comprising or consisting of SEQ ID NO: 319, a LCDR2 comprising or consisting of SEQ ID NO: 129, and a LCDR3 comprising or consisting of SEQ ID NO: 155;

(56) the immunoglobulin heavy chain polypeptide comprises a HCDR1 comprising or consisting of SEQ ID NO: 309, a HCDR2 comprising or consisting of SEQ ID NO: 312, and a HCDR3 comprising or consisting of SEQ ID NO: 318; and/or the immunoglobulin light chain polypeptide comprises a LCDR1 comprising or consisting of SEQ ID NO: 320, a LCDR2 comprising or consisting of SEQ ID NO: 129, and a LCDR3 comprising or consisting of SEQ ID NO: 155;

(57) the immunoglobulin heavy chain polypeptide comprises a HCDR1 comprising or consisting of SEQ ID NO: 309, a HCDR2 comprising or consisting of SEQ ID NO: 312, and a HCDR3 comprising or consisting of SEQ ID NO: 318; and/or the immunoglobulin light chain polypeptide comprises a LCDR1 comprising or consisting of SEQ ID NO: 321, a LCDR2 comprising or consisting of SEQ ID NO: 129, and a LCDR3 comprising or consisting of SEQ ID NO: 155;

(58) the immunoglobulin heavy chain polypeptide comprises a HCDR1 comprising or consisting of SEQ ID NO: 309, a HCDR2 comprising or consisting of SEQ ID NO: 312, and a HCDR3 comprising or consisting of SEQ ID NO: 318; and/or the immunoglobulin light chain polypeptide comprises a LCDR1 comprising or consisting of SEQ ID NO: 322, a LCDR2 comprising or consisting of SEQ ID NO: 129, and a LCDR3 comprising or consisting of SEQ ID NO: 155;

(59) the immunoglobulin heavy chain polypeptide comprises a HCDR1 comprising or consisting of SEQ ID NO: 309, a HCDR2 comprising or consisting of SEQ ID NO: 312, and a HCDR3 comprising or consisting of SEQ ID NO: 318; and/or the immunoglobulin light chain polypeptide comprises a LCDR1 comprising or consisting of SEQ ID NO: 99, a LCDR2 comprising or consisting of SEQ ID NO: 129, and a LCDR3 comprising or consisting of SEQ ID NO: 155;

(60) the immunoglobulin heavy chain polypeptide comprises a HCDR1 comprising or consisting of SEQ ID NO: 309, a HCDR2 comprising or consisting of SEQ ID NO: 312, and a HCDR3 comprising or consisting of SEQ ID NO: 318; and/or the immunoglobulin light chain polypeptide comprises a LCDR1 comprising or consisting of SEQ ID NO: 97, a LCDR2 comprising or consisting of SEQ ID NO: 129, and a LCDR3 comprising or consisting of SEQ ID NO: 155;

(61) the immunoglobulin heavy chain polypeptide comprises a HCDR1 comprising or consisting of SEQ ID NO: 309, a HCDR2 comprising or consisting of SEQ ID NO: 312, and a HCDR3 comprising or consisting of SEQ ID NO: 318; and/or the immunoglobulin light chain polypeptide comprises a LCDR1 comprising or consisting of SEQ ID NO: 323, a LCDR2 comprising or consisting of SEQ ID NO: 129, and a LCDR3 comprising or consisting of SEQ ID NO: 155;

(62) the immunoglobulin heavy chain polypeptide comprises a HCDR1 comprising or consisting of SEQ ID NO: 309, a HCDR2 comprising or consisting of SEQ ID NO: 312, and a HCDR3 comprising or consisting of SEQ ID NO: 318; and/or the immunoglobulin light chain polypeptide comprises a LCDR1 comprising or consisting of SEQ ID NO: 98, a LCDR2 comprising or consisting of SEQ ID NO: 129, and a LCDR3 comprising or consisting of SEQ ID NO: 155;

(63) the immunoglobulin heavy chain polypeptide comprises a HCDR1 comprising or consisting of SEQ ID NO: 309, a HCDR2 comprising or consisting of SEQ ID NO: 312, and a HCDR3 comprising or consisting of SEQ ID NO: 318; and/or the immunoglobulin light chain polypeptide comprises a LCDR1 comprising or consisting of SEQ ID NO: 98, a LCDR2 comprising or consisting of SEQ ID NO: 129, and a LCDR3 comprising or consisting of SEQ ID NO: 165;

(64) the immunoglobulin heavy chain polypeptide comprises a HCDR1 comprising or consisting of SEQ ID NO: 309, a HCDR2 comprising or consisting of SEQ ID NO: 312, and a HCDR3 comprising or consisting of SEQ ID NO: 318; and/or the immunoglobulin light chain polypeptide comprises a LCDR1 comprising or consisting of SEQ ID NO: 98, a LCDR2 comprising or consisting of SEQ ID NO: 129, and a LCDR3 comprising or consisting of SEQ ID NO: 165;

(65) the immunoglobulin heavy chain polypeptide comprises a HCDR1 comprising or consisting of SEQ ID NO: 309, a HCDR2 comprising or consisting of SEQ ID NO: 312, and a HCDR3 comprising or consisting of SEQ ID NO: 318; and/or the immunoglobulin light chain polypeptide comprises a LCDR1 comprising or consisting of SEQ ID NO: 98, a LCDR2 comprising or consisting of SEQ ID NO: 129, and a LCDR3 comprising or consisting of SEQ ID NO: 155;

(66) the immunoglobulin heavy chain polypeptide comprises a HCDR1 comprising or consisting of SEQ ID NO: 2, a HCDR2 comprising or consisting of SEQ ID NO: 346, and a HCDR3 comprising or consisting of SEQ ID NO: 350; and/or the immunoglobulin light chain polypeptide comprises a LCDR1 comprising or consisting of SEQ ID NO: 97, a LCDR2 comprising or consisting of SEQ ID NO: 129, and a LCDR3 comprising or consisting of SEQ ID NO: 165;

(67) the immunoglobulin heavy chain polypeptide comprises a HCDR1 comprising or consisting of SEQ ID NO: 309, a HCDR2 comprising or consisting of SEQ ID NO: 347, and a HCDR3 comprising or consisting of SEQ ID NO: 351; and/or the immunoglobulin light chain polypeptide comprises a LCDR1 comprising or consisting of SEQ ID NO: 97, a LCDR2 comprising or consisting of SEQ ID NO: 357, and a LCDR3 comprising or consisting of SEQ ID NO: 165;

(68) the immunoglobulin heavy chain polypeptide comprises a HCDR1 comprising or consisting of SEQ ID NO: 9, a HCDR2 comprising or consisting of SEQ ID NO: 348, and a HCDR3 comprising or consisting of SEQ ID NO: 352; and/or the immunoglobulin light chain polypeptide comprises a LCDR1 comprising or consisting of SEQ ID NO: 97, a LCDR2 comprising or consisting of SEQ ID NO: 358, and a LCDR3 comprising or consisting of SEQ ID NO: 360;

(69) the immunoglobulin heavy chain polypeptide comprises a HCDR1 comprising or consisting of SEQ ID NO: 2, a HCDR2 comprising or consisting of SEQ ID NO: 310, and a HCDR3 comprising or consisting of SEQ ID NO: 353; and/or the immunoglobulin light chain polypeptide comprises a LCDR1 comprising or consisting of SEQ ID NO: 355, a LCDR2 comprising or consisting of SEQ ID NO: 359, and a LCDR3 comprising or consisting of SEQ ID NO: 152;

(70) the immunoglobulin heavy chain polypeptide comprises a HCDR1 comprising or consisting of SEQ ID NO: 345, a HCDR2 comprising or consisting of SEQ ID NO: 349, and a HCDR3 comprising or consisting of SEQ ID NO: 354; and/or the immunoglobulin light chain polypeptide comprises a LCDR1 comprising or consisting of SEQ ID NO: 356, a LCDR2 comprising or consisting of SEQ ID NO: 129, and a LCDR3 comprising or consisting of SEQ ID NO: 155; and/or

(71) the immunoglobulin heavy chain polypeptide and light chain polypeptide comprises any combination of the CDRs listed in Table 1.

In particular embodiments, the binding agent comprises an immunoglobulin heavy chain polypeptide and an immunoglobulin light chain polypeptide, wherein the immunoglobulin heavy chain polypeptide comprises a first framework region, a second framework region, a third framework region, and/or a fourth framework region; and/or the immunoglobulin light chain polypeptide comprises a first framework region, a second framework region, a third framework region, and/or a fourth framework region; and/or the immunoglobulin heavy chain polypeptide and light chain polypeptide comprises any combination of the framework regions listed in Tables 2 and 3.

TABLE 1

| Binding agent | SEQ ID | HCDR1 | SEQ ID | HCDR2 | SEQ ID | HCDR3 | SEQ ID | LCDR1 | SEQ ID | LCDR2 | SEQ ID | LCDR3 |
|---|---|---|---|---|---|---|---|---|---|---|---|---|
| 1 | 1 | SYAIS | 24 | VINPSAGSTDYAQKFQG | 58 | DLYPYVVVVAAGSYGMDV | 96 | RASQGIDSYLA | 129 | AASSLQS | 152 | QQSYSTPIT |
| 2 | 2 | SYYMH | 25 | WMNPNSDIAGYAQKFQG | 59 | PSIVGAYDAFDI | 97 | RASQSISSWLA | 129 | AASSLQS | 153 | QQSYTTPIT |
| 3 | 3 | RHLLH | 26 | WISPQHGVRNYAQKFQG | 60 | ESVEGYFDL | 98 | RASQSISSYLN | 129 | AASSLQS | 154 | QQIFSTPLT |
| 4 | 4 | SHHMH | 27 | WVSPSHGLTGYAQKFQG | 61 | DNWNVHDAFDI | 99 | RASQGISSYLA | 130 | GASNLQS | 155 | QQSYSTPLT |
| 5 | 5 | RFMH | 28 | WMSLNSGLTGYAQKFQG | 62 | GTYNDAFDI | 100 | RASQTISNYLN | 129 | AASSLQS | 153 | QQSYTTPIT |
| 6 | 6 | SYYIH | 29 | WMKPSSGTTGYAQKFQG | 63 | EQWLVNDAFDI | 101 | RASQSVDRNYVT | 131 | GASTRAT | 156 | QQSYTTPYT |
| 7 | 7 | NYYIH | 30 | WMNPNGDVAGYAQKFQG | 64 | DSSGWMRNDAFDI | 102 | RASQGISQYLA | 132 | GASNLHS | 157 | QQTFTTPLT |
| 8 | 2 | SYYMH | 31 | GIDPNSGGTNYAQKFQG | 65 | SMFPTIFGDNAFDI | 103 | QASQDIGNYLN | 133 | AASSLES | 155 | QQSYSTPLT |
| 9 | 8 | HYYMH | 32 | WMNPDSGSTGYAQKFQG | 66 | ALFPYPFYYYYMDV | 104 | RASQGIRNDLG | 134 | SASNLQS | 158 | QQANSFPFT |
| 10 | 9 | GYYMH | 33 | WMSLNSGLTGYAQKFQG | 67 | DRGWFDP | 97 | RASQSISSWLA | 135 | AASTLES | 159 | QQSYTTPYS |
| 11 | 7 | NYYIH | 34 | WMNPNGDVAGYADSFQG | 64 | DSSGWMRNDAFDI | 102 | RASQGISQYLA | 132 | GASNLHS | 160 | QQTFITPLT |
| 12 | 10 | NYMYH | 35 | WISTYHGSTNYAQKFQG | 68 | DARGYSGYDL | 105 | RASQIIGNYLA | 136 | HASILET | 161 | QQSYSTPT |
| 13 | 2 | SYYMH | 25 | WMNPNSDIAGYAQKFQG | 69 | EGRHGEYLY | 106 | RASQIISSYLN | 129 | AASSLQS | 162 | QQGFSTPFT |
| 14 | 11 | TYYVH | 36 | WMNPNTVYTGSAQKFQG | 70 | EGWGSSGYFDY | 107 | QASQDISNYLN | 129 | AASSLQS | 163 | QQSFTNPVT |

TABLE 1-continued

| Binding agent | SEQ ID | HCDR1 | SEQ ID | HCDR2 | SEQ ID | HCDR3 | SEQ ID | LCDR1 | SEQ ID | LCDR2 | SEQ ID | LCDR3 |
|---|---|---|---|---|---|---|---|---|---|---|---|---|
| 15 | 12 | SYALS | 37 | RIIPAVGSVTYAQKFQG | 71 | HLFPTVFDDYYGMDV | 108 | RASQGISNYLA | 137 | AASTLQS | 164 | QQSYSAPYT |
| 16 | 1 | SYAIS | 38 | GIIPIFGTANYAQKFQG | 72 | GGYSYGSFQH | 109 | RASQGISNNLN | 138 | AATTLQS | 165 | QQSYSTPYT |
| 17 | 13 | RHYVH | 39 | WMSPSSGITGYAQKFQG | 73 | VRWSSDAFDI | 98 | RASQSISSYLN | 129 | AASSLQS | 155 | QQSYSTPLT |
| 18 | 2 | SYYMH | 40 | WMTPSTGNAGYAQKFQG | 74 | EEWLGHFQH | 110 | RASQGISNGLS | 137 | AASTLQS | 166 | QQSHSTPLT |
| 19 | 14 | SHYMH | 41 | WMNPNSGNTGYAQKFQG | 75 | ERFLGGMDV | ill | RASQSITGWLA | 129 | AASSLQS | 165 | QQSYSTPYT |
| 20 | 15 | DYYMH | 42 | WMHPNSGHTGYAQKFQG | 74 | EEWLGHFQH | 97 | RASQSISSWLA | 139 | DATHLET | 152 | QQSYSTPIT |
| 21 | 14 | SHYMH | 43 | WMNPNSGHTGNAQKFQG | 76 | GNWVDAFDI | 112 | RASQGIRNDLA | 137 | AASTLQS | 155 | QQSYSTPLT |
| 22 | 16 | GYTLH | 44 | WIDPNSGVTSSAQKFQG | 77 | ESEVMMAYFQH | 113 | QASQDISSYLN | 140 | AASSLQT | 165 | QQSYSTPYT |
| 23 | 9 | GYYMH | 45 | WISPNSGVTDFTQKFQG | 78 | ESWSGEFDY | 114 | RASQSITTYLN | 141 | AASSLQG | 165 | QQSYSTPYT |
| 24 | 17 | NHYMH | 46 | WMNPNSGHTGYAQRFQG | 79 | EAVAGPMDV | SEQ ID | LCDR1 | SEQ ID | LCDR2 | SEQ ID | LCDR3 |
| 25 | 9 | GYYMH | 25 | WMNPNSDIAGYAQKFQG | 80 | DAWELLAFDI | 98 | RASQSISSYLN | 129 | AASSLQS | 155 | QQSYSTPLT |
| 26 | 17 | NHYMH | 41 | WMNPNSGNTGYAQKFQG | 81 | DRWDGDYYSA | 115 | RASQSVSTWLA | 142 | AASNLES | 165 | QQSYSTPYT |
| 27 | 7 | NYYIH | 47 | WMSPNGGNTGYAQKFQG | 82 | ESWELTGFD | 116 | RASQSISNWLA | 143 | DVSHLES | 167 | QQSYSTPFT |
| 28 | 2 | SYYMH | 41 | WMNPNSGNTGYAQKFQG | 83 | ERFAGGMDA | 117 | QASQGISNYLA | 144 | DASSLQS | 155 | QQSYSTPLT |
| 29 | 18 | NSYMH | 48 | WMDPSSGYTGSAHKFQG | 84 | DSGGAFDI | 118 | RASQSLSSSLA | 131 | GASTRAT | 168 | QQYGSSPFT |
| 30 | 19 | TYYMH | 49 | WMNPHSADTGYAEKFQG | 85 | EVFEGGMDV | 119 | RASEHIANWLA | 145 | GVSSLES | 165 | QQSYSTPYT |
| 31 | 2 | SYYMH | 50 | WLTPSTGHAGYAQKFQG | 86 | EGYGGNYGN | 120 | RASQSVGSWVA | 146 | PASTLQS | 155 | QQSYSTPLT |
| 32 | 2 | SYYMH | 51 | WMNPNSGHTGYAQKFQG | 87 | EDFYGDFDY | 121 | RASQSISPWLA | 147 | DASNLET | 169 | QQTYSTPIT |
| 33 | 20 | RHFIH | 44 | WIDPNSGVTSSAQKFQG | 88 | ELSRWGFDY | 122 | RASQGISRYLA | 137 | AASTLQS | 155 | QQSYSTPLT |

TABLE 1-continued

| Binding agent | SEQ ID | HCDR1 | SEQ ID | HCDR2 | SEQ ID | HCDR3 | SEQ ID | LCDR1 | SEQ ID | LCDR2 | SEQ ID | LCDR3 |
|---|---|---|---|---|---|---|---|---|---|---|---|---|
| 34 | 3 | RHLLH | 52 | WISPQHGV RNYAHKFQ G | 60 | ESVEGYFDL | 123 | RASQTVSS NYLA | 148 | GASTRAS | 170 | QQYYTTPLT |
| 35 | 2 | SYYMH | 53 | MINPSGGST SYAQKFQG | 89 | DIFPTMIAGG GFDL | 98 | RASQSISSY LN | 129 | AASSLQS | 171 | QQSFSTPLT |
| 36 | 21 | TFGIS | 38 | GIIPIFGTAN YAQKFQG | 90 | GGYSYGSFD | 97 | RASQSISSW LA | 147 | DASNLET | 172 | QQSYSTPPT |
| 37 | 22 | SYGIN | 41 | WMNPNSG NTGYAQKF QG | 91 | GSFPLVFTIF GVGDV | 109 | RASQGISN NLN | 150 | ATSTLQS | 165 | QQSYSTPYT |
| 38 | 2 | SYYMH | 54 | WISPRSGVT SYAQKFQG | 92 | DLDYVRAFD 1 | 124 | RSSQGIRND LS | 151 | LASNSHS | 173 | LQHNSYPLT |
| 39 | 2 | SYYMH | 55 | WMDPNSG NTGYAQKF QG | 93 | ESWGGYFDL | 126 | RASQSISR WLA | 129 | AASSLQS | 165 | QQSYSTPYT |
| 40 | 23 | NHYVH | 56 | WMNPTGGI TGYAQKFQ G | 94 | DRTTYAFDI | 97 | RASQSISSW LA | 149 | DSSSLQT | 174 | QQSYSTPVT |
| 41 | 14 | SHYMH | 43 | WMNPNSG HTGNAQKF QG | 76 | GNWVDAFDI | 125 | RDSHSITT WLA | 142 | AASNLES | 175 | QHFYNTQYT |
| 42 | 3 | RHLLH | 57 | WVSPIHGL TGYAPRFQ G | 95 | VHGSGSDG MDV | 127 | RASQVIRN DLA | 137 | AASTLQS | 176 | QQSLQYPSHF |
| 43 | 17 | NHYMH | 46 | WMNPNSG HTGYAQRF QG | 79 | EAVAGPMD V | 98 | RASQSISSY LN | 129 | AASSLQS | 155 | QQSYSTPLT |
| 44 | 14 | SHYMH | 310 | WINPNSGN TGYAQKFQ G | 315 | ERFLGGXMD V | 98 | RASQSISSY LN | 129 | AASSLQS | 155 | QQSYSTPLT |
| 45 | 17 | NHYMH | 311 | WINPNSGH TGYAQKFQ G | 316 | EAVAGPXM DV | 98 | RASQSISSY LN | 129 | AASSLQS | 155 | QQSYSTPLT |
| 46 | 17 | NHYMH | 310 | WINPNSGN TGYAQKFQ G | 317 | DRWGGDYY SA | 98 | RASQSISSY LN | 129 | AASSLQS | 155 | QQSYSTPLT |
| 47 | 309 | THYMH | 312 | WINPNSGN TGYSQKFQ G | 318 | ERLSVAGFD | 98 | RASQSISSY LN | 129 | AASSLQS | 155 | QQSYSTPLT |
| 48 | 17 | NHYMH | 46 | WMNPNSG HTGYAQRF QG | 79 | EAVAGPMD V | 98 | RASQSISSY LN | 129 | AASSLQS | 155 | QQSYSTPLT |
| 49 | 17 | NHYMH | 46 | WMNPNSG HTGYAQRF QG | 79 | EAVAGPMD V | 98 | RASQSISSY LN | 129 | AASSLQS | 155 | QQSYSTPLT |
| 50 | 17 | NHYMH | 51 | WMNPNSG HTGYAQKF QG | 79 | EAVAGPMD V | 98 | RASQSISSY LN | 129 | AASSLQS | 155 | QQSYSTPLT |
| 51 | 17 | NHYMH | 313 | WINPNSGH TGYAQRFQ G | 79 | EAVAGPMD V | 98 | RASQSISSY LN | 129 | AASSLQS | 155 | QQSYSTPLT |
| 52 | 17 | NHYMH | 51 | WMNPNSG HTGYAQKF QG | 79 | EAVAGPMD V | 98 | RASQSISSY LN | 129 | AASSLQS | 155 | QQSYSTPLT |
| 53 | 17 | NHYMH | 311 | WINPNSGH TGYAQKFQ G | 79 | EAVAGPMD V | 98 | RASQSISSY LN | 129 | AASSLQS | 155 | QQSYSTPLT |

TABLE 1-continued

| Binding agent | SEQ ID | HCDR1 | SEQ ID | HCDR2 | SEQ ID | HCDR3 | SEQ ID | LCDR1 | SEQ ID | LCDR2 | SEQ ID | LCDR3 |
|---|---|---|---|---|---|---|---|---|---|---|---|---|
| 54 | 309 | THYMH | 314 | WMNPNSG NTGYSQKF QG | 318 | ERLSVAGFD | 98 | RASQSISSY LN | 129 | AASSLQS | 155 | QQSYSTPLT |
| 55 | 309 | THYMH | 312 | WINPNSGN TGYSQKFQ G | 318 | ERLSVAGFD | 319 | RASQGISSY LN | 129 | AASSLQS | 155 | QQSYSTPLT |
| 56 | 309 | THYMH | 312 | WINPNSGN TGYSQKFQ G | 318 | ERLSVAGFD | 320 | RASQSISSW LN | 129 | AASSLQS | 155 | QQSYSTPLT |
| 57 | 309 | THYMH | 312 | WINPNSGN TGYSQKFQ G | 318 | ERLSVAGFD | 321 | RASQSISSY LA | 129 | AASSLQS | 155 | QQSYSTPLT |
| 58 | 309 | THYMH | 312 | WINPNSGN TGYSQKFQ G | 318 | ERLSVAGFD | 322 | RASQGISS WLN | 129 | AASSLQS | 155 | QQSYSTPLT |
| 59 | 309 | THYMH | 312 | WINPNSGN TGYSQKFQ G | 318 | ERLSVAGFD | 99 | RASQGISSY LA | 129 | AASSLQS | 155 | QQSYSTPLT |
| 60 | 309 | THYMH | 312 | WINPNSGN TGYSQKFQ G | 318 | ERLSVAGFD | 97 | RASQSISSW LA | 129 | AASSLQS | 155 | QQSYSTPLT |
| 61 | 309 | THYMH | 312 | WINPNSGN TGYSQKFQ G | 318 | ERLSVAGFD | 323 | RASQGISS WLA | 129 | AASSLQS | 155 | QQSYSTPLT |
| 62 | 309 | THYMH | 312 | WINPNSGN TGYSQKFQ G | 318 | ERLSVAGFD | 98 | RASQSISSY LN | 129 | AASSLQS | 155 | QQSYSTPLT |
| 63 | 309 | THYMH | 312 | WINPNSGN TGYSQKFQ G | 318 | ERLSVAGFD | 98 | RASQSISSY LN | 129 | AASSLQS | 165 | QQSYSTPYT |
| 64 | 309 | THYMH | 312 | WINPNSGN TGYSQKFQ G | 318 | ERLSVAGFD | 98 | RASQSISSY LN | 129 | AASSLQS | 165 | QQSYSTPYT |
| 65 | 309 | THYMH | 312 | WINPNSGN TGYSQKFQ G | 318 | ERLSVAGFD | 98 | RASQSISSY LN | 129 | AASSLQS | 155 | QQSYSTPLT |
| 66 | 2 | SYYMH | 346 | WITTNSGIT GYAQKFQG | 350 | EGYSSGLDY | 97 | RASQSISSW LA | 129 | AASSLQS | 165 | QQSYSTPYT |
| 67 | 309 | THYMH | 347 | WINPNSGH AGSAQKFQ G | 351 | ESIAVAGYD | 97 | RASQSISSW LA | 357 | AASTLQR | 165 | QQSYSTPYT |
| 68 | 9 | GYYMH | 348 | WINPNSGT TGYAQNFQ G | 352 | EGFGPNAFDI | 97 | RASQSISSW LA | 358 | AASNLQS | 360 | QQYYSTPYT |
| 69 | 2 | SYYMH | 310 | WINPNSGN TGYAQKFQ G | 353 | DDWGGDWF DY | 355 | QASQDISN HLN | 359 | GASNLQR | 152 | QQSYSTPIT |
| 70 | 345 | DHYLH | 349 | WINPNIGNT GYAQKFQG | 354 | EPLQLGGFD | 356 | RASESISSW LA | 129 | AASSLQS | 155 | QQSYSTPLT |

TABLE 2

| Binding Agent | SEQ ID | HFW1 | SEQ ID | HFW2 | SEQ ID | HFW3 | SEQ ID | HFW4 |
|---|---|---|---|---|---|---|---|---|
| 1 | 177 | QVQLVQSGAEVKKPG ASVKVSCKASGGTFS | 192 | WVRQAPG QGLEWMG | 196 | RVTMTRDTSTSTVYMEL SSLRSEDTAVYYCAR | 202 | WGQGTL VTVSS |

TABLE 2-continued

| Binding Agent | SEQ ID | HFW1 | SEQ ID | HFW2 | SEQ ID | HFW3 | SEQ ID | HFW4 |
|---|---|---|---|---|---|---|---|---|
| 2 | 178 | QVQLVQSGAEVKKPG ASVKVSCKASGYTFT | 192 | WVRQAPG QGLEWMG | 197 | RVTMTRDTSTSTVYMEL SSLRSEDTAVYYCAI | 202 | WGQGTL VTVSS |
| 3 | 178 | QVQLVQSGAEVKKPG ASVKVSCKASGYTFT | 192 | WVRQAPG QGLEWMG | 196 | RVTMTRDTSTSTVYMEL SSLRSEDTAVYYCAR | 202 | WGQGTL VTVSS |
| 4 | 178 | QVQLVQSGAEVKKPG ASVKVSCKASGYTFT | 192 | WVRQAPG QGLEWMG | 196 | RVTMTRDTSTSTVYMEL SSLRSEDTAVYYCAR | 202 | WGQGTL VTVSS |
| 5 | 179 | QVQLVQSGAEVKKPG ASVKVSCKASGYTFN | 192 | WVRQAPG QGLEWMG | 198 | RVTMTRDTSTSTVYMEL SSLRSEDTAVYYCTR | 202 | WGQGTL VTVSS |
| 6 | 178 | QVQLVQSGAEVKKPG ASVKVSCKASGYTFT | 192 | WVRQAPG QGLEWMG | 196 | RVTMTRDTSTSTVYMEL SSLRSEDTAVYYCAR | 202 | WGQGTL VTVSS |
| 7 | 178 | QVQLVQSGAEVKKPG ASVKVSCKASGYTFT | 193 | WVRQAPG QGLEWLG | 197 | RVTMTRDTSTSTVYMEL SSLRSEDTAVYYCAI | 202 | WGQGTL VTVSS |
| 8 | 180 | QVQLVQSGAEVKKPG ASVKVSCKASGNTFT | 192 | WVRQAPG QGLEWMG | 196 | RVTMTRDTSTSTVYMEL SSLRSEDTAVYYCAR | 202 | WGQGTL VTVSS |
| 9 | 181 | QVQLVQSGAEVKKPG ASVKVSCKASGHSFT | 192 | WVRQAPG QGLEWMG | 196 | RVTMTRDTSTSTVYMEL SSLRSEDTAVYYCAR | 202 | WGQGTL VTVSS |
| 10 | 178 | QVQLVQSGAEVKKPG ASVKVSCKASGYTFT | 194 | WVRQAPG QGLEWIG | 196 | RVTMTRDTSTSTVYMEL SSLRSEDTAVYYCAR | 202 | WGQGTL VTVSS |
| 11 | 178 | QVQLVQSGAEVKKPG ASVKVSCKASGYTFT | 193 | WVRQAPG QGLEWLG | 197 | RVTMTRDTSTSTVYMEL SSLRSEDTAVYYCAI | 202 | WGQGTL VTVSS |
| 12 | 177 | QVQLVQSGAEVKKPG ASVKVSCKASGGTFS | 192 | WVRQAPG QGLEWMG | 196 | RVTMTRDTSTSTVYMEL SSLRSEDTAVYYCAR | 202 | WGQGTL VTVSS |
| 13 | 182 | QVQLVQSGAEVKKPG ASVKVSCKASGYPFT | 192 | WVRQAPG QGLEWMG | 196 | RVTMTRDTSTSTVYMEL SSLRSEDTAVYYCAR | 202 | WGQGTL VTVSS |
| 14 | 183 | QVQLVQSGAEVKKPG ASVKVSCKASGYRFT | 192 | WVRQAPG QGLEWMG | 196 | RVTMTRDTSTSTVYMEL SSLRSEDTAVYYCAR | 202 | WGQGTL VTVSS |
| 15 | 184 | QVQLVQSGAEVKKPG SSVKVSCKASGGTFS | 192 | WVRQAPG QGLEWMG | 199 | RVTITADESTSTAYMEL SSLRSEDTAVYYCAR | 202 | WGQGTL VTVSS |
| 16 | 184 | QVQLVQSGAEVKKPG SSVKVSCKASGGTFS | 192 | WVRQAPG QGLEWMG | 199 | RVTITADESTSTAYMEL SSLRSEDTAVYYCAR | 202 | WGQGTL VTVSS |
| 17 | 185 | QVQLVQSGAEVKKPG ASVKVSCKASGDTFT | 192 | WVRQAPG QGLEWMG | 196 | RVTMTRDTSTSTVYMEL SSLRSEDTAVYYCAR | 202 | WGQGTL VTVSS |
| 18 | 178 | QVQLVQSGAEVKKPG ASVKVSCKASGYTFT | 195 | WVRQAPG QGLEWVG | 196 | RVTMTRDTSTSTVYMEL SSLRSEDTAVYYCAR | 202 | WGQGTL VTVSS |
| 19 | 178 | QVQLVQSGAEVKKPG ASVKVSCKASGYTFT | 192 | WVRQAPG QGLEWMG | 196 | RVTMTRDTSTSTVYMEL SSLRSEDTAVYYCAR | 203 | WGQGTT VTVSS |
| 20 | 178 | QVQLVQSGAEVKKPG ASVKVSCKASGYTFT | 192 | WVRQAPG QGLEWMG | 200 | RVTMTRDTSTSTVNMEL SSLRSEDTAVYYCAR | 202 | WGQGTL VTVSS |
| 21 | 178 | QVQLVQSGAEVKKPG ASVKVSCKASGYTFT | 192 | WVRQAPG QGLEWMG | 196 | RVTMTRDTSTSTVYMEL SSLRSEDTAVYYCAR | 204 | WGQGTM VTVSS |
| 22 | 178 | QVQLVQSGAEVKKPG ASVKVSCKASGYTFT | 192 | WVRQAPG QGLEWMG | 196 | RVTMTRDTSTSTVYMEL SSLRSEDTAVYYCAR | 202 | WGQGTL VTVSS |
| 23 | 178 | QVQLVQSGAEVKKPG ASVKVSCKASGYTFT | 192 | WVRQAPG QGLEWMG | 196 | RVTMTRDTSTSTVYMEL SSLRSEDTAVYYCAR | 202 | WGQGTL VTVSS |
| 24 | 185 | QVQLVQSGAEVKKPG ASVKVSCKASGDTFT | 192 | WVRQAPG QGLEWMG | 196 | RVTMTRDTSTSTVYMEL SSLRSEDTAVYYCAR | 203 | WGQGTT VTVSS |
| 25 | 178 | QVQLVQSGAEVKKPG ASVKVSCKASGYTFT | 192 | WVRQAPG QGLEWMG | 196 | RVTMTRDTSTSTVYMEL SSLRSEDTAVYYCAR | 202 | WGQGTL VTVSS |
| 26 | 186 | QVQLAQSGAEVKKPG ASVKVSCKASGYTFT | 192 | WVRQAPG QGLEWMG | 196 | RVTMTRDTSTSTVYMEL SSLRSEDTAVYYCAR | 202 | WGQGTL VTVSS |

TABLE 2-continued

| Binding Agent | SEQ ID | HFW1 | SEQ ID | HFW2 | SEQ ID | HFW3 | SEQ ID | HFW4 |
|---|---|---|---|---|---|---|---|---|
| 27 | 178 | QVQLVQSGAEVKKPG ASVKVSCKASGYTFT | 192 | WVRQAPG QGLEWMG | 196 | RVTMTRDTSTSTVYMEL SSLRSEDTAVYYCAR | 202 | WGQGTL VTVSS |
| 28 | 178 | QVQLVQSGAEVKKPG ASVKVSCKASGYTFT | 192 | WVRQAPG QGLEWMG | 196 | RVTMTRDTSTSTVYMEL SSLRSEDTAVYYCAR | 203 | WGQGTT VTVSS |
| 29 | 187 | QVQLVQSGAEVKKPG ASVKVSCKASGYTFS | 192 | WVRQAPG QGLEWMG | 201 | RVTMTRDTSTSTVYMEL SSLRSEDTAVYYCAE | 204 | WGQGTM VTVSS |
| 30 | 188 | QVQLVQSGAEVKKPG ASVKVSCKASGYPFS | 192 | WVRQAPG QGLEWMG | 196 | RVTMTRDTSTSTVYMEL SSLRSEDTAVYYCAR | 203 | WGQGTT VTVSS |
| 31 | 178 | QVQLVQSGAEVKKPG ASVKVSCKASGYTFT | 192 | WVRQAPG QGLEWMG | 196 | RVTMTRDTSTSTVYMEL SSLRSEDTAVYYCAR | 202 | WGQGTL VTVSS |
| 32 | 178 | QVQLVQSGAEVKKPG ASVKVSCKASGYTFT | 192 | WVRQAPG QGLEWMG | 196 | RVTMTRDTSTSTVYMEL SSLRSEDTAVYYCAR | 202 | WGQGTL VTVSS |
| 33 | 178 | QVQLVQSGAEVKKPG ASVKVSCKASGYTFT | 192 | WVRQAPG QGLEWMG | 196 | RVTMTRDTSTSTVYMEL SSLRSEDTAVYYCAR | 205 | WGPGTM VTVSS |
| 34 | 178 | QVQLVQSGAEVKKPG ASVKVSCKASGYTFT | 192 | WVRQAPG QGLEWMG | 196 | RVTMTRDTSTSTVYMEL SSLRSEDTAVYYCAR | 206 | WGRGTL VTVSS |
| 35 | 188 | QVQLVQSGAEVKKPG ASVKVSCKASGYPFS | 192 | WVRQAPG QGLEWMG | 196 | RVTMTRDTSTSTVYMEL SSLRSEDTAVYYCAR | 206 | WGRGTL VTVSS |
| 36 | 184 | QVQLVQSGAEVKKPG SSVKVSCKASGGTFS | 192 | WVRQAPG QGLEWMG | 199 | RVTITADESTSTAYMEL SSLRSEDTAVYYCAR | 202 | WGQGTL VTVSS |
| 37 | 178 | QVQLVQSGAEVKKPG ASVKVSCKASGYTFT | 192 | WVRQAPG QGLEWMG | 196 | RVTMTRDTSTSTVYMEL SSLRSEDTAVYYCAR | 204 | WGQGTM VTVSS |
| 38 | 178 | QVQLVQSGAEVKKPG ASVKVSCKASGYTFT | 192 | WVRQAPG QGLEWMG | 196 | RVTMTRDTSTSTVYMEL SSLRSEDTAVYYCAR | 203 | WGQGTT VTVSS |
| 39 | 189 | QVQLVQSGAEVKKPG ASVKVSCKASGYSFT | 192 | WVRQAPG QGLEWMG | 196 | RVTMTRDTSTSTVYMEL SSLRSEDTAVYYCAR | 206 | WGRGTL VTVSS |
| 40 | 190 | QVQLVQSGAEVKKPG ASVKVSCKASGYTFI | 192 | WVRQAPG QGLEWMG | 196 | RVTMTRDTSTSTVYMEL SSLRSEDTAVYYCAR | 204 | WGQGTM VTVSS |
| 41 | 178 | QVQLVQSGAEVKKPG ASVKVSCKASGYTFT | 192 | WVRQAPG QGLEWMG | 196 | RVTMTRDTSTSTVYMEL SSLRSEDTAVYYCAR | 204 | WGQGTM VTVSS |
| 42 | 191 | QVQLVQSGAEVKKPG SSVKVSCKASGYTFT | 192 | WVRQAPG QGLEWMG | 199 | RVTITADESTSTAYMEL SSLRSEDTAVYYCAR | 203 | WGQGTT VTVSS |
| 43 | 185 | QVQLVQSGAEVKKPG ASVKVSCKASGDTFT | 192 | WVRQAPG QGLEWMG | 196 | RVTMTRDTSTSTVYMEL SSLRSEDTAVYYCAR | 203 | WGQGTT VTVSS |
| 44 | 178 | QVQLVQSGAEVKKPG ASVKVSCKASGYTFT | 192 | WVRQAPG QGLEWMG | 196 | RVTMTRDTSTSTVYMEL SSLRSEDTAVYYCAR | 203 | WGQGTT VTVSS |
| 45 | 178 | QVQLVQSGAEVKKPG ASVKVSCKASGYTFT | 192 | WVRQAPG QGLEWMG | 196 | RVTMTRDTSTSTVYMEL SSLRSEDTAVYYCAR | 203 | WGQGTT VTVSS |
| 46 | 178 | QVQLVQSGAEVKKPG ASVKVSCKASGYTFT | 192 | WVRQAPG QGLEWMG | 196 | RVTMTRDTSTSTVYMEL SSLRSEDTAVYYCAR | 202 | WGQGTL VTVSS |
| 47 | 187 | QVQLVQSGAEVKKPG ASVKVSCKASGYTFS | 192 | WVRQAPG QGLEWMG | 196 | RVTMTRDTSTSTVYMEL SSLRSEDTAVYYCAR | 202 | WGQGTL VTVSS |
| 48 | 178 | QVQLVQSGAEVKKPG ASVKVSCKASGYTFT | 192 | WVRQAPG QGLEWMG | 196 | RVTMTRDTSTSTVYMEL SSLRSEDTAVYYCAR | 203 | WGQGTT VTVSS |
| 49 | 178 | QVQLVQSGAEVKKPG ASVKVSCKASGYTFT | 192 | WVRQAPG QGLEWMG | 196 | RVTMTRDTSTSTVYMEL SSLRSEDTAVYYCAR | 203 | WGQGTT VTVSS |
| 50 | 185 | QVQLVQSGAEVKKPG ASVKVSCKASGDTFT | 192 | WVRQAPG QGLEWMG | 196 | RVTMTRDTSTSTVYMEL SSLRSEDTAVYYCAR | 203 | WGQGTT VTVSS |
| 51 | 178 | QVQLVQSGAEVKKPG ASVKVSCKASGYTFT | 192 | WVRQAPG QGLEWMG | 196 | RVTMTRDTSTSTVYMEL SSLRSEDTAVYYCAR | 203 | WGQGTT VTVSS |

TABLE 2-continued

| Binding Agent | SEQ ID | HFW1 | SEQ ID | HFW2 | SEQ ID | HFW3 | SEQ ID | HFW4 |
|---|---|---|---|---|---|---|---|---|
| 52 | 178 | QVQLVQSGAEVKKPG ASVKVSCKASGYTFT | 192 | WVRQAPG QGLEWMG | 196 | RVTMTRDTSTSTVYMEL SSLRSEDTAVYYCAR | 203 | WGQGTT VTVSS |
| 53 | 185 | QVQLVQSGAEVKKPG ASVKVSCKASGDTFT | 192 | WVRQAPG QGLEWMG | 196 | RVTMTRDTSTSTVYMEL SSLRSEDTAVYYCAR | 203 | WGQGTT VTVSS |
| 54 | 187 | QVQLVQSGAEVKKPG ASVKVSCKASGYTFS | 192 | WVRQAPG QGLEWMG | 196 | RVTMTRDTSTSTVYMEL SSLRSEDTAVYYCAR | 202 | WGQGTL VTVSS |
| 55 | 187 | QVQLVQSGAEVKKPG ASVKVSCKASGYTFS | 192 | WVRQAPG QGLEWMG | 196 | RVTMTRDTSTSTVYMEL SSLRSEDTAVYYCAR | 202 | WGQGTL VTVSS |
| 56 | 187 | QVQLVQSGAEVKKPG ASVKVSCKASGYTFS | 192 | WVRQAPG QGLEWMG | 196 | RVTMTRDTSTSTVYMEL SSLRSEDTAVYYCAR | 202 | WGQGTL VTVSS |
| 57 | 187 | QVQLVQSGAEVKKPG ASVKVSCKASGYTFS | 192 | WVRQAPG QGLEWMG | 196 | RVTMTRDTSTSTVYMEL SSLRSEDTAVYYCAR | 202 | WGQGTL VTVSS |
| 58 | 187 | QVQLVQSGAEVKKPG ASVKVSCKASGYTFS | 192 | WVRQAPG QGLEWMG | 196 | RVTMTRDTSTSTVYMEL SSLRSEDTAVYYCAR | 202 | WGQGTL VTVSS |
| 59 | 187 | QVQLVQSGAEVKKPG ASVKVSCKASGYTFS | 192 | WVRQAPG QGLEWMG | 196 | RVTMTRDTSTSTVYMEL SSLRSEDTAVYYCAR | 202 | WGQGTL VTVSS |
| 60 | 187 | QVQLVQSGAEVKKPG ASVKVSCKASGYTFS | 192 | WVRQAPG QGLEWMG | 196 | RVTMTRDTSTSTVYMEL SSLRSEDTAVYYCAR | 202 | WGQGTL VTVSS |
| 61 | 187 | QVQLVQSGAEVKKPG ASVKVSCKASGYTFS | 192 | WVRQAPG QGLEWMG | 196 | RVTMTRDTSTSTVYMEL SSLRSEDTAVYYCAR | 202 | WGQGTL VTVSS |
| 62 | 187 | QVQLVQSGAEVKKPG ASVKVSCKASGYTFS | 192 | WVRQAPG QGLEWMG | 196 | RVTMTRDTSTSTVYMEL SSLRSEDTAVYYCAR | 202 | WGQGTL VTVSS |
| 63 | 187 | QVQLVQSGAEVKKPG ASVKVSCKASGYTFS | 192 | WVRQAPG QGLEWMG | 196 | RVTMTRDTSTSTVYMEL SSLRSEDTAVYYCAR | 202 | WGQGTL VTVSS |
| 64 | 187 | QVQLVQSGAEVKKPG ASVKVSCKASGYTFS | 192 | WVRQAPG QGLEWMG | 196 | RVTMTRDTSTSTVYMEL SSLRSEDTAVYYCAR | 202 | WGQGTL VTVSS |
| 65 | 187 | QVQLVQSGAEVKKPG ASVKVSCKASGYTFS | 192 | WVRQAPG QGLEWMG | 196 | RVTMTRDTSTSTVYMEL SSLRSEDTAVYYCAR | 202 | WGQGTL VTVSS |
| 66 | 187 | QVQLVQSGAEVKKPG ASVKVSCKASGYTFS | 192 | WVRQAPG QGLEWMG | 196 | RVTMTRDTSTSTVYMEL SSLRSEDTAVYYCAR | 202 | WGQGTL VTVSS |
| 67 | 187 | QVQLVQSGAEVKKPG ASVKVSCKASGYTFS | 192 | WVRQAPG QGLEWMG | 196 | RVTMTRDTSTSTVYMEL SSLRSEDTAVYYCAR | 202 | WGQGTL VTVSS |
| 68 | 178 | QVQLVQSGAEVKKPG ASVKVSCKASGYTFT | 192 | WVRQAPG QGLEWMG | 196 | RVTMTRDTSTSTVYMEL SSLRSEDTAVYYCAR | 203 | WGQGTT VTVSS |
| 69 | 178 | QVQLVQSGAEVKKPG ASVKVSCKASGYTFT | 192 | WVRQAPG QGLEWMG | 196 | RVTMTRDTSTSTVYMEL SSLRSEDTAVYYCAR | 202 | WGQGTL VTVSS |
| 70 | 178 | QVQLVQSGAEVKKPG ASVKVSCKASGYTFT | 192 | WVRQAPG QGLEWMG | 196 | RVTMTRDTSTSTVYMEL SSLRSEDTAVYYCAR | 202 | WGQGTL VTVSS |

TABLE 3

| Binding agent | SEQ ID | LFW1 | SEQ ID | LFW2 | SEQ ID | LFW3 | SEQ ID | LFW4 |
|---|---|---|---|---|---|---|---|---|
| 1 | 207 | DIQMTQSPSSLSASVGDR VTITC | 210 | WYQQKPGKAPKL LIY | 213 | GVPSRFSGSGSGTDFTLTISSLQPED FATYYC | 217 | FGGGTKV EIK |
| 2 | 207 | DIQMTQSPSSLSASVGDR VTITC | 210 | WYQQKPGKAPKL LIY | 213 | GVPSRFSGSGSGTDFTLTISSLQPED FATYYC | 217 | FGGGTKV EIK |
| 3 | 207 | DIQMTQSPSSLSASVGDR VTITC | 210 | WYQQKPGKAPKL LIY | 213 | GVPSRFSGSGSGTDFTLTISSLQPED FATYYC | 217 | FGGGTKV EIK |
| 4 | 207 | DIQMTQSPSSLSASVGDR VTITC | 210 | WYQQKPGKAPKL LIY | 213 | GVPSRFSGSGSGTDFTLTISSLQPED FATYYC | 217 | FGGGTKV EIK |

TABLE 3-continued

| Binding agent | SEQ ID | LFW1 | SEQ ID | LFW2 | SEQ ID | LFW3 | SEQ ID | LFW4 |
|---|---|---|---|---|---|---|---|---|
| 5 | 207 | DIQMTQSPSSLSASVGDRVTITC | 210 | WYQQKPGKAPKLLIY | 213 | GVPSRFSGSGSGTDFTLTISSLQPEDFATYYC | 217 | FGGGTKVEIK |
| 6 | 208 | EIVMTQSPATLSVSPGERATLSC | 211 | WYQQKPGQAPRLLIY | 214 | GIPARFSGSGSGTEFTLTISSLQSEDFAVYYC | 218 | FGQGTKVEIK |
| 7 | 207 | DIQMTQSPSSLSASVGDRVTITC | 210 | WYQQKPGKAPKLLIY | 213 | GVPSRFSGSGSGTDFTLTISSLQPEDFATYYC | 217 | FGGGTKVEIK |
| 8 | 207 | DIQMTQSPSSLSASVGDRVTITC | 210 | WYQQKPGKAPKLLIY | 213 | GVPSRFSGSGSGTDFTLTISSLQPEDFATYYC | 217 | FGGGTKVEIK |
| 9 | 207 | DIQMTQSPSSLSASVGDRVTITC | 210 | WYQQKPGKAPKLLIY | 213 | GVPSRFSGSGSGTDFTLTISSLQPEDFATYYC | 217 | FGGGTKVEIK |
| 10 | 207 | DIQMTQSPSSLSASVGDRVTITC | 210 | WYQQKPGKAPKLLIY | 213 | GVPSRFSGSGSGTDFTLTISSLQPEDFATYYC | 217 | FGGGTKVEIK |
| 11 | 207 | DIQMTQSPSSLSASVGDRVTITC | 210 | WYQQKPGKAPKLLIY | 213 | GVPSRFSGSGSGTDFTLTISSLQPEDFATYYC | 217 | FGGGTKVEIK |
| 12 | 207 | DIQMTQSPSSLSASVGDRVTITC | 210 | WYQQKPGKAPKLLIY | 213 | GVPSRFSGSGSGTDFTLTISSLQPEDFATYYC | 217 | FGGGTKVEIK |
| 13 | 207 | DIQMTQSPSSLSASVGDRVTITC | 210 | WYQQKPGKAPKLLIY | 213 | GVPSRFSGSGSGTDFTLTISSLQPEDFATYYC | 217 | FGGGTKVEIK |
| 14 | 207 | DIQMTQSPSSLSASVGDRVTITC | 210 | WYQQKPGKAPKLLIY | 213 | GVPSRFSGSGSGTDFTLTISSLQPEDFATYYC | 217 | FGGGTKVEIK |
| 15 | 207 | DIQMTQSPSSLSASVGDRVTITC | 210 | WYQQKPGKAPKLLIY | 213 | GVPSRFSGSGSGTDFTLTISSLQPEDFATYYC | 217 | FGGGTKVEIK |
| 16 | 207 | DIQMTQSPSSLSASVGDRVTITC | 210 | WYQQKPGKAPKLLIY | 213 | GVPSRFSGSGSGTDFTLTISSLQPEDFATYYC | 217 | FGGGTKVEIK |
| 17 | 207 | DIQMTQSPSSLSASVGDRVTITC | 210 | WYQQKPGKAPKLLIY | 213 | GVPSRFSGSGSGTDFTLTISSLQPEDFATYYC | 217 | FGGGTKVEIK |
| 18 | 207 | DIQMTQSPSSLSASVGDRVTITC | 210 | WYQQKPGKAPKLLIY | 213 | GVPSRFSGSGSGTDFTLTISSLQPEDFATYYC | 217 | FGGGTKVEIK |
| 19 | 207 | DIQMTQSPSSLSASVGDRVTITC | 210 | WYQQKPGKAPKLLIY | 213 | GVPSRFSGSGSGTDFTLTISSLQPEDFATYYC | 218 | FGQGTKVEIK |
| 20 | 207 | DIQMTQSPSSLSASVGDRVTITC | 210 | WYQQKPGKAPKLLIY | 213 | GVPSRFSGSGSGTDFTLTISSLQPEDFATYYC | 219 | FGQGTRLEIK |
| 21 | 207 | DIQMTQSPSSLSASVGDRVTITC | 210 | WYQQKPGKAPKLLIY | 213 | GVPSRFSGSGSGTDFTLTISSLQPEDFATYYC | 217 | FGGGTKVEIK |
| 22 | 207 | DIQMTQSPSSLSASVGDRVTITC | 210 | WYQQKPGKAPKLLIY | 213 | GVPSRFSGSGSGTDFTLTISSLQPEDFATYYC | 221 | FGQGTKLEIK |
| 23 | 207 | DIQMTQSPSSLSASVGDRVTITC | 210 | WYQQKPGKAPKLLIY | 213 | GVPSRFSGSGSGTDFTLTISSLQPEDFATYYC | 218 | FGQGTKVEIK |
| 24 | 207 | DIQMTQSPSSLSASVGDRVTITC | 210 | WYQQKPGKAPKLLIY | 213 | GVPSRFSGSGSGTDFTLTISSLQPEDFATYYC | 220 | FGGGTKLEIK |
| 25 | 207 | DIQMTQSPSSLSASVGDRVTITC | 210 | WYQQKPGKAPKLLIY | 213 | GVPSRFSGSGSGTDFTLTISSLQPEDFATYYC | 221 | FGQGTKLEIK |
| 26 | 207 | DIQMTQSPSSLSASVGDRVTITC | 210 | WYQQKPGKAPKLLIY | 213 | GVPSRFSGSGSGTDFTLTISSLQPEDFATYYC | 222 | FGPGTKVDIK |
| 27 | 207 | DIQMTQSPSSLSASVGDRVTITC | 210 | WYQQKPGKAPKLLIY | 213 | GVPSRFSGSGSGTDFTLTISSLQPEDFATYYC | 217 | FGGGTKVEIK |
| 28 | 208 | EIVMTQSPATLSVSPGERATLSC | 211 | WYQQKPGQAPRLLIY | 214 | GIPARFSGSGSGTEFTLTISSLQSEDFAVYYC | 222 | FGPGTKVDIK |
| 29 | 207 | DIQMTQSPSSLSASVGDRVTITC | 210 | WYQQKPGKAPKLLIY | 213 | GVPSRFSGSGSGTDFTLTISSLQPEDFATYYC | 221 | FGQGTKLEIK |

TABLE 3-continued

| Binding agent | SEQ ID | LFW1 | SEQ ID | LFW2 | SEQ ID | LFW3 | SEQ ID | LFW4 |
|---|---|---|---|---|---|---|---|---|
| 30 | 207 | DIQMTQSPSSLSASVGDR VTITC | 210 | WYQQKPGKAPKL LIY | 213 | GVPSRFSGSGSGTDFTLTISSLQPED FATYYC | 217 | FGGGTKV EIK |
| 31 | 207 | DIQMTQSPSSLSASVGDR VTITC | 210 | WYQQKPGKAPKL LIY | 213 | GVPSRFSGSGSGTDFTLTISSLQPED FATYYC | 219 | FGQGTRL EIK |
| 32 | 207 | DIQMTQSPSSLSASVGDR VTITC | 210 | WYQQKPGKAPKL LIY | 213 | GVPSRFSGSGSGTDFTLTISSLQPED FATYYC | 218 | FGQGTKV EIK |
| 33 | 208 | EIVMTQSPATLSVSPGER ATLSC | 211 | WYQQKPGQAPRL LIY | 214 | GIPARFSGSGSGTEFTLTISSLQSED FAVYYC | 217 | FGGGTKV EIK |
| 34 | 207 | DIQMTQSPSSLSASVGDR VTITC | 210 | WYQQKPGKAPKL LIY | 213 | GVPSRFSGSGSGTDFTLTISSLQPED FATYYC | 219 | FGQGTRL EIK |
| 35 | 207 | DIQMTQSPSSLSASVGDR VTITC | 210 | WYQQKPGKAPKL LIY | 213 | GVPSRFSGSGSGTDFTLTISSLQPED FATYYC | 218 | FGQGTKV EIK |
| 36 | 207 | DIQMTQSPSSLSASVGDR VTITC | 210 | WYQQKPGKAPKL LIY | 213 | GVPSRFSGSGSGTDFTLTISSLQPED FATYYC | 218 | FGQGTKV EIK |
| 37 | 207 | DIQMTQSPSSLSASVGDR VTITC | 210 | WYQQKPGKAPKL LIY | 213 | GVPSRFSGSGSGTDFTLTISSLQPED FATYYC | 217 | FGGGTKV EIK |
| 38 | 207 | DIQMTQSPSSLSASVGDR VTITC | 210 | WYQQKPGKAPKL LIY | 213 | GVPSRFSGSGSGTDFTLTISSLQPED FATYYC | 221 | FGQGTKL EIK |
| 39 | 207 | DIQMTQSPSSLSASVGDR VTITC | 210 | WYQQKPGKAPKL LIY | 213 | GVPSRFSGSGSGTDFTLTISSLQPED FATYYC | 218 | FGQGTKV EIK |
| 40 | 209 | DIQITHSPSSLSASVGYR LTITC | 212 | WYHQKPWNAPKL MIY | 215 | GVPSRFSGSGSGTYFTLTISSLQPED FATYYC | 218 | FGQGTKV EIK |
| 41 | 207 | DIQMTQSPSSLSASVGDR VTITC | 210 | WYQQKPGKAPKL LIY | 213 | GVPSRFSGSGSGTDFTLTISSLQPED FATYYC | 218 | FGQGTKV EIK |
| 42 | 207 | DIQMTQSPSSLSASVGDR VTITC | 210 | WYQQKPGKAPKL LIY | 216 | GVPSRFSGSGSGTDFTLTISSLQPED FAPYYC | 222 | FGPGTKV DIK |
| 43 | 207 | DIQMTQSPSSLSASVGDR VTITC | 210 | WYQQKPGKAPKL LIY | 213 | GVPSRFSGSGSGTDFTLTISSLQPED FATYYC | 217 | FGGGTKV EIK |
| 44 | 207 | DIQMTQSPSSLSASVGDR VTITC | 210 | WYQQKPGKAPKL LIY | 213 | GVPSRFSGSGSGTDFTLTISSLQPED FATYYC | 217 | FGGGTKV EIK |
| 45 | 207 | DIQMTQSPSSLSASVGDR VTITC | 210 | WYQQKPGKAPKL LIY | 213 | GVPSRFSGSGSGTDFTLTISSLQPED FATYYC | 217 | FGGGTKV EIK |
| 46 | 207 | DIQMTQSPSSLSASVGDR VTITC | 210 | WYQQKPGKAPKL LIY | 213 | GVPSRFSGSGSGTDFTLTISSLQPED FATYYC | 217 | FGGGTKV EIK |
| 47 | 207 | DIQMTQSPSSLSASVGDR VTITC | 210 | WYQQKPGKAPKL LIY | 213 | GVPSRFSGSGSGTDFTLTISSLQPED FATYYC | 217 | FGGGTKV EIK |
| 48 | 207 | DIQMTQSPSSLSASVGDR VTITC | 210 | WYQQKPGKAPKL LIY | 213 | GVPSRFSGSGSGTDFTLTISSLQPED FATYYC | 217 | FGGGTKV EIK |
| 49 | 207 | DIQMTQSPSSLSASVGDR VTITC | 210 | WYQQKPGKAPKL LIY | 213 | GVPSRFSGSGSGTDFTLTISSLQPED FATYYC | 217 | FGGGTKV EIK |
| 50 | 207 | DIQMTQSPSSLSASVGDR VTITC | 210 | WYQQKPGKAPKL LIY | 213 | GVPSRFSGSGSGTDFTLTISSLQPED FATYYC | 217 | FGGGTKV EIK |
| 51 | 207 | DIQMTQSPSSLSASVGDR VTITC | 210 | WYQQKPGKAPKL LIY | 213 | GVPSRFSGSGSGTDFTLTISSLQPED FATYYC | 217 | FGGGTKV EIK |
| 52 | 207 | DIQMTQSPSSLSASVGDR VTITC | 210 | WYQQKPGKAPKL LIY | 213 | GVPSRFSGSGSGTDFTLTISSLQPED FATYYC | 217 | FGGGTKV EIK |
| 53 | 207 | DIQMTQSPSSLSASVGDR VTITC | 210 | WYQQKPGKAPKL LIY | 213 | GVPSRFSGSGSGTDFTLTISSLQPED FATYYC | 217 | FGGGTKV EIK |
| 54 | 207 | DIQMTQSPSSLSASVGDR VTITC | 210 | WYQQKPGKAPKL LIY | 213 | GVPSRFSGSGSGTDFTLTISSLQPED FATYYC | 217 | FGGGTKV EIK |

TABLE 3-continued

| Binding agent | SEQ ID | LFW1 | SEQ ID | LFW2 | SEQ ID | LFW3 | SEQ ID | LFW4 |
|---|---|---|---|---|---|---|---|---|
| 55 | 207 | DIQMTQSPSSLSASVGDR VTITC | 210 | WYQQKPGKAPKL LIY | 213 | GVPSRFSGSGSGTDFTLTISSLQPED FATYYC | 217 | FGGGTKV EIK |
| 56 | 207 | DIQMTQSPSSLSASVGDR VTITC | 210 | WYQQKPGKAPKL LIY | 213 | GVPSRFSGSGSGTDFTLTISSLQPED FATYYC | 217 | FGGGTKV EIK |
| 57 | 207 | DIQMTQSPSSLSASVGDR VTITC | 210 | WYQQKPGKAPKL LIY | 213 | GVPSRFSGSGSGTDFTLTISSLQPED FATYYC | 217 | FGGGTKV EIK |
| 58 | 207 | DIQMTQSPSSLSASVGDR VTITC | 210 | WYQQKPGKAPKL LIY | 213 | GVPSRFSGSGSGTDFTLTISSLQPED FATYYC | 217 | FGGGTKV EIK |
| 59 | 207 | DIQMTQSPSSLSASVGDR VTITC | 210 | WYQQKPGKAPKL LIY | 213 | GVPSRFSGSGSGTDFTLTISSLQPED FATYYC | 217 | FGGGTKV EIK |
| 60 | 207 | DIQMTQSPSSLSASVGDR VTITC | 210 | WYQQKPGKAPKL LIY | 213 | GVPSRFSGSGSGTDFTLTISSLQPED FATYYC | 217 | FGGGTKV EIK |
| 61 | 207 | DIQMTQSPSSLSASVGDR VTITC | 210 | WYQQKPGKAPKL LIY | 213 | GVPSRFSGSGSGTDFTLTISSLQPED FATYYC | 217 | FGGGTKV EIK |
| 62 | 207 | DIQMTQSPSSLSASVGDR VTITC | 210 | WYQQKPGKAPKL LIY | 213 | GVPSRFSGSGSGTDFTLTISSLQPED FATYYC | 217 | FGQGTKV EIK |
| 63 | 207 | DIQMTQSPSSLSASVGDR VTITC | 210 | WYQQKPGKAPKL LIY | 213 | GVPSRFSGSGSGTDFTLTISSLQPED FATYYC | 217 | FGQGTKV EIK |
| 64 | 207 | DIQMTQSPSSLSASVGDR VTITC | 210 | WYQQKPGKAPKL LIY | 213 | GVPSRFSGSGSGTDFTLTISSLQPED FATYYC | 217 | FGGGTKV EIK |
| 65 | 207 | DIQMTQSPSSLSASVGDR VTITC | 210 | WYQQKPGKAPKL LIY | 213 | GVPSRFSGSGSGTDFTLTISSLQPED FATYYC | 217 | FGGGTKV EIK |
| 66 | 207 | DIQMTQSPSSLSASVGDR VTITC | 210 | WYQQKPGKAPKL LIY | 213 | GVPSRFSGSGSGTDFTLTISSLQPED FATYYC | 217 | FGGGTKV EIK |
| 67 | 207 | DIQMTQSPSSLSASVGDR VTITC | 210 | WYQQKPGKAPKL LIY | 213 | GVPSRFSGSGSGTDFTLTISSLQPED FATYYC | 217 | FGQGTKL EIK |
| 68 | 207 | DIQMTQSPSSLSASVGDR VTITC | 210 | WYQQKPGKAPKL LIY | 213 | GVPSRFSGSGSGTDFTLTISSLQPED FATYYC | 217 | FGQGTRL EIK |
| 69 | 207 | DIQMTQSPSSLSASVGDR VTITC | 210 | WYQQKPGKAPKL LIY | 213 | GVPSRFSGSGSGTDFTLTISSLQPED FATYYC | 217 | FGQGTRL EIK |
| 70 | 207 | DIQMTQSPSSLSASVGDR VTITC | 210 | WYQQKPGKAPKL LIY | 213 | GVPSRFSGSGSGTDFTLTISSLQPED FATYYC | 217 | FGQGTKL EIK |

TABLE 4

| Binding agent | SEQ ID | VH |
|---|---|---|
| 1 | 223 | QVQLVQSGAEVKKPGASVKVSCKASGGTFSSYAISWVRQAPGQGLEWMGVINPSAGSTDYAQKFQGRVTMTR DTSTSTVYMELSSLRSEDTAVYYCARDLYPYVVVVAAGSYGMDVWGQGTLVTVSS |
| 2 | 224 | QVQLVQSGAEVKKPGASVKVSCKASGYTFTSYYMHWVRQAPGQGLEWMGWMNPNSDIAGYAQKFQGRVTMTR DTSTSTVYMELSSLRSEDTAVYYCAIPSIVGAYDAFDIWGQGTLVTVSS |
| 3 | 225 | QVQLVQSGAEVKKPGASVKVSCKASGYTFTRHLLHWVRQAPGQGLEWMGWISPQHGVRNYAQKFQGRVTMTR DTSTSTVYMELSSLRSEDTAVYYCARESVEGYFDLWGQGTLVTVSS |
| 4 | 226 | QVQLVQSGAEVKKPGASVKVSCKASGYTFTSHHMHWVRQAPGQGLEWMGWVSPSHGLTGYAQKFQGRVTMTR DTSTSTVYMELSSLRSEDTAVYYCARDNWNVHDAFDIWGQGTLVTVSS |
| 5 | 227 | QVQLVQSGAEVKKPGASVKVSCKASGYTFNRFMHWVRQAPGQGLEWMGWMSLNSGLTGYAQKFQGRVTMTRD TSTSTVYMELSSLRSEDTAVYYCTRGTYNDAFDIWGQGTLVTVSS |
| 6 | 228 | QVQLVQSGAEVKKPGASVKVSCKASGYTFTSYYIHWVRQAPGQGLEWMGWMKPSSGTTGYAQKFQGRVTMTR DTSTSTVYMELSSLRSEDTAVYYCAREQWLVNDAFDIWGQGTLVTVSS |
| 7 | 229 | QVQLVQSGAEVKKPGASVKVSCKASGYTFTSYYIHWVRQAPGQGLEWMGWMKPSSGTTGYAQKFQGRVTMTR DTSTSTVYMELSSLRSEDTAVYYCAREQWLVNDAFDIWGQGTLVTVSS |

TABLE 4-continued

| Binding agent | SEQ ID | VH |
|---|---|---|
| 8 | 230 | QVQLVQSGAEVKKPGASVKVSCKASGNTFTSYYMHWVRQAPGQGLEWMGGIDPNSGGTNYAQKFQGRVTMTR DTSTSTVYMELSSLRSEDTAVYYCARSMFPTIFGDNAFDIWGQGTLVTVSS |
| 9 | 231 | QVQLVQSGAEVKKPGASVKVSCKASGHSFTHYYMHWVRQAPGQGLEWMGWMNPDSGSTGYAQKFQGRVTMTR DTSTSTVYMELSSLRSEDTAVYYCARALFPYPFYYYYMDVWGQGTLVTVSS |
| 10 | 232 | QVQLVQSGAEVKKPGASVKVSCKASGYTFTGYYMHWVRQAPGQGLEWIGWMSLNSGLTGYAQKFQGRVTMTR DTSTSTVYMELSSLRSEDTAVYYCARDRGWFDPWGQGTLVTVSS |
| 11 | 233 | QVQLVQSGAEVKKPGASVKVSCKASGYTFTNYYIHWVRQAPGQGLEWLGWMNPNGDVAGYADSFQGRVTMTR DTSTSTVYMELSSLRSEDTAVYYCAIDSSGWMRNDAFDIWGQGTLVTVSS |
| 12 | 234 | QVQLVQSGAEVKKPGASVKVSCKASGGTFSNYMYHWVRQAPGQGLEWMGWISTYHGSTNYAQKFQGRVTMTR DTSTSTVYMELSSLRSEDTAVYYCARDARGYSGYDLWGQGTLVTVSS |
| 13 | 235 | QVQLVQSGAEVKKPGASVKVSCKASGYPFTSYYMHWVRQAPGQGLEWMGWMNPNSDIAGYAQKFQGRVTMTR DTSTSTVYMELSSLRSEDTAVYYCAREGRHGEYLYWGQGTLVTVSS |
| 14 | 236 | QVQLVQSGAEVKKPGASVKVSCKASGYRFTTYYVHWVRQAPGQGLEWMGWMNPNTVYTGSAQKFQGRVTMTR DTSTSTVYMELSSLRSEDTAVYYCAREGWGSSGYFDYWGQGTLVTVSS |
| 15 | 237 | QVQLVQSGAEVKKPGSSVKVSCKASGGTFSSYALSWVRQAPGQGLEWMGRIIPAVGSVTYAQKFQGRVTITA DESTSTAYMELSSLRSEDTAVYYCARHLFPTVFDDYYGMDVWGQGTLVTVSS |
| 16 | 238 | QVQLVQSGAEVKKPGSSVKVSCKASGGTFSSYAISWVRQAPGQGLEWMGGIIPIFGTANYAQKFQGRVTITA DESTSTAYMELSSLRSEDTAVYYCARGGYSYGSFQHWGQGTLVTVSS |
| 17 | 239 | QVQLVQSGAEVKKPGASVKVSCKASGDTFTRHYVHWVRQAPGQGLEWMGWMSPSSGITGYAQKFQGRVTMTR DTSTSTVYMELSSLRSEDTAVYYCARVRWSSDAFDIWGQGTLVTVSS |
| 18 | 240 | QVQLVQSGAEVKKPGASVKVSCKASGYTFTSYYMHWVRQAPGQGLEWVGWMTPSTGNAGYAQKFQGRVTMTR DTSTSTVYMELSSLRSEDTAVYYCAREEWLGHFQHWGQGTLVTVSS |
| 19 | 241 | QVQLVQSGAEVKKPGASVKVSCKASGYTFTSHYMHWVRQAPGQGLEWMGWMNPNSGNTGYAQKFQGRVTMTR DTSTSTVYMELSSLRSEDTAVYYCARERFLGGMDVWGQGTTVTVSS |
| 20 | 242 | QVQLVQSGAEVKKPGASVKVSCKASGYTFTDYYMHWVRQAPGQGLEWMGWMHPNSGHTGYAQKFQGRVTMTR DTSTSTVNMELSSLRSEDTAVYYCAREEWLGHFQHWGQGTLVTVSS |
| 21 | 243 | QVQLVQSGAEVKKPGASVKVSCKASGYTFTSHYMHWVRQAPGQGLEWMGWMNPNSGHTGNAQKFQGRVTMTR DTSTSTVYMELSSLRSEDTAVYYCARGNWVDAFDIWGQGTMVTVSS |
| 22 | 244 | QVQLVQSGAEVKKPGASVKVSCKASGYTFTGYTLHWVRQAPGQGLEWMGWIDPNSGVTSSAQKFQGRVTMTR DTSTSTVYMELSSLRSEDTAVYYCARESEVMMAYFQHWGQGTLVTVSS |
| 23 | 245 | QVQLVQSGAEVKKPGASVKVSCKASGYTFTGYYMHWVRQAPGQGLEWMGWISPNSGVTDFTQKFQGRVTMTR DTSTSTVYMELSSLRSEDTAVYYCARESWSGEFDYWGQGTLVTVSS |
| 24 | 246 | QVQLVQSGAEVKKPGASVKVSCKASGDTFTNHYMHWVRQAPGQGLEWMGWMNPNSGHTGYAQRFQGRVTMTR DTSTSTVYMELSSLRSEDTAVYYCAREAVAGPMDVWGQGTTVTVSS |
| 25 | 247 | QVQLVQSGAEVKKPGASVKVSCKASGYTFTGYYMHWVRQAPGQGLEWMGWMNPNSDIAGYAQKFQGRVTMTR DTSTSTVYMELSSLRSEDTAVYYCARDAWELLAFDIWGQGTLVTVSS |
| 26 | 248 | QVQLAQSGAEVKKPGASVKVSCKASGYTFTNHYMHWVRQAPGQGLEWMGWMNPNSGNTGYAQKFQGRVTMTR DTSTSTVYMELSSLRSEDTAVYYCARDRWDGDYYSAWGQGTLVTVSS |
| 27 | 249 | QVQLVQSGAEVKKPGASVKVSCKASGYTFTNYYIHWVRQAPGQGLEWMGWMSPNGGNTGYAQKFQGRVTMTR DTSTSTVYMELSSLRSEDTAVYYCARESWELTGFDYWGQGTLVTVSS |
| 28 | 250 | QVQLVQSGAEVKKPGASVKVSCKASGYTFTSYYMHWVRQAPGQGLEWMGWMNPNSGNTGYAQKFQGRVTMTR DTSTSTVYMELSSLRSEDTAVYYCARERFAGGMDAWGQGTTVTVSS |
| 29 | 251 | QVQLVQSGAEVKKPGASVKVSCKASGYTFSNSYMHWVRQAPGQGLEWMGWMDPSSGYTGSAHKFQGRVTMTR DTSTSTVYMELSSLRSEDTAVYYCAEDSGGAFDIWGQGTMVTVSS |
| 30 | 252 | QVQLVQSGAEVKKPGASVKVSCKASGYPFSTYYMHWVRQAPGQGLEWMGWMNPHSADTGYAEKFQGRVTMTR DTSTSTVYMELSSLRSEDTAVYYCAREVFEGGMDVWGQGTTVTVSS |
| 31 | 253 | QVQLVQSGAEVKKPGASVKVSCKASGYTFTSYYMHWVRQAPGQGLEWMGWLTPSTGHAGYAQKFQGRVTMTR DTSTSTVYMELSSLRSEDTAVYYCAREGYGGNYGNWGQGTLVTVSS |
| 32 | 254 | QVQLVQSGAEVKKPGASVKVSCKASGYTFTSYYMHWVRQAPGQGLEWMGWMNPNSGHTGYAQKFQGRVTMTR DTSTSTVYMELSSLRSEDTAVYYCAREDFYGDFDYWGQGTLVTVSS |

TABLE 4-continued

| Binding agent | SEQ ID | VH |
|---|---|---|
| 33 | 255 | QVQLVQSGAEVKKPGASVKVSCKASGYTFTRHFIHWVRQAPGQGLEWMGWIDPNSGVTSSAQKFQGRVTMTR DTSTSTVYMELSSLRSEDTAVYYCARELSRWGFDYWGPGTMVTVSS |
| 34 | 256 | QVQLVQSGAEVKKPGASVKVSCKASGYTFTRHLLHWVRQAPGQGLEWMGWISPQHGVRNYAHKFQGRVTMTR DTSTSTVYMELSSLRSEDTAVYYCARESVEGYFDLWGRGTLVTVSS |
| 35 | 257 | QVQLVQSGAEVKKPGASVKVSCKASGYPFSSYYMHWVRQAPGQGLEWMGMINPSGGSTSYAQKFQGRVTMTR DTSTSTVYMELSSLRSEDTAVYYCARDIFPTMIAGGGFDLWGRGTLVTVSS |
| 36 | 258 | QVQLVQSGAEVKKPGSSVKVSCKASGGTFSTFGISWVRQAPGQGLEWMGGIIPIFGTANYAQKFQGRVTITA DESTSTAYMELSSLRSEDTAVYYCARGGYSYGSFDYWGQGTLVTVSS |
| 37 | 259 | QVQLVQSGAEVKKPGASVKVSCKASGYTFTSYGINWVRQAPGQGLEWMGWMNPNSGNTGYAQKFQGRVTMTR DTSTSTVYMELSSLRSEDTAVYYCARGSFPLVFTIFGVGDVWGQGTMVTVSS |
| 38 | 260 | QVQLVQSGAEVKKPGASVKVSCKASGYTFTSYYMHWVRQAPGQGLEWMGWISPRSGVTSYAQKFQGRVTMTR DTSTSTVYMELSSLRSEDTAVYYCARDLDYVRAFDIWGQGTTVTVSS |
| 39 | 261 | QVQLVQSGAEVKKPGASVKVSCKASGYSFTSYYMHWVRQAPGQGLEWMGWMDPNSGNTGYAQKFQGRVTMTR DTSTSTVYMELSSLRSEDTAVYYCARESWGGYFDLWGRGTLVTVSS |
| 40 | 262 | QVQLVQSGAEVKKPGASVKVSCKASGYTFINHYVHWVRQAPGQGLEWMGWMNPTGGITGYAQKFQGRVTMTR DTSTSTVYMELSSLRSEDTAVYYCARDRTTYAFDIWGQGTMVTVSS |
| 41 | 263 | QVQLVQSGAEVKKPGASVKVSCKASGYTFTSHYMHWVRQAPGQGLEWMGWMNPNSGHTGNAQKFQGRVTMTR DTSTSTVYMELSSLRSEDTAVYYCARGNWVDAFDIWGQGTMVTVSS |
| 42 | 264 | QVQLVQSGAEVKKPGSSVKVSCKASGYTFTRHLLHWVRQAPGQGLEWMGWVSPIHGLTGYAPRFQGRVTITA DESTSTAYMELSSLRSEDTAVYYCARVHGSGSDGMDVWGQGTTVTVSS |
| 43 | 324 | QVQLVQSGAEVKKPGASVKVSCKASGDTFTNHYMHWVRQAPGQGLEWMGWMNPNSGHTGYAQRFQGRVTMTR DTSTSTVYMELSSLRSEDTAVYYCAREAVAGPMDVWGQGTTVTVSS |
| 44 | 325 | QVQLVQSGAEVKKPGASVKVSCKASGYTFTSHYMHWVRQAPGQGLEWMGWINPNSGNTGYAQKFQGRVTMTR DTSTSTVYMELSSLRSEDTAVYYCARERFLGGXMDVWGQGTTVTVSS |
| 45 | 326 | QVQLVQSGAEVKKPGASVKVSCKASGYTFTNHYMHWVRQAPGQGLEWMGWINPNSGHTGYAQKFQGRVTMTR DTSTSTVYMELSSLRSEDTAVYYCAREAVAGPXMDVWGQGTTVTVSS |
| 46 | 327 | QVQLVQSGAEVKKPGASVKVSCKASGYTFTNHYMHWVRQAPGQGLEWMGWINPNSGNTGYAQKFQGRVTMTR DTSTSTVYMELSSLRSEDTAVYYCARDRWGGDYYSAWGQGTLVTVSS |
| 47 | 328 | QVQLVQSGAEVKKPGASVKVSCKASGYTFSTHYMHWVRQAPGQGLEWMGWINPNSGNTGYSQKFQGRVTMTR DTSTSTVYMELSSLRSEDTAVYYCARERLSVAGFDYWGQGTLVTVSS |
| 48 | 329 | QVQLVQSGAEVKKPGASVKVSCKASGYTFTNHYMHWVRQAPGQGLEWMGWMNPNSGHTGYAQRFQGRVTMTR DTSTSTVYMELSSLRSEDTAVYYCAREAVAGPMDVWGQGTTVTVSS |
| 49 | 329 | QVQLVQSGAEVKKPGASVKVSCKASGYTFTNHYMHWVRQAPGQGLEWMGWMNPNSGHTGYAQRFQGRVTMTR DTSTSTVYMELSSLRSEDTAVYYCAREAVAGPMDVWGQGTTVTVSS |
| 50 | 330 | QVQLVQSGAEVKKPGASVKVSCKASGDTFTNHYMHWVRQAPGQGLEWMGWMNPNSGHTGYAQKFQGRVTMTR DTSTSTVYMELSSLRSEDTAVYYCAREAVAGPMDVWGQGTTVTVSS |
| 51 | 331 | QVQLVQSGAEVKKPGASVKVSCKASGYTFTNHYMHWVRQAPGQGLEWMGWINPNSGHTGYAQRFQGRVTMTR DTSTSTVYMELSSLRSEDTAVYYCAREAVAGPMDVWGQGTTVTVSS |
| 52 | 332 | QVQLVQSGAEVKKPGASVKVSCKASGYTFTNHYMHWVRQAPGQGLEWMGWMNPNSGHTGYAQKFQGRVTMTR DTSTSTVYMELSSLRSEDTAVYYCAREAVAGPMDVWGQGTTVTVSS |
| 53 | 333 | QVQLVQSGAEVKKPGASVKVSCKASGDTFTNHYMHWVRQAPGQGLEWMGWINPNSGHTGYAQKFQGRVTMTR DTSTSTVYMELSSLRSEDTAVYYCAREAVAGPMDVWGQGTTVTVSS |
| 54 | 334 | QVQLVQSGAEVKKPGASVKVSCKASGYTFSTHYMHWVRQAPGQGLEWMGWMNPNSGNTGYSQKFQGRVTMTR DTSTSTVYMELSSLRSEDTAVYYCARERLSVAGFDYWGQGTLVTVSS |
| 55 | 328 | QVQLVQSGAEVKKPGASVKVSCKASGYTFSTHYMHWVRQAPGQGLEWMGWINPNSGNTGYSQKFQGRVTMTR DTSTSTVYMELSSLRSEDTAVYYCARERLSVAGFDYWGQGTLVTVSS |
| 56 | 328 | QVQLVQSGAEVKKPGASVKVSCKASGYTFSTHYMHWVRQAPGQGLEWMGWINPNSGNTGYSQKFQGRVTMTR DTSTSTVYMELSSLRSEDTAVYYCARERLSVAGFDYWGQGTLVTVSS |
| 57 | 328 | QVQLVQSGAEVKKPGASVKVSCKASGYTFSTHYMHWVRQAPGQGLEWMGWINPNSGNTGYSQKFQGRVTMTR DTSTSTVYMELSSLRSEDTAVYYCARERLSVAGFDYWGQGTLVTVSS |

TABLE 4-continued

| Binding agent | SEQ ID | VH |
|---|---|---|
| 58 | 328 | QVQLVQSGAEVKKPGASVKVSCKASGYTFSTHYMHWVRQAPGQGLEWMGWINPNSGNTGYSQKFQGRVTMTR DTSTSTVYMELSSLRSEDTAVYYCARERLSVAGFDYWGQGTLVTVSS |
| 59 | 328 | QVQLVQSGAEVKKPGASVKVSCKASGYTFSTHYMHWVRQAPGQGLEWMGWINPNSGNTGYSQKFQGRVTMTR DTSTSTVYMELSSLRSEDTAVYYCARERLSVAGFDYWGQGTLVTVSS |
| 60 | 328 | QVQLVQSGAEVKKPGASVKVSCKASGYTFSTHYMHWVRQAPGQGLEWMGWINPNSGNTGYSQKFQGRVTMTR DTSTSTVYMELSSLRSEDTAVYYCARERLSVAGFDYWGQGTLVTVSS |
| 61 | 328 | QVQLVQSGAEVKKPGASVKVSCKASGYTFSTHYMHWVRQAPGQGLEWMGWINPNSGNTGYSQKFQGRVTMTR DTSTSTVYMELSSLRSEDTAVYYCARERLSVAGFDYWGQGTLVTVSS |
| 62 | 328 | QVQLVQSGAEVKKPGASVKVSCKASGYTFSTHYMHWVRQAPGQGLEWMGWINPNSGNTGYSQKFQGRVTMTR DTSTSTVYMELSSLRSEDTAVYYCARERLSVAGFDYWGQGTLVTVSS |
| 63 | 328 | QVQLVQSGAEVKKPGASVKVSCKASGYTFSTHYMHWVRQAPGQGLEWMGWINPNSGNTGYSQKFQGRVTMTR DTSTSTVYMELSSLRSEDTAVYYCARERLSVAGFDYWGQGTLVTVSS |
| 64 | 328 | QVQLVQSGAEVKKPGASVKVSCKASGYTFSTHYMHWVRQAPGQGLEWMGWINPNSGNTGYSQKFQGRVTMTR DTSTSTVYMELSSLRSEDTAVYYCARERLSVAGFDYWGQGTLVTVSS |
| 65 | 328 | QVQLVQSGAEVKKPGASVKVSCKASGYTFSTHYMHWVRQAPGQGLEWMGWINPNSGNTGYSQKFQGRVTMTR DTSTSTVYMELSSLRSEDTAVYYCARERLSVAGFDYWGQGTLVTVSS |
| 66 | 361 | QVQLVQSGAEVKKPGASVKVSCKASGYTFSSYYMHWVRQAPGQGLEWMGWITTNSGITGYAQKFQGRVTMTR DTSTSTVYMELSSLRSEDTAVYYCAREGYSSGLDYWGQGTLVTVSS |
| 67 | 362 | QVQLVQSGAEVKKPGASVKVSCKASGYTFSTHYMHWVRQAPGQGLEWMGWINPNSGHAGSAQKFQGRVTMTR DTSTSTVYMELSSLRSEDTAVYYCARESIAVAGYDYWGQGTLVTVSS |
| 68 | 363 | QVQLVQSGAEVKKPGASVKVSCKASGYTFTGYYMHWVRQAPGQGLEWMGWINPNSGTTGYAQNFQGRVTMTR DTSTSTVYMELSSLRSEDTAVYYCAREGFGPNAFDIWGQGTTVTVSS |
| 69 | 364 | QVQLVQSGAEVKKPGASVKVSCKASGYTFTSYYMHWVRQAPGQGLEWMGWINPNSGNTGYAQKFQGRVTMTR DTSTSTVYMELSSLRSEDTAVYYCARDDWGGDWFDYWGQGTLVTVSS |
| 70 | 365 | QVQLVQSGAEVKKPGASVKVSCKASGYTFTDHYLHWVRQAPGQGLEWMGWINPNIGNTGYAQKFQGRVTMTR DTSTSTVYMELSSLRSEDTAVYYCAREPLQLGGFDYWGQGTLVTVSS |

| Binding agent | SEQ ID | VL |
|---|---|---|
| 1 | 265 | DIQMTQSPSSLSASVGDRVTITCRASQGIDSYLAWYQQKPGKAPKLLIYAASSLQSGVPSRFSGSGSGTDFTLTISS LQPEDFATYYCQQSYSTPITFGGGTKVEIK |
| 2 | 266 | DIQMTQSPSSLSASVGDRVTITCRASQSISSWLAWYQQKPGKAPKLLIYAASSLQSGVPSRFSGSGSGTDFTLTISS LQPEDFATYYCQQSYTTPITFGGGTKVEIK |
| 3 | 267 | DIQMTQSPSSLSASVGDRVTITCRASQSISSYLNWYQQKPGKAPKLLIYAASSLQSGVPSRFSGSGSGTDFTLTISS LQPEDFATYYCQQIFSTPLTFGGGTKVEIK |
| 4 | 268 | DIQMTQSPSSLSASVGDRVTITCRASQGISSYLAWYQQKPGKAPKLLIYGASNLQSGVPSRFSGSGSGTDFTLTISS LQPEDFATYYCQQSYSTPLTFGGGTKVEIK |
| 5 | 269 | DIQMTQSPSSLSASVGDRVTITCRASQTISNYLNWYQQKPGKAPKLLIYAASSLQSGVPSRFSGSGSGTDFTLTISS LQPEDFATYYCQQSYTTPITFGGGTKVEIK |
| 6 | 270 | EIVMTQSPATLSVSPGERATLSCRASQSVDRNYVTWYQQKPGQAPRLLIYGASTRATGIPARFSGSGSGTEFTLTIS SLQSEDFAVYYCQQSYTTPYTFGQGTKVEIK |
| 7 | 271 | DIQMTQSPSSLSASVGDRVTITCRASQGISQYLAWYQQKPGKAPKLLIYGASNLHSGVPSRFSGSGSGTDFTLTISS LQPEDFATYYCQQTFTTPLTFGGGTKVEIK |
| 8 | 272 | DIQMTQSPSSLSASVGDRVTITCQASQDIGNYLNWYQQKPGKAPKLLIYAASSLESGVPSRFSGSGSGTDFTLTISS LQPEDFATYYCQQSYSTPLTFGGGTKVEIK |
| 9 | 273 | DIQMTQSPSSLSASVGDRVTITCRASQGIRNDLGWYQQKPGKAPKLLIYSASNLQSGVPSRFSGSGSGTDFTLTISS LQPEDFATYYCQQANSFPFTFGGGTKVEIK |
| 10 | 274 | DIQMTQSPSSLSASVGDRVTITCRASQSISSWLAWYQQKPGKAPKLLIYAASTLESGVPSRFSGSGSGTDFTLTISS LQPEDFATYYCQQSYTTPYSFGGGTKVEIK |

-continued

| Binding agent | SEQ ID | VL |
|---|---|---|
| 11 | 275 | DIQMTQSPSSLSASVGDRVTITCRASQGISQYLAWYQQKPGKAPKLLIYGASNLHSGVPSRFSGSGSGTDFTLTISS LQPEDFATYYCQQTFITPLTFGGGTKVEIK |
| 12 | 276 | DIQMTQSPSSLSASVGDRVTITCRASQIIGNYLAWYQQKPGKAPKLLIYHASILETGVPSRFSGSGSGTDFTLTISS LQPEDFATYYCQQSYSTPTFGGGTKVEIK |
| 13 | 277 | DIQMTQSPSSLSASVGDRVTITCRASQIISSYLNWYQQKPGKAPKLLIYAASSLQSGVPSRFSGSGSGTDFTLTISS LQPEDFATYYCQQGFSTPFTFGGGTKVEIK |
| 14 | 278 | DIQMTQSPSSLSASVGDRVTITCQASQDISNYLNWYQQKPGKAPKLLIYAASSLQSGVPSRFSGSGSGTDFTLTISS LQPEDFATYYCQQSFTNPVTFGGGTKVEIK |
| 15 | 279 | DIQMTQSPSSLSASVGDRVTITCRASQGISNYLAWYQQKPGKAPKLLIYAASTLQSGVPSRFSGSGSGTDFTLTISS LQPEDFATYYCQQSYSAPYTFGGGTKVEIK |
| 16 | 280 | DIQMTQSPSSLSASVGDRVTITCRASQGISNNLNWYQQKPGKAPKLLIYAATTLQSGVPSRFSGSGSGTDFTLTISS LQPEDFATYYCQQSYSTPYTFGGGTKVEIK |
| 17 | 281 | DIQMTQSPSSLSASVGDRVTITCRASQSISSYLNWYQQKPGKAPKLLIYAASSLQSGVPSRFSGSGSGTDFTLTISS LQPEDFATYYCQQSYSTPLTFGGGTKVEIK |
| 18 | 282 | DIQMTQSPSSLSASVGDRVTITCRASQGISNGLSWYQQKPGKAPKLLIYAASTLQSGVPSRFSGSGSGTDFTLTISS LQPEDFATYYCQQSHSTPLTFGGGTKVEIK |
| 19 | 283 | DIQMTQSPSSLSASVGDRVTITCRASQSITGWLAWYQQKPGKAPKLLIYAASSLQSGVPSRFSGSGSGTDFTLTISS LQPEDFATYYCQQSYSTPYTFGQGTKVEIK |
| 20 | 284 | DIQMTQSPSSLSASVGDRVTITCRASQSISSWLAWYQQKPGKAPKLLIYDATHLETGVPSRFSGSGSGTDFTLTISS LQPEDFATYYCQQSYSTPITFGQGTRLEIK |
| 21 | 285 | DIQMTQSPSSLSASVGDRVTITCRASQGIRNDLAWYQQKPGKAPKLLIYAASTLQSGVPSRFSGSGSGTDFTLTISS LQPEDFATYYCQQSYSTPLTFGGGTKVEIK |
| 22 | 286 | DIQMTQSPSSLSASVGDRVTITCQASQDISSYLNWYQQKPGKAPKLLIYAASSLQTGVPSRFSGSGSGTDFTLTISS LQPEDFATYYCQQSYSTPYTFGQGTKLEIK |
| 23 | 287 | DIQMTQSPSSLSASVGDRVTITCRASQSITTYLNWYQQKPGKAPKLLIYAASSLQGGVPSRFSGSGSGTDFTLTISS LQPEDFATYYCQQSYSTPYTFGQGTKVEIK |
| 24 | 288 | DIQMTQSPSSLSASVGDRVTITCRASQSISSYLNWYQQKPGKAPKLLIYAASSLQSGVPSRFSGSGSGTDFTLTISS LQPEDFATYYCQQSYSTPLTFGGGTKLEIK |
| 25 | 289 | DIQMTQSPSSLSASVGDRVTITCRASQSVSTWLAWYQQKPGKAPKLLIYAASNLESGVPSRFSGSGSGTDFTLTISS LQPEDFATYYCQQSYSTPYTFGQGTKLEIK |
| 26 | 290 | DIQMTQSPSSLSASVGDRVTITCRASQSISNWLAWYQQKPGKAPKLLIYDVSHLESGVPSRFSGSGSGTDFTLTISS LQPEDFATYYCQQSYSTPFTFGPGTKVDIK |
| 27 | 291 | DIQMTQSPSSLSASVGDRVTITCQASQGISNYLAWYQQKPGKAPKLLIYDASSLQSGVPSRFSGSGSGTDFTLTISS LQPEDFATYYCQQSYSTPLTFGGGTKVEIK |
| 28 | 292 | EIVMTQSPATLSVSPGERATLSCRASQSLSSSSLAWYQQKPGQAPRLLIYGASTRATGIPARFSGSGSGTEFTLTIS SLQSEDFAVYYCQQYGSSPFTFGPGTKVDIK |
| 29 | 293 | DIQMTQSPSSLSASVGDRVTITCRASEHIANWLAWYQQKPGKAPKLLIYGVSSLESGVPSRFSGSGSGTDFTLTISS LQPEDFATYYCQQSYSTPYTFGQGTKLEIK |
| 30 | 294 | DIQMTQSPSSLSASVGDRVTITCRASQSVGSWVAWYQQKPGKAPKLLIYPASTLQSGVPSRFSGSGSGTDFTLTISS LQPEDFATYYCQQSYSTPLTFGGGTKVEIK |
| 31 | 295 | DIQMTQSPSSLSASVGDRVTITCRASQSISPWLAWYQQKPGKAPKLLIYDASNLETGVPSRFSGSGSGTDFTLTISS LQPEDFATYYCQQTYSTPITFGQGTRLEIK |
| 32 | 296 | DIQMTQSPSSLSASVGDRVTITCRASQGISRYLAWYQQKPGKAPKLLIYAASTLQSGVPSRFSGSGSGTDFTLTISS LQPEDFATYYCQQSYSTPLTFGQGTKVEIK |
| 33 | 297 | EIVMTQSPATLSVSPGERATLSCRASQTVSSNYLAWYQQKPGQAPRLLIYGASTRASGIPARFSGSGSGTEFTLTIS SLQSEDFAVYYCQQYYTTPLTFGGGTKVEIK |
| 34 | 298 | DIQMTQSPSSLSASVGDRVTITCRASQSISSYLNWYQQKPGKAPKLLIYAASSLQSGVPSRFSGSGSGTDFTLTISS LQPEDFATYYCQQSFSTPLTFGQGTRLEIK |
| 35 | 299 | DIQMTQSPSSLSASVGDRVTITCRASQSISSWLAWYQQKPGKAPKLLIYDASNLETGVPSRFSGSGSGTDFTLTISS LQPEDFATYYCQQSYSTPPTFGQGTKVEIK |

-continued

| Binding agent | SEQ ID | VL |
|---|---|---|
| 36 | 300 | DIQMTQSPSSLSASVGDRVTITCRASQGISNNLNWYQQKPGKAPKLLIYATSTLQSGVPSRFSGSGSGTDFTLTISS LQPEDFATYYCQQSYSTPYTFGQGTKVEIK |
| 37 | 301 | DIQMTQSPSSLSASVGDRVTITCRSSQGIRNDLSWYQQKPGKAPKLLIYLASNSHSGVPSRFSGSGSGTDFTLTISS LQPEDFATYYCLQHNSYPLTFGGGTKVEIK |
| 38 | 302 | DIQMTQSPSSLSASVGDRVTITCRASQSISRWLAWYQQKPGKAPKLLIYAASSLQSGVPSRFSGSGSGTDFTLTISS LQPEDFATYYCQQSYSTPYTFGQGTKLEIK |
| 39 | 303 | DIQMTQSPSSLSASVGDRVTITCRASQSISSWLAWYQQKPGKAPKLLIYDSSSLQTGVPSRFSGSGSGTDFTLTISS LQPEDFATYYCQQSYSTPYTFGQGTKVEIK |
| 40 | 304 | DIQITHSPSSLSASVGYRLTITCRDSHSITTWLAWYHQKPWNAPKLMIYAASNLESGVPSRFSGSGSGTYFTLTISS LQPEDFATYYCQHFYNTQYTFGQGTKVEIK |
| 41 | 305 | DIQMTQSPSSLSASVGDRVTITCRASQVIRNDLAWYQQKPGKAPKLLIYAASTLQSGVPSRFSGSGSGTDFTLTISS LQPEDFATYYCQQSLQYPSHFFGQGTKVEIK |
| 42 | 306 | DIQMTQSPSSLSASVGDRVTITCRASQSISRYLNWYQQKPGKAPKLLIYAASTLQSGVPSRFSGSGSGTDFTLTISS LQPEDFAPYYCQQSYSTPLTFGPGTKVDIK |
| 43 | 281 | DIQMTQSPSSLSASVGDRVTITCRASQSISSYLNWYQQKPGKAPKLLIYAASSLQSGVPSRFSGSGSGTDFTLTISS LQPEDFATYYCQQSYSTPLTFGGGTKVEIK |
| 44 | 281 | DIQMTQSPSSLSASVGDRVTITCRASQSISSYLNWYQQKPGKAPKLLIYAASSLQSGVPSRFSGSGSGTDFTLTISS LQPEDFATYYCQQSYSTPLTFGGGTKVEIK |
| 45 | 281 | DIQMTQSPSSLSASVGDRVTITCRASQSISSYLNWYQQKPGKAPKLLIYAASSLQSGVPSRFSGSGSGTDFTLTISS LQPEDFATYYCQQSYSTPLTFGGGTKVEIK |
| 46 | 281 | DIQMTQSPSSLSASVGDRVTITCRASQSISSYLNWYQQKPGKAPKLLIYAASSLQSGVPSRFSGSGSGTDFTLTISS LQPEDFATYYCQQSYSTPLTFGGGTKVEIK |
| 47 | 281 | DIQMTQSPSSLSASVGDRVTITCRASQSISSYLNWYQQKPGKAPKLLIYAASSLQSGVPSRFSGSGSGTDFTLTISS LQPEDFATYYCQQSYSTPLTFGGGTKVEIK |
| 48 | 281 | DIQMTQSPSSLSASVGDRVTITCRASQSISSYLNWYQQKPGKAPKLLIYAASSLQSGVPSRFSGSGSGTDFTLTISS LQPEDFATYYCQQSYSTPLTFGGGTKVEIK |
| 49 | 281 | DIQMTQSPSSLSASVGDRVTITCRASQSISSYLNWYQQKPGKAPKLLIYAASSLQSGVPSRFSGSGSGTDFTLTISS LQPEDFATYYCQQSYSTPLTFGGGTKVEIK |
| 50 | 281 | DIQMTQSPSSLSASVGDRVTITCRASQSISSYLNWYQQKPGKAPKLLIYAASSLQSGVPSRFSGSGSGTDFTLTISS LQPEDFATYYCQQSYSTPLTFGGGTKVEIK |
| 51 | 281 | DIQMTQSPSSLSASVGDRVTITCRASQSISSYLNWYQQKPGKAPKLLIYAASSLQSGVPSRFSGSGSGTDFTLTISS LQPEDFATYYCQQSYSTPLTFGGGTKVEIK |
| 52 | 281 | DIQMTQSPSSLSASVGDRVTITCRASQSISSYLNWYQQKPGKAPKLLIYAASSLQSGVPSRFSGSGSGTDFTLTISS LQPEDFATYYCQQSYSTPLTFGGGTKVEIK |
| 53 | 281 | DIQMTQSPSSLSASVGDRVTITCRASQSISSYLNWYQQKPGKAPKLLIYAASSLQSGVPSRFSGSGSGTDFTLTISS LQPEDFATYYCQQSYSTPLTFGGGTKVEIK |
| 54 | 281 | DIQMTQSPSSLSASVGDRVTITCRASQSISSYLNWYQQKPGKAPKLLIYAASSLQSGVPSRFSGSGSGTDFTLTISS LQPEDFATYYCQQSYSTPLTFGGGTKVEIK |
| 55 | 335 | DIQMTQSPSSLSASVGDRVTITCRASQGISSYLNWYQQKPGKAPKLLIYAASSLQSGVPSRFSGSGSGTDFTLTISS LQPEDFATYYCQQSYSTPLTFGGGTKVEIK |
| 56 | 336 | DIQMTQSPSSLSASVGDRVTITCRASQSISSWLNWYQQKPGKAPKLLIYAASSLQSGVPSRFSGSGSGTDFTLTISS LQPEDFATYYCQQSYSTPLTFGGGTKVEIK |
| 57 | 337 | DIQMTQSPSSLSASVGDRVTITCRASQSISSYLAWYQQKPGKAPKLLIYAASSLQSGVPSRFSGSGSGTDFTLTISS LQPEDFATYYCQQSYSTPLTFGGGTKVEIK |
| 58 | 338 | DIQMTQSPSSLSASVGDRVTITCRASQGISSWLNWYQQKPGKAPKLLIYAASSLQSGVPSRFSGSGSGTDFTLTISS LQPEDFATYYCQQSYSTPLTFGGGTKVEIK |
| 59 | 339 | DIQMTQSPSSLSASVGDRVTITCRASQGISSYLAWYQQKPGKAPKLLIYAASSLQSGVPSRFSGSGSGTDFTLTISS LQPEDFATYYCQQSYSTPLTFGGGTKVEIK |
| 60 | 340 | DIQMTQSPSSLSASVGDRVTITCRASQSISSWLAWYQQKPGKAPKLLIYAASSLQSGVPSRFSGSGSGTDFTLTISS LQPEDFATYYCQQSYSTPLTFGGGTKVEIK |

-continued

| Binding agent | SEQ ID | VL |
|---|---|---|
| 61 | 341 | DIQMTQSPSSLSASVGDRVTITCRASQGISSWLAWYQQKPGKAPKLLIYAASSLQSGVPSRFSGSGSGTDFTLTISS LQPEDFATYYCQQSYSTPLTFGGGTKVEIK |
| 62 | 342 | DIQMTQSPSSLSASVGDRVTITCRASQSISSYLNWYQQKPGKAPKLLIYAASSLQSGVPSRFSGSGSGTDFTLTISS LQPEDFATYYCQQSYSTPLTFGGGTKVEIK |
| 63 | 343 | DIQMTQSPSSLSASVGDRVTITCRASQSISSYLNWYQQKPGKAPKLLIYAASSLQSGVPSRFSGSGSGTDFTLTISS LQPEDFATYYCQQSYSTPYTFGGGTKVEIK |
| 64 | 344 | DIQMTQSPSSLSASVGDRVTITCRASQSISSYLNWYQQKPGKAPKLLIYAASSLQSGVPSRFSGSGSGTDFTLTISS LQPEDFATYYCQQSYSTPYTFGGGTKVEIK |
| 65 | 281 | DIQMTQSPSSLSASVGDRVTITCRASQSISSYLNWYQQKPGKAPKLLIYAASSLQSGVPSRFSGSGSGTDFTLTISS LQPEDFATYYCQQSYSTPLTFGGGTKVEIK |
| 66 | 366 | DIQMTQSPSSLSASVGDRVTITCRASQSISSWLAWYQQKPGKAPKLLIYAASSLQSGVPSRFSGSGSGTDFTLTISS LQPEDFATYYCQQSYSTPYTFGGGTKVEIK |
| 67 | 367 | DIQMTQSPSSLSASVGDRVTITCRASQSISSWLAWYQQKPGKAPKLLIYAASTLQRGVPSRFSGSGSGTDFTLTISS LQPEDFATYYCQQSYSTPYTFGQGTKLEIK |
| 68 | 368 | DIQMTQSPSSLSASVGDRVTITCRASQSISSWLAWYQQKPGKAPKLLIYAASNLQSGVPSRFSGSGSGTDFTLTISS LQPEDFATYYCQQYYSTPYTFGQGTKVEIK |
| 69 | 369 | DIQMTQSPSSLSASVGDRVTITCQASQDISNHLNWYQQKPGKAPKLLIYGASNLQRGVPSRFSGSGSGTDFTLTISS LQPEDFATYYCQQSYSTPITFGQGTRLEIK |
| 70 | 370 | DIQMTQSPSSLSASVGDRVTITCRASESISSWLAWYQQKPGKAPKLLIYAASSLQSGVPSRFSGSGSGTDFTLTISS LQPEDFATYYCQQSYSTPLTFGQGTKLEIK |

As mentioned above, the binding agent can comprise an Ig heavy and/or light variable region with at least about 90% identity (e.g. at least about 91%, at least about 92%, at least about 93%, at least about 94%, at least about 95%, at least about 96%, at least about 97%, at least about 98%, or at least about 99% identity) to a specific heavy or light chain variable region sequence provided herein. Similarly, the CDRs of the Ig heavy and/or light chain variable region can have at least about 90% identity (e.g. at least about 91%, at least about 92%, at least about 93%, at least about 94%, at least about 95%, at least about 96%, at least about 97%, at least about 98%, or at least about 99% identity) to a specific CDR sequence provided herein. Thus, the Ig heavy and light chain variable region or CDR sequence can comprise at least one (e.g., 1 or more, 2 or more, 3 or more, 4 or more, 5 or more, 6 or more, 7 or more, 8 or more, 9 or more, or 10 or more, etc., as applicable based on the length of the sequence) amino acid modification (e.g., substitution, addition, or deletion) as compared to the specific sequences provided herein, provided the binding agent maintains the ability to specifically bind PD-L1, optionally wherein the binding agent maintains the affinity of a binding agent with the specified sequences and/or competes with a binding agent having the specified sequences for binding to PD-L1.

The amino acids of the sequences provided can be substituted with any other amino acid. Amino acids include naturally-occurring α-amino acids and their stereoisomers, as well as non-naturally occurring amino acids and their stereoisomers. "Stereoisomers" of a given amino acid refer to isomers having the same molecular formula and intramolecular bonds but different three-dimensional arrangements of bonds and atoms (e.g., an L-amino acid and the corresponding D-amino acid). The amino acids can be glycosylated (e.g., N-linked glycans, O-linked glycans, phosphoglycans, C-linked glycans, or glypiation) or deglycosylated. Naturally-occurring amino acids are those encoded by the genetic code, as well as those amino acids that are later modified, e.g., hydroxyproline, γ-carboxyglutamate, and O-phosphoserine. Naturally-occurring α-amino acids include, without limitation, alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), tyrosine (Tyr), and combinations thereof. Stereoisomers of naturally-occurring α-amino acids include, without limitation, D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof.

Non-naturally occurring amino acids include, without limitation, amino acid analogs, amino acid mimetics, synthetic amino acids, N-substituted glycines, and N-methyl amino acids in either the L- or D-configuration that function in a manner similar to the naturally-occurring amino acids. For example, "amino acid analogs" can be unnatural amino acids that have the same basic chemical structure as naturally-occurring amino acids (i.e., a carbon that is bonded to a hydrogen, a carboxyl group, an amino group) but have modified side-chain groups or modified peptide backbones, e.g., homoserine, norleucine, methionine sulfoxide, and methionine methyl sulfonium. "Amino acid mimetics" refer to chemical compounds that have a structure that is different from the general chemical structure of an amino acid, but that functions in a manner similar to a naturally-occurring amino acid.

Amino acids may be referred to herein by either the commonly known three letter symbols or by the one-letter symbols recommended by the IUPAC-IUB Biochemical Nomenclature Commission.

The amino acid substitution can be conservative, semi-conservative, or non-conservative with respect to the basic properties of the original amino acid residue. A "conservative" substitution refers to the replacement of one amino acid by another amino acid with a common property. A functional way to define common properties between individual amino acids is to analyze the normalized frequencies of amino acid changes between corresponding proteins of homologous organisms (Schulz and Schirmer, *Principles of Protein Structure*, Springer-Verlag, New York (1979)). According to such analyses, groups of amino acids may be defined where amino acids within a group exchange preferentially with each other, and therefore resemble each other most in their impact on the overall protein structure (Schulz and Schirmer, supra).

Amino acids are broadly grouped as "aromatic" or "aliphatic." An aromatic amino acid includes an aromatic ring. Examples of "aromatic" amino acids include histidine (H or His), phenylalanine (F or Phe), tyrosine (Y or Tyr), and tryptophan (W or Trp). Non-aromatic amino acids are broadly grouped as "aliphatic." Examples of "aliphatic" amino acids include glycine (G or Gly), alanine (A or Ala), valine (V or Val), leucine (L or Leu), isoleucine (I or Ile), methionine (M or Met), serine (S or Ser), threonine (T or Thr), cysteine (C or Cys), proline (P or Pro), glutamic acid (E or Glu), aspartic acid (D or Asp), asparagine (N or Asn), glutamine (Q or Gln), lysine (K or Lys), and arginine (R or Arg).

Aliphatic amino acids may be sub-divided into four sub-groups. The "large aliphatic non-polar sub-group" consists of valine, leucine, and isoleucine. The "aliphatic slightly-polar sub-group" consists of methionine, serine, threonine, and cysteine. The "aliphatic polar/charged sub-group" consists of glutamic acid, aspartic acid, asparagine, glutamine, lysine, and arginine. The "small-residue sub-group" consists of glycine and alanine. The group of charged/polar amino acids may be sub-divided into three sub-groups: the "positively-charged sub-group" consisting of lysine and arginine, the "negatively-charged sub-group" consisting of glutamic acid and aspartic acid, and the "polar sub-group" consisting of asparagine and glutamine.

Aromatic amino acids may be sub-divided into two sub-groups: the "nitrogen ring sub-group" consisting of histidine and tryptophan and the "phenyl sub-group" consisting of phenylalanine and tyrosine.

Examples of conservative amino acid substitutions include substitutions of amino acids within the sub-groups described above, for example, lysine for arginine and vice versa such that a positive charge may be maintained, glutamic acid for aspartic acid and vice versa such that a negative charge may be maintained, serine for threonine such that a free —OH can be maintained, and glutamine for asparagine such that a free —NH₂ can be maintained.

"Semi-conservative mutations" include amino acid substitutions of amino acids within the same groups listed above, but not within the same sub-group. For example, the substitution of aspartic acid for asparagine, or asparagine for lysine, involves amino acids within the same group, but different sub-groups. "Non-conservative mutations" involve amino acid substitutions between different groups, for example, lysine for tryptophan, or phenylalanine for serine, etc.

In addition, one or more amino acids can be inserted into the aforementioned immunoglobulin heavy or light chain variable region polypeptides. Any number of any suitable amino acids can be inserted into the amino acid sequence of the immunoglobulin heavy or light chain variable region polypeptide. In this respect, at least one amino acid (e.g., 2 or more, 5 or more, or 10 or more amino acids), but not more than 20 amino acids (e.g., 18 or less, 15 or less, or 12 or less amino acids), can be inserted into the amino acid sequence of the immunoglobulin heavy or light chain variable region polypeptide. Preferably, 1-10 amino acids (e.g., 1, 2, 3, 4, 5, 6, 7, 8, 9, or 10 amino acids) are inserted into the amino acid sequence of the immunoglobulin heavy or light chain variable region polypeptide. In this respect, the amino acid(s) can be inserted into any one of the aforementioned immunoglobulin heavy or light chain variable region polypeptides in any suitable location. In some embodiments, the amino acid(s) are inserted into a CDR (e.g., CDR1, CDR2, or CDR3) of the immunoglobulin heavy or light chain variable region polypeptide; in other embodiments, the amino acids are inserted into a framework region.

Further provided is a PD-L1 binding agent (e.g., antibody or antibody fragment) that competes with a PD-L1 binding agent (e.g., antibody or antibody fragment) having an immunoglobulin heavy and light chain variable region specifically provided herein (e.g., one of binding agents 1-42 provided herein).

The "biological activity" of an PD-L1-binding agent refers to, for example, binding affinity for PD-L1 or a particular PD-L1 epitope, neutralization or inhibition of PD-L1 protein binding to PD-1, neutralization or inhibition of PD-L1 protein activity in vivo (e.g., $IC_{50}$), internalization of PD-L1, pharmacokinetics, and cross-reactivity (e.g., with non-human homologs or orthologs of the PD-L1 protein, or with other proteins or tissues). Other biological properties or characteristics of an antigen-binding agent recognized in the art include, for example, avidity, selectivity, solubility, folding, immunotoxicity, expression, and formulation. The aforementioned properties or characteristics can be observed, measured, and/or assessed using standard techniques including, but not limited to, ELISA, competitive ELISA, surface plasmon resonance analysis (BIACORE™), or KINEXA™, in vitro or in vivo neutralization assays, receptor-ligand binding assays, cytokine or growth factor production and/or secretion assays, and signal transduction and immunohistochemistry assays.

The terms "inhibit" or "neutralize," as used herein with respect to the activity of a PD-L1-binding agent, refer to the ability to substantially antagonize, prohibit, prevent, restrain, slow, disrupt, alter, eliminate, stop, or reverse the progression or severity of, for example, the biological activity of a PD-L1 protein, or a disease or condition associated with an PD-L1 protein. The isolated PD-L1-binding agent of the invention inhibits or neutralizes the activity of a PD-L1 protein by at least about 5%, about 10%, about 15%, about 20%, about 30%, about 40%, about 50%, about 60%, about 70%, about 80%, about 90%, about 95%, about 100%, or a range defined by any two of the foregoing values. In other embodiments, the PD-L1 binding agent does not substantially inhibit the activity of a PD-L1 protein.

In some embodiments, the PD-L1 binding agent (e.g., antibody or antibody fragment) exhibits antibody dependent cell-mediated cytotoxicity (ADCC). ADCC is a mechanism of cell-mediated immune defense whereby an effector cell of the immune system lyses a target cell whose membrane-surface antigens have been bound by specific antibodies. ADCC is independent of the immune complement system that also lyses targets but does not require any other cell and is part of the adaptive immune response.

In some embodiments, the PD-L1 binding agent (e.g., antibody or antibody fragment) promotes antibody dependent cell-mediated phagocytosis (ADCP). ADCP is a cellular process by which effector cells with phagocytic potential, such as monocytes and macrophages, can internalize target cells. Once phagocytosed, the target cell resides in a phagosome, which fuses with a lysosome to begin degradation of the target cell via an oxygen-dependent or independent mechanism. This function is dependent on opsonization, or identification of the target cell with a binding agent, which then also serves as a bridge between the target cell and the phagocytic cell. Mechanistically, the binding agent binds its cognate antigen on the target cell through its antigen recognition domain, and then recruits the phagocytic cell to the target with its Fc region. Once bound to the Fc receptor of the phagocytic cell, the target cell is ingested and degraded. This process also leads to the production of soluble factors by the effector cells that help initiate and drive the immune response.

In some embodiments, the PD-L1 binding agent (e.g., antibody or antibody fragment) exhibits complement dependent cytotoxicity (CDC). CDC is an effector function of IgG and IgM antibodies. When the binding agents are bound to surface antigen, the classical complement pathway is triggered, resulting in formation of a membrane attack complex (MAC) and target cell lysis.

In some embodiments, the binding agents comprising an Fc region contain one or more modifications (e.g., amino acid insertion, deletion, and/or substitution) in the Fc region that results in modulated binding (e.g., increased binding or decreased binding) to one or more Fc receptors (e.g., FcγRI (CD64), FcγRIIA (CD32A), FcγRIIB (CD32B), FcγRIIIA (CD16a), and/or FcγRIIIB (CD16b)) as compared to the a binding agent or antibody with the native Fc region lacking the mutation. In some embodiments, the binding agents contain one or more modifications (e.g., amino acid insertion, deletion, and/or substitution) in the Fc region that reduce the binding of the Fc region to FcγRIIB In some embodiments, the binding agents contain one or more modifications (e.g., amino acid insertion, deletion, and/or substitution) in the Fc region of the antibody that reduce the binding to FcγRIM while maintaining the same binding or having increased binding to FcγRI (CD64), FcγRIIA (CD32A), and/or FcRγIIIA (CD16a) as compared to a binding agent or antibody with a native Fc region lacking the mutation. In some embodiments, the binding agents contain one or more modifications in the Fc region that increase the binding of the Fc region to FcγRIIB In some embodiments, the modifications substantially reduce or eliminate antibody effector functions.

The Fc region mutations can be in a CH2 domain, a CH3 domain, or a combination thereof. A "native Fc region" is synonymous with a "wild-type Fc region" and comprises an amino acid sequence that is identical to the amino acid sequence of an Fc region found in nature or identical to the amino acid sequence of the Fc region found in a native antibody. Native sequence human Fc regions include a native sequence human IgG1 Fc region, native sequence human IgG2 Fc region, native sequence human IgG3 Fc region, and native sequence human IgG4 Fc region, as well as naturally occurring variants thereof. Native sequence Fc includes the various allotypes of Fcs (see, e.g., Jefferis et al., mAbs, 1(4): 332-338 (2009)).

In some embodiments, the mutations in the Fc region that result in modulated binding to one or more Fc receptors can include one or more of the following mutations: SD (S239D), SDIE (S239D/I332E), SE (S267E), SELF (S267E/L328F), SDIE (S239D/I332E), SDIEAL (S239D/I332E/A330L), GA (G236A), ALIE (A330L/I332E), GASDALIE (G236A/S239D/A330L/I332E), V9 (G237D/P238D/

P271G/A330R), and V11 (G237D/P238D/H268D/P271G/A330R), and/or one or more mutations at the following amino acids: E345R, E233, G237, P238, H268, P271, L328 and A330. Additional Fc region modifications for modulating Fc receptor binding are described in, for example, U.S. Patent Application Publication 2016/0145350 and U.S. Pat. Nos. 7,416,726 and 5,624,821, which are hereby incorporated by reference in their entireties herein.

In some embodiments, the Fc region of the binding agents are modified to have an altered glycosylation pattern of the Fc region compared to the native non-modified Fc region.

Human immunoglobulin is glycosylated at the Asn297 residue in the Cy2 domain of each heavy chain. This N-linked oligosaccharide is composed of a core heptasaccharide, N-acetylglucosamine4Mannose3 (GlcNAc4Man3). Removal of the heptasaccharide with endoglycosidase or PNGase F is known to lead to conformational changes in the Fc region, which can significantly reduce binding affinity to activating FcγR and lead to decreased effector function. The core heptasaccharide is often decorated with galactose, bisecting GlcNAc, fucose, or sialic acid, which differentially impacts Fc binding to activating and inhibitory FcγR. Additionally, it has been demonstrated that α2,6-sialyation enhances anti-inflammatory activity in vivo, while defucosylation leads to improved FcγRIIIa binding and a 10-fold increase in antibody-dependent cellular cytotoxicity and antibody-dependent phagocytosis. Specific glycosylation patterns, therefore, can be used to control inflammatory effector functions.

In some embodiments, the modification to alter the glycosylation pattern is a mutation. For example, a substitution at Asn297. In some embodiments, Asn297 is mutated to glutamine (N297Q). Methods for controlling immune response with antibodies that modulate FcγR-regulated signaling are described, for example, in U.S. Pat. No. 7,416,726 and U.S. Patent Application Publications 2007/0014795 and 2008/0286819, which are hereby incorporated by reference in their entireties.

In some embodiments, the binding agents are modified to contain an engineered Fab region with a non-naturally occurring glycosylation pattern. For example, hybridomas can be genetically engineered to secrete afucosylated mAb, desialylated mAb or deglycosylated Fc with specific mutations that enable increased FcRγIIIa binding and effector function. In some embodiments, the binding agents are engineered to be afucosylated.

In some embodiments, the entire Fc region is exchanged with a different Fc region, so that the Fab region is conjugated to a non-native Fc region. For example, the Fab region of atezolizumab, which normally comprises an IgG1 Fc region, can be conjugated to IgG2, IgG3, IgG4, or IgA, or the Fab region of nivolumab, which normally comprises an IgG4 Fc region, can be conjugated to IgG1, IgG2, IgG3, IgA1, or IgG2. In some embodiments, the Fc modified binding agent with a non-native Fc domain also comprises one or more additional amino acid modification, such as the S228P mutation within the IgG4 Fc, that modulate the stability of the Fc domain described. In some embodiments, the Fc modified binding agent with a non-native Fc domain also comprises one or more amino acid modifications described herein that modulate Fc binding to FcR.

In some embodiments, the modifications that modulate the binding of the Fc region to FcR do not alter the binding of the Fab region to its antigen when compared to the non-modified Fab. In other embodiments, the modifications that modulate the binding of the Fc region to FcR also increase the binding of the Fab region to its antigen when compared to the non-modified Fab.

In some embodiments, the Fc region is modified by attachment or inclusion of a transforming growth factor beta 1 (TGFβ1) receptor, or a fragment thereof, that is capable of binding TGFβ1. For example, the receptor can be TGFβ receptor II (TGFβRII) (see U.S. Pat. No. 9,676,863, incorporated herein in its entirety). In some embodiments, the TGFβ receptor is a human TGFβ receptor. In some embodiments, the Fc region (e.g., IgG) has a C-terminal fusion to a TGFβ receptor (e.g., TGFβRII) extracellular domain (ECD; e.g., amino acids 24-159 of SEQ ID NO: 9 of U.S. Pat. No. 9,676,863). An "Fc linker" may be used to attach the IgG to the TGFβR extracellular domain, for example, a G$_4$S$_4$G Fc linker. The Fc linker may be a short, flexible peptide that allows for the proper three-dimensional folding of the molecule while maintaining the binding-specificity to the targets. In some embodiments, the N-terminus of the TGFβ receptor is fused to the Fc region (with or without an Fc linker). In some embodiments, the C-terminus of the immunoglobulin heavy chain is fused to the TGFβ receptor (with or without an Fc linker). In some embodiments, the C-terminal lysine residue of the antibody heavy chain is mutated to alanine. In some embodiments, the antibody includes SEQ ID NO: 308.

The PD-L1 binding agent can have any suitable affinity to a PD-L1 protein or an epitope thereof. The term "affinity" refers to the equilibrium constant for the reversible binding of two agents and is expressed as the dissociation constant ($K_D$). Affinity of a binding agent to a ligand, such as affinity of an antibody for an epitope, can be, for example, from about 1 picomolar (pM) to about 100 micromolar (μM) (e.g., from about 1 picomolar (pM) to about 1 nanomolar (nM), from about 1 nM to about 1 micromolar (μM), or from about 1 μM to about 100 μM). In one embodiment, the PD-L1-binding agent can bind to an PD-L1 protein with a $K_D$ less than or equal to 1 nanomolar (e.g., 0.9 nM, 0.8 nM, 0.7 nM, 0.6 nM, 0.5 nM, 0.4 nM, 0.3 nM, 0.2 nM, 0.1 nM, 0.05 nM, 0.025 nM, 0.01 nM, 0.001 nM, or a range defined by any two of the foregoing values). In another embodiment, the PD-L1-binding agent can bind to PD-L1 with a $K_D$ less than or equal to 200 pM (e.g., 190 pM, 175 pM, 150 pM, 125 pM, 110 pM, 100 pM, 90 pM, 80 pM, 75 pM, 60 pM, 50 pM, 40 pM, 30 pM, 25 pM, 20 pM, 15 pM, 10 pM, 5 pM, 1 pM, or a range defined by any two of the foregoing values). Immunoglobulin affinity for an antigen or epitope of interest can be measured using any art-recognized assay. Such methods include, for example, fluorescence activated cell sorting (FACS), separable beads (e.g., magnetic beads), surface plasmon resonance (SPR), solution phase competition (KINEXA™), antigen panning, and/or ELISA (see, Janeway et al. (eds.), *Immunobiology, 9th Ed.*, Garland Publishing, New York, NY (2017)).

Nucleic Acids

The invention also provides nucleic acids that encode the immunoglobulin heavy chain polypeptide and/or the immunoglobulin light chain polypeptide of the PD-L1-binding agent.

The term "nucleic acid sequence" is intended to encompass a polymer of DNA or RNA, i.e., a polynucleotide, which can be single-stranded or double-stranded and which can contain non-natural or altered nucleotides. The terms "nucleic acid" and "polynucleotide" as used herein refer to a polymeric form of nucleotides of any length, either ribonucleotides (RNA) or deoxyribonucleotides (DNA). These terms refer to the primary structure of the molecule, and thus include double- and single-stranded DNA, and double- and single-stranded RNA. The terms include, as equivalents, analogs of either RNA or DNA made from nucleotide analogs and modified polynucleotides such as, though not limited to, methylated and/or capped polynucleotides. Nucleic acids are typically linked via phosphate bonds to form nucleic acid sequences or polynucleotides, though many other linkages are known in the art (e.g., phosphorothioates, boranophosphates, and the like).

The nucleic acid can be part of a vector. Thus, also provided is a vector comprising one or more nucleic acid sequences encoding the immunoglobulin heavy chain polypeptide, the immunoglobulin light chain polypeptide, or both, of the PD-L1 binding agent. Any type of vector can be used, particularly an expression vector useful for expressing the polypeptides in a cell. The vector can be, for example, a plasmid, episome, cosmid, viral vector (e.g., retroviral or adenoviral), or phage. Suitable vectors and methods of vector preparation are well known in the art (see, e.g., Sambrook et al., *Molecular Cloning, a Laboratory Manual, 3rd edition*, Cold Spring Harbor Press, Cold Spring Harbor, N.Y. (2001), and Ausubel et al., *Current Protocols in Molecular Biology*, Greene Publishing Associates and John Wiley & Sons, New York, N.Y. (1994)).

The vector preferably comprises expression control sequences, such as promoters, enhancers, polyadenylation signals, transcription terminators, internal ribosome entry sites (IRES), and the like, that provide for the expression of the coding sequence in a host cell. Exemplary expression control sequences are known in the art and described in, for example, Goeddel, *Gene Expression Technology: Methods in Enzymology*, Vol. 185, Academic Press, San Diego, Calif. (1990).

A large number of promoters, including constitutive, inducible, and repressible promoters, from a variety of different sources are well known in the art. Representative sources of promoters include for example, virus, mammal, insect, plant, yeast, and bacteria, and suitable promoters from these sources are readily available, or can be made synthetically, based on sequences publicly available, for example, from depositories such as the American Type Culture Collection (ATCC) as well as other commercial or individual sources. Promoters can be unidirectional (i.e., initiate transcription in one direction) or bi-directional (i.e., initiate transcription in either a 3' or 5' direction). Non-limiting examples of promoters include, for example, the T7 bacterial expression system, pBAD (araA) bacterial expression system, the cytomegalovirus (CMV) promoter, the SV40 promoter, the RSV promoter. Inducible promoters include, for example, the Tet system (U.S. Pat. Nos. 5,464, 758 and 5,814,618), the Ecdysone inducible system (No et al., *Proc. Natl. Acad. Sci.,* 93: 3346-3351 (1996)), the T-REX™ system (Invitrogen, Carlsbad, CA), LACSWITCH™ system (Stratagene, San Diego, CA), and the Cre-ERT tamoxifen inducible recombinase system (Indra et al., *Nuc. Acid. Res.,* 27: 4324-4327 (1999); *Nuc. Acid. Res.,* 28: e99 (2000); U.S. Pat. No. 7,112,715; and Kramer & Fussenegger, *Methods Mol. Biol.,* 308: 123-144 (2005)).

The term "enhancer" as used herein, refers to a DNA sequence that increases transcription of, for example, a nucleic acid sequence to which it is operably linked. Enhancers can be located many kilobases away from the coding region of the nucleic acid sequence and can mediate the binding of regulatory factors, patterns of DNA methylation, or changes in DNA structure. A large number of enhancers from a variety of different sources are well known in the art and are available as or within cloned polynucleotides (from, e.g., depositories such as the ATCC as well as other commercial or individual sources). A number of poly-nucleotides comprising promoters (such as the commonly-used CMV promoter) also comprise enhancer sequences. Enhancers can be located upstream, within, or downstream of coding sequences.

The vector also can comprise a "selectable marker gene." The term "selectable marker gene," as used herein, refers to a nucleic acid sequence that allow cells expressing the nucleic acid sequence to be specifically selected for or against, in the presence of a corresponding selective agent. Suitable selectable marker genes are known in the art and described in, e.g., International Patent Application Publications WO 1992/008796 and WO 1994/028143; Wigler et al., *Proc. Natl. Acad. Sci. USA,* 77: 3567-3570 (1980); O'Hare et al., *Proc. Natl. Acad. Sci. USA,* 78: 1527-1531 (1981); Mulligan & Berg, *Proc. Natl. Acad. Sci. USA,* 78: 2072-2076 (1981); Colberre-Garapin et al., *J. Mol. Biol.,* 150: 1-14 (1981); Santerre et al., *Gene,* 30: 147-156 (1984); Kent et al., *Science,* 237: 901-903 (1987); Wigler et al., *Cell,* 11: 223-232 (1977); Szybalska & Szybalski, *Proc. Natl. Acad. Sci. USA,* 48: 2026-2034 (1962); Lowy et al., *Cell,* 22: 817-823 (1980); and U.S. Pat. Nos. 5,122,464 and 5,770,359.

In some embodiments, the vector is an "episomal expression vector" or "episome," which is able to replicate in a host cell, and persists as an extrachromosomal segment of DNA within the host cell in the presence of appropriate selective pressure (see, e.g., Conese et al., *Gene Therapy,* 11: 1735-1742 (2004)). Representative commercially available episomal expression vectors include, but are not limited to, episomal plasmids that utilize Epstein Barr Nuclear Antigen 1 (EBNA1) and the Epstein Barr Virus (EBV) origin of replication (oriP). The vectors pREP4, pCEP4, pREP7, and pcDNA3.1 from Invitrogen (Carlsbad, CA) and pBK-CMV from Stratagene (La Jolla, CA) represent non-limiting examples of an episomal vector that uses T-antigen and the SV40 origin of replication in lieu of EBNA1 and oriP.

Other suitable vectors include integrating expression vectors, which may randomly integrate into the host cell's DNA, or may include a recombination site to enable the specific recombination between the expression vector and the host cell's chromosome. Such integrating expression vectors may utilize the endogenous expression control sequences of the host cell's chromosomes to effect expression of the desired protein. Examples of vectors that integrate in a site specific manner include, for example, components of the flp-in system from Invitrogen (Carlsbad, CA) (e.g., pcDNA™5/FRT), or the cre-lox system, such as can be found in the pExchange-6 Core Vectors from Stratagene (La Jolla, CA). Examples of vectors that randomly integrate into host cell chromosomes include, for example, pcDNA3.1 (when introduced in the absence of T-antigen) from Invitrogen (Carlsbad, CA), UCOE from Millipore (Billerica, MA), and pCI or pFN10A (ACT) FLEXI™ from Promega (Madison, WI).

Viral vectors also can be used. Representative commercially available viral expression vectors include, but are not limited to, the adenovirus-based Per.C6 system available from Crucell, Inc. (Leiden, The Netherlands), the lentiviral-based pLP1 from Invitrogen (Carlsbad, CA), and the retro-viral vectors pFB-ERV plus pCFB-EGSH from Stratagene (La Jolla, CA).

Cells

Nucleic acid sequences encoding the heavy and light chain immunoglobulin sequences can be provided to a cell on the same vector (i.e., in cis). A unidirectional promoter can be used to control expression of each nucleic acid sequence. In another embodiment, a combination of bidi-rectional and unidirectional promoters can be used to control expression of multiple nucleic acid sequences. Nucleic acid sequences encoding the inventive amino acid sequences alternatively can be provided to the population of cells on separate vectors (i.e., in trans). Each of the nucleic acid sequences in each of the separate vectors can comprise the same or different expression control sequences. The separate vectors can be provided to cells simultaneously or sequen-tially.

The vector(s) comprising the nucleic acid(s) encoding the inventive amino acid sequences can be introduced into a host cell that is capable of expressing the polypeptides encoded thereby, including any suitable prokaryotic or eukaryotic cell. As such, the invention provides an in vitro (isolated) cell or cell line comprising the inventive vector, which expresses the immunoglobulin heavy and light chain polypeptides. Preferred host cells are those that can be easily and reliably grown, have reasonably fast growth rates, have well characterized expression systems, and can be trans-formed or transfected easily and efficiently.

Examples of suitable prokaryotic cells include, but are not limited to, cells from the genera *Bacillus* (such as *Bacillus subtilis* and *Bacillus brevis*), *Escherichia* (such as *E. coli*), *Pseudomonas, Streptomyces, Salmonella,* and *Erwinia.* Par-ticularly useful prokaryotic cells include the various strains of *Escherichia coli* (e.g., K12, HB101 (ATCC No. 33694), DH5α, DH10, MC1061 (ATCC No. 53338), and CC102).

Preferably, the vector is introduced into a eukaryotic cell. Suitable eukaryotic cells are known in the art and include, for example, yeast cells, insect cells, and mammalian cells. Examples of suitable yeast cells include those from the genera *Kluyveromyces, Pichia, Rhino-sporidium, Saccharo-myces,* and *Schizosaccharomyces.* Preferred yeast cells include, for example, *Saccharomyces cerivisae* and *Pichia pastoris.*

Suitable insect cells are described in, for example, Kitts et al., *Biotechniques,* 14: 810-817 (1993); Lucklow, *Curr. Opin. Biotechnol.,* 4: 564-572 (1993); and Lucklow et al., *J. Virol.,* 67: 4566-4579 (1993). Preferred insect cells include Sf-9 and HI5 (Invitrogen, Carlsbad, CA).

Preferably, mammalian cells are utilized in the invention. A number of suitable mammalian host cells are known in the art, and many are available from ATCC. Examples of suitable mammalian cells include, but are not limited to, Chinese hamster ovary cells (CHO) cells, such as CHO-K1 cells (ATCC No. CCL61), CHO DHFR-cells (Urlaub et al., *Proc. Natl. Acad. Sci. USA,* 97: 4216-4220 (1980)), human embryonic kidney (HEK) 293 or 293T cells (ATCC No. CRL1573), JIMT-1, and 3T3 cells (ATCC No. CCL92). Other suitable mammalian cell lines are the monkey COS-1 (ATCC No. CRL1650) and COS-7 cell lines (ATCC No. CRL1651), as well as the CV-1 cell line (ATCC No. CCL70). Further exemplary mammalian host cells include primate cell lines and rodent cell lines, including trans-formed cell lines. Normal diploid cells, cell strains derived from in vitro culture of primary tissue, as well as primary explants, are also suitable. Other suitable mammalian cell lines include, but are not limited to, mouse neuroblastoma N2A cells, HeLa, mouse L-929 cells, and BHK or HaK hamster cell lines, all of which are available from the ATCC. Methods for selecting suitable mammalian host cells and methods for transformation, culture, amplification, screen-ing, and purification of cells are known in the art.

The mammalian cell can be a human cell. For example, the mammalian cell can be a human lymphoid or lymphoid derived cell line, such as a cell line of pre-B lymphocyte origin. Examples of human lymphoid cells lines include, without limitation, RAMOS (CRL-1596), Daudi (CCL-213), EB-3 (CCL-85), DT40 (CRL-2111), 18-81 (Jack et al., *Proc. Natl. Acad. Sci. USA,* 85: 1581-1585 (1988)), Raji cells (CCL-86), and derivatives thereof.

A nucleic acid sequence encoding the inventive amino acid sequence may be introduced into a cell by "transfection," "transformation," or "transduction." "Transfection," "transformation," or "transduction," as used herein, refer to the introduction of one or more exogenous polynucleotides into a host cell by using physical or chemical methods. Many transfection techniques are known in the art and include, for example, calcium phosphate DNA co-precipitation (see, e.g., Murray E. J. (ed.), *Methods in Molecular Biology, Vol. 7, Gene Transfer and Expression Protocols,* Humana Press (1991)); DEAE-dextran; electroporation; cationic liposome-mediated transfection; tungsten particle-facilitated microparticle bombardment (Johnston, *Nature,* 346: 776-777 (1990)); and strontium phosphate DNA co-precipitation (Brash et al., *Mol. Cell Biol.,* 7: 2031-2034 (1987)). Phage or viral vectors can be introduced into host cells, after growth of infectious particles in suitable packaging cells, many of which are commercially available.

Compositions

The invention provides a composition comprising the PD-L1-binding agent or nucleic acid(s) encoding same optionally in a vector. Preferably, the composition is a pharmaceutically acceptable (e.g., physiologically acceptable) composition, which comprises a carrier, preferably a pharmaceutically acceptable (e.g., physiologically acceptable) carrier, and the PD-L1 binding agent or nucleic acid(s) encoding same. Any suitable carrier can be used within the context of the invention, and such carriers are well known in the art. The choice of carrier will be determined, in part, by the particular site to which the composition may be administered and the particular method used to administer the composition. The composition optionally can be sterile. The composition can be frozen or lyophilized for storage and reconstituted in a suitable sterile carrier prior to use. The compositions can be generated in accordance with conventional techniques described in, e.g., Remington: *The Science and Practice of Pharmacy,* 21*st Edition,* Lippincott Williams & Wilkins, Philadelphia, PA (2001).

The composition can be formulated for parenteral administration, such as IV administration or administration into a body cavity or lumen of an organ. Alternatively, the composition can be injected intra-tumorally. Compositions for injection will commonly comprise the active ingredient dissolved or suspended in a pharmaceutically acceptable carrier. Among the acceptable vehicles and solvents that can be employed are water and an isotonic solution of one or more salts such as sodium chloride, e.g., Ringer's solution. In addition, sterile fixed oils can conventionally be employed as a solvent or suspending medium. For this purpose, any bland fixed oil can be employed, including synthetic monoglycerides or diglycerides. In addition, fatty acids such as oleic acid can likewise be used in the preparation of injectables. These compositions desirably are sterile and generally free of undesirable matter. These compositions can be sterilized by conventional, well known sterilization techniques. The compositions can contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like.

The composition can contain any suitable concentration of the PD-L1-binding agent or nucleic acid(s) encoding same optionally in a vector, in some embodiments, a concentration effective to elicit a therapeutic response. The concentration can vary widely, and will be selected primarily based on fluid volumes, viscosities, body weight, and the like, in accordance with the particular mode of administration selected and the patient's needs. In certain embodiments, the concentration of the inventive immunoglobulin heavy chain polypeptide, the inventive immunoglobulin light chain polypeptide, the inventive PD-L1-binding agent, the inventive nucleic acid sequence encoding any of the foregoing, or the inventive vector comprising the inventive nucleic acid sequence in a solution formulation for injection will range from about 0.1% (w/w) to about 10% (w/w).

Methods

The PD-L1 binding agents provided herein can be used for any suitable purpose. For instance, the PD-L1 binding agents can target PD-L1 expressing cells, and be used to deliver a payload to such cells. The payload can be any agent that is desired to be delivered to the cell (e.g., therapeutic agent, diagnostic/imaging agent, etc.). According, one aspect of the disclosure provides a method of delivering a payload to a cell expressing PD-L1, the method comprising administering to the cell, or mammal comprising the cell, a PD-L1 binding agent provided herein conjugated to the payload.

Provided herein is a method of enhancing (e.g., increasing) an immune response in a mammal comprising administering a PD-L1 binding agent alone or conjugated to an appropriate drug or other agent suitable for increasing an immune response, or composition comprising same, as described herein to the mammal. The immune response can be an immune response to any type of antigen for use in any application in which it is desirable to enhance an immune response to the antigen. In some embodiments, the antigen can be an infectious agent or pathogen (e.g., a virus or bacteria) or a cancer antigen (e.g., an endogenous cancer antigen in the cell, an administered antigen, such as a peptide vaccine, or a neoantigen).

In another embodiment, there is provided a method of reducing (e.g., inhibiting) an immune response in a mammal comprising administering a PD-L1 binding agent alone or conjugated to an appropriate drug or other agent suitable for reducing an immune response, or composition comprising same, as described herein to the mammal. The immune response can be, for instance, an autoimmune response.

In this respect, the invention also provides a method of treating a disease, condition, or disorder responsive to PD-L1 inhibition in a mammal by administering a PD-L1 binding agent, or composition comprising same, as described herein to the mammal. In some embodiments, the disease or disorder is characterized by the improper expression (e.g., overexpression) or increased activity of a PD-L1 protein, which causes or contributes to the pathological effects of the disease, such that a decrease in PD-L1 protein levels or activity has a therapeutic benefit in mammals, preferably humans.

As used herein, the terms "treat," "treatment," and "treating" refer to any indicia of success in the treatment or amelioration of an injury, pathology, condition (e.g., cancer, infection, or autoimmune disorder), or symptom (e.g., cognitive impairment), including any objective or subjective parameter such as abatement; remission; diminishing of symptoms or making the symptom, injury, pathology, or condition more tolerable to the patient; reduction in the rate of symptom progression; decreasing the frequency or duration of the symptom or condition; or, in some situations, preventing the onset of the symptom. The treatment or amelioration of symptoms can be based on any objective or subjective parameter, including, for example, the result of a physical examination.

The terms "cancer," "neoplasm," and "tumor" are used herein to refer to cells which exhibit autonomous, unregulated growth, such that the cells exhibit an aberrant growth phenotype characterized by a significant loss of control over cell proliferation. Cells of interest for detection, analysis, and/or treatment in the context of the invention include cancer cells (e.g., cancer cells from an individual with cancer), malignant cancer cells, pre-metastatic cancer cells, metastatic cancer cells, and non-metastatic cancer cells. Cancers of virtually every tissue are known. The phrase "cancer burden" refers to the quantum of cancer cells or cancer volume in a subject. Reducing cancer burden accordingly refers to reducing the number of cancer cells or the cancer cell volume in a subject. The term "cancer cell" as used herein refers to any cell that is a cancer cell (e.g., from any of the cancers for which an individual can be treated, e.g., isolated from an individual having cancer) or is derived from a cancer cell, e.g., clone of a cancer cell. For example, a cancer cell can be from an established cancer cell line, can be a primary cell isolated from an individual with cancer, can be a progeny cell from a primary cell isolated from an individual with cancer, and the like. In some embodiments, the term can also refer to a portion of a cancer cell, such as a sub-cellular portion, a cell membrane portion, or a cell lysate of a cancer cell. Many types of cancers are known to those of skill in the art, including solid tumors such as carcinomas, sarcomas, glioblastomas, melanomas, lymphomas, and myelomas, and circulating cancers such as leukemias.

As used herein, the term "cancer" includes any form of cancer, including but not limited to, solid tumor cancers (e.g., skin, lung, prostate, breast, gastric, bladder, colon, ovarian, pancreas, kidney, liver, glioblastoma, medulloblastoma, leiomyosarcoma, head & neck squamous cell carcinomas, melanomas, and neuroendocrine) and liquid cancers (e.g., hematological cancers); carcinomas; soft tissue tumors; sarcomas; teratomas; melanomas; leukemias; lymphomas; and brain cancers, including minimal residual disease, and including both primary and metastatic tumors.

Any PD-L1 expressing or overexpressing cancer is a suitable cancer to be treated by the subject methods and compositions. As used herein "PD-L1 expression" refers to a cell that has a PD-L1 receptor on the cell's surface. As used herein "PD-L1 overexpression" refers to a cell that has more PD-L1 receptors as compared to corresponding non-cancer cell of the same type.

As used herein "internalizing binding agent" is a binding agent that, upon binding to a receptor or other ligand on a cell surface is transported into the cell (e.g., into a vacuole or other organelle or into the cytoplasm of the cell). In some embodiments, the internalizing binding agent is an internalizing antibody.

Carcinomas are malignancies that originate in the epithelial tissues. Epithelial cells cover the external surface of the body, line the internal cavities, and form the lining of glandular tissues. Examples of carcinomas include, but are not limited to, adenocarcinoma (cancer that begins in glandular (secretory) cells such as cancers of the breast, pancreas, lung, prostate, stomach, gastroesophageal junction, and colon); adrenocortical carcinoma; hepatocellular carcinoma; renal cell carcinoma; ovarian carcinoma; carcinoma in situ; ductal carcinoma; carcinoma of the breast; basal cell carcinoma; squamous cell carcinoma (e.g., head and neck squamous cell carcinoma); transitional cell carcinoma; colon carcinoma; nasopharyngeal carcinoma; multilocular cystic renal cell carcinoma; oat cell carcinoma; large cell lung carcinoma; small cell lung carcinoma; non-small cell lung carcinoma; and the like. Carcinomas may be found in prostrate, pancreas, colon, brain (usually as secondary metastases), lung, breast, and skin.

Soft tissue tumors are a highly diverse group of rare tumors that are derived from connective tissue. Examples of soft tissue tumors include, but are not limited to, alveolar soft part sarcoma; angiomatoid fibrous histiocytoma; chondromyoxid fibroma; skeletal chondrosarcoma; extraskeletal myxoid chondrosarcoma; clear cell sarcoma; desmoplastic small round-cell tumor; dermatofibrosarcoma protuberans; endometrial stromal tumor; Ewing's sarcoma; fibromatosis (Desmoid); fibrosarcoma, infantile; gastrointestinal stromal tumor; bone giant cell tumor; tenosynovial giant cell tumor; inflammatory myofibroblastic tumor; uterine leiomyoma; leiomyosarcoma; lipoblastoma; typical lipoma; spindle cell or pleomorphic lipoma; atypical lipoma; chondroid lipoma; well-differentiated liposarcoma; myxoid/round cell liposarcoma; pleomorphic liposarcoma; myxoid malignant fibrous histiocytoma; high-grade malignant fibrous histiocytoma; myxofibrosarcoma; malignant peripheral nerve sheath tumor; mesothelioma; neuroblastoma; osteochondroma; osteosarcoma; primitive neuroectodermal tumor; alveolar rhabdomyosarcoma; embryonal rhabdomyosarcoma; benign or malignant schwannoma; synovial sarcoma; Evan's tumor; nodular fasciitis; desmoid-type fibromatosis; solitary fibrous tumor; dermatofibrosarcoma protuberans (DF SP); angiosarcoma; epithelioid hemangioendothelioma; tenosynovial giant cell tumor (TGCT); pigmented villonodular synovitis (PVNS); fibrous dysplasia; myxofibrosarcoma; fibrosarcoma; synovial sarcoma; malignant peripheral nerve sheath tumor; neurofibroma; pleomorphic adenoma of soft tissue; and neoplasias derived from fibroblasts, myofibroblasts, histiocytes, vascular cells/endothelial cells, and nerve sheath cells.

A sarcoma is a rare type of cancer that arises in cells of mesenchymal origin, e.g., in bone or in the soft tissues of the body, including cartilage, fat, muscle, blood vessels, fibrous tissue, or other connective or supportive tissue. Different types of sarcoma are based on where the cancer forms. For example, osteosarcoma forms in bone, liposarcoma forms in fat, and rhabdomyosarcoma forms in muscle. Examples of sarcomas include, but are not limited to, askin's tumor; sarcoma botryoides; chondrosarcoma; ewing's sarcoma; malignant hemangioendothelioma; malignant schwannoma; osteosarcoma; and soft tissue sarcomas (e.g., alveolar soft part sarcoma; angiosarcoma; cystosarcoma phyllodesdermatofibrosarcoma protuberans (DFSP); desmoid tumor; desmoplastic small round cell tumor; epithelioid sarcoma; extraskeletal chondrosarcoma; extraskeletal osteosarcoma; fibrosarcoma; gastrointestinal stromal tumor (GIST); hemangiopericytoma; hemangiosarcoma (more commonly referred to as "angiosarcoma"); kaposi's sarcoma; leiomyosarcoma; liposarcoma; lymphangiosarcoma; malignant peripheral nerve sheath tumor (MPNST); neurofibrosarcoma; synovial sarcoma; and undifferentiated pleomorphic sarcoma).

A teratoma is a type of germ cell tumor that may contain several different types of tissue (e.g., can include tissues derived from any and/or all of the three germ layers: endoderm, mesoderm, and ectoderm), including, for example, hair, muscle, and bone. Teratomas occur most often in the ovaries in women, the testicles in men, and the tailbone in children.

Melanoma is a form of cancer that begins in melanocytes (cells that make the pigment melanin). Melanoma may begin in a mole (skin melanoma), but can also begin in other pigmented tissues, such as in the eye or in the intestines.

Merkel cell carcinoma is a rare type of skin cancer that usually appears as a flesh-colored or bluish-red nodule. It frequently appears on the face, head or neck. Merkel cell carcinoma is also called neuroendocrine carcinoma of the skin. In some embodiments, the Merkel cell carcinoma has metastasized when administration occurs.

Leukemias are cancers that start in blood-forming tissue, such as the bone marrow, and cause large numbers of abnormal blood cells to be produced and enter the bloodstream. For example, leukemias can originate in bone marrow-derived cells that normally mature in the bloodstream. Leukemias are named for how quickly the disease develops and progresses (e.g., acute versus chronic) and for the type of white blood cell that is affected (e.g., myeloid versus lymphoid). Myeloid leukemias are also called myelogenous or myeloblastic leukemias. Lymphoid leukemias are also called lymphoblastic or lymphocytic leukemia. Lymphoid leukemia cells may collect in the lymph nodes, which can become swollen. Examples of leukemias include, but are not limited to, Acute myeloid leukemia (AML), Acute lymphoblastic leukemia (ALL), Chronic myeloid leukemia (CIVIL), and Chronic lymphocytic leukemia (CLL).

Lymphomas are cancers that begin in cells of the immune system. For example, lymphomas can originate in bone marrow-derived cells that normally mature in the lymphatic system. There are two basic categories of lymphomas. One category of lymphoma is Hodgkin lymphoma (HL), which is marked by the presence of a type of cell called the Reed-Sternberg cell. There are currently 6 recognized types of HL. Examples of Hodgkin lymphomas include nodular sclerosis classical Hodgkin lymphoma (CHL), mixed cellularity CHL, lymphocyte-depletion CHL, lymphocyte-rich CHL, and nodular lymphocyte predominant HL.

The other category of lymphoma is non-Hodgkin lymphomas (NHL), which includes a large, diverse group of cancers of immune system cells. Non-Hodgkin lymphomas can be further divided into cancers that have an indolent (slow-growing) course and those that have an aggressive (fast-growing) course. There are currently 61 recognized types of NHL. Examples of non-Hodgkin lymphomas include, but are not limited to, AIDS-related Lymphomas, anaplastic large-cell lymphoma, angioimmunoblastic lymphoma, blastic NK-cell lymphoma, Burkitt's lymphoma, Burkitt-like lymphoma (small non-cleaved cell lymphoma), chronic lymphocytic leukemia/small lymphocytic lymphoma, cutaneous T-Cell lymphoma, diffuse large B-Cell lymphoma, enteropathy-type T-Cell lymphoma, follicular lymphoma, hepatosplenic gamma-delta T-Cell lymphomas, T-Cell leukemias, lymphoblastic lymphoma, mantle cell lymphoma, marginal zone lymphoma, nasal T-Cell lymphoma, pediatric lymphoma, peripheral T-Cell lymphomas, primary central nervous system lymphoma, transformed lymphomas, treatment-related T-Cell lymphomas, and Waldenstrom's macroglobulinemia.

Brain cancers include any cancer of the brain tissues. Examples of brain cancers include, but are not limited to, gliomas (e.g., glioblastomas, astrocytomas, oligodendrogliomas, ependymomas, and the like), meningiomas, pituitary adenomas, and vestibular schwannomas, primitive neuroectodermal tumors (medulloblastomas).

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, and invasion of surrounding or distant tissues or organs, such as lymph nodes.

As used herein, the phrases "cancer recurrence" and "tumor recurrence," and grammatical variants thereof, refer to further growth of neoplastic or cancerous cells after diagnosis of cancer. Particularly, recurrence may occur when further cancerous cell growth occurs in the cancerous tissue. "Tumor spread," similarly, occurs when the cells of a tumor disseminate into local or distant tissues and organs, therefore, tumor spread encompasses tumor metastasis. "Tumor invasion" occurs when the tumor growth spread out locally to compromise the function of involved tissues by compression, destruction, or prevention of normal organ function.

As used herein, the term "metastasis" refers to the growth of a cancerous tumor in an organ or body part, which is not directly connected to the organ of the original cancerous tumor. Metastasis will be understood to include micrometastasis, which is the presence of an undetectable amount of cancerous cells in an organ or body part that is not directly connected to the organ of the original cancerous tumor. Metastasis can also be defined as several steps of a process, such as the departure of cancer cells from an original tumor site, and migration and/or invasion of cancer cells to other parts of the body.

As used herein, the phrase "autoimmune disorder" refers to means a disease or disorder caused by a reaction produced by the body against its own tissues or organs or cosegregation or manifestation of these disorders or condition associated with them. Examples of autoimmune diseases or disorders include, but are not limited to, arthritis (rheumatoid arthritis such as acute arthritis, chronic rheumatoid arthritis, gouty arthritis, acute gouty arthritis, chronic inflammatory arthritis, degenerative arthritis, infectious arthritis, Lyme arthritis, proliferative arthritis, psoriatic arthritis, vertebral arthritis, and juvenile rheumatoid arthritis, osteoarthritis, a progressive chronic arthritis, deforming arthritis, primary chronic arthritis, reactive arthritis and ankylosing spondylitis), inflammatory hyperproliferative skin diseases, psoriasis such as plaque psoriasis, guttate psoriasis, pustular psoriasis and psoriasis of nails; dermatitis including contact dermatitis, chronic contact dermatitis, allergic dermatitis, allergic contact dermatitis, dermatitis herpetiformis, and atopic dermatitis; coupled with X-linked hyper-IgM-syndrome, urticaria such as chronic allergic urticaria and chronic idiopathic urticaria, including chronic autoimmune urticaria, polymyositis/dermatomyositis, juvenile dermatomyositis, toxic epidermal necrolysis, scleroderma (including systemic scleroderma), sclerosis such as systemic sclerosis, multiple sclerosis (MS) such as MS, is accompanied by breach of the spinal cord and visual organs, primary progressive MS (APP) to and relapsing-remitting MS (RRMS), progressive systemic sclerosis, atherosclerosis, arteriosclerosis, multiple sclerosis, and ataxic sclerosis; inflammatory bowel disease (IBD) (e.g., Crohn's disease, autoimmune gastrointestinal disorders, colitis such as ulcerative colitis, ulcerative colitis, microscopic colitis, collagenous colitis, polypoid colitis, nekroziruyuschy enterocolitis, and transmural colitis, and autoimmune inflammatory bowel disease); pyoderma gangrenosum, erythema nodosum, primary sclerosing cholangitis, episcleritis), respiratory distress syndrome, including adult respiratory distress syndrome (ARDS) or acute respiratory distress syndrome, meningitis, inflammation of all or part of the uveal tract, iritis, choroiditis, an autoimmune hematological disorder, rheumatoid spondylitis, sudden hearing loss, IgE-mediated diseases such as anaphylaxis and allergic and atopic rhinitis, encephalitis such as Rasmussen's encephalitis and encephalitis with lesions limbs and/or the brain stem, uveitis, such as anterior uveitis, acute anterior uveitis, granulomatous uveitis, negranulomatozny uveitis fakoantigenny uveitis, posterior uveitis, or autoimmune uveitis, glomerulonephritis (GN) with nephrotic syndrome or without nephrotic syndrome such as chronic or acute glomerulonephritis such as primary GN, immune-mediated GN, membranous GN (membranous nephropathy), idiopathic membranous GN or idiopathic membranous nephropathy, membranous proliferative or membranoproliferative ativnost GN (MPGN), including glumerulonefrit type I and type II, and rapidly progressive GN, allergic conditions, allergic reaction, eczema including allergic or atopic eczema; asthma, such as bronchial asthma and autoimmune asthma; conditions caused by infiltration of T cells and chronic inflammatory responses; chronic inflammatory lung disease, autoimmune myocarditis, leukocyte adhesion is insufficient; systemic lupus erythematosus (systemic lupus erythematodes) (SLE) such as cutaneous SLE or subacute cutaneous SLE, lupus neonatal syndrome (HRV), disseminated lupus erythematosus, lupus (including nephritis, cerebritis, child lupus, non-renal lupus, extrarenal lupus, discoid lupus, alopecia); juvenile diabetes (type I), including child insulin dependent diabetes mellitus (IDDM), adult diabetes mellitus (diabetes type II), autoimmune diabetes, idiopathic diabetes insipidus, immune responses associated with acute hypersensitivity and delayed type hypersensitivity mediated by cytokines and T lymphocytes; tuberculosis, sarcoidosis, granulomatosis including lymphomatoid granulomatosis, Wegener's granulomatosis, agranulocytosis; vasculitides including vasculitis (including vasculitis, large blood vessels (including polymyalgia rheumatica and giant cell arteritis (Takayasu's)), vasculitis secondary blood vessels (including Kavazaki disease and polyarteritis nodosa), polyarteritis capillary vasculitis CNS nekroziruyuschy vasculitis, cutaneous vasculitis or vasculitis associated hypersensitivity nekroziruyuschy systemic vasculitis and ANCA-associated vasculitis, such as vasculitis or Cherga-Strauss syndrome (SCHSH), temporal arteritis, aplastic anemia, auto mmunnaya aplastic anemia, a positive anemia, Coombs, anemia, Diamond-Blekfana, hemolytic anemia or immune hemolytic anemia including autoimmune hemolytic anemia (AIHA), pernicious anemia (pernicious anemia), Addison's disease, pure red cell anemia or aplasia (PRCA), Factor VIII deficiency, hemophilia A, autoimmune neutropenia, pancytopenia, leukopenia, diseases that lead to leukocyte diapedesis, CNS inflammatory disorder, multiple organ injury syndrome, such as a secondary syndrome, as of dissociated with sepsis, trauma or hemorrhage; diseases mediated by complex formation "antigen-antibody" disease glomerular basement membranes, catalysed reaction of the antibody-antigen, antiphospholipid syndrome, allergic neurite disease/Behcet's syndrome, Castleman's syndrome, Goodpasture's syndrome, Reynaud's syndrome, Sjogren's syndrome, Stevens-Johnson syndrome, pemphigoid such as pemphigoid bullous and skin pemphigoid, pemphigus (including pemphigus vulgar, leaf-pemphigus, pemphigoid, mucous membrane pemphigoid membranous and pemphigus erythematosus), utoimmunnaya poliendokrinopatiya disease or Reiter's syndrome, nephritis associated with immune complexes, antibody-mediated nephritis, neuromyelitis optica, polyneuropathies, chronic neuropathy such as IgM-polyneuropathy or IgM-mediated neuropathy, thrombocytopenia (e.g., developing in a patient with myocardial infarction), including thrombotic thrombocytopenic purpura (TTP) and autoimmune or immune-mediated thrombocytopenia such as idiopathic thrombocytopenic purpura (ITP) including chromel matic or acute ITP; autoimmune disease testis and ovary including autoimmune orchitis and oophoritis, primary hypothyroid, gipoparatireoidit, autoimmune endocrine diseases including thyroiditis such as autoimmune thyroiditis, Hashimoto's disease, chronic thyroiditis (Hashimoto's thyroiditis), or subacute thyroiditis, autoimmune thyroid disease, idiopathic hypothyroid, Grave's disease, polyglandular syndromes such as autoimmune polyglandular syndromes (or polyglandular endocrinopathy syndromes), paraneoplastic syndromes, including neurologic paraneoplastic syndromes such as myasthenic syndrome, Lambert-Eaton syndrome or Eaton-Lambert syndrome "stiff-man," encephalomyelitis such as allergic encephalomyelitis (or encephalomyelitis allergica) and experimental allergic encephalomyelitis (EAE), myasthenia gravis such as myasthenia gravis associated with thymoma, cerebellar degeneration, nevromiotoniya, opsoclonus or syndrome (LNG) and senses neuropathy, multifocal motor neuropathy, the system We, Sheehan's syndrome, autoimmune hepatitis, chronic hepatitis, lupoid hepatitis, giant cell hepatitis, chronic active hepatitis or autoimmune chronic active hepatitis, lymphoid interstitial pneumonitis, bronchiolitis obliterans (non-transmissible, unlike NSIP); Guillain-Barre syndrome, Berger's disease (IgA-nephropathy), idiopathic IgA-nephropathy, linear IgA-dermatosis, primary biliary cirrhosis, pnevmonotsirroz, autoimmune enteropathy syndrome, bowel disease or celiac disease, intestinal sprue (gluten enteropathy), not amenable sprue treatment, idiopathic sprue, cryoglobulinemia, amilotrofichesky lateral sclerosis (ALS; Louis Gehrig's disease), coronary heart disease; autoimmune ear disease such as autoimmune inner ear disease (AZVU); autoimmune hearing loss; "Dancing eye" syndrome (LNG), polychondritis such as refractory, or relapsing polychondritis; pulmonary alveolar proteinosis, amyloidosis, scleritis, non-cancerous lymphocytosis, a primary lymphocytosis, including monoclonal B cell lymphocytosis (e.g., benign monoclonal gammopathy and monoclonal gammopathy of unknown etiology, MGUS); peripheral neuropathy, paraneoplastic syndrome; "Channelopathy," such as epilepsy, migraine, arrhythmia, muscular disorders, deafness, blindness, periodic paralysis and "channelopathy" CNS, autism, inflammatory myopathy, focal and segmental glomerulosclerosis (OSGS), endocrine ophthalmopathy, uveoretinitis, chorioretinitis, autoimmune liver disease, fibromyalgia, multiple endocrine failure, Schmidt's syndrome, adrenalit, gastric atrophy, presenile dementia, demyelinating diseases such as autoimmune demyelinating diseases, diabetic nefropa ment, Dressler's syndrome, alopecia areata, CREST syndrome (calcinosis, Raynau's phenomenon, impaired esophageal motility, sclerodactyly, and telangiectasia), autoimmune infertility in both men and women, mixed connective tissue disease, Chagas' disease, rheumatic fever, recurrent miscarriage, lung disease farmers, erythema multiforme, cardiotomy syndrome, Cushing's syndrome, pulmonary disease, bird lovers, allergic granulomatous vasculitis, benign lymphocytic angiitis, Alport syndrome, alveolitis, such as allergies cal alveolitis and fibrosing alveolitis, interstitial lung disease, transfusion disease, leprosy, malaria, leishmaniasis, kipanosomoz, schistosomiasis, askarioz, aspergillosis, Semptera syndrome, Caplan's syndrome, dengue, endocarditis, endomyocardial fibrosis, diffuse interstitial pulmonary fibrosis, interstitial pulmonary fibrosis, idiopathic pulmonary fibrosis, cystic fibrosis, endophthalmitis, erythema elevated resistant, fetal erythroblastosis, eosinophilic fasciitis, Shulman's syndrome, Felty's syndrome, flyarioz, cyclitis such as cartilage onichesky cycles geterohronichesky cycles or cycles iridotsyklit Fuchs, Henoch-Schonlein purpura, infection caused by the human immunodeficiency virus (HIV) infections caused by echovirus; cardiomyopathy, Alzheime's disease, infections caused by parvovirus; infections caused by rubella virus; syndrome that develops after vaccination; hereditary infection caused by rubella virus; infections caused by Epstein-Barr virus; Mumps, Evans syndrome, autoimmune gonadal failure, Sydenham's chorea, post-streptococcal nephritis, thromboangiitis obliterans, thyrotoxicosis, tabes, choroiditis, giant cell polymyalgia, endocrine ophthalmopathy, pneumonitis associated with chronic hypersensitivity, keratoconjunctivitis sicca, epidemic keratoconjunctivitis, idiopathic nephritis syndrome, nephropathy, characterized by minimal changes of renal tissue, benign hereditary caused by ischemia and rap rfuzionnye lesions, autoimmune disease of the retina, inflammation of the joints, bronchitis, chronic obstructive airway disease, silicosis, aphthae, aphthous stomatitis, arteriosclerotic disorders, aspermiogenez, autoimmune hemolysis, Beck disease, cryoglobulinemia, Dupuytren's contracture, fakoanafilakticheskaya endophthalmitis, allergic enteritis, nodose lepromatous erythema, idiopathic facial paralysis, chronic fatigue syndrome, rheumatic fever, Hamman Rich syndrome; sensorineural hearing loss, paroxysmal hemoglobinuria, hypogonadism, regional ileitis, leukopenia, infectious mononucleosis, transverse myelitis, primary idiopathic miksidema, nephrosis, sympathetic ophthalmia, granulomatous orchitis, pancreatitis, acute polyradiculitis, pyoderma gangrenosum, thyroiditis Quervain acquired atrophy of the spinal cord, infertility, caused by anti-sperm, non-malignant thymoma, vitiligo, severe combined immunodeficiency (SCID) and diseases caused by a virus Epstein and Barra; acquired immunodeficiency syndrome (AIDS), parasitic diseases such as leishmaniasis, toxic shock syndrome, food poisoning, conditions caused by infiltration of T-cells, the lack of leukocyte adhesion, immune responses associated with acute hypersensitivity and delayed type hypersensitivity mediated by cytokines and T-lymphocytes, diseases associated with leukocyte diapedesis, multiple organ injury syndrome, a disease mediated by the formation of the complex antigen-antibody Disease glomerular basement membranes, allergic neuritis, autoimmune poliendokrinopatiya, oophoritis, primary myxedema, autoimmune atrophic gastritis, sympathetic ophthalmia, rheumatic diseases, mixed connective tissue disease, nephrotic syndrome, insulitis, polyendocrine failure, neuropathy of peripheral organs, autoimmune polyglandular syndrome type I, idiopathic gipoparatireoidit adults (IIV), total alopecia, congestive cardiomyopathy, acquired epidermolysis bullosa (PBE), hemochromatosis, myocarditis, nephrotic syndrome, primary sclerosing cholangitis, purulent or non-purulent sinusitis, acute or chronic sinusitis; grid sinusitis, frontal sinusitis, maxillary sinusitis or sphenoiditis; eozonofilnye disorder such as eosinophilia, pulmonary infiltrating eosinophilia, eosinophilia-myalgia syndrome, Leffler syndrome, chronic eosinophilic pneumonia, tropical pulmonary eosinophilia, allergic pulmonary aspergillosis, aspergilloma, or granulomas containing eosinophils; anaphylaxis, seronegative spondylitis, multiple endocrine autoimmune disease, sclerosing cholangitis, scleritis, episcleritis, chronic mucocutaneous candidiasis, Bruton's syndrome, transient hypogammaglobulinemia in children with Wiskott-Aldrich syndrome, ataxia-telangiectasia syndrome, autoimmune disorders associated with collagen disease, rheumatism, neurological disease, ischemic reperfusion injury, reaction to a drop in blood pressure, vascular dysfunction, angiodysplasia, tissue damage, vascular ischemia, hyperalgesia, cerebral ischemia, and disease accompanied by vascularization, allergic disorders associated with hypersensitivity, glomerulonephritis, reperfusion injury, reperfusion injury of myocardial or other tissues, dermatoses with the components of acute inflammation, acute purulent meningitis or other inflammatory disorders of the central nervous system, inflammatory diseases of the eye and orbit; syndromes associated with granulocyte transfusion; toxicity induced by cytokines, acute serous inflammation, chronic intractable inflammation, pyelitis, diabetic retinopathy, diabetic lesion of large arteries, peripheral arterial hyperplasia, peptic ulcer, and endometriosis.

As used herein, the phrase "infection" refers to a condition caused by an infectious pathogen, e.g., virus, bacteria, fungus, or parasite.

As used herein the phrases "effective amount" and "therapeutically effective amount" refer to a dose of a substance such as a binding agent that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); *Goodman & Gilman's The Pharmacological Basis of Therapeutics,* 11th Edition (McGraw-Hill, 2006); and *Remington: The Science and Practice of Pharmacy,* 22nd Edition, (Pharmaceutical Press, London, 2012)).

As used herein, the terms "recipient," "individual," "subject," "host," and "patient" are used interchangeably and refer to any mammalian subject for whom diagnosis, treatment, or therapy is desired (e.g., humans). "Mammal" for purposes of treatment refers to any animal classified as a mammal, including humans, domestic and farm animals, and zoo, sports, or pet animals, such as dogs, horses, cats, cows, sheep, goats, pigs, camels, etc. In certain embodiments, the mammal is human.

As used herein, the term "administering" refers to parenteral, intravenous, intraperitoneal, intramuscular, intratumoral, intralesional, intranasal, or subcutaneous administration, oral administration, administration as a suppository, topical contact, intrathecal administration, or the implantation of a slow-release device, e.g., a mini-osmotic pump, to the subject.

The inventive method also can be used to treat any type of infectious disease (i.e., a disease or disorder caused by a bacterium, a virus, a fungus, or a parasite). Examples of infectious diseases that can be treated by the inventive method include, but are not limited to, diseases caused by a human immunodeficiency virus (HIV), a respiratory syncytial virus (RSV), an influenza virus, a dengue virus, a hepatitis B virus (HBV, or a hepatitis C virus (HCV)). Administration of a composition comprising the inventive immunoglobulin heavy chain polypeptide, the inventive immunoglobulin light chain polypeptide, the inventive PD-L1-binding agent, the inventive nucleic acid sequence encoding any of the foregoing, or the inventive vector comprising the inventive nucleic acid sequence induces an immune response against a cancer or infectious disease in a mammal. An "immune response" can entail, for example, antibody production and/or the activation of immune effector cells (e.g., T-cells).

The inventive methods comprise administering a "therapeutically effective amount" of the binding agent. A "therapeutically effective amount" refers to an amount effective, at dosages and for periods of time necessary, to achieve a desired therapeutic result. The therapeutically effective amount may vary according to factors such as the disease state, age, sex, and weight of the individual, and the ability of the binding agent to elicit a desired response in the individual. For example, a therapeutically effective amount of a binding agent of the invention is an amount which decreases PD-L1 protein bioactivity in a human and/or enhances the immune response against a cancer or infectious disease.

Alternatively, the pharmacologic and/or physiologic effect may be prophylactic, i.e., the effect completely or partially prevents a disease or symptom thereof. In this respect, the inventive method comprises administering a "prophylactically effective amount" of the binding agent. A "prophylactically effective amount" refers to an amount effective, at dosages and for periods of time necessary, to achieve a desired prophylactic result (e.g., prevention of disease onset).

A typical dose can be, for example, in the range of 1 μg/kg to 20 mg/kg of animal or human body weight; however, doses below or above this exemplary range are within the scope of the invention. The daily parenteral dose can be about 0.00001 μg/kg to about 20 mg/kg of total body weight (e.g., about 0.001 μg/kg, about 0.1 μg/kg, about 1 μg/kg, about 5 μg/kg, about 10 μg/kg, about 100 μg/kg, about 500 μg/kg, about 1 mg/kg, about 5 mg/kg, about 10 mg/kg, or a range defined by any two of the foregoing values), preferably from about 0.1 μg/kg to about 10 mg/kg of total body weight (e.g., about 0.5 μg/kg, about 1 μg/kg, about 50 μg/kg, about 150 μg/kg, about 300 μg/kg, about 750 μg/kg, about 1.5 mg/kg, about 5 mg/kg, or a range defined by any two of the foregoing values), more preferably from about 1 μg/kg to 5 mg/kg of total body weight (e.g., about 3 μg/kg, about 15 μg/kg, about 75 μg/kg, about 300 μg/kg, about 900 μg/kg, about 2 mg/kg, about 4 mg/kg, or a range defined by any two of the foregoing values), and even more preferably from about 0.5 to 15 mg/kg body weight per day (e.g., about 1 mg/kg, about 2.5 mg/kg, about 3 mg/kg, about 6 mg/kg, about 9 mg/kg, about 11 mg/kg, about 13 mg/kg, or a range defined by any two of the foregoing values). Therapeutic or prophylactic efficacy can be monitored by periodic assessment of treated patients. For repeated administrations over several days or longer, depending on the condition, the treatment can be repeated until a desired suppression of disease symptoms occurs. However, other dosage regimens may be useful and are within the scope of the invention. The desired dosage can be delivered by a single bolus administration of the composition, by multiple bolus administrations of the composition, or by continuous infusion administration of the composition.

The composition comprising an effective amount of the inventive immunoglobulin heavy chain polypeptide, the inventive immunoglobulin light chain polypeptide, the inventive binding agent, the inventive nucleic acid sequence encoding any of the foregoing, or the inventive vector comprising the inventive nucleic acid sequence can be administered to a mammal using standard administration techniques, including oral, intravenous, intraperitoneal, subcutaneous, pulmonary, transdermal, intramuscular, intranasal, buccal, sublingual, or suppository administration. The composition preferably is suitable for parenteral administration. The term "parenteral," as used herein, includes intravenous, intramuscular, subcutaneous, rectal, vaginal, and intraperitoneal administration. More preferably, the composition is administered to a mammal using peripheral systemic delivery by intravenous, intraperitoneal, or subcutaneous injection.

Once administered to a mammal (e.g., a human), the biological activity of the inventive binding agent can be measured by any suitable method known in the art. For example, the biological activity can be assessed by determining the stability of a particular binding agent. In one embodiment of the invention, the binding agent (e.g., an antibody) has an in vivo half-life between about 30 minutes and 45 days (e.g., about 30 minutes, about 45 minutes, about 1 hour, about 2 hours, about 4 hours, about 6 hours, about 10 hours, about 12 hours, about 1 day, about 5 days, about 10 days, about 15 days, about 25 days, about 35 days, about 40 days, about 45 days, or a range defined by any two of the foregoing values). In another embodiment, the PD-L1-binding agent has an in vivo half-life between about 2 hours and 20 days (e.g., about 5 hours, about 10 hours, about 15 hours, about 20 hours, about 2 days, about 3 days, about 7 days, about 12 days, about 14 days, about 17 days, about 19 days, or a range defined by any two of the foregoing values). In another embodiment, the binding agent has an in vivo half-life between about 10 days and about 40 days (e.g., about 10 days, about 13 days, about 16 days, about 18 days, about 20 days, about 23 days, about 26 days, about 29 days, about 30 days, about 33 days, about 37 days, about 38 days, about 39 days, about 40 days, or a range defined by any two of the foregoing values).

The PD-L1 binding agent of the invention may be administered alone or in combination with other drugs, either as separate moieties or as a conjugate with the PD-L1 binding agent. For example, the binding agent can be administered in combination with other agents for the treatment or prevention of the diseases disclosed herein. In this respect, the binding agent can be used in combination with at least one other anticancer agent including, for example, any chemotherapeutic agent known in the art, ionization radiation, small molecule anticancer agents, cancer vaccines, biological therapies (e.g., other monoclonal antibodies, cancer-killing viruses, gene therapy, and adoptive T-cell transfer, immune conjugates or cytotoxic antibody drug conjugates), and/or surgery. When the inventive method treats an infectious disease, the binding agent can be administered in combination with at least one anti-bacterial agent or at least one anti-viral agent. In this respect, the anti-bacterial agent can be any suitable antibiotic known in the art. The anti-viral agent can be any vaccine of any suitable type that specifically targets a particular virus (e.g., live-attenuated vaccines, subunit vaccines, recombinant vector vaccines, and small molecule anti-viral therapies (e.g., viral replication inhibitors and nucleoside analogs).

In another embodiment, the inventive binding agent can be administered in combination with other agents that inhibit innate and adaptive immune checkpoint pathways. For example, the inventive binding agent can be administered in combination with agents that inhibit or antagonize the CTLA-4, TIM-3, LAG-3, CD47, CD24, and SIRPA pathways.

In addition to therapeutic uses, the binding agent described herein can be used in diagnostic or research applications. In this respect, the binding agent can be used in a method to diagnose a cancer or infectious disease. In a similar manner, the binding agent can be used in an assay to monitor PD-L1 protein levels in a subject being tested for a disease or disorder that is associated with abnormal PD-L1 expression. Research applications include, for example, methods that utilize the binding agent and a label to detect a PD-L1 protein in a sample, e.g., in a human body fluid or in a cell or tissue extract. The binding agent can be used with or without modification, such as covalent or non-covalent labeling with a detectable moiety. For example, the detectable moiety can be a radioisotope (e.g., $^3$H, $^{14}$C, $^{32}$P, $^{35}$S, or $^{125}$I), a fluorescent or chemiluminescent compound (e.g., fluorescein isothiocyanate, rhodamine, or luciferin), an enzyme (e.g., alkaline phosphatase, beta-galactosidase, or horseradish peroxidase), or prosthetic groups. Any method known in the art for separately conjugating an antigen-binding agent (e.g., an antibody) to a detectable moiety may be employed in the context of the invention (see, e.g., Hunter et al., *Nature,* 194: 495-496 (1962); David et al., *Biochemistry,* 13: 1014-1021 (1974); Pain et al., *J. Immunol. Meth.,* 40: 219-230 (1981); and Nygren, *J. Histochem. and Cytochem.,* 30: 407-412 (1982)).

PD-L1 protein levels can be measured using the inventive binding agent by any suitable method known in the art. Such methods include, for example, immunohistochemistry, immunofluorescence, radioimmunoassay (RIA), and FACS. Normal or standard expression values of PD-L1 protein can be established using any suitable technique, e.g., by combining a sample comprising, or suspected of comprising, a PD-L1 polypeptide with a PD-L1-specific antibody under conditions suitable to form an antigen-antibody complex. The antibody is directly or indirectly labeled with a detectable substance to facilitate detection of the bound or unbound antibody. Suitable detectable substances include various enzymes, prosthetic groups, fluorescent materials, luminescent materials, and radioactive materials (see, e.g., Zola, *Monoclonal Antibodies: A Manual of Techniques,* CRC Press, Inc. (1987)). The amount of PD-L1 polypeptide expressed in a sample is then compared with a standard value.

Kits

The binding agent can be provided in a kit, i.e., a packaged combination of reagents in predetermined amounts with instructions for performing a diagnostic assay. If the binding agent is labeled with an enzyme, the kit desirably includes substrates and cofactors required by the enzyme (e.g., a substrate precursor which provides a detectable chromophore or fluorophore). In addition, other additives may be included in the kit, such as stabilizers, buffers (e.g., a blocking buffer or lysis buffer), and the like. The relative amounts of the various reagents can be varied to provide for concentrations in solution of the reagents which substantially optimize the sensitivity of the assay. The reagents may be provided as dry powders (typically lyophilized), including excipients which on dissolution will provide a reagent solution having the appropriate concentration.

Examples of Non-Limiting Aspects of the Disclosure

Aspects, including embodiments, of the invention described herein may be beneficial alone or in combination, with one or more other aspects or embodiments. Without limiting the foregoing description, certain non-limiting aspects of the disclosure numbered (1)-(32) are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

(1) A programmed death-ligand 1 (PD-L1) binding agent comprising an immunoglobulin heavy chain variable region polypeptide and an immunoglobulin light chain variable region polypeptide, wherein:

the immunoglobulin heavy chain variable region polypeptide comprises a complementarity determining region 1 (HCDR1) comprising any one of SEQ ID NOs: 1-23, 309, or 345, a complementarity determining region 2 (HCDR2) comprising any one of SEQ ID NOs: 24-57, 310-314, or 346-349, and a complementarity determining region 3 (HCDR3) comprising any one of SEQ ID NOs: 58-95, 315-318, or 350-354; or the immunoglobulin light chain variable region polypeptide comprises a complementarity determining region 1 (LCDR1) comprising any one of SEQ ID NOs: 96-128, 319-323, 355, or 356, a complementarity determining region 2 (LCDR2) comprising any one of SEQ ID NOs: 129-151 or 357-359, and a complementarity determining region 3 (LCDR3) comprising any one of SEQ ID NOs: 152-176 or 360.

(2) A PD-L1 binding agent comprising an immunoglobulin heavy chain variable region of any one of SEQ ID NOs: 223-264, 324-334, or 361-365 or at least the CDRs thereof; and an immunoglobulin light chain variable region of any one of SEQ ID NOs: 265-306, 335-344, or 366-370 or at least the CDRs thereof.

(3) A PD-L1 binding agent comprising an immunoglobulin heavy chain variable region polypeptide with an amino acid sequence that is at least 90% identical to any one of SEQ ID NOs: 223-264, 324-334, or 361-365, and an immunoglobulin light chain variable region polypeptide with an amino acid sequence that is at least 90% identical to any one of SEQ ID NOs: 265-306, 335-344, or 366-370.

(4) The PD-L1 binding agent of any one of aspects 1-3, which comprises the heavy and light chain immunoglobulin polypeptides, or at least the CDRs thereof, of a PD-L1 binding agent of Table 1.

(5) The PD-L1 binding agent of any one of aspects 1-4, wherein the binding agent is an antibody, an antibody conjugate, or an antigen-binding fragment thereof.

(6) The PD-L1 binding agent of aspect 5, wherein the binding agent is an antibody fragment selected from F(ab')$_2$, Fab', Fab, Fv, scFv, dsFv, dAb, and a single chain binding polypeptide.

(7) The PD-L1 binding agent of aspect 5, wherein the binding agent is an antibody.

(8) The PD-L1 binding agent of any of aspects 1-7, further comprising an immunoglobulin Fc region.

(9) The PD-L1 binding agent of aspect 8, further comprising a transforming growth factor beta 1 (TGFβ1) receptor, or a fragment thereof that binds TGFβ1, attached to the Fc region.

(10) The PD-L1 binding agent of any one of aspects 7-9, wherein the antibody is an IgG, IgM, IgA, IgD or IgE antibody.

(11) The PD-L1 binding agent of any one of aspects 7-9, wherein the antibody is an IgG antibody.

(12) The PD-L1 binding agent of any one of aspects 7-11, wherein the antibody exhibits antibody dependent cell-mediated cytotoxicity (ADCC), antibody-dependent cell-mediated phagocytosis (ADCP), or complement dependent cytotoxicity (CDC).

(13) The PD-L1 binding agent of any of aspects 1-12, wherein the binding agent is part of a bispecific antibody, chimeric antigen receptor, chimeric T cell receptor, or bispecific T-cell engager.

(14) The PD-L1 binding agent of any of aspects 1-12, wherein the binding agent is an internalizing binding agent.

(15) A nucleic acid encoding the heavy chain immunoglobulin polypeptide of the anti-PD-L1 binding agent of any one of aspects 1-14.

(16) A nucleic acid encoding the light chain immunoglobulin polypeptide of the anti-PD-L1 binding agent of any one of aspects 1-14.

(17) A nucleic acid encoding the heavy chain immunoglobulin polypeptide and the light chain immunoglobulin polypeptide of the PD-L1 binding agent of any one of aspects 1-14.

(18) A vector comprising the nucleic acid sequence of any one of aspects 15-17.

(19) An isolated cell comprising the nucleic acid of any one of aspects 15-17, optionally in a vector.

(20) A method of providing a PD-L1 binding agent of any of aspects 1-14, the method comprising expressing in a cell in vitro one or more nucleic acids encoding the immunoglobulin heavy and light chain polypeptides thereof.

(21) A composition comprising the PD-L1 binding agent of any one of aspects 1-14 or nucleic acid of any one of aspects 15-17, optionally in a vector, and a pharmaceutically acceptable carrier.

(22) The PD-L1 binding agent of any one of aspects 1-14 or the composition of aspect 21 for use as a medicament for treating a disease, disorder, or condition in a mammal that is responsive to PD-L1 inhibition or binding.

(23) The PD-L1 binding agent or composition of aspect 22, wherein the disease, disorder, or condition is cancer.

(24) The PD-L1 binding agent of any one of aspects 1-14 or the composition of aspect 19 for use as a medicament for enhancing or reducing or inhibiting an immune response in a mammal.

(25) The PD-L1 binding agent for use according to aspect 24, wherein the immune response is an anti-cancer immune response.

(26) A method for treating a disease, disorder, or condition in a mammal that is responsive to PD-L1 inhibition or binding, the method comprising administering the PD-L1 binding agent of any one of aspects 1-14 or the composition of aspect 21 to the mammal.

(27) The method of aspect 26, wherein the disease, disorder, or condition is cancer.

(28) The method of aspect 26, wherein the disease, disorder, or condition is an autoimmune disorder.

(29) The method of aspect 26, wherein the disease, disorder, or condition is an infection.

(30) A method for enhancing or reducing or inhibiting an immune response in a mammal comprising administering the PD-L1 binding agent of any one of aspects 1-14 or the composition of aspect 21 to the mammal.

(31) The method of aspect 30, wherein the immune response is an anti-cancer immune response.

(32) A method of delivering a payload to a cell expressing PD-L1, the method comprising administering to the cell, or a mammal comprising the cell, a conjugate comprising a (1) PD-L1 binding agent of any one of aspects 1-14 and a (2) payload to the mammal.

(33) A hybridoma or cell line that expresses a PD-L1 binding agent of any of aspects 1-14.

The following examples further illustrate the invention but, of course, should not be construed as in any way limiting its scope.

EXAMPLES

Example 1

This example demonstrates that the binding agents according to embodiments of the invention are effective at binding human PD-L1 (hPD-L1) on a cell surface.

Binding of the binding agents of an embodiment of the invention to human PD-L1 (hPD-L1) on cell surfaces was assessed by incubating the binding agents with JIMT1 cells that express endogenous hPD-L1. Briefly, the binding agents were diluted serially in FACS buffer (PBS+1% FBS+5 mM EDTA, pH 7.4) at 4° C. Diluted binding agents were applied to JIMT1 cells (~$1\times10^5$-$2\times10^5$ per well) and incubated at 4° C. Cells were subsequently washed twice to remove unbound binding agents and subsequently incubated with a fluorescent anti-human IgG Fc antibody at 4° C. to detect cell-bound anti-PD-L1 binding agents. After unbound secondary antibody was washed out, cells were resuspended in FACS buffer plus 2% formaldehyde and analyzed by flow cytometry. The intensity of fluorescence, expressed as geometric mean fluorescence intensity, was used to determine anti-PDL1 binding agent binding to hPD-L1 on cell surface.

Figure 2:
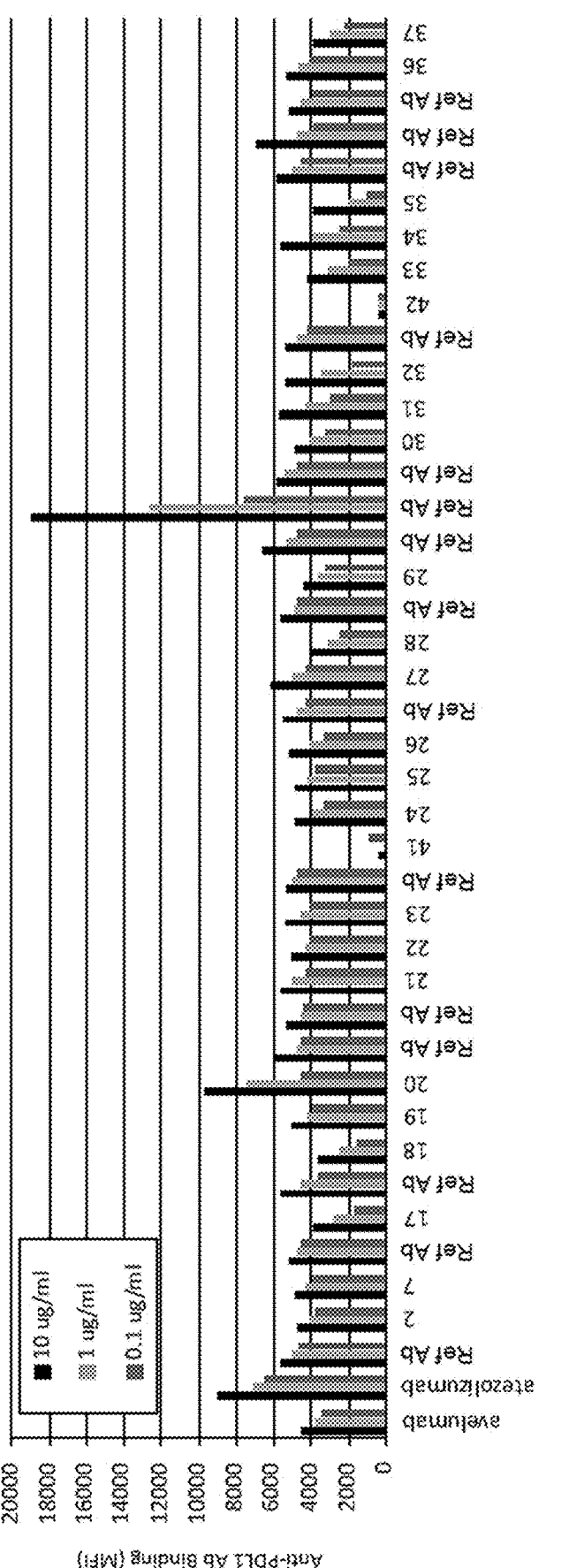
FIG. 2 depicts experimental data illustrating the affinity for binding agents of an embodiment of the invention for human PD-L1 using JIMT-1 cells.
Figure 4:
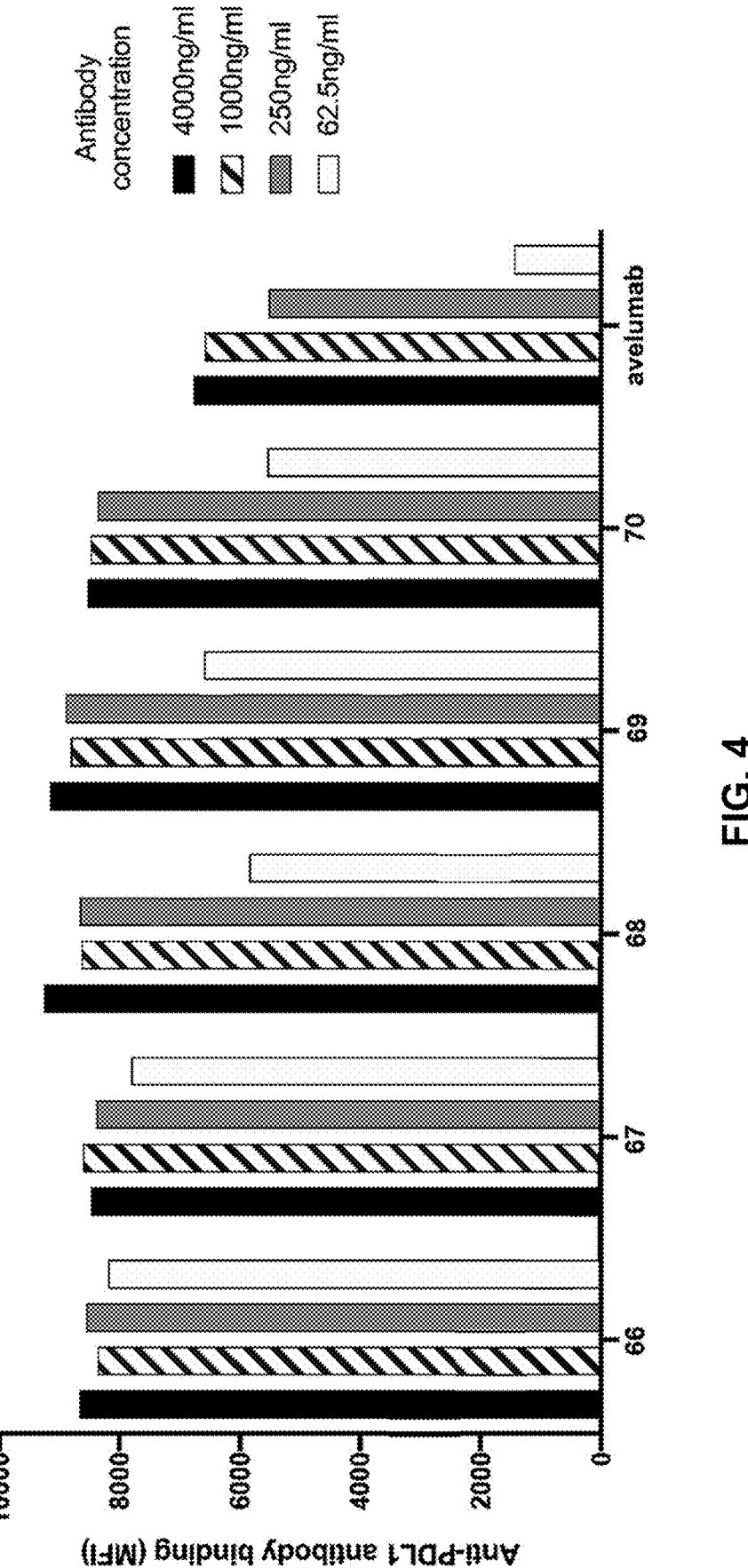
FIG. 4 depicts experimental data illustrating the affinity for binding agents of an embodiment of the invention for human PD-L1 on JIMT-1 cell surface.

As shown by the data presented in FIGS. 1, 2, and 4, the binding agents according to embodiments of the present invention were successful at binding human PD-L1. The numbers along the x-axis correlate to the numbers of the binding agents according to embodiments of the invention. "Ref Ab" in the figures refers to reference binding agents that are not embodiments of the present invention. The binding agent concentrations are listed in the figure legends.

Example 2

This example demonstrates that binding agents according to embodiments of the invention were internalized when exposed to cells with PD-L1 on the cells' surface.

Anti-PDL1 binding agent internalization was measured by estimating their extent of cell surface persistence upon incubation of cells with pre-bound antibodies at 37° C. over a prolonged time course. Briefly, to measure anti-PDL1 antibody surface persistence, JIMT-1 cells were seeded at $2\times10^5$-$4\times10^5$ cells per well. On day 1, one set of samples (the "chase" set) was generated by incubating JIMT-1 cells for 60 minutes at 4° C. with anti-PDL1 antibodies at 10 μg/ml in cell culture medium. After the incubation, unbound binding agents were removed by successive washes with culture medium, then cell were incubated at 37° C. in fresh culture medium for 24 hr. On day 2, cells were recovered from the microtiter plates by brief incubation with PBS+10 mM EDTA. The second set of samples (the "no chase" set) was generated on day 2 by incubating JIMT-1 cells with anti-PDL1 binding agents as described above, removing the unbound antibodies and then immediately recovering the cells using PBS+10 mM EDTA.

Recovered JIMT-1 cells were transferred to 96-well microtiter plates, pelleted, and incubated with a fluorescent anti-human IgG Fc antibody in FACS buffer (PBS+1% FBS+5 mM EDTA, pH 7.4) for at least 45 minutes at 4° C. to detect cell-bound anti-PDL1 antibodies. Unbound binding agents were removed by washing cells twice, and cells were resuspended in FACS buffer+2% formaldehyde and analyzed by flow cytometry.

The intensity of fluorescence in the secondary anti-Fc channel, expressed as geometric mean fluorescence intensity, was used to determine anti-PDL1 binding. The ratio in fluorescence intensity of cells incubated with a given anti-PDL1 binding agent followed by a 24 hr chase versus no chase is a measure of the surface persistence of that binding agents. For example, a ratio of 1.0 indicates no loss of surface-bound binding agents over the course of the 24 hr chase, while a ratio <1 indicates that a proportion of binding agents was internalized.

Figure 3:
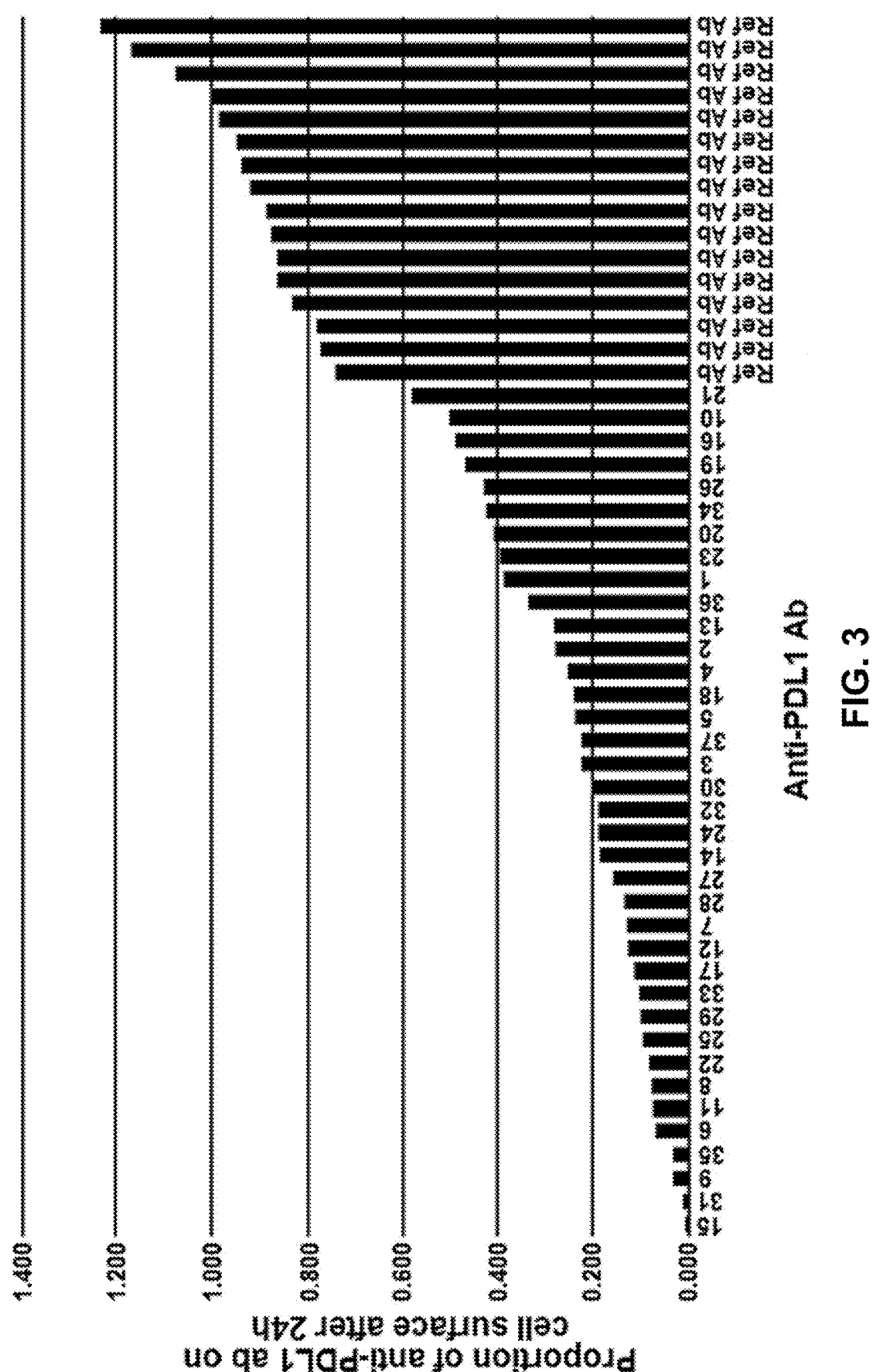
FIG. 3 depicts experimental data illustrating the level of cellular internalization of binding agents of an embodiment of the invention.

As shown by the data presented in FIG. 3, the binding agents according to embodiments of the present invention were successful at being internalized. The numbers along the x-axis correlate to the numbers of the binding agents according to embodiments of the invention. "Ref Ab" in the figure refers to reference binding agents that are not embodiments of the present invention. The binding agent concentrations are listed in the figure legend.

Example 3

This example demonstrates that binding agents according to embodiments of the invention inhibit PD-L1/PD-1 binding.

The effects of the binding agents and two commercially available antibodies, avelumab and atezolizumab, on the PD-L1/PD-1 interaction were determined using a reporter assay (Promega). The assay was performed according to the manufacturer's instructions. Briefly, cells expressing both PD-L1 and T cell receptor (TCR) activating alphaAPC at the surface were incubated with cells expressing surface recombinant TCR and PD-1 and bearing a luciferase gene that is under the control of the NFAT (nuclear factor of activated T cells) response element.

A trans PD-L1/PD-1 interaction prevents the induction of luciferase expression that occurs through trans alphaAPC-TCR binding, TCR signaling, and NFAT response element activation. Anti-PDL1 antibodies that block the interaction with PD-1 thereby allow TCR signaling and luciferase expression. Luciferase expression is measured using a bio-luminescent substrate and a plate reader set in luminescence detection mode.

Stimulator CHO-K1/PD-L1/alphaAPC cells were suspended into Ham's F-12 medium supplemented with 10% fetal bovine serum (FBS) and plated into wells of six 96-well, clear bottom, white wall plates (Corning). Plates were placed into a 37° C. incubator under 5% $CO_2$ atmosphere for fourteen hours. Culture medium was removed, and test articles diluted to 2× final concentration in RPMI-1640 medium supplemented with 1% FBS were added to the wells. An equal volume of reporter Jurkat/PD-1/luciferase cells suspended in RPMI-1640+1% FBS was then added to each well. The final concentrations ranged from 4.12 to 27,000 ng/ml in three-fold increments. Avelumab was included as a reference. After eight hours in a 37° C. incubator under 5% $CO_2$ atmosphere, plates were removed and allowed to equilibrate to room temperature for ten minutes. Wells then received BIOGLOW cell-permeabilizing luciferase substrate (Promega) for ten minutes with gentle agitation.

Luminescence was measured using a Molecular Devices M3 plate reader.

Luminescence data were analyzed with GraphPad PRISM v8 for four-parameter sigmoidal dose-response curve fitting and determination of EC50 values. The concentrations were converted to log 10 values for EC50 determinations and for graphing; the "no test article" concentration was converted to (lowest concentration tested)/3 to allow log 10 transformation. Conversion of EC50 values from ng/ml to nM was done using IgG molecular weight data.

PD-L1/PD-1 blockade was demonstrated by the increase in luminescence (RLU=relative luminescence units) induced by increasing concentrations of anti-PDL1 antibodies. Dose-response curves were closely fit using a four-parameter sigmoidal model, consistent with saturable antibody binding.

TABLE 5

Examples of PD-L1/PD-1 blockade EC50 values (ng/mL, nM) for anti-PDL1 binding agents

| Binding agent | plate | EC50 (ng/ml) | MW (Da) | EC50 (nM) |
|---|---|---|---|---|
| Ref Ab | 1 | 106.5 | 144705 | 0.74 |
| Ref Ab | 1 | 123.6 | 144840 | 0.85 |
| Ref Ab | 1 | 97.3 | 144886 | 0.67 |
| Avelumab | 2 | 67.5 | 143540 | 0.47 |
| Ref Ab | 2 | 106.3 | 145265 | 0.73 |
| Ref Ab | 2 | 180.6 | 144205 | 1.25 |
| 10 | 3 | 290.8 | 144209 | 2.02 |
| Ref Ab | 3 | 105.8 | 144977 | 0.73 |
| Ref Ab | 3 | 67.4 | 144797 | 0.47 |
| Ref Ab | 4 | 54.3 | 144808 | 0.37 |
| Avelumab | 4 | 73.1 | 143540 | 0.51 |
| Ref Ab | 4 | 166.0 | 144329 | 1.15 |
| Ref Ab | 5 | 47.3 | 144447 | 0.33 |
| 21 | 5 | 129.4 | 144437 | 0.9 |
| Atezolizumab | 5 | 57.1 | 144355 | 0.4 |
| Ref Ab | 6 | 53.6 | 144813 | 0.37 |
| Ref Ab | 6 | 163.9 | 145130 | 1.13 |
| Avelumab | 6 | 55.2 | 143540 | 0.38 |

In summary, binding agents according to embodiments of the invention inhibited protein binding, with EC50 values ranging from 129.4 to 290.8 ng/ml (0.33 to 2.02 nM).

The terms "about" and "around," as used herein to modify a numerical value, indicate a close range surrounding the numerical value. Thus, if "X" is the value, "about X" or "around X" indicates a value of from 0.9X to 1.1X, e.g., from 0.95X to 1.05X or from 0.99X to 1.01X. A reference to "about X" or "around X" specifically indicates at least the values X, 0.95X, 0.96X, 0.97X, 0.98X, 0.99X, 1.01X, 1.02X, 1.03X, 1.04X, and 1.05X. Accordingly, "about X" and "around X" are intended to teach and provide written description support for a claim limitation of, e.g., "0.98X."

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A programmed death-ligand 1 (PD-L1) binding agent comprising an immunoglobulin heavy chain variable region polypeptide and an immunoglobulin light chain variable region polypeptide, wherein:

(a) the immunoglobulin heavy chain variable region polypeptide comprises a complementarity determining region 1 (HCDR1) comprising SEQ ID NO: 17, a complementarity determining region 2 (HCDR2) comprising SEQ ID NO: 311, and a complementarity determining region 3 (HCDR3) comprising SEQ ID NO: 79, and the immunoglobulin light chain variable region polypeptide comprises a complementarity determining region 1 (LCDR1) comprising SEQ ID NO: 98, a complementarity determining region 2 (LCDR2) comprising SEQ ID NO: 129, and a complementarity determining region 3 (LCDR3) comprising SEQ ID NO: 155, or (b) the immunoglobulin heavy chain variable region polypeptide comprises a HCDR1 comprising SEQ ID NO: 9, a HCDR2 comprising SEQ ID NO: 348, and a HCDR3 comprising SEQ ID NO: 352, and the immunoglobulin light chain variable region polypeptide comprises a LCDR1 comprising SEQ ID NO: 97, a LCDR2 comprising SEQ ID NO: 358, and a LCDR3 comprising SEQ ID NO: 360.

2. A programmed death-ligand 1 (PD-L1) binding agent comprising (a) an immunoglobulin heavy chain variable region of SEQ ID NO: 333 or at least the complementarity determining regions (CDRs) thereof; and an immunoglobulin light chain variable region of SEQ ID NO: 281 or at least the CDRs thereof, or (b) an immunoglobulin heavy chain variable region of SEQ ID NO: 363 or at least the CDRs thereof; and an immunoglobulin light chain variable region of SEQ ID NO: 368 or at least the CDRs thereof.

3. A programmed death-ligand 1 (PD-L1) binding agent comprising (a) an immunoglobulin heavy chain variable region polypeptide with an amino acid sequence that is at least 90% identical to SEQ ID NO: 333, and an immunoglobulin light chain variable region polypeptide with an amino acid sequence that is at least 90% identical to SEQ ID NO: 281, or (b) an immunoglobulin light chain variable region polypeptide with an amino acid sequence that is at least 90% identical to SEQ ID NO: 363, and an immunoglobulin light chain variable region polypeptide with an amino acid sequence that is at least 90% identical to SEQ ID NO: 368.

4. The PD-L1 binding agent of claim 1, wherein the binding agent is an antibody, an antibody conjugate, or an antigen-binding fragment thereof.

5. The PD-L1 binding agent of claim 4, wherein the binding agent is an antibody fragment selected from F(ab')$_2$, Fab', Fab, Fv, scFv, dsFv, dAb, and a single chain binding polypeptide.

6. The PD-L1 binding agent of claim 4, wherein the binding agent is an antibody.

7. The PD-L1 binding agent of claim 1, further comprising an immunoglobulin Fc region.

8. The PD-L1 binding agent of claim 7, further comprising a transforming growth factor beta 1 (TGFβ1) receptor, or a fragment thereof that binds TGFβ1, attached to the Fc region.

9. The PD-L1 binding agent of claim 6, wherein the antibody is an IgG, IgM, IgA, IgD or IgE antibody.

10. The PD-L1 binding agent of claim 6, wherein the antibody is an IgG antibody.

11. The PD-L1 binding agent of claim 6, wherein the antibody exhibits antibody dependent cell-mediated cytotoxicity (ADCC), antibody-dependent cell-mediated phagocytosis (ADCP), or complement dependent cytotoxicity (CDC).

12. The PD-L1 binding agent of claim 1, wherein the binding agent is part of a bispecific antibody, chimeric antigen receptor, chimeric T cell receptor, or bispecific T-cell engager.

13. The PD-L1 binding agent of claim 1, wherein the binding agent is an internalizing binding agent.

14. A nucleic acid encoding the heavy chain immunoglobulin polypeptide of the anti-PD-L1 binding agent of claim 1.

15. A nucleic acid encoding the light chain immunoglobulin polypeptide of the anti-PD-L1 binding agent of claim 1.

16. A nucleic acid encoding the heavy chain immunoglobulin polypeptide and the light chain immunoglobulin polypeptide of the PD-L1 binding agent of claim 1.

17. A vector comprising the nucleic acid sequence encoding the heavy and/or light chains of the anti-PD-L1 binding agent of claim 1.

18. An isolated cell comprising the nucleic acid encoding the heavy and/or light chains of the anti-PD-L1 binding agent of claim 1, optionally in a vector.

19. A method of providing a PD-L1 binding agent of claim 1, the method comprising expressing in a cell in vitro one or more nucleic acids encoding the immunoglobulin heavy and light chain polypeptides thereof.

20. A composition comprising the PD-L1 binding agent of claim 1 or a nucleic acid encoding the heavy and/or light chains of same, optionally in a vector, and a pharmaceutically acceptable carrier.

21. A method for treating a disease, disorder, or condition in a mammal that is responsive to PD-L1 inhibition or binding, the method comprising administering the PD-L1 binding agent of claim 1 or conjugate comprising same, or a composition comprising the PD-L1 binding agent or conjugate comprising same, to the mammal.

22. The method of claim 21, wherein the disease, disorder, or condition is cancer.

23. The method of claim 21, wherein the disease, disorder, or condition is an autoimmune disorder.

24. The method of claim 21, wherein the disease, disorder, or condition is an infection.

25. A method for enhancing or inhibiting an immune response in a mammal comprising administering the PD-L1 binding agent of claim 1 or conjugate comprising same, or a composition comprising the PD-L1 binding agent or conjugate comprising same, to the mammal.

26. The method of claim 25, wherein the immune response is an anti-cancer immune response.

27. A method of delivering a payload to a cell expressing PD-L1, the method comprising administering to the cell, or a mammal comprising the cell, a conjugate comprising a PD-L1 binding agent of claim 1 and a payload to the mammal.

28. A hybridoma or cell line that expresses a PD-L1 binding agent of claim 1.

29. A programmed death-ligand 1 (PD-L1) binding agent comprising an immunoglobulin heavy chain variable region polypeptide and an immunoglobulin light chain variable region polypeptide, wherein the immunoglobulin heavy chain variable region poly-
peptide comprises a complementarity determining
region 1 (HCDR1) comprising SEQ ID NO: 17, a
complementarity determining region 2 (HCDR2) com-
prising SEQ ID NO: 311, and a complementarity
determining region 3 (HCDR3) comprising SEQ ID
NO: 79, and
the immunoglobulin light chain variable region polypep-
tide comprises a complementarity determining region 1
(LCDR1) comprising SEQ ID NO: 98, a complemen-
tarity determining region 2 (LCDR2) comprising SEQ
ID NO: 129, and a complementarity determining region
3 (LCDR3) comprising SEQ ID NO: 155.

\* \* \* \* \*

SEQUENCE LISTING

```
<160> NUMBER OF SEQ ID NOS: 370

<210> SEQ ID NO 1
<211> LENGTH: 5
<212> TYPE: PRT
<213> ORGANISM: Artificial Sequence
<220> FEATURE:
<223> OTHER INFORMATION: synthetic

<400> SEQUENCE: 1

Ser Tyr Ala Ile Ser
1               5

<210> SEQ ID NO 2
<211> LENGTH: 5
<212> TYPE: PRT
<213> ORGANISM: Artificial Sequence
<220> FEATURE:
<223> OTHER INFORMATION: synthetic

<400> SEQUENCE: 2

Ser Tyr Tyr Met His
1               5

<210> SEQ ID NO 3
<211> LENGTH: 5
<212> TYPE: PRT
<213> ORGANISM: Artificial Sequence
<220> FEATURE:
<223> OTHER INFORMATION: synthetic

<400> SEQUENCE: 3

Arg His Leu Leu His
1               5

<210> SEQ ID NO 4
<211> LENGTH: 5
<212> TYPE: PRT
<213> ORGANISM: Artificial Sequence
<220> FEATURE:
<223> OTHER INFORMATION: synthetic

<400> SEQUENCE: 4

Ser His His Met His
1               5

<210> SEQ ID NO 5
<211> LENGTH: 4
<212> TYPE: PRT
<213> ORGANISM: Artificial Sequence
<220> FEATURE:
<223> OTHER INFORMATION: synthetic
```

```
<400> SEQUENCE: 5

Arg Phe Met His
1

<210> SEQ ID NO 6
<211> LENGTH: 5
<212> TYPE: PRT
<213> ORGANISM: Artificial Sequence
<220> FEATURE:
<223> OTHER INFORMATION: synthetic

<400> SEQUENCE: 6

Ser Tyr Tyr Ile His
1               5

<210> SEQ ID NO 7
<211> LENGTH: 5
<212> TYPE: PRT
<213> ORGANISM: Artificial Sequence
<220> FEATURE:
<223> OTHER INFORMATION: synthetic

<400> SEQUENCE: 7

Asn Tyr Tyr Ile His
1               5

<210> SEQ ID NO 8
<211> LENGTH: 5
<212> TYPE: PRT
<213> ORGANISM: Artificial Sequence
<220> FEATURE:
<223> OTHER INFORMATION: synthetic

<400> SEQUENCE: 8

His Tyr Tyr Met His
1               5

<210> SEQ ID NO 9
<211> LENGTH: 5
<212> TYPE: PRT
<213> ORGANISM: Artificial Sequence
<220> FEATURE:
<223> OTHER INFORMATION: synthetic

<400> SEQUENCE: 9

Gly Tyr Tyr Met His
1               5

<210> SEQ ID NO 10
<211> LENGTH: 5
<212> TYPE: PRT
<213> ORGANISM: Artificial Sequence
<220> FEATURE:
<223> OTHER INFORMATION: synthetic

<400> SEQUENCE: 10

Asn Tyr Met Tyr His
1               5

<210> SEQ ID NO 11
<211> LENGTH: 5
<212> TYPE: PRT
<213> ORGANISM: Artificial Sequence
<220> FEATURE:
<223> OTHER INFORMATION: synthetic

<400> SEQUENCE: 11
```

```
Thr Tyr Tyr Val His
1               5

<210> SEQ ID NO 12
<211> LENGTH: 5
<212> TYPE: PRT
<213> ORGANISM: Artificial Sequence
<220> FEATURE:
<223> OTHER INFORMATION: synthetic

<400> SEQUENCE: 12

Ser Tyr Ala Leu Ser
1               5

<210> SEQ ID NO 13
<211> LENGTH: 5
<212> TYPE: PRT
<213> ORGANISM: Artificial Sequence
<220> FEATURE:
<223> OTHER INFORMATION: synthetic

<400> SEQUENCE: 13

Arg His Tyr Val His
1               5

<210> SEQ ID NO 14
<211> LENGTH: 5
<212> TYPE: PRT
<213> ORGANISM: Artificial Sequence
<220> FEATURE:
<223> OTHER INFORMATION: synthetic

<400> SEQUENCE: 14

Ser His Tyr Met His
1               5

<210> SEQ ID NO 15
<211> LENGTH: 5
<212> TYPE: PRT
<213> ORGANISM: Artificial Sequence
<220> FEATURE:
<223> OTHER INFORMATION: synthetic

<400> SEQUENCE: 15

Asp Tyr Tyr Met His
1               5

<210> SEQ ID NO 16
<211> LENGTH: 5
<212> TYPE: PRT
<213> ORGANISM: Artificial Sequence
<220> FEATURE:
<223> OTHER INFORMATION: synthetic

<400> SEQUENCE: 16

Gly Tyr Thr Leu His
1               5

<210> SEQ ID NO 17
<211> LENGTH: 5
<212> TYPE: PRT
<213> ORGANISM: Artificial Sequence
<220> FEATURE:
<223> OTHER INFORMATION: synthetic

<400> SEQUENCE: 17
```

Asn His Tyr Met His
1               5

<210> SEQ ID NO 18
<211> LENGTH: 5
<212> TYPE: PRT
<213> ORGANISM: Artificial Sequence
<220> FEATURE:
<223> OTHER INFORMATION: synthetic

<400> SEQUENCE: 18

Asn Ser Tyr Met His
1               5

<210> SEQ ID NO 19
<211> LENGTH: 5
<212> TYPE: PRT
<213> ORGANISM: Artificial Sequence
<220> FEATURE:
<223> OTHER INFORMATION: synthetic

<400> SEQUENCE: 19

Thr Tyr Tyr Met His
1               5

<210> SEQ ID NO 20
<211> LENGTH: 5
<212> TYPE: PRT
<213> ORGANISM: Artificial Sequence
<220> FEATURE:
<223> OTHER INFORMATION: synthetic

<400> SEQUENCE: 20

Arg His Phe Ile His
1               5

<210> SEQ ID NO 21
<211> LENGTH: 5
<212> TYPE: PRT
<213> ORGANISM: Artificial Sequence
<220> FEATURE:
<223> OTHER INFORMATION: synthetic

<400> SEQUENCE: 21

Thr Phe Gly Ile Ser
1               5

<210> SEQ ID NO 22
<211> LENGTH: 5
<212> TYPE: PRT
<213> ORGANISM: Artificial Sequence
<220> FEATURE:
<223> OTHER INFORMATION: synthetic

<400> SEQUENCE: 22

Ser Tyr Gly Ile Asn
1               5

<210> SEQ ID NO 23
<211> LENGTH: 5
<212> TYPE: PRT
<213> ORGANISM: Artificial Sequence
<220> FEATURE:
<223> OTHER INFORMATION: synthetic

<400> SEQUENCE: 23

Asn His Tyr Val His

-continued 1                   5

<210> SEQ ID NO 24
<211> LENGTH: 17
<212> TYPE: PRT
<213> ORGANISM: Artificial Sequence
<220> FEATURE:
<223> OTHER INFORMATION: synthetic

<400> SEQUENCE: 24

Val Ile Asn Pro Ser Ala Gly Ser Thr Asp Tyr Ala Gln Lys Phe Gln
1                   5                   10                  15

Gly

<210> SEQ ID NO 25
<211> LENGTH: 17
<212> TYPE: PRT
<213> ORGANISM: Artificial Sequence
<220> FEATURE:
<223> OTHER INFORMATION: synthetic

<400> SEQUENCE: 25

Trp Met Asn Pro Asn Ser Asp Ile Ala Gly Tyr Ala Gln Lys Phe Gln
1                   5                   10                  15

Gly

<210> SEQ ID NO 26
<211> LENGTH: 17
<212> TYPE: PRT
<213> ORGANISM: Artificial Sequence
<220> FEATURE:
<223> OTHER INFORMATION: synthetic

<400> SEQUENCE: 26

Trp Ile Ser Pro Gln His Gly Val Arg Asn Tyr Ala Gln Lys Phe Gln
1                   5                   10                  15

Gly

<210> SEQ ID NO 27
<211> LENGTH: 17
<212> TYPE: PRT
<213> ORGANISM: Artificial Sequence
<220> FEATURE:
<223> OTHER INFORMATION: synthetic

<400> SEQUENCE: 27

Trp Val Ser Pro Ser His Gly Leu Thr Gly Tyr Ala Gln Lys Phe Gln
1                   5                   10                  15

Gly

<210> SEQ ID NO 28
<211> LENGTH: 17
<212> TYPE: PRT
<213> ORGANISM: Artificial Sequence
<220> FEATURE:
<223> OTHER INFORMATION: synthetic

<400> SEQUENCE: 28

Trp Met Ser Leu Asn Ser Gly Leu Thr Gly Tyr Ala Gln Lys Phe Gln
1                   5                   10                  15

Gly

<210> SEQ ID NO 29

```
<211> LENGTH: 17
<212> TYPE: PRT
<213> ORGANISM: Artificial Sequence
<220> FEATURE:
<223> OTHER INFORMATION: synthetic

<400> SEQUENCE: 29

Trp Met Lys Pro Ser Ser Gly Thr Thr Gly Tyr Ala Gln Lys Phe Gln
1               5                   10                  15

Gly

<210> SEQ ID NO 30
<211> LENGTH: 17
<212> TYPE: PRT
<213> ORGANISM: Artificial Sequence
<220> FEATURE:
<223> OTHER INFORMATION: synthetic

<400> SEQUENCE: 30

Trp Met Asn Pro Asn Gly Asp Val Ala Gly Tyr Ala Gln Lys Phe Gln
1               5                   10                  15

Gly

<210> SEQ ID NO 31
<211> LENGTH: 17
<212> TYPE: PRT
<213> ORGANISM: Artificial Sequence
<220> FEATURE:
<223> OTHER INFORMATION: synthetic

<400> SEQUENCE: 31

Gly Ile Asp Pro Asn Ser Gly Gly Thr Asn Tyr Ala Gln Lys Phe Gln
1               5                   10                  15

Gly

<210> SEQ ID NO 32
<211> LENGTH: 17
<212> TYPE: PRT
<213> ORGANISM: Artificial Sequence
<220> FEATURE:
<223> OTHER INFORMATION: synthetic

<400> SEQUENCE: 32

Trp Met Asn Pro Asp Ser Gly Ser Thr Gly Tyr Ala Gln Lys Phe Gln
1               5                   10                  15

Gly

<210> SEQ ID NO 33
<211> LENGTH: 17
<212> TYPE: PRT
<213> ORGANISM: Artificial Sequence
<220> FEATURE:
<223> OTHER INFORMATION: synthetic

<400> SEQUENCE: 33

Trp Met Ser Leu Asn Ser Gly Leu Thr Gly Tyr Ala Gln Lys Phe Gln
1               5                   10                  15

Gly

<210> SEQ ID NO 34
<211> LENGTH: 17
<212> TYPE: PRT
<213> ORGANISM: Artificial Sequence
<220> FEATURE:
```

-continued

<223> OTHER INFORMATION: synthetic

<400> SEQUENCE: 34

Trp Met Asn Pro Asn Gly Asp Val Ala Gly Tyr Ala Asp Ser Phe Gln
1               5                   10                  15

Gly

<210> SEQ ID NO 35
<211> LENGTH: 17
<212> TYPE: PRT
<213> ORGANISM: Artificial Sequence
<220> FEATURE:
<223> OTHER INFORMATION: synthetic

<400> SEQUENCE: 35

Trp Ile Ser Thr Tyr His Gly Ser Thr Asn Tyr Ala Gln Lys Phe Gln
1               5                   10                  15

Gly

<210> SEQ ID NO 36
<211> LENGTH: 17
<212> TYPE: PRT
<213> ORGANISM: Artificial Sequence
<220> FEATURE:
<223> OTHER INFORMATION: synthetic

<400> SEQUENCE: 36

Trp Met Asn Pro Asn Thr Val Tyr Thr Gly Ser Ala Gln Lys Phe Gln
1               5                   10                  15

Gly

<210> SEQ ID NO 37
<211> LENGTH: 17
<212> TYPE: PRT
<213> ORGANISM: Artificial Sequence
<220> FEATURE:
<223> OTHER INFORMATION: synthetic

<400> SEQUENCE: 37

Arg Ile Ile Pro Ala Val Gly Ser Val Thr Tyr Ala Gln Lys Phe Gln
1               5                   10                  15

Gly

<210> SEQ ID NO 38
<211> LENGTH: 17
<212> TYPE: PRT
<213> ORGANISM: Artificial Sequence
<220> FEATURE:
<223> OTHER INFORMATION: synthetic

<400> SEQUENCE: 38

Gly Ile Ile Pro Ile Phe Gly Thr Ala Asn Tyr Ala Gln Lys Phe Gln
1               5                   10                  15

Gly

<210> SEQ ID NO 39
<211> LENGTH: 17
<212> TYPE: PRT
<213> ORGANISM: Artificial Sequence
<220> FEATURE:
<223> OTHER INFORMATION: synthetic

<400> SEQUENCE: 39

```
Trp Met Ser Pro Ser Ser Gly Ile Thr Gly Tyr Ala Gln Lys Phe Gln
1               5                   10                  15

Gly

<210> SEQ ID NO 40
<211> LENGTH: 17
<212> TYPE: PRT
<213> ORGANISM: Artificial Sequence
<220> FEATURE:
<223> OTHER INFORMATION: synthetic

<400> SEQUENCE: 40

Trp Met Thr Pro Ser Thr Gly Asn Ala Gly Tyr Ala Gln Lys Phe Gln
1               5                   10                  15

Gly

<210> SEQ ID NO 41
<211> LENGTH: 17
<212> TYPE: PRT
<213> ORGANISM: Artificial Sequence
<220> FEATURE:
<223> OTHER INFORMATION: synthetic

<400> SEQUENCE: 41

Trp Met Asn Pro Asn Ser Gly Asn Thr Gly Tyr Ala Gln Lys Phe Gln
1               5                   10                  15

Gly

<210> SEQ ID NO 42
<211> LENGTH: 17
<212> TYPE: PRT
<213> ORGANISM: Artificial Sequence
<220> FEATURE:
<223> OTHER INFORMATION: synthetic

<400> SEQUENCE: 42

Trp Met His Pro Asn Ser Gly His Thr Gly Tyr Ala Gln Lys Phe Gln
1               5                   10                  15

Gly

<210> SEQ ID NO 43
<211> LENGTH: 17
<212> TYPE: PRT
<213> ORGANISM: Artificial Sequence
<220> FEATURE:
<223> OTHER INFORMATION: synthetic

<400> SEQUENCE: 43

Trp Met Asn Pro Asn Ser Gly His Thr Gly Asn Ala Gln Lys Phe Gln
1               5                   10                  15

Gly

<210> SEQ ID NO 44
<211> LENGTH: 17
<212> TYPE: PRT
<213> ORGANISM: Artificial Sequence
<220> FEATURE:
<223> OTHER INFORMATION: synthetic

<400> SEQUENCE: 44

Trp Ile Asp Pro Asn Ser Gly Val Thr Ser Ser Ala Gln Lys Phe Gln
1               5                   10                  15

Gly
```

```
<210> SEQ ID NO 45
<211> LENGTH: 17
<212> TYPE: PRT
<213> ORGANISM: Artificial Sequence
<220> FEATURE:
<223> OTHER INFORMATION: synthetic

<400> SEQUENCE: 45

Trp Ile Ser Pro Asn Ser Gly Val Thr Asp Phe Thr Gln Lys Phe Gln
1               5                   10                  15

Gly

<210> SEQ ID NO 46
<211> LENGTH: 17
<212> TYPE: PRT
<213> ORGANISM: Artificial Sequence
<220> FEATURE:
<223> OTHER INFORMATION: synthetic

<400> SEQUENCE: 46

Trp Met Asn Pro Asn Ser Gly His Thr Gly Tyr Ala Gln Arg Phe Gln
1               5                   10                  15

Gly

<210> SEQ ID NO 47
<211> LENGTH: 17
<212> TYPE: PRT
<213> ORGANISM: Artificial Sequence
<220> FEATURE:
<223> OTHER INFORMATION: synthetic

<400> SEQUENCE: 47

Trp Met Ser Pro Asn Gly Gly Asn Thr Gly Tyr Ala Gln Lys Phe Gln
1               5                   10                  15

Gly

<210> SEQ ID NO 48
<211> LENGTH: 17
<212> TYPE: PRT
<213> ORGANISM: Artificial Sequence
<220> FEATURE:
<223> OTHER INFORMATION: synthetic

<400> SEQUENCE: 48

Trp Met Asp Pro Ser Ser Gly Tyr Thr Gly Ser Ala His Lys Phe Gln
1               5                   10                  15

Gly

<210> SEQ ID NO 49
<211> LENGTH: 17
<212> TYPE: PRT
<213> ORGANISM: Artificial Sequence
<220> FEATURE:
<223> OTHER INFORMATION: synthetic

<400> SEQUENCE: 49

Trp Met Asn Pro His Ser Ala Asp Thr Gly Tyr Ala Glu Lys Phe Gln
1               5                   10                  15

Gly

<210> SEQ ID NO 50
<211> LENGTH: 17
```

<212> TYPE: PRT
<213> ORGANISM: Artificial Sequence
<220> FEATURE:
<223> OTHER INFORMATION: synthetic

<400> SEQUENCE: 50

Trp Leu Thr Pro Ser Thr Gly His Ala Gly Tyr Ala Gln Lys Phe Gln
1               5                   10                  15

Gly

<210> SEQ ID NO 51
<211> LENGTH: 17
<212> TYPE: PRT
<213> ORGANISM: Artificial Sequence
<220> FEATURE:
<223> OTHER INFORMATION: synthetic

<400> SEQUENCE: 51

Trp Met Asn Pro Asn Ser Gly His Thr Gly Tyr Ala Gln Lys Phe Gln
1               5                   10                  15

Gly

<210> SEQ ID NO 52
<211> LENGTH: 17
<212> TYPE: PRT
<213> ORGANISM: Artificial Sequence
<220> FEATURE:
<223> OTHER INFORMATION: synthetic

<400> SEQUENCE: 52

Trp Ile Ser Pro Gln His Gly Val Arg Asn Tyr Ala His Lys Phe Gln
1               5                   10                  15

Gly

<210> SEQ ID NO 53
<211> LENGTH: 17
<212> TYPE: PRT
<213> ORGANISM: Artificial Sequence
<220> FEATURE:
<223> OTHER INFORMATION: synthetic

<400> SEQUENCE: 53

Met Ile Asn Pro Ser Gly Gly Ser Thr Ser Tyr Ala Gln Lys Phe Gln
1               5                   10                  15

Gly

<210> SEQ ID NO 54
<211> LENGTH: 17
<212> TYPE: PRT
<213> ORGANISM: Artificial Sequence
<220> FEATURE:
<223> OTHER INFORMATION: synthetic

<400> SEQUENCE: 54

Trp Ile Ser Pro Arg Ser Gly Val Thr Ser Tyr Ala Gln Lys Phe Gln
1               5                   10                  15

Gly

<210> SEQ ID NO 55
<211> LENGTH: 17
<212> TYPE: PRT
<213> ORGANISM: Artificial Sequence
<220> FEATURE:
<223> OTHER INFORMATION: synthetic -continued

<400> SEQUENCE: 55

Trp Met Asp Pro Asn Ser Gly Asn Thr Gly Tyr Ala Gln Lys Phe Gln
1               5                   10                  15

Gly

<210> SEQ ID NO 56
<211> LENGTH: 17
<212> TYPE: PRT
<213> ORGANISM: Artificial Sequence
<220> FEATURE:
<223> OTHER INFORMATION: synthetic

<400> SEQUENCE: 56

Trp Met Asn Pro Thr Gly Gly Ile Thr Gly Tyr Ala Gln Lys Phe Gln
1               5                   10                  15

Gly

<210> SEQ ID NO 57
<211> LENGTH: 17
<212> TYPE: PRT
<213> ORGANISM: Artificial Sequence
<220> FEATURE:
<223> OTHER INFORMATION: synthetic

<400> SEQUENCE: 57

Trp Val Ser Pro Ile His Gly Leu Thr Gly Tyr Ala Pro Arg Phe Gln
1               5                   10                  15

Gly

<210> SEQ ID NO 58
<211> LENGTH: 18
<212> TYPE: PRT
<213> ORGANISM: Artificial Sequence
<220> FEATURE:
<223> OTHER INFORMATION: synthetic

<400> SEQUENCE: 58

Asp Leu Tyr Pro Tyr Val Val Val Val Ala Ala Gly Ser Tyr Gly Met
1               5                   10                  15

Asp Val

<210> SEQ ID NO 59
<211> LENGTH: 12
<212> TYPE: PRT
<213> ORGANISM: Artificial Sequence
<220> FEATURE:
<223> OTHER INFORMATION: synthetic

<400> SEQUENCE: 59

Pro Ser Ile Val Gly Ala Tyr Asp Ala Phe Asp Ile
1               5                   10

<210> SEQ ID NO 60
<211> LENGTH: 9
<212> TYPE: PRT
<213> ORGANISM: Artificial Sequence
<220> FEATURE:
<223> OTHER INFORMATION: synthetic

<400> SEQUENCE: 60

Glu Ser Val Glu Gly Tyr Phe Asp Leu
1               5

<210> SEQ ID NO 61
<211> LENGTH: 11
<212> TYPE: PRT
<213> ORGANISM: Artificial Sequence
<220> FEATURE:
<223> OTHER INFORMATION: synthetic

<400> SEQUENCE: 61

Asp Asn Trp Asn Val His Asp Ala Phe Asp Ile
1               5                   10

<210> SEQ ID NO 62
<211> LENGTH: 9
<212> TYPE: PRT
<213> ORGANISM: Artificial Sequence
<220> FEATURE:
<223> OTHER INFORMATION: synthetic

<400> SEQUENCE: 62

Gly Thr Tyr Asn Asp Ala Phe Asp Ile
1               5

<210> SEQ ID NO 63
<211> LENGTH: 11
<212> TYPE: PRT
<213> ORGANISM: Artificial Sequence
<220> FEATURE:
<223> OTHER INFORMATION: synthetic

<400> SEQUENCE: 63

Glu Gln Trp Leu Val Asn Asp Ala Phe Asp Ile
1               5                   10

<210> SEQ ID NO 64
<211> LENGTH: 13
<212> TYPE: PRT
<213> ORGANISM: Artificial Sequence
<220> FEATURE:
<223> OTHER INFORMATION: synthetic

<400> SEQUENCE: 64

Asp Ser Ser Gly Trp Met Arg Asn Asp Ala Phe Asp Ile
1               5                   10

<210> SEQ ID NO 65
<211> LENGTH: 14
<212> TYPE: PRT
<213> ORGANISM: Artificial Sequence
<220> FEATURE:
<223> OTHER INFORMATION: synthetic

<400> SEQUENCE: 65

Ser Met Phe Pro Thr Ile Phe Gly Asp Asn Ala Phe Asp Ile
1               5                   10

<210> SEQ ID NO 66
<211> LENGTH: 14
<212> TYPE: PRT
<213> ORGANISM: Artificial Sequence
<220> FEATURE:
<223> OTHER INFORMATION: synthetic

<400> SEQUENCE: 66

Ala Leu Phe Pro Tyr Pro Phe Tyr Tyr Tyr Met Asp Val
1               5                   10

```
<210> SEQ ID NO 67
<211> LENGTH: 7
<212> TYPE: PRT
<213> ORGANISM: Artificial Sequence
<220> FEATURE:
<223> OTHER INFORMATION: synthetic

<400> SEQUENCE: 67

Asp Arg Gly Trp Phe Asp Pro
1               5

<210> SEQ ID NO 68
<211> LENGTH: 10
<212> TYPE: PRT
<213> ORGANISM: Artificial Sequence
<220> FEATURE:
<223> OTHER INFORMATION: synthetic

<400> SEQUENCE: 68

Asp Ala Arg Gly Tyr Ser Gly Tyr Asp Leu
1               5                   10

<210> SEQ ID NO 69
<211> LENGTH: 9
<212> TYPE: PRT
<213> ORGANISM: Artificial Sequence
<220> FEATURE:
<223> OTHER INFORMATION: synthetic

<400> SEQUENCE: 69

Glu Gly Arg His Gly Glu Tyr Leu Tyr
1               5

<210> SEQ ID NO 70
<211> LENGTH: 11
<212> TYPE: PRT
<213> ORGANISM: Artificial Sequence
<220> FEATURE:
<223> OTHER INFORMATION: synthetic

<400> SEQUENCE: 70

Glu Gly Trp Gly Ser Ser Gly Tyr Phe Asp Tyr
1               5                   10

<210> SEQ ID NO 71
<211> LENGTH: 15
<212> TYPE: PRT
<213> ORGANISM: Artificial Sequence
<220> FEATURE:
<223> OTHER INFORMATION: synthetic

<400> SEQUENCE: 71

His Leu Phe Pro Thr Val Phe Asp Asp Tyr Tyr Gly Met Asp Val
1               5                   10                  15

<210> SEQ ID NO 72
<211> LENGTH: 10
<212> TYPE: PRT
<213> ORGANISM: Artificial Sequence
<220> FEATURE:
<223> OTHER INFORMATION: synthetic

<400> SEQUENCE: 72

Gly Gly Tyr Ser Tyr Gly Ser Phe Gln His
1               5                   10

<210> SEQ ID NO 73
```

```
<211> LENGTH: 10
<212> TYPE: PRT
<213> ORGANISM: Artificial Sequence
<220> FEATURE:
<223> OTHER INFORMATION: synthetic

<400> SEQUENCE: 73

Val Arg Trp Ser Ser Asp Ala Phe Asp Ile
1               5                   10

<210> SEQ ID NO 74
<211> LENGTH: 9
<212> TYPE: PRT
<213> ORGANISM: Artificial Sequence
<220> FEATURE:
<223> OTHER INFORMATION: synthetic

<400> SEQUENCE: 74

Glu Glu Trp Leu Gly His Phe Gln His
1               5

<210> SEQ ID NO 75
<211> LENGTH: 9
<212> TYPE: PRT
<213> ORGANISM: Artificial Sequence
<220> FEATURE:
<223> OTHER INFORMATION: synthetic

<400> SEQUENCE: 75

Glu Arg Phe Leu Gly Gly Met Asp Val
1               5

<210> SEQ ID NO 76
<211> LENGTH: 9
<212> TYPE: PRT
<213> ORGANISM: Artificial Sequence
<220> FEATURE:
<223> OTHER INFORMATION: synthetic

<400> SEQUENCE: 76

Gly Asn Trp Val Asp Ala Phe Asp Ile
1               5

<210> SEQ ID NO 77
<211> LENGTH: 11
<212> TYPE: PRT
<213> ORGANISM: Artificial Sequence
<220> FEATURE:
<223> OTHER INFORMATION: synthetic

<400> SEQUENCE: 77

Glu Ser Glu Val Met Met Ala Tyr Phe Gln His
1               5                   10

<210> SEQ ID NO 78
<211> LENGTH: 9
<212> TYPE: PRT
<213> ORGANISM: Artificial Sequence
<220> FEATURE:
<223> OTHER INFORMATION: synthetic

<400> SEQUENCE: 78

Glu Ser Trp Ser Gly Glu Phe Asp Tyr
1               5

<210> SEQ ID NO 79
<211> LENGTH: 9
```

-continued

```
<212> TYPE: PRT
<213> ORGANISM: Artificial Sequence
<220> FEATURE:
<223> OTHER INFORMATION: synthetic

<400> SEQUENCE: 79

Glu Ala Val Ala Gly Pro Met Asp Val
1               5

<210> SEQ ID NO 80
<211> LENGTH: 10
<212> TYPE: PRT
<213> ORGANISM: Artificial Sequence
<220> FEATURE:
<223> OTHER INFORMATION: synthetic

<400> SEQUENCE: 80

Asp Ala Trp Glu Leu Leu Ala Phe Asp Ile
1               5                   10

<210> SEQ ID NO 81
<211> LENGTH: 10
<212> TYPE: PRT
<213> ORGANISM: Artificial Sequence
<220> FEATURE:
<223> OTHER INFORMATION: synthetic

<400> SEQUENCE: 81

Asp Arg Trp Asp Gly Asp Tyr Tyr Ser Ala
1               5                   10

<210> SEQ ID NO 82
<211> LENGTH: 10
<212> TYPE: PRT
<213> ORGANISM: Artificial Sequence
<220> FEATURE:
<223> OTHER INFORMATION: synthetic

<400> SEQUENCE: 82

Glu Ser Trp Glu Leu Thr Gly Phe Asp Tyr
1               5                   10

<210> SEQ ID NO 83
<211> LENGTH: 9
<212> TYPE: PRT
<213> ORGANISM: Artificial Sequence
<220> FEATURE:
<223> OTHER INFORMATION: synthetic

<400> SEQUENCE: 83

Glu Arg Phe Ala Gly Gly Met Asp Ala
1               5

<210> SEQ ID NO 84
<211> LENGTH: 8
<212> TYPE: PRT
<213> ORGANISM: Artificial Sequence
<220> FEATURE:
<223> OTHER INFORMATION: synthetic

<400> SEQUENCE: 84

Asp Ser Gly Gly Ala Phe Asp Ile
1               5

<210> SEQ ID NO 85
<211> LENGTH: 9
<212> TYPE: PRT
```

<213> ORGANISM: Artificial Sequence
<220> FEATURE:
<223> OTHER INFORMATION: synthetic

<400> SEQUENCE: 85

Glu Val Phe Glu Gly Gly Met Asp Val
1               5

<210> SEQ ID NO 86
<211> LENGTH: 9
<212> TYPE: PRT
<213> ORGANISM: Artificial Sequence
<220> FEATURE:
<223> OTHER INFORMATION: synthetic

<400> SEQUENCE: 86

Glu Gly Tyr Gly Gly Asn Tyr Gly Asn
1               5

<210> SEQ ID NO 87
<211> LENGTH: 9
<212> TYPE: PRT
<213> ORGANISM: Artificial Sequence
<220> FEATURE:
<223> OTHER INFORMATION: synthetic

<400> SEQUENCE: 87

Glu Asp Phe Tyr Gly Asp Phe Asp Tyr
1               5

<210> SEQ ID NO 88
<211> LENGTH: 9
<212> TYPE: PRT
<213> ORGANISM: Artificial Sequence
<220> FEATURE:
<223> OTHER INFORMATION: synthetic

<400> SEQUENCE: 88

Glu Leu Ser Arg Trp Gly Phe Asp Tyr
1               5

<210> SEQ ID NO 89
<211> LENGTH: 14
<212> TYPE: PRT
<213> ORGANISM: Artificial Sequence
<220> FEATURE:
<223> OTHER INFORMATION: synthetic

<400> SEQUENCE: 89

Asp Ile Phe Pro Thr Met Ile Ala Gly Gly Gly Phe Asp Leu
1               5                   10

<210> SEQ ID NO 90
<211> LENGTH: 10
<212> TYPE: PRT
<213> ORGANISM: Artificial Sequence
<220> FEATURE:
<223> OTHER INFORMATION: synthetic

<400> SEQUENCE: 90

Gly Gly Tyr Ser Tyr Gly Ser Phe Asp Tyr
1               5                   10

<210> SEQ ID NO 91
<211> LENGTH: 15
<212> TYPE: PRT
<213> ORGANISM: Artificial Sequence
<220> FEATURE:
<223> OTHER INFORMATION: synthetic

<400> SEQUENCE: 91

Gly Ser Phe Pro Leu Val Phe Thr Ile Phe Gly Val Gly Asp Val
1               5                   10                  15

<210> SEQ ID NO 92
<211> LENGTH: 10
<212> TYPE: PRT
<213> ORGANISM: Artificial Sequence
<220> FEATURE:
<223> OTHER INFORMATION: synthetic

<400> SEQUENCE: 92

Asp Leu Asp Tyr Val Arg Ala Phe Asp Ile
1               5                   10

<210> SEQ ID NO 93
<211> LENGTH: 9
<212> TYPE: PRT
<213> ORGANISM: Artificial Sequence
<220> FEATURE:
<223> OTHER INFORMATION: synthetic

<400> SEQUENCE: 93

Glu Ser Trp Gly Gly Tyr Phe Asp Leu
1               5

<210> SEQ ID NO 94
<211> LENGTH: 9
<212> TYPE: PRT
<213> ORGANISM: Artificial Sequence
<220> FEATURE:
<223> OTHER INFORMATION: synthetic

<400> SEQUENCE: 94

Asp Arg Thr Thr Tyr Ala Phe Asp Ile
1               5

<210> SEQ ID NO 95
<211> LENGTH: 11
<212> TYPE: PRT
<213> ORGANISM: Artificial Sequence
<220> FEATURE:
<223> OTHER INFORMATION: synthetic

<400> SEQUENCE: 95

Val His Gly Ser Gly Ser Asp Gly Met Asp Val
1               5                   10

<210> SEQ ID NO 96
<211> LENGTH: 11
<212> TYPE: PRT
<213> ORGANISM: Artificial Sequence
<220> FEATURE:
<223> OTHER INFORMATION: synthetic

<400> SEQUENCE: 96

Arg Ala Ser Gln Gly Ile Asp Ser Tyr Leu Ala
1               5                   10

<210> SEQ ID NO 97
<211> LENGTH: 11
<212> TYPE: PRT
<213> ORGANISM: Artificial Sequence
<220> FEATURE:

<223> OTHER INFORMATION: synthetic

<400> SEQUENCE: 97

Arg Ala Ser Gln Ser Ile Ser Ser Trp Leu Ala
1               5                   10

<210> SEQ ID NO 98
<211> LENGTH: 11
<212> TYPE: PRT
<213> ORGANISM: Artificial Sequence
<220> FEATURE:
<223> OTHER INFORMATION: synthetic

<400> SEQUENCE: 98

Arg Ala Ser Gln Ser Ile Ser Ser Tyr Leu Asn
1               5                   10

<210> SEQ ID NO 99
<211> LENGTH: 11
<212> TYPE: PRT
<213> ORGANISM: Artificial Sequence
<220> FEATURE:
<223> OTHER INFORMATION: synthetic

<400> SEQUENCE: 99

Arg Ala Ser Gln Gly Ile Ser Ser Tyr Leu Ala
1               5                   10

<210> SEQ ID NO 100
<211> LENGTH: 11
<212> TYPE: PRT
<213> ORGANISM: Artificial Sequence
<220> FEATURE:
<223> OTHER INFORMATION: synthetic

<400> SEQUENCE: 100

Arg Ala Ser Gln Thr Ile Ser Asn Tyr Leu Asn
1               5                   10

<210> SEQ ID NO 101
<211> LENGTH: 12
<212> TYPE: PRT
<213> ORGANISM: Artificial Sequence
<220> FEATURE:
<223> OTHER INFORMATION: synthetic

<400> SEQUENCE: 101

Arg Ala Ser Gln Ser Val Asp Arg Asn Tyr Val Thr
1               5                   10

<210> SEQ ID NO 102
<211> LENGTH: 11
<212> TYPE: PRT
<213> ORGANISM: Artificial Sequence
<220> FEATURE:
<223> OTHER INFORMATION: synthetic

<400> SEQUENCE: 102

Arg Ala Ser Gln Gly Ile Ser Gln Tyr Leu Ala
1               5                   10

<210> SEQ ID NO 103
<211> LENGTH: 11
<212> TYPE: PRT
<213> ORGANISM: Artificial Sequence
<220> FEATURE:
<223> OTHER INFORMATION: synthetic

<400> SEQUENCE: 103

Gln Ala Ser Gln Asp Ile Gly Asn Tyr Leu Asn
1               5                   10

<210> SEQ ID NO 104
<211> LENGTH: 11
<212> TYPE: PRT
<213> ORGANISM: Artificial Sequence
<220> FEATURE:
<223> OTHER INFORMATION: synthetic

<400> SEQUENCE: 104

Arg Ala Ser Gln Gly Ile Arg Asn Asp Leu Gly
1               5                   10

<210> SEQ ID NO 105
<211> LENGTH: 11
<212> TYPE: PRT
<213> ORGANISM: Artificial Sequence
<220> FEATURE:
<223> OTHER INFORMATION: synthetic

<400> SEQUENCE: 105

Arg Ala Ser Gln Ile Ile Gly Asn Tyr Leu Ala
1               5                   10

<210> SEQ ID NO 106
<211> LENGTH: 11
<212> TYPE: PRT
<213> ORGANISM: Artificial Sequence
<220> FEATURE:
<223> OTHER INFORMATION: synthetic

<400> SEQUENCE: 106

Arg Ala Ser Gln Ile Ile Ser Ser Tyr Leu Asn
1               5                   10

<210> SEQ ID NO 107
<211> LENGTH: 11
<212> TYPE: PRT
<213> ORGANISM: Artificial Sequence
<220> FEATURE:
<223> OTHER INFORMATION: synthetic

<400> SEQUENCE: 107

Gln Ala Ser Gln Asp Ile Ser Asn Tyr Leu Asn
1               5                   10

<210> SEQ ID NO 108
<211> LENGTH: 11
<212> TYPE: PRT
<213> ORGANISM: Artificial Sequence
<220> FEATURE:
<223> OTHER INFORMATION: synthetic

<400> SEQUENCE: 108

Arg Ala Ser Gln Gly Ile Ser Asn Tyr Leu Ala
1               5                   10

<210> SEQ ID NO 109
<211> LENGTH: 11
<212> TYPE: PRT
<213> ORGANISM: Artificial Sequence
<220> FEATURE:
<223> OTHER INFORMATION: synthetic

```
<400> SEQUENCE: 109

Arg Ala Ser Gln Gly Ile Ser Asn Asn Leu Asn
1               5                   10

<210> SEQ ID NO 110
<211> LENGTH: 11
<212> TYPE: PRT
<213> ORGANISM: Artificial Sequence
<220> FEATURE:
<223> OTHER INFORMATION: synthetic

<400> SEQUENCE: 110

Arg Ala Ser Gln Gly Ile Ser Asn Gly Leu Ser
1               5                   10

<210> SEQ ID NO 111
<211> LENGTH: 11
<212> TYPE: PRT
<213> ORGANISM: Artificial Sequence
<220> FEATURE:
<223> OTHER INFORMATION: synthetic

<400> SEQUENCE: 111

Arg Ala Ser Gln Ser Ile Thr Gly Trp Leu Ala
1               5                   10

<210> SEQ ID NO 112
<211> LENGTH: 11
<212> TYPE: PRT
<213> ORGANISM: Artificial Sequence
<220> FEATURE:
<223> OTHER INFORMATION: synthetic

<400> SEQUENCE: 112

Arg Ala Ser Gln Gly Ile Arg Asn Asp Leu Ala
1               5                   10

<210> SEQ ID NO 113
<211> LENGTH: 11
<212> TYPE: PRT
<213> ORGANISM: Artificial Sequence
<220> FEATURE:
<223> OTHER INFORMATION: synthetic

<400> SEQUENCE: 113

Gln Ala Ser Gln Asp Ile Ser Ser Tyr Leu Asn
1               5                   10

<210> SEQ ID NO 114
<211> LENGTH: 11
<212> TYPE: PRT
<213> ORGANISM: Artificial Sequence
<220> FEATURE:
<223> OTHER INFORMATION: synthetic

<400> SEQUENCE: 114

Arg Ala Ser Gln Ser Ile Thr Thr Tyr Leu Asn
1               5                   10

<210> SEQ ID NO 115
<211> LENGTH: 11
<212> TYPE: PRT
<213> ORGANISM: Artificial Sequence
<220> FEATURE:
<223> OTHER INFORMATION: synthetic

<400> SEQUENCE: 115
```

-continued

```
Arg Ala Ser Gln Ser Val Ser Thr Trp Leu Ala
1               5                   10

<210> SEQ ID NO 116
<211> LENGTH: 11
<212> TYPE: PRT
<213> ORGANISM: Artificial Sequence
<220> FEATURE:
<223> OTHER INFORMATION: synthetic

<400> SEQUENCE: 116

Arg Ala Ser Gln Ser Ile Ser Asn Trp Leu Ala
1               5                   10

<210> SEQ ID NO 117
<211> LENGTH: 11
<212> TYPE: PRT
<213> ORGANISM: Artificial Sequence
<220> FEATURE:
<223> OTHER INFORMATION: synthetic

<400> SEQUENCE: 117

Gln Ala Ser Gln Gly Ile Ser Asn Tyr Leu Ala
1               5                   10

<210> SEQ ID NO 118
<211> LENGTH: 12
<212> TYPE: PRT
<213> ORGANISM: Artificial Sequence
<220> FEATURE:
<223> OTHER INFORMATION: synthetic

<400> SEQUENCE: 118

Arg Ala Ser Gln Ser Leu Ser Ser Ser Ser Leu Ala
1               5                   10

<210> SEQ ID NO 119
<211> LENGTH: 11
<212> TYPE: PRT
<213> ORGANISM: Artificial Sequence
<220> FEATURE:
<223> OTHER INFORMATION: synthetic

<400> SEQUENCE: 119

Arg Ala Ser Glu His Ile Ala Asn Trp Leu Ala
1               5                   10

<210> SEQ ID NO 120
<211> LENGTH: 11
<212> TYPE: PRT
<213> ORGANISM: Artificial Sequence
<220> FEATURE:
<223> OTHER INFORMATION: synthetic

<400> SEQUENCE: 120

Arg Ala Ser Gln Ser Val Gly Ser Trp Val Ala
1               5                   10

<210> SEQ ID NO 121
<211> LENGTH: 11
<212> TYPE: PRT
<213> ORGANISM: Artificial Sequence
<220> FEATURE:
<223> OTHER INFORMATION: synthetic

<400> SEQUENCE: 121
```

-continued

```
Arg Ala Ser Gln Ser Ile Ser Pro Trp Leu Ala
1               5                   10

<210> SEQ ID NO 122
<211> LENGTH: 11
<212> TYPE: PRT
<213> ORGANISM: Artificial Sequence
<220> FEATURE:
<223> OTHER INFORMATION: synthetic

<400> SEQUENCE: 122

Arg Ala Ser Gln Gly Ile Ser Arg Tyr Leu Ala
1               5                   10

<210> SEQ ID NO 123
<211> LENGTH: 12
<212> TYPE: PRT
<213> ORGANISM: Artificial Sequence
<220> FEATURE:
<223> OTHER INFORMATION: synthetic

<400> SEQUENCE: 123

Arg Ala Ser Gln Thr Val Ser Ser Asn Tyr Leu Ala
1               5                   10

<210> SEQ ID NO 124
<211> LENGTH: 11
<212> TYPE: PRT
<213> ORGANISM: Artificial Sequence
<220> FEATURE:
<223> OTHER INFORMATION: synthetic

<400> SEQUENCE: 124

Arg Ser Ser Gln Gly Ile Arg Asn Asp Leu Ser
1               5                   10

<210> SEQ ID NO 125
<211> LENGTH: 11
<212> TYPE: PRT
<213> ORGANISM: Artificial Sequence
<220> FEATURE:
<223> OTHER INFORMATION: synthetic

<400> SEQUENCE: 125

Arg Asp Ser His Ser Ile Thr Thr Trp Leu Ala
1               5                   10

<210> SEQ ID NO 126
<211> LENGTH: 11
<212> TYPE: PRT
<213> ORGANISM: Artificial Sequence
<220> FEATURE:
<223> OTHER INFORMATION: synthetic

<400> SEQUENCE: 126

Arg Ala Ser Gln Ser Ile Ser Arg Trp Leu Ala
1               5                   10

<210> SEQ ID NO 127
<211> LENGTH: 11
<212> TYPE: PRT
<213> ORGANISM: Artificial Sequence
<220> FEATURE:
<223> OTHER INFORMATION: synthetic

<400> SEQUENCE: 127

Arg Ala Ser Gln Val Ile Arg Asn Asp Leu Ala
```

-continued

```
1               5                    10

<210> SEQ ID NO 128
<211> LENGTH: 11
<212> TYPE: PRT
<213> ORGANISM: Artificial Sequence
<220> FEATURE:
<223> OTHER INFORMATION: synthetic

<400> SEQUENCE: 128

Arg Ala Ser Gln Ser Ile Ser Arg Tyr Leu Asn
1               5                    10

<210> SEQ ID NO 129
<211> LENGTH: 7
<212> TYPE: PRT
<213> ORGANISM: Artificial Sequence
<220> FEATURE:
<223> OTHER INFORMATION: synthetic

<400> SEQUENCE: 129

Ala Ala Ser Ser Leu Gln Ser
1               5

<210> SEQ ID NO 130
<211> LENGTH: 7
<212> TYPE: PRT
<213> ORGANISM: Artificial Sequence
<220> FEATURE:
<223> OTHER INFORMATION: synthetic

<400> SEQUENCE: 130

Gly Ala Ser Asn Leu Gln Ser
1               5

<210> SEQ ID NO 131
<211> LENGTH: 7
<212> TYPE: PRT
<213> ORGANISM: Artificial Sequence
<220> FEATURE:
<223> OTHER INFORMATION: synthetic

<400> SEQUENCE: 131

Gly Ala Ser Thr Arg Ala Thr
1               5

<210> SEQ ID NO 132
<211> LENGTH: 7
<212> TYPE: PRT
<213> ORGANISM: Artificial Sequence
<220> FEATURE:
<223> OTHER INFORMATION: synthetic

<400> SEQUENCE: 132

Gly Ala Ser Asn Leu His Ser
1               5

<210> SEQ ID NO 133
<211> LENGTH: 7
<212> TYPE: PRT
<213> ORGANISM: Artificial Sequence
<220> FEATURE:
<223> OTHER INFORMATION: synthetic

<400> SEQUENCE: 133

Ala Ala Ser Ser Leu Glu Ser
1               5
```

```
<210> SEQ ID NO 134
<211> LENGTH: 7
<212> TYPE: PRT
<213> ORGANISM: Artificial Sequence
<220> FEATURE:
<223> OTHER INFORMATION: synthetic

<400> SEQUENCE: 134

Ser Ala Ser Asn Leu Gln Ser
1               5

<210> SEQ ID NO 135
<211> LENGTH: 7
<212> TYPE: PRT
<213> ORGANISM: Artificial Sequence
<220> FEATURE:
<223> OTHER INFORMATION: synthetic

<400> SEQUENCE: 135

Ala Ala Ser Thr Leu Glu Ser
1               5

<210> SEQ ID NO 136
<211> LENGTH: 7
<212> TYPE: PRT
<213> ORGANISM: Artificial Sequence
<220> FEATURE:
<223> OTHER INFORMATION: synthetic

<400> SEQUENCE: 136

His Ala Ser Ile Leu Glu Thr
1               5

<210> SEQ ID NO 137
<211> LENGTH: 7
<212> TYPE: PRT
<213> ORGANISM: Artificial Sequence
<220> FEATURE:
<223> OTHER INFORMATION: synthetic

<400> SEQUENCE: 137

Ala Ala Ser Thr Leu Gln Ser
1               5

<210> SEQ ID NO 138
<211> LENGTH: 7
<212> TYPE: PRT
<213> ORGANISM: Artificial Sequence
<220> FEATURE:
<223> OTHER INFORMATION: synthetic

<400> SEQUENCE: 138

Ala Ala Thr Thr Leu Gln Ser
1               5

<210> SEQ ID NO 139
<211> LENGTH: 7
<212> TYPE: PRT
<213> ORGANISM: Artificial Sequence
<220> FEATURE:
<223> OTHER INFORMATION: synthetic

<400> SEQUENCE: 139

Asp Ala Thr His Leu Glu Thr
1               5
```

```
<210> SEQ ID NO 140
<211> LENGTH: 7
<212> TYPE: PRT
<213> ORGANISM: Artificial Sequence
<220> FEATURE:
<223> OTHER INFORMATION: synthetic

<400> SEQUENCE: 140

Ala Ala Ser Ser Leu Gln Thr
1               5

<210> SEQ ID NO 141
<211> LENGTH: 7
<212> TYPE: PRT
<213> ORGANISM: Artificial Sequence
<220> FEATURE:
<223> OTHER INFORMATION: synthetic

<400> SEQUENCE: 141

Ala Ala Ser Ser Leu Gln Gly
1               5

<210> SEQ ID NO 142
<211> LENGTH: 7
<212> TYPE: PRT
<213> ORGANISM: Artificial Sequence
<220> FEATURE:
<223> OTHER INFORMATION: synthetic

<400> SEQUENCE: 142

Ala Ala Ser Asn Leu Glu Ser
1               5

<210> SEQ ID NO 143
<211> LENGTH: 7
<212> TYPE: PRT
<213> ORGANISM: Artificial Sequence
<220> FEATURE:
<223> OTHER INFORMATION: synthetic

<400> SEQUENCE: 143

Asp Val Ser His Leu Glu Ser
1               5

<210> SEQ ID NO 144
<211> LENGTH: 7
<212> TYPE: PRT
<213> ORGANISM: Artificial Sequence
<220> FEATURE:
<223> OTHER INFORMATION: synthetic

<400> SEQUENCE: 144

Asp Ala Ser Ser Leu Gln Ser
1               5

<210> SEQ ID NO 145
<211> LENGTH: 7
<212> TYPE: PRT
<213> ORGANISM: Artificial Sequence
<220> FEATURE:
<223> OTHER INFORMATION: synthetic

<400> SEQUENCE: 145

Gly Val Ser Ser Leu Glu Ser
1               5
```

-continued

```
<210> SEQ ID NO 146
<211> LENGTH: 7
<212> TYPE: PRT
<213> ORGANISM: Artificial Sequence
<220> FEATURE:
<223> OTHER INFORMATION: synthetic

<400> SEQUENCE: 146

Pro Ala Ser Thr Leu Gln Ser
1               5

<210> SEQ ID NO 147
<211> LENGTH: 7
<212> TYPE: PRT
<213> ORGANISM: Artificial Sequence
<220> FEATURE:
<223> OTHER INFORMATION: synthetic

<400> SEQUENCE: 147

Asp Ala Ser Asn Leu Glu Thr
1               5

<210> SEQ ID NO 148
<211> LENGTH: 7
<212> TYPE: PRT
<213> ORGANISM: Artificial Sequence
<220> FEATURE:
<223> OTHER INFORMATION: synthetic

<400> SEQUENCE: 148

Gly Ala Ser Thr Arg Ala Ser
1               5

<210> SEQ ID NO 149
<211> LENGTH: 7
<212> TYPE: PRT
<213> ORGANISM: Artificial Sequence
<220> FEATURE:
<223> OTHER INFORMATION: synthetic

<400> SEQUENCE: 149

Asp Ser Ser Ser Leu Gln Thr
1               5

<210> SEQ ID NO 150
<211> LENGTH: 7
<212> TYPE: PRT
<213> ORGANISM: Artificial Sequence
<220> FEATURE:
<223> OTHER INFORMATION: synthetic

<400> SEQUENCE: 150

Ala Thr Ser Thr Leu Gln Ser
1               5

<210> SEQ ID NO 151
<211> LENGTH: 7
<212> TYPE: PRT
<213> ORGANISM: Artificial Sequence
<220> FEATURE:
<223> OTHER INFORMATION: synthetic

<400> SEQUENCE: 151

Leu Ala Ser Asn Ser His Ser
1               5

<210> SEQ ID NO 152
```

```
<211> LENGTH: 9
<212> TYPE: PRT
<213> ORGANISM: Artificial Sequence
<220> FEATURE:
<223> OTHER INFORMATION: synthetic

<400> SEQUENCE: 152

Gln Gln Ser Tyr Ser Thr Pro Ile Thr
1               5

<210> SEQ ID NO 153
<211> LENGTH: 9
<212> TYPE: PRT
<213> ORGANISM: Artificial Sequence
<220> FEATURE:
<223> OTHER INFORMATION: synthetic

<400> SEQUENCE: 153

Gln Gln Ser Tyr Thr Thr Pro Ile Thr
1               5

<210> SEQ ID NO 154
<211> LENGTH: 9
<212> TYPE: PRT
<213> ORGANISM: Artificial Sequence
<220> FEATURE:
<223> OTHER INFORMATION: synthetic

<400> SEQUENCE: 154

Gln Gln Ile Phe Ser Thr Pro Leu Thr
1               5

<210> SEQ ID NO 155
<211> LENGTH: 9
<212> TYPE: PRT
<213> ORGANISM: Artificial Sequence
<220> FEATURE:
<223> OTHER INFORMATION: synthetic

<400> SEQUENCE: 155

Gln Gln Ser Tyr Ser Thr Pro Leu Thr
1               5

<210> SEQ ID NO 156
<211> LENGTH: 9
<212> TYPE: PRT
<213> ORGANISM: Artificial Sequence
<220> FEATURE:
<223> OTHER INFORMATION: synthetic

<400> SEQUENCE: 156

Gln Gln Ser Tyr Thr Thr Pro Tyr Thr
1               5

<210> SEQ ID NO 157
<211> LENGTH: 9
<212> TYPE: PRT
<213> ORGANISM: Artificial Sequence
<220> FEATURE:
<223> OTHER INFORMATION: synthetic

<400> SEQUENCE: 157

Gln Gln Thr Phe Thr Thr Pro Leu Thr
1               5

<210> SEQ ID NO 158
<211> LENGTH: 9
```

-continued

```
<212> TYPE: PRT
<213> ORGANISM: Artificial Sequence
<220> FEATURE:
<223> OTHER INFORMATION: synthetic

<400> SEQUENCE: 158

Gln Gln Ala Asn Ser Phe Pro Phe Thr
1               5

<210> SEQ ID NO 159
<211> LENGTH: 9
<212> TYPE: PRT
<213> ORGANISM: Artificial Sequence
<220> FEATURE:
<223> OTHER INFORMATION: synthetic

<400> SEQUENCE: 159

Gln Gln Ser Tyr Thr Thr Pro Tyr Ser
1               5

<210> SEQ ID NO 160
<211> LENGTH: 9
<212> TYPE: PRT
<213> ORGANISM: Artificial Sequence
<220> FEATURE:
<223> OTHER INFORMATION: synthetic

<400> SEQUENCE: 160

Gln Gln Thr Phe Ile Thr Pro Leu Thr
1               5

<210> SEQ ID NO 161
<211> LENGTH: 8
<212> TYPE: PRT
<213> ORGANISM: Artificial Sequence
<220> FEATURE:
<223> OTHER INFORMATION: synthetic

<400> SEQUENCE: 161

Gln Gln Ser Tyr Ser Thr Pro Thr
1               5

<210> SEQ ID NO 162
<211> LENGTH: 9
<212> TYPE: PRT
<213> ORGANISM: Artificial Sequence
<220> FEATURE:
<223> OTHER INFORMATION: synthetic

<400> SEQUENCE: 162

Gln Gln Gly Phe Ser Thr Pro Phe Thr
1               5

<210> SEQ ID NO 163
<211> LENGTH: 9
<212> TYPE: PRT
<213> ORGANISM: Artificial Sequence
<220> FEATURE:
<223> OTHER INFORMATION: synthetic

<400> SEQUENCE: 163

Gln Gln Ser Phe Thr Asn Pro Val Thr
1               5

<210> SEQ ID NO 164
<211> LENGTH: 9
<212> TYPE: PRT
```

-continued

```
<213> ORGANISM: Artificial Sequence
<220> FEATURE:
<223> OTHER INFORMATION: synthetic

<400> SEQUENCE: 164

Gln Gln Ser Tyr Ser Ala Pro Tyr Thr
1               5

<210> SEQ ID NO 165
<211> LENGTH: 9
<212> TYPE: PRT
<213> ORGANISM: Artificial Sequence
<220> FEATURE:
<223> OTHER INFORMATION: synthetic

<400> SEQUENCE: 165

Gln Gln Ser Tyr Ser Thr Pro Tyr Thr
1               5

<210> SEQ ID NO 166
<211> LENGTH: 9
<212> TYPE: PRT
<213> ORGANISM: Artificial Sequence
<220> FEATURE:
<223> OTHER INFORMATION: synthetic

<400> SEQUENCE: 166

Gln Gln Ser His Ser Thr Pro Leu Thr
1               5

<210> SEQ ID NO 167
<211> LENGTH: 9
<212> TYPE: PRT
<213> ORGANISM: Artificial Sequence
<220> FEATURE:
<223> OTHER INFORMATION: synthetic

<400> SEQUENCE: 167

Gln Gln Ser Tyr Ser Thr Pro Phe Thr
1               5

<210> SEQ ID NO 168
<211> LENGTH: 9
<212> TYPE: PRT
<213> ORGANISM: Artificial Sequence
<220> FEATURE:
<223> OTHER INFORMATION: synthetic

<400> SEQUENCE: 168

Gln Gln Tyr Gly Ser Ser Pro Phe Thr
1               5

<210> SEQ ID NO 169
<211> LENGTH: 9
<212> TYPE: PRT
<213> ORGANISM: Artificial Sequence
<220> FEATURE:
<223> OTHER INFORMATION: synthetic

<400> SEQUENCE: 169

Gln Gln Thr Tyr Ser Thr Pro Ile Thr
1               5

<210> SEQ ID NO 170
<211> LENGTH: 9
<212> TYPE: PRT
<213> ORGANISM: Artificial Sequence
```

<220> FEATURE:
<223> OTHER INFORMATION: synthetic

<400> SEQUENCE: 170

Gln Gln Tyr Tyr Thr Thr Pro Leu Thr
1               5

<210> SEQ ID NO 171
<211> LENGTH: 9
<212> TYPE: PRT
<213> ORGANISM: Artificial Sequence
<220> FEATURE:
<223> OTHER INFORMATION: synthetic

<400> SEQUENCE: 171

Gln Gln Ser Phe Ser Thr Pro Leu Thr
1               5

<210> SEQ ID NO 172
<211> LENGTH: 9
<212> TYPE: PRT
<213> ORGANISM: Artificial Sequence
<220> FEATURE:
<223> OTHER INFORMATION: synthetic

<400> SEQUENCE: 172

Gln Gln Ser Tyr Ser Thr Pro Pro Thr
1               5

<210> SEQ ID NO 173
<211> LENGTH: 9
<212> TYPE: PRT
<213> ORGANISM: Artificial Sequence
<220> FEATURE:
<223> OTHER INFORMATION: synthetic

<400> SEQUENCE: 173

Leu Gln His Asn Ser Tyr Pro Leu Thr
1               5

<210> SEQ ID NO 174
<211> LENGTH: 9
<212> TYPE: PRT
<213> ORGANISM: Artificial Sequence
<220> FEATURE:
<223> OTHER INFORMATION: synthetic

<400> SEQUENCE: 174

Gln Gln Ser Tyr Ser Thr Pro Val Thr
1               5

<210> SEQ ID NO 175
<211> LENGTH: 9
<212> TYPE: PRT
<213> ORGANISM: Artificial Sequence
<220> FEATURE:
<223> OTHER INFORMATION: synthetic

<400> SEQUENCE: 175

Gln His Phe Tyr Asn Thr Gln Tyr Thr
1               5

<210> SEQ ID NO 176
<211> LENGTH: 10
<212> TYPE: PRT
<213> ORGANISM: Artificial Sequence
<220> FEATURE:

-continued

```
<223> OTHER INFORMATION: synthetic

<400> SEQUENCE: 176

Gln Gln Ser Leu Gln Tyr Pro Ser His Phe
1               5                   10

<210> SEQ ID NO 177
<211> LENGTH: 30
<212> TYPE: PRT
<213> ORGANISM: Artificial Sequence
<220> FEATURE:
<223> OTHER INFORMATION: synthetic

<400> SEQUENCE: 177

Gln Val Gln Leu Val Gln Ser Gly Ala Glu Val Lys Lys Pro Gly Ala
1               5                   10                  15

Ser Val Lys Val Ser Cys Lys Ala Ser Gly Gly Thr Phe Ser
            20                  25                  30

<210> SEQ ID NO 178
<211> LENGTH: 30
<212> TYPE: PRT
<213> ORGANISM: Artificial Sequence
<220> FEATURE:
<223> OTHER INFORMATION: synthetic

<400> SEQUENCE: 178

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 179
<211> LENGTH: 30
<212> TYPE: PRT
<213> ORGANISM: Artificial Sequence
<220> FEATURE:
<223> OTHER INFORMATION: synthetic

<400> SEQUENCE: 179

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn
            20                  25                  30

<210> SEQ ID NO 180
<211> LENGTH: 30
<212> TYPE: PRT
<213> ORGANISM: Artificial Sequence
<220> FEATURE:
<223> OTHER INFORMATION: synthetic

<400> SEQUENCE: 180

Gln Val Gln Leu Val Gln Ser Gly Ala Glu Val Lys Lys Pro Gly Ala
1               5                   10                  15

Ser Val Lys Val Ser Cys Lys Ala Ser Gly Asn Thr Phe Thr
            20                  25                  30

<210> SEQ ID NO 181
<211> LENGTH: 30
<212> TYPE: PRT
<213> ORGANISM: Artificial Sequence
<220> FEATURE:
<223> OTHER INFORMATION: synthetic
```

-continued

```
<400> SEQUENCE: 181

Gln Val Gln Leu Val Gln Ser Gly Ala Glu Val Lys Lys Pro Gly Ala
1               5                   10                  15

Ser Val Lys Val Ser Cys Lys Ala Ser Gly His Ser Phe Thr
            20                  25                  30

<210> SEQ ID NO 182
<211> LENGTH: 30
<212> TYPE: PRT
<213> ORGANISM: Artificial Sequence
<220> FEATURE:
<223> OTHER INFORMATION: synthetic

<400> SEQUENCE: 182

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Pro Phe Thr
            20                  25                  30

<210> SEQ ID NO 183
<211> LENGTH: 30
<212> TYPE: PRT
<213> ORGANISM: Artificial Sequence
<220> FEATURE:
<223> OTHER INFORMATION: synthetic

<400> SEQUENCE: 183

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Arg Phe Thr
            20                  25                  30

<210> SEQ ID NO 184
<211> LENGTH: 30
<212> TYPE: PRT
<213> ORGANISM: Artificial Sequence
<220> FEATURE:
<223> OTHER INFORMATION: synthetic

<400> SEQUENCE: 184

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser
            20                  25                  30

<210> SEQ ID NO 185
<211> LENGTH: 30
<212> TYPE: PRT
<213> ORGANISM: Artificial Sequence
<220> FEATURE:
<223> OTHER INFORMATION: synthetic

<400> SEQUENCE: 185

Gln Val Gln Leu Val Gln Ser Gly Ala Glu Val Lys Lys Pro Gly Ala
1               5                   10                  15

Ser Val Lys Val Ser Cys Lys Ala Ser Gly Asp Thr Phe Thr
            20                  25                  30

<210> SEQ ID NO 186
<211> LENGTH: 30
<212> TYPE: PRT
<213> ORGANISM: Artificial Sequence
<220> FEATURE:
<223> OTHER INFORMATION: synthetic
```

<400> SEQUENCE: 186

```
Gln Val Gln Leu Ala Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30
```

<210> SEQ ID NO 187
<211> LENGTH: 30
<212> TYPE: PRT
<213> ORGANISM: Artificial Sequence
<220> FEATURE:
<223> OTHER INFORMATION: synthetic

<400> SEQUENCE: 187

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser
            20                  25                  30
```

<210> SEQ ID NO 188
<211> LENGTH: 30
<212> TYPE: PRT
<213> ORGANISM: Artificial Sequence
<220> FEATURE:
<223> OTHER INFORMATION: synthetic

<400> SEQUENCE: 188

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Pro Phe Ser
            20                  25                  30
```

<210> SEQ ID NO 189
<211> LENGTH: 30
<212> TYPE: PRT
<213> ORGANISM: Artificial Sequence
<220> FEATURE:
<223> OTHER INFORMATION: synthetic

<400> SEQUENCE: 189

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr
            20                  25                  30
```

<210> SEQ ID NO 190
<211> LENGTH: 30
<212> TYPE: PRT
<213> ORGANISM: Artificial Sequence
<220> FEATURE:
<223> OTHER INFORMATION: synthetic

<400> SEQUENCE: 190

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ile
            20                  25                  30
```

<210> SEQ ID NO 191
<211> LENGTH: 30
<212> TYPE: PRT
<213> ORGANISM: Artificial Sequence
<220> FEATURE:

<223> OTHER INFORMATION: synthetic

<400> SEQUENCE: 191

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr
            20                  25                  30

<210> SEQ ID NO 192
<211> LENGTH: 14
<212> TYPE: PRT
<213> ORGANISM: Artificial Sequence
<220> FEATURE:
<223> OTHER INFORMATION: synthetic

<400> SEQUENCE: 192

Trp Val Arg Gln Ala Pro Gly Gln Gly Leu Glu Trp Met Gly
1               5                   10

<210> SEQ ID NO 193
<211> LENGTH: 14
<212> TYPE: PRT
<213> ORGANISM: Artificial Sequence
<220> FEATURE:
<223> OTHER INFORMATION: synthetic

<400> SEQUENCE: 193

Trp Val Arg Gln Ala Pro Gly Gln Gly Leu Glu Trp Leu Gly
1               5                   10

<210> SEQ ID NO 194
<211> LENGTH: 14
<212> TYPE: PRT
<213> ORGANISM: Artificial Sequence
<220> FEATURE:
<223> OTHER INFORMATION: synthetic

<400> SEQUENCE: 194

Trp Val Arg Gln Ala Pro Gly Gln Gly Leu Glu Trp Ile Gly
1               5                   10

<210> SEQ ID NO 195
<211> LENGTH: 14
<212> TYPE: PRT
<213> ORGANISM: Artificial Sequence
<220> FEATURE:
<223> OTHER INFORMATION: synthetic

<400> SEQUENCE: 195

Trp Val Arg Gln Ala Pro Gly Gln Gly Leu Glu Trp Val Gly
1               5                   10

<210> SEQ ID NO 196
<211> LENGTH: 32
<212> TYPE: PRT
<213> ORGANISM: Artificial Sequence
<220> FEATURE:
<223> OTHER INFORMATION: synthetic

<400> SEQUENCE: 196

Arg Val Thr Met Thr Arg Asp Thr Ser Thr Ser Thr Val Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 197
<211> LENGTH: 32
<212> TYPE: PRT
<213> ORGANISM: Artificial Sequence
<220> FEATURE:
<223> OTHER INFORMATION: synthetic

<400> SEQUENCE: 197

Arg Val Thr Met Thr Arg Asp Thr Ser Thr Ser Thr Val Tyr Met Glu
1               5                   10                  15

Leu Ser Ser Leu Arg Ser Glu Asp Thr Ala Val Tyr Tyr Cys Ala Ile
            20                  25                  30

<210> SEQ ID NO 198
<211> LENGTH: 32
<212> TYPE: PRT
<213> ORGANISM: Artificial Sequence
<220> FEATURE:
<223> OTHER INFORMATION: synthetic

<400> SEQUENCE: 198

Arg Val Thr Met Thr Arg Asp Thr Ser Thr Ser Thr Val Tyr Met Glu
1               5                   10                  15

Leu Ser Ser Leu Arg Ser Glu Asp Thr Ala Val Tyr Tyr Cys Thr Arg
            20                  25                  30

<210> SEQ ID NO 199
<211> LENGTH: 32
<212> TYPE: PRT
<213> ORGANISM: Artificial Sequence
<220> FEATURE:
<223> OTHER INFORMATION: synthetic

<400> SEQUENCE: 199

Arg Val Thr Ile Thr Ala Asp Glu Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 200
<211> LENGTH: 32
<212> TYPE: PRT
<213> ORGANISM: Artificial Sequence
<220> FEATURE:
<223> OTHER INFORMATION: synthetic

<400> SEQUENCE: 200

Arg Val Thr Met Thr Arg Asp Thr Ser Thr Ser Thr Val Asn Met Glu
1               5                   10                  15

Leu Ser Ser Leu Arg Ser Glu Asp Thr Ala Val Tyr Tyr Cys Ala Arg
            20                  25                  30

<210> SEQ ID NO 201
<211> LENGTH: 32
<212> TYPE: PRT
<213> ORGANISM: Artificial Sequence
<220> FEATURE:
<223> OTHER INFORMATION: synthetic

<400> SEQUENCE: 201

Arg Val Thr Met Thr Arg Asp Thr Ser Thr Ser Thr Val Tyr Met Glu
1               5                   10                  15

Leu Ser Ser Leu Arg Ser Glu Asp Thr Ala Val Tyr Tyr Cys Ala Glu
            20                  25                  30

```
<210> SEQ ID NO 202
<211> LENGTH: 11
<212> TYPE: PRT
<213> ORGANISM: Artificial Sequence
<220> FEATURE:
<223> OTHER INFORMATION: synthetic

<400> SEQUENCE: 202

Trp Gly Gln Gly Thr Leu Val Thr Val Ser Ser
1               5                   10

<210> SEQ ID NO 203
<211> LENGTH: 11
<212> TYPE: PRT
<213> ORGANISM: Artificial Sequence
<220> FEATURE:
<223> OTHER INFORMATION: synthetic

<400> SEQUENCE: 203

Trp Gly Gln Gly Thr Thr Val Thr Val Ser Ser
1               5                   10

<210> SEQ ID NO 204
<211> LENGTH: 11
<212> TYPE: PRT
<213> ORGANISM: Artificial Sequence
<220> FEATURE:
<223> OTHER INFORMATION: synthetic

<400> SEQUENCE: 204

Trp Gly Gln Gly Thr Met Val Thr Val Ser Ser
1               5                   10

<210> SEQ ID NO 205
<211> LENGTH: 11
<212> TYPE: PRT
<213> ORGANISM: Artificial Sequence
<220> FEATURE:
<223> OTHER INFORMATION: synthetic

<400> SEQUENCE: 205

Trp Gly Pro Gly Thr Met Val Thr Val Ser Ser
1               5                   10

<210> SEQ ID NO 206
<211> LENGTH: 11
<212> TYPE: PRT
<213> ORGANISM: Artificial Sequence
<220> FEATURE:
<223> OTHER INFORMATION: synthetic

<400> SEQUENCE: 206

Trp Gly Arg Gly Thr Leu Val Thr Val Ser Ser
1               5                   10

<210> SEQ ID NO 207
<211> LENGTH: 23
<212> TYPE: PRT
<213> ORGANISM: Artificial Sequence
<220> FEATURE:
<223> OTHER INFORMATION: synthetic

<400> SEQUENCE: 207

Asp Ile Gln Met Thr Gln Ser Pro Ser Ser Leu Ser Ala Ser Val Gly
1               5                   10                  15

Asp Arg Val Thr Ile Thr Cys
```

-continued

```
              20

<210> SEQ ID NO 208
<211> LENGTH: 23
<212> TYPE: PRT
<213> ORGANISM: Artificial Sequence
<220> FEATURE:
<223> OTHER INFORMATION: synthetic

<400> SEQUENCE: 208

Glu Ile Val Met Thr Gln Ser Pro Ala Thr Leu Ser Val Ser Pro Gly
1               5                   10                  15

Glu Arg Ala Thr Leu Ser Cys
            20

<210> SEQ ID NO 209
<211> LENGTH: 23
<212> TYPE: PRT
<213> ORGANISM: Artificial Sequence
<220> FEATURE:
<223> OTHER INFORMATION: synthetic

<400> SEQUENCE: 209

Asp Ile Gln Ile Thr His Ser Pro Ser Ser Leu Ser Ala Ser Val Gly
1               5                   10                  15

Tyr Arg Leu Thr Ile Thr Cys
            20

<210> SEQ ID NO 210
<211> LENGTH: 15
<212> TYPE: PRT
<213> ORGANISM: Artificial Sequence
<220> FEATURE:
<223> OTHER INFORMATION: synthetic

<400> SEQUENCE: 210

Trp Tyr Gln Gln Lys Pro Gly Lys Ala Pro Lys Leu Leu Ile Tyr
1               5                   10                  15

<210> SEQ ID NO 211
<211> LENGTH: 15
<212> TYPE: PRT
<213> ORGANISM: Artificial Sequence
<220> FEATURE:
<223> OTHER INFORMATION: synthetic

<400> SEQUENCE: 211

Trp Tyr Gln Gln Lys Pro Gly Gln Ala Pro Arg Leu Leu Ile Tyr
1               5                   10                  15

<210> SEQ ID NO 212
<211> LENGTH: 15
<212> TYPE: PRT
<213> ORGANISM: Artificial Sequence
<220> FEATURE:
<223> OTHER INFORMATION: synthetic

<400> SEQUENCE: 212

Trp Tyr His Gln Lys Pro Trp Asn Ala Pro Lys Leu Met Ile Tyr
1               5                   10                  15

<210> SEQ ID NO 213
<211> LENGTH: 32
<212> TYPE: PRT
<213> ORGANISM: Artificial Sequence
<220> FEATURE:
```

-continued

<223> OTHER INFORMATION: synthetic

<400> SEQUENCE: 213

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 214
<211> LENGTH: 32
<212> TYPE: PRT
<213> ORGANISM: Artificial Sequence
<220> FEATURE:
<223> OTHER INFORMATION: synthetic

<400> SEQUENCE: 214

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30

<210> SEQ ID NO 215
<211> LENGTH: 32
<212> TYPE: PRT
<213> ORGANISM: Artificial Sequence
<220> FEATURE:
<223> OTHER INFORMATION: synthetic

<400> SEQUENCE: 215

Gly Val Pro Ser Arg Phe Ser Gly Ser Gly Ser Gly Thr Tyr Phe Thr
1               5                   10                  15

Leu Thr Ile Ser Ser Leu Gln Pro Glu Asp Phe Ala Thr Tyr Tyr Cys
            20                  25                  30

<210> SEQ ID NO 216
<211> LENGTH: 32
<212> TYPE: PRT
<213> ORGANISM: Artificial Sequence
<220> FEATURE:
<223> OTHER INFORMATION: synthetic

<400> SEQUENCE: 216

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Pro Tyr Tyr Cys
            20                  25                  30

<210> SEQ ID NO 217
<211> LENGTH: 10
<212> TYPE: PRT
<213> ORGANISM: Artificial Sequence
<220> FEATURE:
<223> OTHER INFORMATION: synthetic

<400> SEQUENCE: 217

Phe Gly Gly Gly Thr Lys Val Glu Ile Lys
1               5                   10

<210> SEQ ID NO 218
<211> LENGTH: 10
<212> TYPE: PRT
<213> ORGANISM: Artificial Sequence
<220> FEATURE:
<223> OTHER INFORMATION: synthetic

<400> SEQUENCE: 218

Phe Gly Gln Gly Thr Lys Val Glu Ile Lys
1               5                   10

<210> SEQ ID NO 219
<211> LENGTH: 10
<212> TYPE: PRT
<213> ORGANISM: Artificial Sequence
<220> FEATURE:
<223> OTHER INFORMATION: synthetic

<400> SEQUENCE: 219

Phe Gly Gln Gly Thr Arg Leu Glu Ile Lys
1               5                   10

<210> SEQ ID NO 220
<211> LENGTH: 10
<212> TYPE: PRT
<213> ORGANISM: Artificial Sequence
<220> FEATURE:
<223> OTHER INFORMATION: synthetic

<400> SEQUENCE: 220

Phe Gly Gly Gly Thr Lys Leu Glu Ile Lys
1               5                   10

<210> SEQ ID NO 221
<211> LENGTH: 10
<212> TYPE: PRT
<213> ORGANISM: Artificial Sequence
<220> FEATURE:
<223> OTHER INFORMATION: synthetic

<400> SEQUENCE: 221

Phe Gly Gln Gly Thr Lys Leu Glu Ile Lys
1               5                   10

<210> SEQ ID NO 222
<211> LENGTH: 10
<212> TYPE: PRT
<213> ORGANISM: Artificial Sequence
<220> FEATURE:
<223> OTHER INFORMATION: synthetic

<400> SEQUENCE: 222

Phe Gly Pro Gly Thr Lys Val Asp Ile Lys
1               5                   10

<210> SEQ ID NO 223
<211> LENGTH: 127
<212> TYPE: PRT
<213> ORGANISM: Artificial Sequence
<220> FEATURE:
<223> OTHER INFORMATION: synthetic

<400> SEQUENCE: 223

Gln Val Gln Leu Val Gln Ser Gly Ala Glu Val Lys Lys Pro Gly Ala
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Val Ile Asn Pro Ser Ala Gly Ser Thr Asp Tyr Ala Gln Lys Phe
    50                  55                  60

```
Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Leu Tyr Pro Tyr Val Val Val Val Ala Ala Gly Ser Tyr
                100                 105                 110

Gly Met Asp Val Trp Gly Gln Gly Thr Leu Val Thr Val Ser Ser
            115                 120                 125
```

```
<210> SEQ ID NO 224
<211> LENGTH: 121
<212> TYPE: PRT
<213> ORGANISM: Artificial Sequence
<220> FEATURE:
<223> OTHER INFORMATION: synthetic
```

```
<400> SEQUENCE: 224
```

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Trp Met Asn Pro Asn Ser Asp Ile Ala Gly Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ile Pro Ser Ile Val Gly Ala Tyr Asp Ala Phe Asp Ile Trp Gly
                100                 105                 110

Gln Gly Thr Leu Val Thr Val Ser Ser
            115                 120
```

```
<210> SEQ ID NO 225
<211> LENGTH: 118
<212> TYPE: PRT
<213> ORGANISM: Artificial Sequence
<220> FEATURE:
<223> OTHER INFORMATION: synthetic
```

```
<400> SEQUENCE: 225
```

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg His
                20                  25                  30

Leu Leu His Trp Val Arg Gln Ala Pro Gly Gln Gly Leu Glu Trp Met
            35                  40                  45

Gly Trp Ile Ser Pro Gln His Gly Val Arg Asn Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ser Val Glu Gly Tyr Phe Asp Leu Trp Gly Gln Gly Thr
                100                 105                 110

Leu Val Thr Val Ser Ser
            115
```

<210> SEQ ID NO 226
<211> LENGTH: 120
<212> TYPE: PRT
<213> ORGANISM: Artificial Sequence
<220> FEATURE:
<223> OTHER INFORMATION: synthetic

<400> SEQUENCE: 226

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

His Met His Trp Val Arg Gln Ala Pro Gly Gln Gly Leu Glu Trp Met
        35                  40                  45

Gly Trp Val Ser Pro Ser His Gly Leu Thr Gly Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Asn Trp Asn Val His Asp Ala Phe Asp Ile Trp Gly Gln
            100                 105                 110

Gly Thr Leu Val Thr Val Ser Ser
        115                 120

<210> SEQ ID NO 227
<211> LENGTH: 117
<212> TYPE: PRT
<213> ORGANISM: Artificial Sequence
<220> FEATURE:
<223> OTHER INFORMATION: synthetic

<400> SEQUENCE: 227

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn Arg Phe
            20                  25                  30

Met His Trp Val Arg Gln Ala Pro Gly Gln Gly Leu Glu Trp Met Gly
        35                  40                  45

Trp Met Ser Leu Asn Ser Gly Leu Thr Gly Tyr Ala Gln Lys Phe Gln
    50                  55                  60

Gly Arg Val Thr Met Thr Arg Asp Thr Ser Thr Ser Thr Val Tyr Met
65                  70                  75                  80

Glu Leu Ser Ser Leu Arg Ser Glu Asp Thr Ala Val Tyr Tyr Cys Thr
                85                  90                  95

Arg Gly Thr Tyr Asn Asp Ala Phe Asp Ile Trp Gly Gln Gly Thr Leu
            100                 105                 110

Val Thr Val Ser Ser
        115

<210> SEQ ID NO 228
<211> LENGTH: 120
<212> TYPE: PRT
<213> ORGANISM: Artificial Sequence
<220> FEATURE:
<223> OTHER INFORMATION: synthetic

<400> SEQUENCE: 228

-continued

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Met Lys Pro Ser Ser Gly Thr Thr Gly Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Gln Trp Leu Val Asn Asp Ala Phe Asp Ile Trp Gly Gln
                100                 105                 110

Gly Thr Leu Val Thr Val Ser Ser
            115                 120
```

<210> SEQ ID NO 229
<211> LENGTH: 120
<212> TYPE: PRT
<213> ORGANISM: Artificial Sequence
<220> FEATURE:
<223> OTHER INFORMATION: synthetic

<400> SEQUENCE: 229

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Met Lys Pro Ser Ser Gly Thr Thr Gly Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Gln Trp Leu Val Asn Asp Ala Phe Asp Ile Trp Gly Gln
                100                 105                 110

Gly Thr Leu Val Thr Val Ser Ser
            115                 120
```

<210> SEQ ID NO 230
<211> LENGTH: 123
<212> TYPE: PRT
<213> ORGANISM: Artificial Sequence
<220> FEATURE:
<223> OTHER INFORMATION: synthetic

<400> SEQUENCE: 230

```
Gln Val Gln Leu Val Gln Ser Gly Ala Glu Val Lys Lys Pro Gly Ala
1               5                   10                  15

Ser Val Lys Val Ser Cys Lys Ala Ser Gly Asn Thr Phe Thr Ser Tyr
            20                  25                  30

Tyr Met His Trp Val Arg Gln Ala Pro Gly Gln Gly Leu Glu Trp Met
        35                  40                  45

Gly Gly Ile Asp Pro Asn Ser Gly Gly Thr Asn Tyr Ala Gln Lys Phe
    50                  55                  60
```

```
Gln Gly Arg Val Thr Met Thr Arg Asp Thr Ser Thr Ser Thr Val Tyr
65              70              75                  80

Met Glu Leu Ser Ser Leu Arg Ser Glu Asp Thr Ala Val Tyr Tyr Cys
                85              90                  95

Ala Arg Ser Met Phe Pro Thr Ile Phe Gly Asp Asn Ala Phe Asp Ile
            100             105             110

Trp Gly Gln Gly Thr Leu Val Thr Val Ser Ser
        115             120
```

<210> SEQ ID NO 231
<211> LENGTH: 123
<212> TYPE: PRT
<213> ORGANISM: Artificial Sequence
<220> FEATURE:
<223> OTHER INFORMATION: synthetic

<400> SEQUENCE: 231

```
Gln Val Gln Leu Val Gln Ser Gly Ala Glu Val Lys Lys Pro Gly Ala
1               5               10                  15

Ser Val Lys Val Ser Cys Lys Ala Ser Gly His Ser Phe Thr His Tyr
            20              25              30

Tyr Met His Trp Val Arg Gln Ala Pro Gly Gln Gly Leu Glu Trp Met
        35              40              45

Gly Trp Met Asn Pro Asp Ser Gly Ser Thr Gly Tyr Ala Gln Lys Phe
    50              55              60

Gln Gly Arg Val Thr Met Thr Arg Asp Thr Ser Thr Ser Thr Val Tyr
65              70              75                  80

Met Glu Leu Ser Ser Leu Arg Ser Glu Asp Thr Ala Val Tyr Tyr Cys
                85              90                  95

Ala Arg Ala Leu Phe Pro Tyr Pro Phe Tyr Tyr Tyr Tyr Met Asp Val
            100             105             110

Trp Gly Gln Gly Thr Leu Val Thr Val Ser Ser
        115             120
```

<210> SEQ ID NO 232
<211> LENGTH: 116
<212> TYPE: PRT
<213> ORGANISM: Artificial Sequence
<220> FEATURE:
<223> OTHER INFORMATION: synthetic

<400> SEQUENCE: 232

```
Gln Val Gln Leu Val Gln Ser Gly Ala Glu Val Lys Lys Pro Gly Ala
1               5               10                  15

Ser Val Lys Val Ser Cys Lys Ala Ser Gly Tyr Thr Phe Thr Gly Tyr
            20              25              30

Tyr Met His Trp Val Arg Gln Ala Pro Gly Gln Gly Leu Glu Trp Ile
        35              40              45

Gly Trp Met Ser Leu Asn Ser Gly Leu Thr Gly Tyr Ala Gln Lys Phe
    50              55              60

Gln Gly Arg Val Thr Met Thr Arg Asp Thr Ser Thr Ser Thr Val Tyr
65              70              75                  80

Met Glu Leu Ser Ser Leu Arg Ser Glu Asp Thr Ala Val Tyr Tyr Cys
                85              90                  95

Ala Arg Asp Arg Gly Trp Phe Asp Pro Trp Gly Gln Gly Thr Leu Val
            100             105             110

Thr Val Ser Ser
```

-continued

115

<210> SEQ ID NO 233
<211> LENGTH: 122
<212> TYPE: PRT
<213> ORGANISM: Artificial Sequence
<220> FEATURE:
<223> OTHER INFORMATION: synthetic

<400> SEQUENCE: 233

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Ile His Trp Val Arg Gln Ala Pro Gly Gln Gly Leu Glu Trp Leu
        35                  40                  45

Gly Trp Met Asn Pro Asn Gly Asp Val Ala Gly Tyr Ala Asp Ser Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
            85                  90                  95

Ala Ile Asp Ser Ser Gly Trp Met Arg Asn Asp Ala Phe Asp Ile Trp
            100                 105                 110

Gly Gln Gly Thr Leu Val Thr Val Ser Ser
        115                 120

<210> SEQ ID NO 234
<211> LENGTH: 119
<212> TYPE: PRT
<213> ORGANISM: Artificial Sequence
<220> FEATURE:
<223> OTHER INFORMATION: synthetic

<400> SEQUENCE: 234

Gln Val Gln Leu Val Gln Ser Gly Ala Glu Val Lys Lys Pro Gly Ala
1               5                   10                  15

Ser Val Lys Val Ser Cys Lys Ala Ser Gly Gly Thr Phe Ser Asn Tyr
            20                  25                  30

Met Tyr His Trp Val Arg Gln Ala Pro Gly Gln Gly Leu Glu Trp Met
        35                  40                  45

Gly Trp Ile Ser Thr Tyr His Gly Ser Thr Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
            85                  90                  95

Ala Arg Asp Ala Arg Gly Tyr Ser Gly Tyr Asp Leu Trp Gly Gln Gly
            100                 105                 110

Thr Leu Val Thr Val Ser Ser
        115

<210> SEQ ID NO 235
<211> LENGTH: 118
<212> TYPE: PRT
<213> ORGANISM: Artificial Sequence
<220> FEATURE:
<223> OTHER INFORMATION: synthetic

<400> SEQUENCE: 235

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Pro Phe Thr Ser Tyr
            20                  25                  30

Tyr Met His Trp Val Arg Gln Ala Pro Gly Gln Gly Leu Glu Trp Met
        35                  40                  45

Gly Trp Met Asn Pro Asn Ser Asp Ile Ala Gly Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Gly Arg His Gly Glu Tyr Leu Tyr Trp Gly Gln Gly Thr
            100                 105                 110

Leu Val Thr Val Ser Ser
            115
```

```
<210> SEQ ID NO 236
<211> LENGTH: 120
<212> TYPE: PRT
<213> ORGANISM: Artificial Sequence
<220> FEATURE:
<223> OTHER INFORMATION: synthetic

<400> SEQUENCE: 236
```

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Arg Phe Thr Thr Tyr
            20                  25                  30

Tyr Val His Trp Val Arg Gln Ala Pro Gly Gln Gly Leu Glu Trp Met
        35                  40                  45

Gly Trp Met Asn Pro Asn Thr Val Tyr Thr Gly Ser Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Gly Trp Gly Ser Ser Gly Tyr Phe Asp Tyr Trp Gly Gln
            100                 105                 110

Gly Thr Leu Val Thr Val Ser Ser
        115                 120
```

```
<210> SEQ ID NO 237
<211> LENGTH: 124
<212> TYPE: PRT
<213> ORGANISM: Artificial Sequence
<220> FEATURE:
<223> OTHER INFORMATION: synthetic

<400> SEQUENCE: 237
```

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Leu Ser Trp Val Arg Gln Ala Pro Gly Gln Gly Leu Glu Trp Met
        35                  40                  45

Gly Arg Ile Ile Pro Ala Val Gly Ser Val Thr Tyr Ala Gln Lys Phe
```

```
         50                    55                    60

Gln Gly Arg Val Thr Ile Thr Ala Asp Glu Ser Thr Ser Thr Ala Tyr
65                    70                    75                    80

Met Glu Leu Ser Ser Leu Arg Ser Glu Asp Thr Ala Val Tyr Tyr Cys
                  85                    90                    95

Ala Arg His Leu Phe Pro Thr Val Phe Asp Asp Tyr Tyr Gly Met Asp
              100                   105                   110

Val Trp Gly Gln Gly Thr Leu Val Thr Val Ser Ser
          115                   120
```

<210> SEQ ID NO 238
<211> LENGTH: 119
<212> TYPE: PRT
<213> ORGANISM: Artificial Sequence
<220> FEATURE:
<223> OTHER INFORMATION: synthetic

<400> SEQUENCE: 238

```
Gln Val Gln Leu Val Gln Ser Gly Ala Glu Val Lys Lys Pro Gly Ser
1                   5                     10                    15

Ser Val Lys Val Ser Cys Lys Ala Ser Gly Gly Thr Phe Ser Ser Tyr
                  20                    25                    30

Ala Ile Ser Trp Val Arg Gln Ala Pro Gly Gln Gly Leu Glu Trp Met
              35                    40                    45

Gly Gly Ile Ile Pro Ile Phe Gly Thr Ala Asn Tyr Ala Gln Lys Phe
          50                    55                    60

Gln Gly Arg Val Thr Ile Thr Ala Asp Glu Ser Thr Ser Thr Ala Tyr
65                    70                    75                    80

Met Glu Leu Ser Ser Leu Arg Ser Glu Asp Thr Ala Val Tyr Tyr Cys
                  85                    90                    95

Ala Arg Gly Gly Tyr Ser Tyr Gly Ser Phe Gln His Trp Gly Gln Gly
              100                   105                   110

Thr Leu Val Thr Val Ser Ser
          115
```

<210> SEQ ID NO 239
<211> LENGTH: 119
<212> TYPE: PRT
<213> ORGANISM: Artificial Sequence
<220> FEATURE:
<223> OTHER INFORMATION: synthetic

<400> SEQUENCE: 239

```
Gln Val Gln Leu Val Gln Ser Gly Ala Glu Val Lys Lys Pro Gly Ala
1                   5                     10                    15

Ser Val Lys Val Ser Cys Lys Ala Ser Gly Asp Thr Phe Thr Arg His
                  20                    25                    30

Tyr Val His Trp Val Arg Gln Ala Pro Gly Gln Gly Leu Glu Trp Met
              35                    40                    45

Gly Trp Met Ser Pro Ser Ser Gly Ile Thr Gly Tyr Ala Gln Lys Phe
          50                    55                    60

Gln Gly Arg Val Thr Met Thr Arg Asp Thr Ser Thr Ser Thr Val Tyr
65                    70                    75                    80

Met Glu Leu Ser Ser Leu Arg Ser Glu Asp Thr Ala Val Tyr Tyr Cys
                  85                    90                    95

Ala Arg Val Arg Trp Ser Ser Asp Ala Phe Asp Ile Trp Gly Gln Gly
              100                   105                   110
```

-continued

Thr Leu Val Thr Val Ser Ser
        115

<210> SEQ ID NO 240
<211> LENGTH: 118
<212> TYPE: PRT
<213> ORGANISM: Artificial Sequence
<220> FEATURE:
<223> OTHER INFORMATION: synthetic

<400> SEQUENCE: 240

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Val
        35                  40                  45

Gly Trp Met Thr Pro Ser Thr Gly Asn Ala Gly Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Glu Trp Leu Gly His Phe Gln His Trp Gly Gln Gly Thr
            100                 105                 110

Leu Val Thr Val Ser Ser
        115

<210> SEQ ID NO 241
<211> LENGTH: 118
<212> TYPE: PRT
<213> ORGANISM: Artificial Sequence
<220> FEATURE:
<223> OTHER INFORMATION: synthetic

<400> SEQUENCE: 241

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Tyr Met His Trp Val Arg Gln Ala Pro Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Arg Phe Leu Gly Gly Met Asp Val Trp Gly Gln Gly Thr
            100                 105                 110

Thr Val Thr Val Ser Ser
        115

<210> SEQ ID NO 242
<211> LENGTH: 118
<212> TYPE: PRT
<213> ORGANISM: Artificial Sequence
<220> FEATURE:
<223> OTHER INFORMATION: synthetic

<400> SEQUENCE: 242

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Met
        35                  40                  45

Gly Trp Met His Pro Asn Ser Gly His Thr Gly Tyr Ala Gln Lys Phe
    50                  55                  60

Gln Gly Arg Val Thr Met Thr Arg Asp Thr Ser Thr Ser Thr Val Asn
65                  70                  75                  80

Met Glu Leu Ser Ser Leu Arg Ser Glu Asp Thr Ala Val Tyr Tyr Cys
                85                  90                  95

Ala Arg Glu Glu Trp Leu Gly His Phe Gln His Trp Gly Gln Gly Thr
            100                 105                 110

Leu Val Thr Val Ser Ser
        115

<210> SEQ ID NO 243
<211> LENGTH: 118
<212> TYPE: PRT
<213> ORGANISM: Artificial Sequence
<220> FEATURE:
<223> OTHER INFORMATION: synthetic

<400> SEQUENCE: 243

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Tyr Met His Trp Val Arg Gln Ala Pro Gly Gln Gly Leu Glu Trp Met
        35                  40                  45

Gly Trp Met Asn Pro Asn Ser Gly His Thr Gly Asn Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Asn Trp Val Asp Ala Phe Asp Ile Trp Gly Gln Gly Thr
            100                 105                 110

Met Val Thr Val Ser Ser
        115

<210> SEQ ID NO 244
<211> LENGTH: 120
<212> TYPE: PRT
<213> ORGANISM: Artificial Sequence
<220> FEATURE:
<223> OTHER INFORMATION: synthetic

<400> SEQUENCE: 244

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Thr Leu His Trp Val Arg Gln Ala Pro Gly Gln Gly Leu Glu Trp Met
        35                  40                  45

```
Gly Trp Ile Asp Pro Asn Ser Gly Val Thr Ser Ser Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ser Glu Val Met Met Ala Tyr Phe Gln His Trp Gly Gln
                100                 105                 110

Gly Thr Leu Val Thr Val Ser Ser
        115                 120

<210> SEQ ID NO 245
<211> LENGTH: 118
<212> TYPE: PRT
<213> ORGANISM: Artificial Sequence
<220> FEATURE:
<223> OTHER INFORMATION: synthetic

<400> SEQUENCE: 245

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
        35                  40                  45

Gly Trp Ile Ser Pro Asn Ser Gly Val Thr Asp Phe Thr Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ser Trp Ser Gly Glu Phe Asp Tyr Trp Gly Gln Gly Thr
                100                 105                 110

Leu Val Thr Val Ser Ser
        115

<210> SEQ ID NO 246
<211> LENGTH: 118
<212> TYPE: PRT
<213> ORGANISM: Artificial Sequence
<220> FEATURE:
<223> OTHER INFORMATION: synthetic

<400> SEQUENCE: 246

Gln Val Gln Leu Val Gln Ser Gly Ala Glu Val Lys Lys Pro Gly Ala
1               5                   10                  15

Ser Val Lys Val Ser Cys Lys Ala Ser Gly Asp Thr Phe Thr Asn His
                20                  25                  30

Tyr Met His Trp Val Arg Gln Ala Pro Gly Gln Gly Leu Glu Trp Met
        35                  40                  45

Gly Trp Met Asn Pro Asn Ser Gly His Thr Gly Tyr Ala Gln Arg Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ala Val Ala Gly Pro Met Asp Val Trp Gly Gln Gly Thr
                100                 105                 110
```

Thr Val Thr Val Ser Ser
        115

<210> SEQ ID NO 247
<211> LENGTH: 119
<212> TYPE: PRT
<213> ORGANISM: Artificial Sequence
<220> FEATURE:
<223> OTHER INFORMATION: synthetic

<400> SEQUENCE: 247

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Met Asn Pro Asn Ser Asp Ile Ala Gly Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Ala Trp Glu Leu Leu Ala Phe Asp Ile Trp Gly Gln Gly
            100                 105                 110

Thr Leu Val Thr Val Ser Ser
        115

<210> SEQ ID NO 248
<211> LENGTH: 119
<212> TYPE: PRT
<213> ORGANISM: Artificial Sequence
<220> FEATURE:
<223> OTHER INFORMATION: synthetic

<400> SEQUENCE: 248

Gln Val Gln Leu Ala Gln Ser Gly Ala Glu Val Lys Lys Pro Gly Ala
1               5                   10                  15

Ser Val Lys Val Ser Cys Lys Ala Ser Gly Tyr Thr Phe Thr Asn His
            20                  25                  30

Tyr Met His Trp Val Arg Gln Ala Pro Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Arg Trp Asp Gly Asp Tyr Tyr Ser Ala Trp Gly Gln Gly
            100                 105                 110

Thr Leu Val Thr Val Ser Ser
        115

<210> SEQ ID NO 249
<211> LENGTH: 119
<212> TYPE: PRT
<213> ORGANISM: Artificial Sequence
<220> FEATURE:
<223> OTHER INFORMATION: synthetic

<400> SEQUENCE: 249

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Tyr Ile His Trp Val Arg Gln Ala Pro Gly Gln Gly Leu Glu Trp Met
        35                  40                  45

Gly Trp Met Ser Pro Asn Gly Gly Asn Thr Gly Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ser Trp Glu Leu Thr Gly Phe Asp Tyr Trp Gly Gln Gly
                100                 105                 110

Thr Leu Val Thr Val Ser Ser
        115

<210> SEQ ID NO 250
<211> LENGTH: 118
<212> TYPE: PRT
<213> ORGANISM: Artificial Sequence
<220> FEATURE:
<223> OTHER INFORMATION: synthetic

<400> SEQUENCE: 250

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Arg Phe Ala Gly Gly Met Asp Ala Trp Gly Gln Gly Thr
                100                 105                 110

Thr Val Thr Val Ser Ser
        115

<210> SEQ ID NO 251
<211> LENGTH: 117
<212> TYPE: PRT
<213> ORGANISM: Artificial Sequence
<220> FEATURE:
<223> OTHER INFORMATION: synthetic

<400> SEQUENCE: 251

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asn Ser
                20                  25                  30

Tyr Met His Trp Val Arg Gln Ala Pro Gly Gln Gly Leu Glu Trp Met
        35                  40                  45

-continued

```
Gly Trp Met Asp Pro Ser Ser Gly Tyr Thr Gly Ser Ala His Lys Phe
    50              55              60

Gln Gly Arg Val Thr Met Thr Arg Asp Thr Ser Thr Ser Thr Val Tyr
65              70              75              80

Met Glu Leu Ser Ser Leu Arg Ser Glu Asp Thr Ala Val Tyr Tyr Cys
                85              90              95

Ala Glu Asp Ser Gly Gly Ala Phe Asp Ile Trp Gly Gln Gly Thr Met
            100             105             110

Val Thr Val Ser Ser
        115

<210> SEQ ID NO 252
<211> LENGTH: 118
<212> TYPE: PRT
<213> ORGANISM: Artificial Sequence
<220> FEATURE:
<223> OTHER INFORMATION: synthetic

<400> SEQUENCE: 252

Gln Val Gln Leu Val Gln Ser Gly Ala Glu Val Lys Lys Pro Gly Ala
1               5               10              15

Ser Val Lys Val Ser Cys Lys Ala Ser Gly Tyr Pro Phe Ser Thr Tyr
            20              25              30

Tyr Met His Trp Val Arg Gln Ala Pro Gly Gln Gly Leu Glu Trp Met
        35              40              45

Gly Trp Met Asn Pro His Ser Ala Asp Thr Gly Tyr Ala Glu Lys Phe
    50              55              60

Gln Gly Arg Val Thr Met Thr Arg Asp Thr Ser Thr Ser Thr Val Tyr
65              70              75              80

Met Glu Leu Ser Ser Leu Arg Ser Glu Asp Thr Ala Val Tyr Tyr Cys
                85              90              95

Ala Arg Glu Val Phe Glu Gly Gly Met Asp Val Trp Gly Gln Gly Thr
            100             105             110

Thr Val Thr Val Ser Ser
        115

<210> SEQ ID NO 253
<211> LENGTH: 118
<212> TYPE: PRT
<213> ORGANISM: Artificial Sequence
<220> FEATURE:
<223> OTHER INFORMATION: synthetic

<400> SEQUENCE: 253

Gln Val Gln Leu Val Gln Ser Gly Ala Glu Val Lys Lys Pro Gly Ala
1               5               10              15

Ser Val Lys Val Ser Cys Lys Ala Ser Gly Tyr Thr Phe Thr Ser Tyr
            20              25              30

Tyr Met His Trp Val Arg Gln Ala Pro Gly Gln Gly Leu Glu Trp Met
        35              40              45

Gly Trp Leu Thr Pro Ser Thr Gly His Ala Gly Tyr Ala Gln Lys Phe
    50              55              60

Gln Gly Arg Val Thr Met Thr Arg Asp Thr Ser Thr Ser Thr Val Tyr
65              70              75              80

Met Glu Leu Ser Ser Leu Arg Ser Glu Asp Thr Ala Val Tyr Tyr Cys
                85              90              95

Ala Arg Glu Gly Tyr Gly Gly Asn Tyr Gly Asn Trp Gly Gln Gly Thr
```

-continued

```
                100                105                110

Leu Val Thr Val Ser Ser
        115

<210> SEQ ID NO 254
<211> LENGTH: 118
<212> TYPE: PRT
<213> ORGANISM: Artificial Sequence
<220> FEATURE:
<223> OTHER INFORMATION: synthetic

<400> SEQUENCE: 254

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Met Asn Pro Asn Ser Gly His Thr Gly Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Asp Phe Tyr Gly Asp Phe Asp Tyr Trp Gly Gln Gly Thr
            100                 105                 110

Leu Val Thr Val Ser Ser
        115

<210> SEQ ID NO 255
<211> LENGTH: 118
<212> TYPE: PRT
<213> ORGANISM: Artificial Sequence
<220> FEATURE:
<223> OTHER INFORMATION: synthetic

<400> SEQUENCE: 255

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg His
            20                  25                  30

Phe Ile His Trp Val Arg Gln Ala Pro Gly Gln Gly Leu Glu Trp Met
        35                  40                  45

Gly Trp Ile Asp Pro Asn Ser Gly Val Thr Ser Ser Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Leu Ser Arg Trp Gly Phe Asp Tyr Trp Gly Pro Gly Thr
            100                 105                 110

Met Val Thr Val Ser Ser
        115

<210> SEQ ID NO 256
<211> LENGTH: 118
<212> TYPE: PRT
<213> ORGANISM: Artificial Sequence
<220> FEATURE:
```

<223> OTHER INFORMATION: synthetic

<400> SEQUENCE: 256

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg His
                20                  25                  30

Leu Leu His Trp Val Arg Gln Ala Pro Gly Gln Gly Leu Glu Trp Met
            35                  40                  45

Gly Trp Ile Ser Pro Gln His Gly Val Arg Asn Tyr Ala His Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ser Val Glu Gly Tyr Phe Asp Leu Trp Gly Arg Gly Thr
                100                 105                 110

Leu Val Thr Val Ser Ser
        115

<210> SEQ ID NO 257
<211> LENGTH: 123
<212> TYPE: PRT
<213> ORGANISM: Artificial Sequence
<220> FEATURE:
<223> OTHER INFORMATION: synthetic

<400> SEQUENCE: 257

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Pro Phe Ser Ser Tyr
                20                  25                  30

Tyr Met His Trp Val Arg Gln Ala Pro Gly Gln Gly Leu Glu Trp Met
            35                  40                  45

Gly Met Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Ile Phe Pro Thr Met Ile Ala Gly Gly Gly Phe Asp Leu
                100                 105                 110

Trp Gly Arg Gly Thr Leu Val Thr Val Ser Ser
        115                 120

<210> SEQ ID NO 258
<211> LENGTH: 119
<212> TYPE: PRT
<213> ORGANISM: Artificial Sequence
<220> FEATURE:
<223> OTHER INFORMATION: synthetic

<400> SEQUENCE: 258

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Phe
                20                  25                  30

Gly Ile Ser Trp Val Arg Gln Ala Pro Gly Gln Gly Leu Glu Trp Met

-continued

```
              35                  40                  45
Gly Gly Ile Ile Pro Ile Phe Gly Thr Ala Asn Tyr Ala Gln Lys Phe
        50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                    85                  90                  95
Ala Arg Gly Gly Tyr Ser Tyr Gly Ser Phe Asp Tyr Trp Gly Gln Gly
                100                 105                 110
Thr Leu Val Thr Val Ser Ser
            115
```

<210> SEQ ID NO 259
<211> LENGTH: 124
<212> TYPE: PRT
<213> ORGANISM: Artificial Sequence
<220> FEATURE:
<223> OTHER INFORMATION: synthetic

<400> SEQUENCE: 259

```
Gln Val Gln Leu Val Gln Ser Gly Ala Glu Val Lys Lys Pro Gly Ala
1                   5                   10                  15
Ser Val Lys Val Ser Cys Lys Ala Ser Gly Tyr Thr Phe Thr Ser Tyr
                20                  25                  30
Gly Ile Asn Trp Val Arg Gln Ala Pro Gly Gln Gly Leu Glu Trp Met
            35                  40                  45
Gly Trp Met Asn Pro Asn Ser Gly Asn Thr Gly Tyr Ala Gln Lys Phe
        50                  55                  60
Gln Gly Arg Val Thr Met Thr Arg Asp Thr Ser Thr Ser Thr Val Tyr
65                  70                  75                  80
Met Glu Leu Ser Ser Leu Arg Ser Glu Asp Thr Ala Val Tyr Tyr Cys
                    85                  90                  95
Ala Arg Gly Ser Phe Pro Leu Val Phe Thr Ile Phe Gly Val Gly Asp
                100                 105                 110
Val Trp Gly Gln Gly Thr Met Val Thr Val Ser Ser
            115                 120
```

<210> SEQ ID NO 260
<211> LENGTH: 119
<212> TYPE: PRT
<213> ORGANISM: Artificial Sequence
<220> FEATURE:
<223> OTHER INFORMATION: synthetic

<400> SEQUENCE: 260

```
Gln Val Gln Leu Val Gln Ser Gly Ala Glu Val Lys Lys Pro Gly Ala
1                   5                   10                  15
Ser Val Lys Val Ser Cys Lys Ala Ser Gly Tyr Thr Phe Thr Ser Tyr
                20                  25                  30
Tyr Met His Trp Val Arg Gln Ala Pro Gly Gln Gly Leu Glu Trp Met
            35                  40                  45
Gly Trp Ile Ser Pro Arg Ser Gly Val Thr Ser Tyr Ala Gln Lys Phe
        50                  55                  60
Gln Gly Arg Val Thr Met Thr Arg Asp Thr Ser Thr Ser Thr Val Tyr
65                  70                  75                  80
Met Glu Leu Ser Ser Leu Arg Ser Glu Asp Thr Ala Val Tyr Tyr Cys
                    85                  90                  95
```

-continued

```
Ala Arg Asp Leu Asp Tyr Val Arg Ala Phe Asp Ile Trp Gly Gln Gly
            100                 105                 110

Thr Thr Val Thr Val Ser Ser
        115

<210> SEQ ID NO 261
<211> LENGTH: 118
<212> TYPE: PRT
<213> ORGANISM: Artificial Sequence
<220> FEATURE:
<223> OTHER INFORMATION: synthetic

<400> SEQUENCE: 261

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
            20                  25                  30

Tyr Met His Trp Val Arg Gln Ala Pro Gly Gln Gly Leu Glu Trp Met
        35                  40                  45

Gly Trp Met Asp Pro Asn Ser Gly Asn Thr Gly Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ser Trp Gly Gly Tyr Phe Asp Leu Trp Gly Arg Gly Thr
            100                 105                 110

Leu Val Thr Val Ser Ser
        115

<210> SEQ ID NO 262
<211> LENGTH: 118
<212> TYPE: PRT
<213> ORGANISM: Artificial Sequence
<220> FEATURE:
<223> OTHER INFORMATION: synthetic

<400> SEQUENCE: 262

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ile Asn His
            20                  25                  30

Tyr Val His Trp Val Arg Gln Ala Pro Gly Gln Gly Leu Glu Trp Met
        35                  40                  45

Gly Trp Met Asn Pro Thr Gly Gly Ile Thr Gly Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Arg Thr Thr Tyr Ala Phe Asp Ile Trp Gly Gln Gly Thr
            100                 105                 110

Met Val Thr Val Ser Ser
        115

<210> SEQ ID NO 263
<211> LENGTH: 118
<212> TYPE: PRT
<213> ORGANISM: Artificial Sequence
```

<220> FEATURE:
<223> OTHER INFORMATION: synthetic

<400> SEQUENCE: 263

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
                20                  25                  30

Tyr Met His Trp Val Arg Gln Ala Pro Gly Gln Gly Leu Glu Trp Met
            35                  40                  45

Gly Trp Met Asn Pro Asn Ser Gly His Thr Gly Asn Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Asn Trp Val Asp Ala Phe Asp Ile Trp Gly Gln Gly Thr
            100                 105                 110

Met Val Thr Val Ser Ser
        115

<210> SEQ ID NO 264
<211> LENGTH: 120
<212> TYPE: PRT
<213> ORGANISM: Artificial Sequence
<220> FEATURE:
<223> OTHER INFORMATION: synthetic

<400> SEQUENCE: 264

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Arg His
                20                  25                  30

Leu Leu His Trp Val Arg Gln Ala Pro Gly Gln Gly Leu Glu Trp Met
            35                  40                  45

Gly Trp Val Ser Pro Ile His Gly Leu Thr Gly Tyr Ala Pro Arg Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val His Gly Ser Gly Ser Asp Gly Met Asp Val Trp Gly Gln
            100                 105                 110

Gly Thr Thr Val Thr Val Ser Ser
        115                 120

<210> SEQ ID NO 265
<211> LENGTH: 107
<212> TYPE: PRT
<213> ORGANISM: Artificial Sequence
<220> FEATURE:
<223> OTHER INFORMATION: synthetic

<400> SEQUENCE: 265

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asp Ser Tyr
            20                  25                  30

```
Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ile
                85                  90                  95

Thr Phe Gly Gly Gly Thr Lys Val Glu Ile Lys
            100                 105
```

<210> SEQ ID NO 266
<211> LENGTH: 107
<212> TYPE: PRT
<213> ORGANISM: Artificial Sequence
<220> FEATURE:
<223> OTHER INFORMATION: synthetic

<400> SEQUENCE: 266

```
Asp Ile Gln Met Thr Gln Ser Pro Ser Ser Leu Ser Ala Ser Val Gly
1                   5                   10                  15

Asp Arg Val Thr Ile Thr Cys Arg Ala Ser Gln Ser Ile Ser Ser Trp
        20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Ile
                85                  90                  95

Thr Phe Gly Gly Gly Thr Lys Val Glu Ile Lys
            100                 105
```

<210> SEQ ID NO 267
<211> LENGTH: 107
<212> TYPE: PRT
<213> ORGANISM: Artificial Sequence
<220> FEATURE:
<223> OTHER INFORMATION: synthetic

<400> SEQUENCE: 267

```
Asp Ile Gln Met Thr Gln Ser Pro Ser Ser Leu Ser Ala Ser Val Gly
1                   5                   10                  15

Asp Arg Val Thr Ile Thr Cys Arg Ala Ser Gln Ser Ile Ser Ser Tyr
        20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ile Phe Ser Thr Pro Leu
                85                  90                  95

Thr Phe Gly Gly Gly Thr Lys Val Glu Ile Lys
            100                 105
```

<210> SEQ ID NO 268

```
<211> LENGTH: 107
<212> TYPE: PRT
<213> ORGANISM: Artificial Sequence
<220> FEATURE:
<223> OTHER INFORMATION: synthetic

<400> SEQUENCE: 268

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Gly Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105

<210> SEQ ID NO 269
<211> LENGTH: 107
<212> TYPE: PRT
<213> ORGANISM: Artificial Sequence
<220> FEATURE:
<223> OTHER INFORMATION: synthetic

<400> SEQUENCE: 269

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Ile
                85                  90                  95

Thr Phe Gly Gly Gly Thr Lys Val Glu Ile Lys
            100                 105

<210> SEQ ID NO 270
<211> LENGTH: 108
<212> TYPE: PRT
<213> ORGANISM: Artificial Sequence
<220> FEATURE:
<223> OTHER INFORMATION: synthetic

<400> SEQUENCE: 270

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Asp Arg Asn
            20                  25                  30

Tyr Val Thr Trp Tyr Gln Gln Lys Pro Gly Gln Ala Pro Arg Leu Leu
        35                  40                  45
```

```
Ile Tyr Gly Ala Ser Thr Arg Ala Thr Gly Ile Pro Ala Arg Phe Ser
    50                  55                  60

Gly Ser Gly Ser Gly Thr Glu Phe Thr Leu Thr Ile Ser Ser Leu Gln
65                  70                  75                  80

Ser Glu Asp Phe Ala Val Tyr Tyr Cys Gln Gln Ser Tyr Thr Thr Pro
                85                  90                  95

Tyr Thr Phe Gly Gln Gly Thr Lys Val Glu Ile Lys
            100                 105
```

```
<210> SEQ ID NO 271
<211> LENGTH: 107
<212> TYPE: PRT
<213> ORGANISM: Artificial Sequence
<220> FEATURE:
<223> OTHER INFORMATION: synthetic

<400> SEQUENCE: 271

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Gln Tyr
                20                  25                  30

Leu Ala Trp Tyr Gln Gln Lys Pro Gly Lys Ala Pro Lys Leu Leu Ile
            35                  40                  45

Tyr Gly Ala Ser Asn Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Phe Thr Thr Pro Leu
                85                  90                  95

Thr Phe Gly Gly Gly Thr Lys Val Glu Ile Lys
            100                 105
```

```
<210> SEQ ID NO 272
<211> LENGTH: 107
<212> TYPE: PRT
<213> ORGANISM: Artificial Sequence
<220> FEATURE:
<223> OTHER INFORMATION: synthetic

<400> SEQUENCE: 272

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Gly Asn Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105
```

```
<210> SEQ ID NO 273
<211> LENGTH: 107
<212> TYPE: PRT
<213> ORGANISM: Artificial Sequence
```

```
<220> FEATURE:
<223> OTHER INFORMATION: synthetic

<400> SEQUENCE: 273

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ser Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Phe
                85                  90                  95

Thr Phe Gly Gly Gly Thr Lys Val Glu Ile Lys
            100                 105

<210> SEQ ID NO 274
<211> LENGTH: 107
<212> TYPE: PRT
<213> ORGANISM: Artificial Sequence
<220> FEATURE:
<223> OTHER INFORMATION: synthetic

<400> SEQUENCE: 274

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Tyr
                85                  90                  95

Ser Phe Gly Gly Gly Thr Lys Val Glu Ile Lys
            100                 105

<210> SEQ ID NO 275
<211> LENGTH: 107
<212> TYPE: PRT
<213> ORGANISM: Artificial Sequence
<220> FEATURE:
<223> OTHER INFORMATION: synthetic

<400> SEQUENCE: 275

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Gln Tyr
            20                  25                  30

Leu Ala Trp Tyr Gln Gln Lys Pro Gly Lys Ala Pro Lys Leu Leu Ile
        35                  40                  45

Tyr Gly Ala Ser Asn Leu His Ser Gly Val Pro Ser Arg Phe Ser Gly
    50                  55                  60
```

```
Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Phe Ile Thr Pro Leu
                85                  90                  95

Thr Phe Gly Gly Gly Thr Lys Val Glu Ile Lys
            100                 105

<210> SEQ ID NO 276
<211> LENGTH: 106
<212> TYPE: PRT
<213> ORGANISM: Artificial Sequence
<220> FEATURE:
<223> OTHER INFORMATION: synthetic

<400> SEQUENCE: 276

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ile Ile Gly Asn Tyr
                20                  25                  30

Leu Ala Trp Tyr Gln Gln Lys Pro Gly Lys Ala Pro Lys Leu Leu Ile
            35                  40                  45

Tyr His Ala Ser Ile Leu Glu Thr Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Thr
                85                  90                  95

Phe Gly Gly Gly Thr Lys Val Glu Ile Lys
            100                 105

<210> SEQ ID NO 277
<211> LENGTH: 107
<212> TYPE: PRT
<213> ORGANISM: Artificial Sequence
<220> FEATURE:
<223> OTHER INFORMATION: synthetic

<400> SEQUENCE: 277

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ile Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Phe Ser Thr Pro Phe
                85                  90                  95

Thr Phe Gly Gly Gly Thr Lys Val Glu Ile Lys
            100                 105

<210> SEQ ID NO 278
<211> LENGTH: 107
<212> TYPE: PRT
<213> ORGANISM: Artificial Sequence
<220> FEATURE:
<223> OTHER INFORMATION: synthetic
```

```
<400> SEQUENCE: 278

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Phe Thr Asn Pro Val
            85                  90                  95

Thr Phe Gly Gly Gly Thr Lys Val Glu Ile Lys
            100                 105

<210> SEQ ID NO 279
<211> LENGTH: 107
<212> TYPE: PRT
<213> ORGANISM: Artificial Sequence
<220> FEATURE:
<223> OTHER INFORMATION: synthetic

<400> SEQUENCE: 279

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ala Pro Tyr
            85                  90                  95

Thr Phe Gly Gly Gly Thr Lys Val Glu Ile Lys
            100                 105

<210> SEQ ID NO 280
<211> LENGTH: 107
<212> TYPE: PRT
<213> ORGANISM: Artificial Sequence
<220> FEATURE:
<223> OTHER INFORMATION: synthetic

<400> SEQUENCE: 280

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Asn
            20                  25                  30

Leu Asn Trp Tyr Gln Gln Lys Pro Gly Lys Ala Pro Lys Leu Leu Ile
        35                  40                  45

Tyr Ala Ala Thr Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Ser Tyr Ser Thr Pro Tyr
                85                  90                  95

Thr Phe Gly Gly Gly Thr Lys Val Glu Ile Lys
            100                 105

<210> SEQ ID NO 281
<211> LENGTH: 107
<212> TYPE: PRT
<213> ORGANISM: Artificial Sequence
<220> FEATURE:
<223> OTHER INFORMATION: synthetic

<400> SEQUENCE: 281

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105

<210> SEQ ID NO 282
<211> LENGTH: 107
<212> TYPE: PRT
<213> ORGANISM: Artificial Sequence
<220> FEATURE:
<223> OTHER INFORMATION: synthetic

<400> SEQUENCE: 282

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Gly
                20                  25                  30

Leu Ser Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser His Ser Thr Pro Leu
                85                  90                  95

Thr Phe Gly Gly Gly Thr Lys Val Glu Ile Lys
            100                 105

<210> SEQ ID NO 283
<211> LENGTH: 107
<212> TYPE: PRT
<213> ORGANISM: Artificial Sequence
<220> FEATURE:
<223> OTHER INFORMATION: synthetic

<400> SEQUENCE: 283

Asp Ile Gln Met Thr Gln Ser Pro Ser Ser Leu Ser Ala Ser Val Gly
```

-continued

```
1                5                    10                   15

Asp Arg Val Thr Ile Thr Cys Arg Ala Ser Gln Ser Ile Thr Gly Trp
                20                   25                   30

Leu Ala Trp Tyr Gln Gln Lys Pro Gly Lys Ala Pro Lys Leu Leu Ile
            35                   40                   45

Tyr Ala Ala Ser Ser Leu Gln Ser Gly Val Pro Ser Arg Phe Ser Gly
        50                   55                   60

Ser Gly Ser Gly Thr Asp Phe Thr Leu Thr Ile Ser Ser Leu Gln Pro
65                   70                   75                   80

Glu Asp Phe Ala Thr Tyr Tyr Cys Gln Gln Ser Tyr Ser Thr Pro Tyr
                85                   90                   95

Thr Phe Gly Gln Gly Thr Lys Val Glu Ile Lys
            100                  105
```

```
<210> SEQ ID NO 284
<211> LENGTH: 107
<212> TYPE: PRT
<213> ORGANISM: Artificial Sequence
<220> FEATURE:
<223> OTHER INFORMATION: synthetic

<400> SEQUENCE: 284

Asp Ile Gln Met Thr Gln Ser Pro Ser Ser Leu Ser Ala Ser Val Gly
1                5                    10                   15

Asp Arg Val Thr Ile Thr Cys Arg Ala Ser Gln Ser Ile Ser Ser Trp
                20                   25                   30

Leu Ala Trp Tyr Gln Gln Lys Pro Gly Lys Ala Pro Lys Leu Leu Ile
            35                   40                   45

Tyr Asp Ala Thr His Leu Glu Thr Gly Val Pro Ser Arg Phe Ser Gly
        50                   55                   60

Ser Gly Ser Gly Thr Asp Phe Thr Leu Thr Ile Ser Ser Leu Gln Pro
65                   70                   75                   80

Glu Asp Phe Ala Thr Tyr Tyr Cys Gln Gln Ser Tyr Ser Thr Pro Ile
                85                   90                   95

Thr Phe Gly Gln Gly Thr Arg Leu Glu Ile Lys
            100                  105
```

```
<210> SEQ ID NO 285
<211> LENGTH: 107
<212> TYPE: PRT
<213> ORGANISM: Artificial Sequence
<220> FEATURE:
<223> OTHER INFORMATION: synthetic

<400> SEQUENCE: 285

Asp Ile Gln Met Thr Gln Ser Pro Ser Ser Leu Ser Ala Ser Val Gly
1                5                    10                   15

Asp Arg Val Thr Ile Thr Cys Arg Ala Ser Gln Gly Ile Arg Asn Asp
                20                   25                   30

Leu Ala Trp Tyr Gln Gln Lys Pro Gly Lys Ala Pro Lys Leu Leu Ile
            35                   40                   45

Tyr Ala Ala Ser Thr Leu Gln Ser Gly Val Pro Ser Arg Phe Ser Gly
        50                   55                   60

Ser Gly Ser Gly Thr Asp Phe Thr Leu Thr Ile Ser Ser Leu Gln Pro
65                   70                   75                   80

Glu Asp Phe Ala Thr Tyr Tyr Cys Gln Gln Ser Tyr Ser Thr Pro Leu
                85                   90                   95
```

```
Thr Phe Gly Gly Gly Thr Lys Val Glu Ile Lys
            100                 105

<210> SEQ ID NO 286
<211> LENGTH: 107
<212> TYPE: PRT
<213> ORGANISM: Artificial Sequence
<220> FEATURE:
<223> OTHER INFORMATION: synthetic

<400> SEQUENCE: 286

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Leu Glu Ile Lys
            100                 105

<210> SEQ ID NO 287
<211> LENGTH: 107
<212> TYPE: PRT
<213> ORGANISM: Artificial Sequence
<220> FEATURE:
<223> OTHER INFORMATION: synthetic

<400> SEQUENCE: 287

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Thr Thr Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Gly Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Val Glu Ile Lys
            100                 105

<210> SEQ ID NO 288
<211> LENGTH: 107
<212> TYPE: PRT
<213> ORGANISM: Artificial Sequence
<220> FEATURE:
<223> OTHER INFORMATION: synthetic

<400> SEQUENCE: 288

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
```

```
                20              25              30

Leu Asn Trp Tyr Gln Gln Lys Pro Gly Lys Ala Pro Lys Leu Leu Ile
        35              40              45

Tyr Ala Ala Ser Ser Leu Gln Ser Gly Val Pro Ser Arg Phe Ser Gly
    50              55              60

Ser Gly Ser Gly Thr Asp Phe Thr Leu Thr Ile Ser Ser Leu Gln Pro
65              70              75              80

Glu Asp Phe Ala Thr Tyr Tyr Cys Gln Gln Ser Tyr Ser Thr Pro Leu
                85              90              95

Thr Phe Gly Gly Gly Thr Lys Leu Glu Ile Lys
            100             105

<210> SEQ ID NO 289
<211> LENGTH: 107
<212> TYPE: PRT
<213> ORGANISM: Artificial Sequence
<220> FEATURE:
<223> OTHER INFORMATION: synthetic

<400> SEQUENCE: 289

Asp Ile Gln Met Thr Gln Ser Pro Ser Ser Leu Ser Ala Ser Val Gly
1               5               10              15

Asp Arg Val Thr Ile Thr Cys Arg Ala Ser Gln Ser Val Ser Thr Trp
            20              25              30

Leu Ala Trp Tyr Gln Gln Lys Pro Gly Lys Ala Pro Lys Leu Leu Ile
        35              40              45

Tyr Ala Ala Ser Asn Leu Glu Ser Gly Val Pro Ser Arg Phe Ser Gly
    50              55              60

Ser Gly Ser Gly Thr Asp Phe Thr Leu Thr Ile Ser Ser Leu Gln Pro
65              70              75              80

Glu Asp Phe Ala Thr Tyr Tyr Cys Gln Gln Ser Tyr Ser Thr Pro Tyr
                85              90              95

Thr Phe Gly Gln Gly Thr Lys Leu Glu Ile Lys
            100             105

<210> SEQ ID NO 290
<211> LENGTH: 107
<212> TYPE: PRT
<213> ORGANISM: Artificial Sequence
<220> FEATURE:
<223> OTHER INFORMATION: synthetic

<400> SEQUENCE: 290

Asp Ile Gln Met Thr Gln Ser Pro Ser Ser Leu Ser Ala Ser Val Gly
1               5               10              15

Asp Arg Val Thr Ile Thr Cys Arg Ala Ser Gln Ser Ile Ser Asn Trp
            20              25              30

Leu Ala Trp Tyr Gln Gln Lys Pro Gly Lys Ala Pro Lys Leu Leu Ile
        35              40              45

Tyr Asp Val Ser His Leu Glu Ser Gly Val Pro Ser Arg Phe Ser Gly
    50              55              60

Ser Gly Ser Gly Thr Asp Phe Thr Leu Thr Ile Ser Ser Leu Gln Pro
65              70              75              80

Glu Asp Phe Ala Thr Tyr Tyr Cys Gln Gln Ser Tyr Ser Thr Pro Phe
                85              90              95

Thr Phe Gly Pro Gly Thr Lys Val Asp Ile Lys
            100             105
```

<210> SEQ ID NO 291
<211> LENGTH: 107
<212> TYPE: PRT
<213> ORGANISM: Artificial Sequence
<220> FEATURE:
<223> OTHER INFORMATION: synthetic

<400> SEQUENCE: 291

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Gly Ile Ser Asn Tyr
            20                  25                  30

Leu Ala Trp Tyr Gln Gln Lys Pro Gly Lys Ala Pro Lys Leu Leu Ile
        35                  40                  45

Tyr Asp Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105

<210> SEQ ID NO 292
<211> LENGTH: 108
<212> TYPE: PRT
<213> ORGANISM: Artificial Sequence
<220> FEATURE:
<223> OTHER INFORMATION: synthetic

<400> SEQUENCE: 292

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Leu Ser Ser Ser
            20                  25                  30

Ser Leu Ala Trp Tyr Gln Gln Lys Pro Gly Gln Ala Pro Arg Leu Leu
        35                  40                  45

Ile Tyr Gly Ala Ser Thr Arg Ala Thr Gly Ile Pro Ala Arg Phe Ser
    50                  55                  60

Gly Ser Gly Ser Gly Thr Glu Phe Thr Leu Thr Ile Ser Ser Leu Gln
65                  70                  75                  80

Ser Glu Asp Phe Ala Val Tyr Tyr Cys Gln Gln Tyr Gly Ser Ser Pro
                85                  90                  95

Phe Thr Phe Gly Pro Gly Thr Lys Val Asp Ile Lys
            100                 105

<210> SEQ ID NO 293
<211> LENGTH: 107
<212> TYPE: PRT
<213> ORGANISM: Artificial Sequence
<220> FEATURE:
<223> OTHER INFORMATION: synthetic

<400> SEQUENCE: 293

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu His Ile Ala Asn Trp
            20                  25                  30

Leu Ala Trp Tyr Gln Gln Lys Pro Gly Lys Ala Pro Lys Leu Leu Ile

-continued

```
                35                40                45

Tyr Gly Val Ser Ser Leu Glu Ser Gly Val Pro Ser Arg Phe Ser Gly
    50                55                60

Ser Gly Ser Gly Thr Asp Phe Thr Leu Thr Ile Ser Ser Leu Gln Pro
65                70                75                80

Glu Asp Phe Ala Thr Tyr Tyr Cys Gln Gln Ser Tyr Ser Thr Pro Tyr
                85                90                95

Thr Phe Gly Gln Gly Thr Lys Leu Glu Ile Lys
            100                105

<210> SEQ ID NO 294
<211> LENGTH: 107
<212> TYPE: PRT
<213> ORGANISM: Artificial Sequence
<220> FEATURE:
<223> OTHER INFORMATION: synthetic

<400> SEQUENCE: 294

Asp Ile Gln Met Thr Gln Ser Pro Ser Ser Leu Ser Ala Ser Val Gly
1                5                10                15

Asp Arg Val Thr Ile Thr Cys Arg Ala Ser Gln Ser Val Gly Ser Trp
                20                25                30

Val Ala Trp Tyr Gln Gln Lys Pro Gly Lys Ala Pro Lys Leu Leu Ile
            35                40                45

Tyr Pro Ala Ser Thr Leu Gln Ser Gly Val Pro Ser Arg Phe Ser Gly
    50                55                60

Ser Gly Ser Gly Thr Asp Phe Thr Leu Thr Ile Ser Ser Leu Gln Pro
65                70                75                80

Glu Asp Phe Ala Thr Tyr Tyr Cys Gln Gln Ser Tyr Ser Thr Pro Leu
                85                90                95

Thr Phe Gly Gly Gly Thr Lys Val Glu Ile Lys
            100                105

<210> SEQ ID NO 295
<211> LENGTH: 107
<212> TYPE: PRT
<213> ORGANISM: Artificial Sequence
<220> FEATURE:
<223> OTHER INFORMATION: synthetic

<400> SEQUENCE: 295

Asp Ile Gln Met Thr Gln Ser Pro Ser Ser Leu Ser Ala Ser Val Gly
1                5                10                15

Asp Arg Val Thr Ile Thr Cys Arg Ala Ser Gln Ser Ile Ser Pro Trp
                20                25                30

Leu Ala Trp Tyr Gln Gln Lys Pro Gly Lys Ala Pro Lys Leu Leu Ile
            35                40                45

Tyr Asp Ala Ser Asn Leu Glu Thr Gly Val Pro Ser Arg Phe Ser Gly
    50                55                60

Ser Gly Ser Gly Thr Asp Phe Thr Leu Thr Ile Ser Ser Leu Gln Pro
65                70                75                80

Glu Asp Phe Ala Thr Tyr Tyr Cys Gln Gln Thr Tyr Ser Thr Pro Ile
                85                90                95

Thr Phe Gly Gln Gly Thr Arg Leu Glu Ile Lys
            100                105

<210> SEQ ID NO 296
<211> LENGTH: 107
```

<212> TYPE: PRT
<213> ORGANISM: Artificial Sequence
<220> FEATURE:
<223> OTHER INFORMATION: synthetic

<400> SEQUENCE: 296

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Arg Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys
            100                 105

<210> SEQ ID NO 297
<211> LENGTH: 108
<212> TYPE: PRT
<213> ORGANISM: Artificial Sequence
<220> FEATURE:
<223> OTHER INFORMATION: synthetic

<400> SEQUENCE: 297

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Thr Val Ser Ser Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Thr Arg Ala Ser Gly Ile Pro Ala Arg Phe Ser
    50                  55                  60

Gly Ser Gly Ser Gly Thr Glu Phe Thr Leu Thr Ile Ser Ser Leu Gln
65                  70                  75                  80

Ser Glu Asp Phe Ala Val Tyr Tyr Cys Gln Gln Tyr Tyr Thr Thr Pro
                85                  90                  95

Leu Thr Phe Gly Gly Gly Thr Lys Val Glu Ile Lys
            100                 105

<210> SEQ ID NO 298
<211> LENGTH: 107
<212> TYPE: PRT
<213> ORGANISM: Artificial Sequence
<220> FEATURE:
<223> OTHER INFORMATION: synthetic

<400> SEQUENCE: 298

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly 50                    55                    60

Ser Gly Ser Gly Thr Asp Phe Thr Leu Thr Ile Ser Ser Leu Gln Pro
65                    70                    75                    80

Glu Asp Phe Ala Thr Tyr Tyr Cys Gln Gln Ser Phe Ser Thr Pro Leu
                    85                    90                    95

Thr Phe Gly Gln Gly Thr Arg Leu Glu Ile Lys
                    100                   105

<210> SEQ ID NO 299
<211> LENGTH: 107
<212> TYPE: PRT
<213> ORGANISM: Artificial Sequence
<220> FEATURE:
<223> OTHER INFORMATION: synthetic

<400> SEQUENCE: 299

Asp Ile Gln Met Thr Gln Ser Pro Ser Ser Leu Ser Ala Ser Val Gly
1                     5                     10                    15

Asp Arg Val Thr Ile Thr Cys Arg Ala Ser Gln Ser Ile Ser Ser Trp
                    20                    25                    30

Leu Ala Trp Tyr Gln Gln Lys Pro Gly Lys Ala Pro Lys Leu Leu Ile
              35                    40                    45

Tyr Asp Ala Ser Asn Leu Glu Thr Gly Val Pro Ser Arg Phe Ser Gly
        50                    55                    60

Ser Gly Ser Gly Thr Asp Phe Thr Leu Thr Ile Ser Ser Leu Gln Pro
65                    70                    75                    80

Glu Asp Phe Ala Thr Tyr Tyr Cys Gln Gln Ser Tyr Ser Thr Pro Pro
                    85                    90                    95

Thr Phe Gly Gln Gly Thr Lys Val Glu Ile Lys
                    100                   105

<210> SEQ ID NO 300
<211> LENGTH: 107
<212> TYPE: PRT
<213> ORGANISM: Artificial Sequence
<220> FEATURE:
<223> OTHER INFORMATION: synthetic

<400> SEQUENCE: 300

Asp Ile Gln Met Thr Gln Ser Pro Ser Ser Leu Ser Ala Ser Val Gly
1                     5                     10                    15

Asp Arg Val Thr Ile Thr Cys Arg Ala Ser Gln Gly Ile Ser Asn Asn
                    20                    25                    30

Leu Asn Trp Tyr Gln Gln Lys Pro Gly Lys Ala Pro Lys Leu Leu Ile
              35                    40                    45

Tyr Ala Thr Ser Thr Leu Gln Ser Gly Val Pro Ser Arg Phe Ser Gly
        50                    55                    60

Ser Gly Ser Gly Thr Asp Phe Thr Leu Thr Ile Ser Ser Leu Gln Pro
65                    70                    75                    80

Glu Asp Phe Ala Thr Tyr Tyr Cys Gln Gln Ser Tyr Ser Thr Pro Tyr
                    85                    90                    95

Thr Phe Gly Gln Gly Thr Lys Val Glu Ile Lys
                    100                   105

<210> SEQ ID NO 301
<211> LENGTH: 107
<212> TYPE: PRT
<213> ORGANISM: Artificial Sequence
<220> FEATURE:

<223> OTHER INFORMATION: synthetic

<400> SEQUENCE: 301

```
Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Gly Ile Arg Asn Asp
            20                  25                  30

Leu Ser Trp Tyr Gln Gln Lys Pro Gly Lys Ala Pro Lys Leu Leu Ile
        35                  40                  45

Tyr Leu Ala Ser Asn Ser His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln His Asn Ser Tyr Pro Leu
                85                  90                  95

Thr Phe Gly Gly Gly Thr Lys Val Glu Ile Lys
            100                 105
```

<210> SEQ ID NO 302
<211> LENGTH: 107
<212> TYPE: PRT
<213> ORGANISM: Artificial Sequence
<220> FEATURE:
<223> OTHER INFORMATION: synthetic

<400> SEQUENCE: 302

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Arg Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Leu Glu Ile Lys
            100                 105
```

<210> SEQ ID NO 303
<211> LENGTH: 107
<212> TYPE: PRT
<213> ORGANISM: Artificial Sequence
<220> FEATURE:
<223> OTHER INFORMATION: synthetic

<400> SEQUENCE: 303

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ser Ser Ser Leu Gln Thr Gly Val Pro Ser Arg Phe Ser Gly
    50                  55                  60

Ser Gly Ser Gly Thr Asp Phe Thr Leu Thr Ile Ser Ser Leu Gln Pro
```

```
65              70              75              80

Glu Asp Phe Ala Thr Tyr Tyr Cys Gln Gln Ser Tyr Ser Thr Pro Val
                85              90              95

Thr Phe Gly Gln Gly Thr Lys Val Glu Ile Lys
            100             105

<210> SEQ ID NO 304
<211> LENGTH: 107
<212> TYPE: PRT
<213> ORGANISM: Artificial Sequence
<220> FEATURE:
<223> OTHER INFORMATION: synthetic

<400> SEQUENCE: 304

Asp Ile Gln Ile Thr His Ser Pro Ser Ser Leu Ser Ala Ser Val Gly
1               5               10              15

Tyr Arg Leu Thr Ile Thr Cys Arg Asp Ser His Ser Ile Thr Thr Trp
                20              25              30

Leu Ala Trp Tyr His Gln Lys Pro Trp Asn Ala Pro Lys Leu Met Ile
            35              40              45

Tyr Ala Ala Ser Asn Leu Glu Ser Gly Val Pro Ser Arg Phe Ser Gly
        50              55              60

Ser Gly Ser Gly Thr Tyr Phe Thr Leu Thr Ile Ser Ser Leu Gln Pro
65              70              75              80

Glu Asp Phe Ala Thr Tyr Tyr Cys Gln His Phe Tyr Asn Thr Gln Tyr
                85              90              95

Thr Phe Gly Gln Gly Thr Lys Val Glu Ile Lys
            100             105

<210> SEQ ID NO 305
<211> LENGTH: 108
<212> TYPE: PRT
<213> ORGANISM: Artificial Sequence
<220> FEATURE:
<223> OTHER INFORMATION: synthetic

<400> SEQUENCE: 305

Asp Ile Gln Met Thr Gln Ser Pro Ser Ser Leu Ser Ala Ser Val Gly
1               5               10              15

Asp Arg Val Thr Ile Thr Cys Arg Ala Ser Gln Val Ile Arg Asn Asp
                20              25              30

Leu Ala Trp Tyr Gln Gln Lys Pro Gly Lys Ala Pro Lys Leu Leu Ile
            35              40              45

Tyr Ala Ala Ser Thr Leu Gln Ser Gly Val Pro Ser Arg Phe Ser Gly
        50              55              60

Ser Gly Ser Gly Thr Asp Phe Thr Leu Thr Ile Ser Ser Leu Gln Pro
65              70              75              80

Glu Asp Phe Ala Thr Tyr Tyr Cys Gln Gln Ser Leu Gln Tyr Pro Ser
                85              90              95

His Phe Phe Gly Gln Gly Thr Lys Val Glu Ile Lys
            100             105

<210> SEQ ID NO 306
<211> LENGTH: 107
<212> TYPE: PRT
<213> ORGANISM: Artificial Sequence
<220> FEATURE:
<223> OTHER INFORMATION: synthetic

<400> SEQUENCE: 306
```

-continued

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Arg Tyr
            20                  25                  30

Leu Asn Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Pro Tyr Tyr Cys Gln Gln Ser Tyr Ser Thr Pro Leu
                85                  90                  95

Thr Phe Gly Pro Gly Thr Lys Val Asp Ile Lys
            100                 105

<210> SEQ ID NO 307
<211> LENGTH: 290
<212> TYPE: PRT
<213> ORGANISM: Artificial Sequence
<220> FEATURE:
<223> OTHER INFORMATION: synthetic

<400> SEQUENCE: 307

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
            115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255
```

```
Phe Ile Phe Arg Leu Arg Lys Gly Arg Met Met Asp Val Lys Lys Cys
            260                 265             270

Gly Ile Gln Asp Thr Asn Ser Lys Lys Gln Ser Asp Thr His Leu Glu
        275             280             285

Glu Thr
    290

<210> SEQ ID NO 308
<211> LENGTH: 607
<212> TYPE: PRT
<213> ORGANISM: Artificial Sequence
<220> FEATURE:
<223> OTHER INFORMATION: synthetic

<400> SEQUENCE: 308

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
            35                  40                  45

Ser Ser Ile Tyr Pro Ser Gly Gly Ile Thr Phe Tyr Ala Asp Thr Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Lys Leu Gly Thr Val Thr Thr Val Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
        210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320
```

```
Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Ala Gly Gly Gly Ser Gly Gly Gly Gly Ser Gly Gly Gly Gly
    450                 455                 460

Ser Gly Gly Gly Gly Ser Gly Ile Pro Pro His Val Gln Lys Ser Val
465                 470                 475                 480

Asn Asn Asp Met Ile Val Thr Asp Asn Asn Gly Ala Val Lys Phe Pro
                485                 490                 495

Gln Leu Cys Lys Phe Cys Asp Val Arg Phe Ser Thr Cys Asp Asn Gln
            500                 505                 510

Lys Ser Cys Met Ser Asn Cys Ser Ile Thr Ser Ile Cys Glu Lys Pro
            515                 520                 525

Gln Glu Val Cys Val Ala Val Trp Arg Lys Asn Asp Glu Asn Ile Thr
    530                 535                 540

Leu Glu Thr Val Cys His Asp Pro Lys Leu Pro Tyr His Asp Phe Ile
545                 550                 555                 560

Leu Glu Asp Ala Ala Ser Pro Lys Cys Ile Met Lys Glu Lys Lys Lys
                565                 570                 575

Pro Gly Glu Thr Phe Phe Met Cys Ser Cys Ser Ser Asp Glu Cys Asn
            580                 585                 590

Asp Asn Ile Ile Phe Ser Glu Glu Tyr Asn Thr Ser Asn Pro Asp
        595                 600                 605
```

<210> SEQ ID NO 309
<211> LENGTH: 5
<212> TYPE: PRT
<213> ORGANISM: Artificial Sequence
<220> FEATURE:
<223> OTHER INFORMATION: Synthetic

<400> SEQUENCE: 309

```
Thr His Tyr Met His
1               5
```

<210> SEQ ID NO 310
<211> LENGTH: 17
<212> TYPE: PRT
<213> ORGANISM: Artificial Sequence
<220> FEATURE:
<223> OTHER INFORMATION: Synthetic

<400> SEQUENCE: 310

```
Trp Ile Asn Pro Asn Ser Gly Asn Thr Gly Tyr Ala Gln Lys Phe Gln
```

-continued

```
1               5               10              15

Gly

<210> SEQ ID NO 311
<211> LENGTH: 17
<212> TYPE: PRT
<213> ORGANISM: Artificial Sequence
<220> FEATURE:
<223> OTHER INFORMATION: Synthetic

<400> SEQUENCE: 311

Trp Ile Asn Pro Asn Ser Gly His Thr Gly Tyr Ala Gln Lys Phe Gln
1               5               10              15

Gly

<210> SEQ ID NO 312
<211> LENGTH: 17
<212> TYPE: PRT
<213> ORGANISM: Artificial Sequence
<220> FEATURE:
<223> OTHER INFORMATION: Synthetic

<400> SEQUENCE: 312

Trp Ile Asn Pro Asn Ser Gly Asn Thr Gly Tyr Ser Gln Lys Phe Gln
1               5               10              15

Gly

<210> SEQ ID NO 313
<211> LENGTH: 17
<212> TYPE: PRT
<213> ORGANISM: Artificial Sequence
<220> FEATURE:
<223> OTHER INFORMATION: Synthetic

<400> SEQUENCE: 313

Trp Ile Asn Pro Asn Ser Gly His Thr Gly Tyr Ala Gln Arg Phe Gln
1               5               10              15

Gly

<210> SEQ ID NO 314
<211> LENGTH: 17
<212> TYPE: PRT
<213> ORGANISM: Artificial Sequence
<220> FEATURE:
<223> OTHER INFORMATION: Synthetic

<400> SEQUENCE: 314

Trp Met Asn Pro Asn Ser Gly Asn Thr Gly Tyr Ser Gln Lys Phe Gln
1               5               10              15

Gly

<210> SEQ ID NO 315
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 315

Glu Arg Phe Leu Gly Gly Xaa Met Asp Val
```

```
1               5                    10
```

```
<210> SEQ ID NO 316
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 316

Glu Ala Val Ala Gly Pro Xaa Met Asp Val
1               5                    10

<210> SEQ ID NO 317
<211> LENGTH: 10
<212> TYPE: PRT
<213> ORGANISM: Artificial Sequence
<220> FEATURE:
<223> OTHER INFORMATION: Synthetic

<400> SEQUENCE: 317

Asp Arg Trp Gly Gly Asp Tyr Tyr Ser Ala
1               5                    10

<210> SEQ ID NO 318
<211> LENGTH: 10
<212> TYPE: PRT
<213> ORGANISM: Artificial Sequence
<220> FEATURE:
<223> OTHER INFORMATION: Synthetic

<400> SEQUENCE: 318

Glu Arg Leu Ser Val Ala Gly Phe Asp Tyr
1               5                    10

<210> SEQ ID NO 319
<211> LENGTH: 11
<212> TYPE: PRT
<213> ORGANISM: Artificial Sequence
<220> FEATURE:
<223> OTHER INFORMATION: Synthetic

<400> SEQUENCE: 319

Arg Ala Ser Gln Gly Ile Ser Ser Tyr Leu Asn
1               5                    10

<210> SEQ ID NO 320
<211> LENGTH: 11
<212> TYPE: PRT
<213> ORGANISM: Artificial Sequence
<220> FEATURE:
<223> OTHER INFORMATION: Synthetic

<400> SEQUENCE: 320

Arg Ala Ser Gln Ser Ile Ser Ser Trp Leu Asn
1               5                    10

<210> SEQ ID NO 321
<211> LENGTH: 11
<212> TYPE: PRT
<213> ORGANISM: Artificial Sequence
<220> FEATURE:
<223> OTHER INFORMATION: Synthetic
```

-continued

<400> SEQUENCE: 321

Arg Ala Ser Gln Ser Ile Ser Ser Tyr Leu Ala
1               5                   10

<210> SEQ ID NO 322
<211> LENGTH: 11
<212> TYPE: PRT
<213> ORGANISM: Artificial Sequence
<220> FEATURE:
<223> OTHER INFORMATION: Synthetic

<400> SEQUENCE: 322

Arg Ala Ser Gln Gly Ile Ser Ser Trp Leu Asn
1               5                   10

<210> SEQ ID NO 323
<211> LENGTH: 11
<212> TYPE: PRT
<213> ORGANISM: Artificial Sequence
<220> FEATURE:
<223> OTHER INFORMATION: Synthetic

<400> SEQUENCE: 323

Arg Ala Ser Gln Gly Ile Ser Ser Trp Leu Ala
1               5                   10

<210> SEQ ID NO 324
<211> LENGTH: 118
<212> TYPE: PRT
<213> ORGANISM: Artificial Sequence
<220> FEATURE:
<223> OTHER INFORMATION: Synthetic

<400> SEQUENCE: 324

Gln Val Gln Leu Val Gln Ser Gly Ala Glu Val Lys Lys Pro Gly Ala
1               5                   10                  15

Ser Val Lys Val Ser Cys Lys Ala Ser Gly Asp Thr Phe Thr Asn His
            20                  25                  30

Tyr Met His Trp Val Arg Gln Ala Pro Gly Gln Gly Leu Glu Trp Met
        35                  40                  45

Gly Trp Met Asn Pro Asn Ser Gly His Thr Gly Tyr Ala Gln Arg Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ala Val Ala Gly Pro Met Asp Val Trp Gly Gln Gly Thr
            100                 105                 110

Thr Val Thr Val Ser Ser
        115

<210> SEQ ID NO 325
<211> LENGTH: 119
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (105)..(105)
<223> OTHER INFORMATION: Xaa can be any naturally occurring amino acid

<400> SEQUENCE: 325

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Tyr Met His Trp Val Arg Gln Ala Pro Gly Gln Gly Leu Glu Trp Met
        35                  40                  45

Gly Trp Ile Asn Pro Asn Ser Gly Asn Thr Gly Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Arg Phe Leu Gly Gly Xaa Met Asp Val Trp Gly Gln Gly
            100                 105                 110

Thr Thr Val Thr Val Ser Ser
        115
```

<210> SEQ ID NO 326
<211> LENGTH: 119
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (105)..(105)
<223> OTHER INFORMATION: Xaa can be any naturally occurring amino acid

<400> SEQUENCE: 326

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn His
            20                  25                  30

Tyr Met His Trp Val Arg Gln Ala Pro Gly Gln Gly Leu Glu Trp Met
        35                  40                  45

Gly Trp Ile Asn Pro Asn Ser Gly His Thr Gly Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ala Val Ala Gly Pro Xaa Met Asp Val Trp Gly Gln Gly
            100                 105                 110

Thr Thr Val Thr Val Ser Ser
        115
```

<210> SEQ ID NO 327
<211> LENGTH: 119
<212> TYPE: PRT
<213> ORGANISM: Artificial Sequence
<220> FEATURE:
<223> OTHER INFORMATION: Synthetic

<400> SEQUENCE: 327

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn His
            20                  25                  30

Tyr Met His Trp Val Arg Gln Ala Pro Gly Gln Gly Leu Glu Trp Met
```

-continued

```
              35                    40                    45
Gly Trp Ile Asn Pro Asn Ser Gly Asn Thr Gly Tyr Ala Gln Lys Phe
    50                    55                    60
Gln Gly Arg Val Thr Met Thr Arg Asp Thr Ser Thr Ser Thr Val Tyr
65                    70                    75                    80
Met Glu Leu Ser Ser Leu Arg Ser Glu Asp Thr Ala Val Tyr Tyr Cys
                  85                    90                    95
Ala Arg Asp Arg Trp Gly Gly Asp Tyr Tyr Ser Ala Trp Gly Gln Gly
                 100                   105                   110
Thr Leu Val Thr Val Ser Ser
             115
```

<210> SEQ ID NO 328
<211> LENGTH: 119
<212> TYPE: PRT
<213> ORGANISM: Artificial Sequence
<220> FEATURE:
<223> OTHER INFORMATION: Synthetic

<400> SEQUENCE: 328

```
Gln Val Gln Leu Val Gln Ser Gly Ala Glu Val Lys Lys Pro Gly Ala
1                 5                    10                    15
Ser Val Lys Val Ser Cys Lys Ala Ser Gly Tyr Thr Phe Ser Thr His
                  20                    25                    30
Tyr Met His Trp Val Arg Gln Ala Pro Gly Gln Gly Leu Glu Trp Met
              35                    40                    45
Gly Trp Ile Asn Pro Asn Ser Gly Asn Thr Gly Tyr Ser Gln Lys Phe
    50                    55                    60
Gln Gly Arg Val Thr Met Thr Arg Asp Thr Ser Thr Ser Thr Val Tyr
65                    70                    75                    80
Met Glu Leu Ser Ser Leu Arg Ser Glu Asp Thr Ala Val Tyr Tyr Cys
                  85                    90                    95
Ala Arg Glu Arg Leu Ser Val Ala Gly Phe Asp Tyr Trp Gly Gln Gly
                 100                   105                   110
Thr Leu Val Thr Val Ser Ser
             115
```

<210> SEQ ID NO 329
<211> LENGTH: 118
<212> TYPE: PRT
<213> ORGANISM: Artificial Sequence
<220> FEATURE:
<223> OTHER INFORMATION: Synthetic

<400> SEQUENCE: 329

```
Gln Val Gln Leu Val Gln Ser Gly Ala Glu Val Lys Lys Pro Gly Ala
1                 5                    10                    15
Ser Val Lys Val Ser Cys Lys Ala Ser Gly Tyr Thr Phe Thr Asn His
                  20                    25                    30
Tyr Met His Trp Val Arg Gln Ala Pro Gly Gln Gly Leu Glu Trp Met
              35                    40                    45
Gly Trp Met Asn Pro Asn Ser Gly His Thr Gly Tyr Ala Gln Arg Phe
    50                    55                    60
Gln Gly Arg Val Thr Met Thr Arg Asp Thr Ser Thr Ser Thr Val Tyr
65                    70                    75                    80
Met Glu Leu Ser Ser Leu Arg Ser Glu Asp Thr Ala Val Tyr Tyr Cys
                  85                    90                    95
```

```
Ala Arg Glu Ala Val Ala Gly Pro Met Asp Val Trp Gly Gln Gly Thr
            100                 105                 110

Thr Val Thr Val Ser Ser
        115

<210> SEQ ID NO 330
<211> LENGTH: 118
<212> TYPE: PRT
<213> ORGANISM: Artificial Sequence
<220> FEATURE:
<223> OTHER INFORMATION: Synthetic

<400> SEQUENCE: 330

Gln Val Gln Leu Val Gln Ser Gly Ala Glu Val Lys Lys Pro Gly Ala
1               5                   10                  15

Ser Val Lys Val Ser Cys Lys Ala Ser Gly Asp Thr Phe Thr Asn His
            20                  25                  30

Tyr Met His Trp Val Arg Gln Ala Pro Gly Gln Gly Leu Glu Trp Met
        35                  40                  45

Gly Trp Met Asn Pro Asn Ser Gly His Thr Gly Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ala Val Ala Gly Pro Met Asp Val Trp Gly Gln Gly Thr
            100                 105                 110

Thr Val Thr Val Ser Ser
        115

<210> SEQ ID NO 331
<211> LENGTH: 118
<212> TYPE: PRT
<213> ORGANISM: Artificial Sequence
<220> FEATURE:
<223> OTHER INFORMATION: Synthetic

<400> SEQUENCE: 331

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn His
            20                  25                  30

Tyr Met His Trp Val Arg Gln Ala Pro Gly Gln Gly Leu Glu Trp Met
        35                  40                  45

Gly Trp Ile Asn Pro Asn Ser Gly His Thr Gly Tyr Ala Gln Arg Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ala Val Ala Gly Pro Met Asp Val Trp Gly Gln Gly Thr
            100                 105                 110

Thr Val Thr Val Ser Ser
        115

<210> SEQ ID NO 332
<211> LENGTH: 118
<212> TYPE: PRT
<213> ORGANISM: Artificial Sequence
```

-continued

```
<220> FEATURE:
<223> OTHER INFORMATION: Synthetic

<400> SEQUENCE: 332

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn His
                20                  25                  30

Tyr Met His Trp Val Arg Gln Ala Pro Gly Gln Gly Leu Glu Trp Met
            35                  40                  45

Gly Trp Met Asn Pro Asn Ser Gly His Thr Gly Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ala Val Ala Gly Pro Met Asp Val Trp Gly Gln Gly Thr
            100                 105                 110

Thr Val Thr Val Ser Ser
        115

<210> SEQ ID NO 333
<211> LENGTH: 118
<212> TYPE: PRT
<213> ORGANISM: Artificial Sequence
<220> FEATURE:
<223> OTHER INFORMATION: Synthetic

<400> SEQUENCE: 333

Gln Val Gln Leu Val Gln Ser Gly Ala Glu Val Lys Lys Pro Gly Ala
1               5                   10                  15

Ser Val Lys Val Ser Cys Lys Ala Ser Gly Asp Thr Phe Thr Asn His
                20                  25                  30

Tyr Met His Trp Val Arg Gln Ala Pro Gly Gln Gly Leu Glu Trp Met
            35                  40                  45

Gly Trp Ile Asn Pro Asn Ser Gly His Thr Gly Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ala Val Ala Gly Pro Met Asp Val Trp Gly Gln Gly Thr
            100                 105                 110

Thr Val Thr Val Ser Ser
        115

<210> SEQ ID NO 334
<211> LENGTH: 119
<212> TYPE: PRT
<213> ORGANISM: Artificial Sequence
<220> FEATURE:
<223> OTHER INFORMATION: Synthetic

<400> SEQUENCE: 334

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Thr His
                20                  25                  30
```

```
Tyr Met His Trp Val Arg Gln Ala Pro Gly Gln Gly Leu Glu Trp Met
        35                  40                  45

Gly Trp Met Asn Pro Asn Ser Gly Asn Thr Gly Tyr Ser Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Arg Leu Ser Val Ala Gly Phe Asp Tyr Trp Gly Gln Gly
            100                 105                 110

Thr Leu Val Thr Val Ser Ser
        115
```

```
<210> SEQ ID NO 335
<211> LENGTH: 107
<212> TYPE: PRT
<213> ORGANISM: Artificial Sequence
<220> FEATURE:
<223> OTHER INFORMATION: Synthetic

<400> SEQUENCE: 335

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105
```

```
<210> SEQ ID NO 336
<211> LENGTH: 107
<212> TYPE: PRT
<213> ORGANISM: Artificial Sequence
<220> FEATURE:
<223> OTHER INFORMATION: Synthetic

<400> SEQUENCE: 336

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Trp
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105
```

```
<210> SEQ ID NO 337
<211> LENGTH: 107
<212> TYPE: PRT
<213> ORGANISM: Artificial Sequence
<220> FEATURE:
<223> OTHER INFORMATION: Synthetic

<400> SEQUENCE: 337

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105

<210> SEQ ID NO 338
<211> LENGTH: 107
<212> TYPE: PRT
<213> ORGANISM: Artificial Sequence
<220> FEATURE:
<223> OTHER INFORMATION: Synthetic

<400> SEQUENCE: 338

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105

<210> SEQ ID NO 339
<211> LENGTH: 107
<212> TYPE: PRT
<213> ORGANISM: Artificial Sequence
<220> FEATURE:
<223> OTHER INFORMATION: Synthetic

<400> SEQUENCE: 339

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30
```

```
Leu Ala Trp Tyr Gln Gln Lys Pro Gly Lys Ala Pro Lys Leu Leu Ile
        35              40              45

Tyr Ala Ala Ser Ser Leu Gln Ser Gly Val Pro Ser Arg Phe Ser Gly
    50              55              60

Ser Gly Ser Gly Thr Asp Phe Thr Leu Thr Ile Ser Ser Leu Gln Pro
65              70              75              80

Glu Asp Phe Ala Thr Tyr Tyr Cys Gln Gln Ser Tyr Ser Thr Pro Leu
                85              90              95

Thr Phe Gly Gly Gly Thr Lys Val Glu Ile Lys
            100             105
```

<210> SEQ ID NO 340
<211> LENGTH: 107
<212> TYPE: PRT
<213> ORGANISM: Artificial Sequence
<220> FEATURE:
<223> OTHER INFORMATION: Synthetic

<400> SEQUENCE: 340

```
Asp Ile Gln Met Thr Gln Ser Pro Ser Ser Leu Ser Ala Ser Val Gly
1               5               10              15

Asp Arg Val Thr Ile Thr Cys Arg Ala Ser Gln Ser Ile Ser Ser Trp
            20              25              30

Leu Ala Trp Tyr Gln Gln Lys Pro Gly Lys Ala Pro Lys Leu Leu Ile
        35              40              45

Tyr Ala Ala Ser Ser Leu Gln Ser Gly Val Pro Ser Arg Phe Ser Gly
    50              55              60

Ser Gly Ser Gly Thr Asp Phe Thr Leu Thr Ile Ser Ser Leu Gln Pro
65              70              75              80

Glu Asp Phe Ala Thr Tyr Tyr Cys Gln Gln Ser Tyr Ser Thr Pro Leu
                85              90              95

Thr Phe Gly Gly Gly Thr Lys Val Glu Ile Lys
            100             105
```

<210> SEQ ID NO 341
<211> LENGTH: 107
<212> TYPE: PRT
<213> ORGANISM: Artificial Sequence
<220> FEATURE:
<223> OTHER INFORMATION: Synthetic

<400> SEQUENCE: 341

```
Asp Ile Gln Met Thr Gln Ser Pro Ser Ser Leu Ser Ala Ser Val Gly
1               5               10              15

Asp Arg Val Thr Ile Thr Cys Arg Ala Ser Gln Gly Ile Ser Ser Trp
            20              25              30

Leu Ala Trp Tyr Gln Gln Lys Pro Gly Lys Ala Pro Lys Leu Leu Ile
        35              40              45

Tyr Ala Ala Ser Ser Leu Gln Ser Gly Val Pro Ser Arg Phe Ser Gly
    50              55              60

Ser Gly Ser Gly Thr Asp Phe Thr Leu Thr Ile Ser Ser Leu Gln Pro
65              70              75              80

Glu Asp Phe Ala Thr Tyr Tyr Cys Gln Gln Ser Tyr Ser Thr Pro Leu
                85              90              95

Thr Phe Gly Gly Gly Thr Lys Val Glu Ile Lys
            100             105
```

<210> SEQ ID NO 342

<211> LENGTH: 107
<212> TYPE: PRT
<213> ORGANISM: Artificial Sequence
<220> FEATURE:
<223> OTHER INFORMATION: Synthetic

<400> SEQUENCE: 342

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys
            100                 105
```

<210> SEQ ID NO 343
<211> LENGTH: 107
<212> TYPE: PRT
<213> ORGANISM: Artificial Sequence
<220> FEATURE:
<223> OTHER INFORMATION: Synthetic

<400> SEQUENCE: 343

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Val Glu Ile Lys
            100                 105
```

<210> SEQ ID NO 344
<211> LENGTH: 107
<212> TYPE: PRT
<213> ORGANISM: Artificial Sequence
<220> FEATURE:
<223> OTHER INFORMATION: Synthetic

<400> SEQUENCE: 344

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45
```

```
Tyr Ala Ala Ser Ser Leu Gln Ser Gly Val Pro Ser Arg Phe Ser Gly
    50              55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln Ser Tyr Ser Thr Pro Tyr
                85                  90                  95

Thr Phe Gly Gly Gly Thr Lys Val Glu Ile Lys
            100                 105

<210> SEQ ID NO 345
<211> LENGTH: 5
<212> TYPE: PRT
<213> ORGANISM: Artificial Sequence
<220> FEATURE:
<223> OTHER INFORMATION: Synthetic

<400> SEQUENCE: 345

Asp His Tyr Leu His
1               5

<210> SEQ ID NO 346
<211> LENGTH: 17
<212> TYPE: PRT
<213> ORGANISM: Artificial Sequence
<220> FEATURE:
<223> OTHER INFORMATION: Synthetic

<400> SEQUENCE: 346

Trp Ile Thr Thr Asn Ser Gly Ile Thr Gly Tyr Ala Gln Lys Phe Gln
1               5                   10                  15

Gly

<210> SEQ ID NO 347
<211> LENGTH: 17
<212> TYPE: PRT
<213> ORGANISM: Artificial Sequence
<220> FEATURE:
<223> OTHER INFORMATION: Synthetic

<400> SEQUENCE: 347

Trp Ile Asn Pro Asn Ser Gly His Ala Gly Ser Ala Gln Lys Phe Gln
1               5                   10                  15

Gly

<210> SEQ ID NO 348
<211> LENGTH: 17
<212> TYPE: PRT
<213> ORGANISM: Artificial Sequence
<220> FEATURE:
<223> OTHER INFORMATION: Synthetic

<400> SEQUENCE: 348

Trp Ile Asn Pro Asn Ser Gly Thr Thr Gly Tyr Ala Gln Asn Phe Gln
1               5                   10                  15

Gly

<210> SEQ ID NO 349
<211> LENGTH: 17
<212> TYPE: PRT
<213> ORGANISM: Artificial Sequence
<220> FEATURE:
<223> OTHER INFORMATION: Synthetic

<400> SEQUENCE: 349
```

Trp Ile Asn Pro Asn Ile Gly Asn Thr Gly Tyr Ala Gln Lys Phe Gln
1               5                   10                  15

Gly

<210> SEQ ID NO 350
<211> LENGTH: 9
<212> TYPE: PRT
<213> ORGANISM: Artificial Sequence
<220> FEATURE:
<223> OTHER INFORMATION: Synthetic

<400> SEQUENCE: 350

Glu Gly Tyr Ser Ser Gly Leu Asp Tyr
1               5

<210> SEQ ID NO 351
<211> LENGTH: 10
<212> TYPE: PRT
<213> ORGANISM: Artificial Sequence
<220> FEATURE:
<223> OTHER INFORMATION: Synthetic

<400> SEQUENCE: 351

Glu Ser Ile Ala Val Ala Gly Tyr Asp Tyr
1               5                   10

<210> SEQ ID NO 352
<211> LENGTH: 10
<212> TYPE: PRT
<213> ORGANISM: Artificial Sequence
<220> FEATURE:
<223> OTHER INFORMATION: Synthetic

<400> SEQUENCE: 352

Glu Gly Phe Gly Pro Asn Ala Phe Asp Ile
1               5                   10

<210> SEQ ID NO 353
<211> LENGTH: 10
<212> TYPE: PRT
<213> ORGANISM: Artificial Sequence
<220> FEATURE:
<223> OTHER INFORMATION: Synthetic

<400> SEQUENCE: 353

Asp Asp Trp Gly Gly Asp Trp Phe Asp Tyr
1               5                   10

<210> SEQ ID NO 354
<211> LENGTH: 10
<212> TYPE: PRT
<213> ORGANISM: Artificial Sequence
<220> FEATURE:
<223> OTHER INFORMATION: Synthetic

<400> SEQUENCE: 354

Glu Pro Leu Gln Leu Gly Gly Phe Asp Tyr
1               5                   10

<210> SEQ ID NO 355
<211> LENGTH: 11
<212> TYPE: PRT
<213> ORGANISM: Artificial Sequence
<220> FEATURE:
<223> OTHER INFORMATION: Synthetic

```
<400> SEQUENCE: 355

Gln Ala Ser Gln Asp Ile Ser Asn His Leu Asn
1               5                   10

<210> SEQ ID NO 356
<211> LENGTH: 11
<212> TYPE: PRT
<213> ORGANISM: Artificial Sequence
<220> FEATURE:
<223> OTHER INFORMATION: Synthetic

<400> SEQUENCE: 356

Arg Ala Ser Glu Ser Ile Ser Ser Trp Leu Ala
1               5                   10

<210> SEQ ID NO 357
<211> LENGTH: 7
<212> TYPE: PRT
<213> ORGANISM: Artificial Sequence
<220> FEATURE:
<223> OTHER INFORMATION: Synthetic

<400> SEQUENCE: 357

Ala Ala Ser Thr Leu Gln Arg
1               5

<210> SEQ ID NO 358
<211> LENGTH: 7
<212> TYPE: PRT
<213> ORGANISM: Artificial Sequence
<220> FEATURE:
<223> OTHER INFORMATION: Synthetic

<400> SEQUENCE: 358

Ala Ala Ser Asn Leu Gln Ser
1               5

<210> SEQ ID NO 359
<211> LENGTH: 7
<212> TYPE: PRT
<213> ORGANISM: Artificial Sequence
<220> FEATURE:
<223> OTHER INFORMATION: Synthetic

<400> SEQUENCE: 359

Gly Ala Ser Asn Leu Gln Arg
1               5

<210> SEQ ID NO 360
<211> LENGTH: 9
<212> TYPE: PRT
<213> ORGANISM: Artificial Sequence
<220> FEATURE:
<223> OTHER INFORMATION: Synthetic

<400> SEQUENCE: 360

Gln Gln Tyr Tyr Ser Thr Pro Tyr Thr
1               5

<210> SEQ ID NO 361
<211> LENGTH: 118
<212> TYPE: PRT
<213> ORGANISM: Artificial Sequence
<220> FEATURE:
<223> OTHER INFORMATION: Synthetic

<400> SEQUENCE: 361
```

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Ser Tyr
            20                  25                  30

Tyr Met His Trp Val Arg Gln Ala Pro Gly Gln Gly Leu Glu Trp Met
        35                  40                  45

Gly Trp Ile Thr Thr Asn Ser Gly Ile Thr Gly Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Gly Tyr Ser Ser Gly Leu Asp Tyr Trp Gly Gln Gly Thr
            100                 105                 110

Leu Val Thr Val Ser Ser
        115
```

```
<210> SEQ ID NO 362
<211> LENGTH: 119
<212> TYPE: PRT
<213> ORGANISM: Artificial Sequence
<220> FEATURE:
<223> OTHER INFORMATION: Synthetic

<400> SEQUENCE: 362
```

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Thr His
            20                  25                  30

Tyr Met His Trp Val Arg Gln Ala Pro Gly Gln Gly Leu Glu Trp Met
        35                  40                  45

Gly Trp Ile Asn Pro Asn Ser Gly His Ala Gly Ser Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ser Ile Ala Val Ala Gly Tyr Asp Tyr Trp Gly Gln Gly
            100                 105                 110

Thr Leu Val Thr Val Ser Ser
        115
```

```
<210> SEQ ID NO 363
<211> LENGTH: 119
<212> TYPE: PRT
<213> ORGANISM: Artificial Sequence
<220> FEATURE:
<223> OTHER INFORMATION: Synthetic

<400> SEQUENCE: 363
```

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Thr Thr Gly Tyr Ala Gln Asn Phe
```

```
        50              55              60

Gln Gly Arg Val Thr Met Thr Arg Asp Thr Ser Thr Ser Thr Val Tyr
65              70              75              80

Met Glu Leu Ser Ser Leu Arg Ser Glu Asp Thr Ala Val Tyr Tyr Cys
                85              90              95

Ala Arg Glu Gly Phe Gly Pro Asn Ala Phe Asp Ile Trp Gly Gln Gly
            100             105             110

Thr Thr Val Thr Val Ser Ser
        115

<210> SEQ ID NO 364
<211> LENGTH: 119
<212> TYPE: PRT
<213> ORGANISM: Artificial Sequence
<220> FEATURE:
<223> OTHER INFORMATION: Synthetic

<400> SEQUENCE: 364

Gln Val Gln Leu Val Gln Ser Gly Ala Glu Val Lys Lys Pro Gly Ala
1               5               10              15

Ser Val Lys Val Ser Cys Lys Ala Ser Gly Tyr Thr Phe Thr Ser Tyr
            20              25              30

Tyr Met His Trp Val Arg Gln Ala Pro Gly Gln Gly Leu Glu Trp Met
        35              40              45

Gly Trp Ile Asn Pro Asn Ser Gly Asn Thr Gly Tyr Ala Gln Lys Phe
    50              55              60

Gln Gly Arg Val Thr Met Thr Arg Asp Thr Ser Thr Ser Thr Val Tyr
65              70              75              80

Met Glu Leu Ser Ser Leu Arg Ser Glu Asp Thr Ala Val Tyr Tyr Cys
                85              90              95

Ala Arg Asp Asp Trp Gly Gly Asp Trp Phe Asp Tyr Trp Gly Gln Gly
            100             105             110

Thr Leu Val Thr Val Ser Ser
        115

<210> SEQ ID NO 365
<211> LENGTH: 119
<212> TYPE: PRT
<213> ORGANISM: Artificial Sequence
<220> FEATURE:
<223> OTHER INFORMATION: Synthetic

<400> SEQUENCE: 365

Gln Val Gln Leu Val Gln Ser Gly Ala Glu Val Lys Lys Pro Gly Ala
1               5               10              15

Ser Val Lys Val Ser Cys Lys Ala Ser Gly Tyr Thr Phe Thr Asp His
            20              25              30

Tyr Leu His Trp Val Arg Gln Ala Pro Gly Gln Gly Leu Glu Trp Met
        35              40              45

Gly Trp Ile Asn Pro Asn Ile Gly Asn Thr Gly Tyr Ala Gln Lys Phe
    50              55              60

Gln Gly Arg Val Thr Met Thr Arg Asp Thr Ser Thr Ser Thr Val Tyr
65              70              75              80

Met Glu Leu Ser Ser Leu Arg Ser Glu Asp Thr Ala Val Tyr Tyr Cys
                85              90              95

Ala Arg Glu Pro Leu Gln Leu Gly Gly Phe Asp Tyr Trp Gly Gln Gly
            100             105             110
```

-continued

```
Thr Leu Val Thr Val Ser Ser
        115

<210> SEQ ID NO 366
<211> LENGTH: 107
<212> TYPE: PRT
<213> ORGANISM: Artificial Sequence
<220> FEATURE:
<223> OTHER INFORMATION: Synthetic

<400> SEQUENCE: 366

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gly Gly Thr Lys Val Glu Ile Lys
            100                 105

<210> SEQ ID NO 367
<211> LENGTH: 107
<212> TYPE: PRT
<213> ORGANISM: Artificial Sequence
<220> FEATURE:
<223> OTHER INFORMATION: Synthetic

<400> SEQUENCE: 367

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Arg Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Leu Glu Ile Lys
            100                 105

<210> SEQ ID NO 368
<211> LENGTH: 107
<212> TYPE: PRT
<213> ORGANISM: Artificial Sequence
<220> FEATURE:
<223> OTHER INFORMATION: Synthetic

<400> SEQUENCE: 368

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Trp
```

-continued

```
              20                  25                  30

Leu Ala Trp Tyr Gln Gln Lys Pro Gly Lys Ala Pro Lys Leu Leu Ile
         35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Thr Pro Tyr
                   85                  90                  95

Thr Phe Gly Gln Gly Thr Lys Val Glu Ile Lys
              100                 105

<210> SEQ ID NO 369
<211> LENGTH: 107
<212> TYPE: PRT
<213> ORGANISM: Artificial Sequence
<220> FEATURE:
<223> OTHER INFORMATION: Synthetic

<400> SEQUENCE: 369

Asp Ile Gln Met Thr Gln Ser Pro Ser Ser Leu Ser Ala Ser Val Gly
1                   5                  10                  15

Asp Arg Val Thr Ile Thr Cys Gln Ala Ser Gln Asp Ile Ser Asn His
              20                  25                  30

Leu Asn Trp Tyr Gln Gln Lys Pro Gly Lys Ala Pro Lys Leu Leu Ile
         35                  40                  45

Tyr Gly Ala Ser Asn Leu Gln Arg Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ile
                   85                  90                  95

Thr Phe Gly Gln Gly Thr Arg Leu Glu Ile Lys
              100                 105

<210> SEQ ID NO 370
<211> LENGTH: 107
<212> TYPE: PRT
<213> ORGANISM: Artificial Sequence
<220> FEATURE:
<223> OTHER INFORMATION: Synthetic

<400> SEQUENCE: 370

Asp Ile Gln Met Thr Gln Ser Pro Ser Ser Leu Ser Ala Ser Val Gly
1                   5                  10                  15

Asp Arg Val Thr Ile Thr Cys Arg Ala Ser Glu Ser Ile Ser Ser Trp
              20                  25                  30

Leu Ala Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                   85                  90                  95

Thr Phe Gly Gln Gly Thr Lys Leu Glu Ile Lys
              100                 105
```